(12) United States Patent
Bischoff et al.

(10) Patent No.: US 10,562,897 B2
(45) Date of Patent: *Feb. 18, 2020

(54) SUBSTITUTED 3,4-DIHYDRO-2H-PYRIDO[1,2-A]PYRAZINE-1,6-DIONES AS GAMMA SECRETASE MODULATORS

(71) Applicant: Janssen Pharmaceutica NV, Beerse (BE)

(72) Inventors: François Paul Bischoff, Vosselaar (BE); Adriana Ingrid Velter, Antwerp (BE); Frederik Jan Rita Rombouts, Wilrijk (BE); Michel Anna Jozef De Cleyn, Lille (BE); Sven Franciscus Anna Van Brandt, Beerse (BE); Henricus Jacobus Maria Gijsen, Breda (NL); Chiara Zavattaro, Zonhoven (BE); Frans Alfons Maria Van den Keybus, Essen (BE)

(73) Assignee: JANSSEN PHARMACEUTICA NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 16/038,761

(22) Filed: Jul. 18, 2018

(65) Prior Publication Data

US 2018/0319797 A1 Nov. 8, 2018

Related U.S. Application Data

(63) Continuation of application No. 14/761,801, filed as application No. PCT/EP2014/050787 on Jan. 16, 2014, now Pat. No. 10,246,454.

(51) Int. Cl.
| | | |
|---|---|---|
| *A61K 31/4985* | (2006.01) | |
| *C07D 487/04* | (2006.01) | |
| *C07D 471/04* | (2006.01) | |

(52) U.S. Cl.
CPC .................. *C07D 471/04* (2013.01)

(58) Field of Classification Search
CPC .......... A61K 31/4985; C07D 487/04
USPC .......................... 514/249; 544/349
See application file for complete search history.

(56) References Cited

U.S. PATENT DOCUMENTS

| | | | |
|---|---|---|---|
| 5,565,453 A | 10/1996 | Bright et al. | |
| 5,767,144 A | 6/1998 | Winn et al. | |
| 6,114,334 A | 9/2000 | Kerrigan et al. | |
| 6,995,155 B2 | 2/2006 | Churcher et al. | |
| 7,517,532 B2 | 4/2009 | Wai et al. | |
| 7,923,563 B2 | 4/2011 | Kushida et al. | |
| 8,598,353 B2 | 12/2013 | Mjalli et al. | |
| 8,664,411 B2 | 3/2014 | Wu et al. | |
| 8,916,564 B2 | 3/2014 | Pettersson et al. | |
| 2002/0128319 A1 | 9/2002 | Galasko et al. | |
| 2006/0004013 A1 | 1/2006 | Kimura et al. | |
| 2006/0223849 A1 | 10/2006 | Mjalli et al. | |
| 2008/0280948 A1 | 11/2008 | Baumann et al. | |
| 2009/0062529 A1 | 3/2009 | Doko et al. | |
| 2010/0137320 A1 | 6/2010 | Huang et al. | |
| 2011/0015175 A1 | 1/2011 | Marcin et al. | |
| 2012/0053165 A1 | 3/2012 | Allen et al. | |

FOREIGN PATENT DOCUMENTS

| | | |
|---|---|---|
| CA | 2118936 A1 | 4/2001 |
| CN | 101142194 | 3/2008 |
| EP | 1757591 | 2/2007 |
| EP | 1992618 A1 | 11/2008 |
| JP | 2003/502313 | 1/2003 |
| WO | WO 01/78721 | 10/2001 |
| WO | WO 01/87845 | 11/2001 |
| WO | WO 02/22574 A1 | 3/2002 |
| WO | WO 2002/069946 | 9/2002 |
| WO | WO 04/024078 A1 | 3/2004 |
| WO | WO 2004/017963 | 3/2004 |
| WO | WO 2004/076448 | 9/2004 |
| WO | WO 2004/110350 | 12/2004 |
| WO | WO 2005/016892 | 5/2005 |
| WO | WO 2005/085245 | 9/2005 |
| WO | WO 2006/099379 | 9/2006 |
| WO | WO 2005/115990 | 12/2006 |
| WO | WO 2006/135667 | 12/2006 |
| WO | WO 2007/038314 | 4/2007 |
| WO | WO 2007/043786 | 4/2007 |
| WO | WO 2007/044895 | 4/2007 |
| WO | WO 2007/034252 | 5/2007 |
| WO | WO 2007/058942 | 5/2007 |
| WO | WO 2001/102580 | 9/2007 |
| WO | WO 2007/105953 | 9/2007 |
| WO | WO 2007/113276 | 10/2007 |
| WO | WO 2007/131991 | 11/2007 |

(Continued)

OTHER PUBLICATIONS

Jordan, V. C. Nature Reviews: Drug Discovery, 2, 2003, 205.*

(Continued)

*Primary Examiner* — Douglas M Willis

(57) ABSTRACT

The present invention is concerned with novel substituted pyrido-piperazinone derivatives of Formula (I)

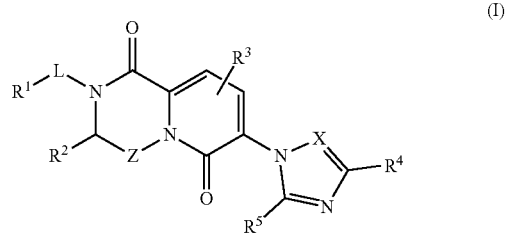

wherein $R^1$, $R^2$, $R^3$, $R^4$, $R^5$, L, Z and X have the meaning defined in the claims. The compounds according to the present invention are useful as gamma secretase modulators. The invention further relates to processes for preparing such novel compounds, pharmaceutical compositions comprising said compounds as an active ingredient as well as the use of said compounds as a medicament.

11 Claims, No Drawings

(56) References Cited

FOREIGN PATENT DOCUMENTS

| | | |
|---|---|---|
| WO | WO 2008/065199 | 6/2008 |
| WO | WO 2008/073370 | 6/2008 |
| WO | WO 2008/082490 | 7/2008 |
| WO | WO 2008/097538 | 8/2008 |
| WO | WO 2008/099210 | 8/2008 |
| WO | WO 2008/100412 | 8/2008 |
| WO | WO 2008/137139 | 11/2008 |
| WO | WO 2008/156580 | 12/2008 |
| WO | WO 2009/005729 | 1/2009 |
| WO | WO 2009/028588 | 3/2009 |
| WO | WO 2009/032277 | 3/2009 |
| WO | WO 2009/050227 | 4/2009 |
| WO | WO 2009/073777 | 6/2009 |
| WO | WO 2009/076352 | 6/2009 |
| WO | WO 2009/103652 | 8/2009 |
| WO | WO 2009/155551 | 12/2009 |
| WO | WO 2010/010188 | 1/2010 |
| WO | WO 2010/038488 | 3/2010 |
| WO | WO 2010/052199 A1 | 5/2010 |
| WO | WO 2010/054067 | 5/2010 |
| WO | WO 2010/065310 | 6/2010 |
| WO | WO 2010/070008 | 6/2010 |
| WO | WO 2010/083141 | 7/2010 |
| WO | WO 2010/089292 | 8/2010 |
| WO | WO 2010/094647 | 8/2010 |
| WO | WO 2010/098487 | 9/2010 |
| WO | WO 2010/098495 | 9/2010 |
| WO | WO 2010/100606 | 9/2010 |
| WO | WO 2010/106745 | 9/2010 |
| WO | WO 2010/114971 A1 | 10/2010 |
| WO | WO 2010/126745 | 11/2010 |
| WO | WO 2010/137320 | 12/2010 |
| WO | WO 2010/145883 | 12/2010 |
| WO | WO 2011/006903 | 1/2011 |
| WO | WO 2011/048525 A1 | 4/2011 |
| WO | WO 2011/086098 | 7/2011 |
| WO | WO 2011/086099 | 7/2011 |
| WO | WO 2011/094823 A1 | 8/2011 |
| WO | WO 2012/126984 | 9/2012 |
| WO | WO 2012/131539 | 10/2012 |
| WO | WO 2013/010904 | 1/2013 |
| WO | WO 2013/171712 | 11/2013 |
| WO | WO 2014/045156 A1 | 3/2014 |
| WO | WO 2014/096212 A1 | 6/2014 |
| WO | WO 2014/111457 A1 | 6/2014 |

OTHER PUBLICATIONS

Vippagunta, et al. Advanced Drug Delivery Reviews, 48, 2001, 18.*
"Crystallization", Kirk-Othmer Encyclopedia of Chemical Technology, 2002, 8, 95-147.
Dorwald, "Side Reactions in Organic Synthesis", Wiley: VCH Weinheim Preface, Chapter 8, 45 pages.
Dyatkin et al., "Determination of the Absolute Configuration of a Key Tricyclic Component of a Novel Vasopressin Receptor Antagonist by Use of Vibrational Circular Dichroism", Chirality, 2002, 14, 215-219.
Garofalo, "Patents Targeting Gamma-Secretase Inhibition and Modulation for the Treatment of Alzheimer's Disease: 2004-2008", Expert Opinion Ther. Patents, 2008, 18(7), 693-703.
Guillory (Brittain Ed.). "Polymorphism in Pharmaceutical Solids" Marcel Dekker. Inc., NY, 1999, 50 pages.
International Patent Application No. PCT/EP2011/050350: International Search Report dated Feb. 23, 2011, 3 pages.
Jadhav et al, "Ammonium Metavanadate: A Novel Catalyst for Synthesis of 2-Substituted Benzimidazole Derivatives", Chinese Chemical Letters, 2009, 20, 292-295.
Jain et al., "Polymorphism in Pharmacy", Indian Drugs, 1986, 23(6), 315-329.
Matthews et al., "A Convenient Procedure for the Preparation of 4(5)-Cyanoimidazoles", J. Org. Chem., 1986 51, 3228-3231.
Moechars et al., "Early Phenotypic Changes in Transgenic Mice That Overexpress Different Mutants of Amyloid Precursor Protein in Brain", J. Biol. Chem., 1999, 274(10), 6483-6492.
Eimer et al., Neuron loss in the 5XFAD mouse model of Alzheimer's disease correlates with intraneuronal $A\beta_{42}$ accumulation and Caspase-3 activation, Molecular Neurodegeneration, 2013, 8:2.
Arnold Reissert, Chemische Berichte, 30_1897_1030-1045 (English Translation).
International Search Report for PCT/EP2014/050787 dated Feb. 21, 2014.
SIPO Search Report dated Mar. 16, 2016.
Office Action for (Application No. 201380066966.9) dated Apr. 5, 2016.
Office Action for (Application No. 2015-546580) dated Sep. 19, 2017.
ACS Symposium Series, 870 (Chemical Process Research), Willemsens American Chemical Society, 125-139, 2004.
Citron et al (1997) Nature Medicine 3: 67.
Eriksen (2003) J. Clin. Invest. 112, 440.
Greene and P. G. M. Wuts in "Protective Groups in Organic Chemistry", John Wiley and Sons, 1999.
Larner, 2004. Secretases as therapeutics targets in AD: patents 2000-2004. Expert Opin. Ther. Patents 14, 1403-1420.
Li, Org. Lett. 2010, 12, 3332.
Marjaux et al., 2004. Drug Discovery Today: Therapeutic Strategies, vol. 1, 1-6.
Peretto et al., 2005, J. Med. Chem. 48, 5705-5720.
Schweisguth F (2004) Curr. Biol. 14, R129.
Steiner, 2004. Curr. Alzheimer Research 1(3): 175-181.
Tanzi and Bertram 2005, Cell 120, 545.
Waldvogel, Helv. Chim. Acta, 1992, 907.
International Search Report for PCT/IB2013/054014 dated Aug. 20, 2013.
Notice of Allowance for U.S. Appl. No. 14/654,397 dated Oct. 12, 2016.
Notice of Allowance for U.S. Appl. No. 14/654,397 dated Apr. 26, 2016.
Office Action for U.S. Appl. No. 14/654,397 dated Jan. 6, 2016.
Notice of Allowance for U.S. Appl. No. 14/400,663 dated Jul. 17, 2015.
Office Action for U.S. Appl. No. 14/400,663 dated Apr. 14, 2015.
Morihara et al., "Selective inhibition of Aβ42 Production by NSAID R-Enantiomers", Journal of Neurochemistry, 2002, 83, 1009-1012.
Oumata et al., "Roscovitine-Derived, Dual-Specificity Inhibitors of Cyclin-Dependent Kinases and Casein Kinases 1", J. Med. Chem., 2008, 51, 5229-5242.
Sechi et al., "Design and Synthesis of Novel Indole β-Diketo Acid Derivatives as HIV-1 Integrase Inhibitors", J. Med. Chem., 2004, 47, 5298-5310.
Vippagonta et al., "Crystalline Solids", Advanced Drug Delivery Reviews, 2001, 48, 3-26.
Wang et al., "Preparation of a-Chloroketones by the Chloracetate Claisen Reaction", Synlett, 2000, 6, 902-904.
Weggen et al., "A Subset of NSAIDs Lower Amyloidegenic Aβ42 Independently of Cyclooxygenase Activity", Nature, Nov. 2001, 411, 212-216.
Wermuth, "Chapter 13—Molecular Variations Based On Isosteric Replacements", The Practice of Medicinal Chemistry, 1996, 35 pages.
West, "Solid State Chemistry and its Applications", Wiley, New York, 1988, 16 pages (see pp. 358 & 365).
Yu et al. "Physical Characterization of Polymorphic Drugs: An Integrated Characterization Strategy", PSTT, 1998, 1(3), 118-127.
Zettl et al., "Exporing the Chemical Space of γ-Secretase Modulators", Trends in Pharmaceutical Sciences, 2010, 31(9), 402-410.
Hackam, et al. JAMA, 296(14), 2006, 1731-1732.

* cited by examiner

SUBSTITUTED 3,4-DIHYDRO-2H-PYRIDO[1,2-A]PYRAZINE-1,6-DIONES AS GAMMA SECRETASE MODULATORS

CROSS REFERENCE TO RELATED APPLICATIONS

This application is a continuation application of U.S. patent application Ser. No. 14/761,801 filed Jul. 17, 2015, which is a 371 National Stage Application of PCT/EP2014/050787 with an international filing date of Jan. 16, 2014, and claims the benefit of European Patent Application No. 13151654.4 filed Jan. 17, 2013, the entire disclosures of each of which are hereby incorporated in their entirety

FIELD OF THE INVENTION

The present invention is concerned with novel substituted pyrido-piperazinone derivatives useful as gamma secretase modulators. The invention further relates to processes for preparing such novel compounds, pharmaceutical compositions comprising said compounds as an active ingredient as well as the use of said compounds as a medicament.

BACKGROUND OF THE INVENTION

Alzheimer's Disease (AD) is a progressive neurodegenerative disorder marked by loss of memory, cognition, and behavioral stability. AD afflicts 6-10% of the population over age 65 and up to 50% over age 85. It is the leading cause of dementia and the third leading cause of death after cardiovascular disease and cancer. There is currently no effective treatment for AD. The total net cost related to AD in the U.S. exceeds $100 billion annually.

AD does not have a simple etiology, however, it has been associated with certain risk factors including (1) age, (2) family history and (3) head trauma; other factors include environmental toxins and low levels of education. Specific neuropathological lesions in the limbic and cerebral cortices include intracellular neurofibrillary tangles consisting of hyperphosphorylated tau protein and the extracellular deposition of fibrillar aggregates of amyloid beta peptides (amyloid plaques). The major components of amyloid plaques are the amyloid beta (A-beta, Abeta or Aß) peptides of various lengths. A variant thereof, which is the Aß1-42-peptide (Abeta-42), is believed to be the major causative agent for amyloid formation. Another variant is the Aß1-40-peptide (Abeta-40). Aß is the proteolytic product of a precursor protein, beta amyloid precursor protein (beta-APP or APP).

Familial, early onset autosomal dominant forms of AD have been linked to missense mutations in the β-amyloid precursor protein (β-APP or APP) and in the presenilin proteins 1 and 2. In some patients, late onset forms of AD have been correlated with a specific allele of the apolipoprotein E (ApoE) gene, and, more recently, the finding of a mutation in alpha2-macroglobulin, which may be linked to at least 30% of the AD population. Despite this heterogeneity, all forms of AD exhibit similar pathological findings. Genetic analysis has provided the best clues for a logical therapeutic approach to AD. All mutations found to date, affect the quantitative or qualitative production of the amyloidogenic peptides known as Abeta-peptides (Aβ), specifically Aβ42, and have given strong support to the "amyloid cascade hypothesis" of AD (Tanzi and Bertram, 2005, Cell 120, 545). The likely link between Aβ peptide generation and AD pathology emphasizes the need for a better understanding of the mechanisms of Aβ production and strongly warrants a therapeutic approach at modulating Aβ levels.

The release of Aβ peptides is modulated by at least two proteolytic activities referred to as β- and γ-secretase cleavage at the N-terminus (Met-Asp bond) and the C-terminus (residues 37-42) of the Aβ peptide, respectively. In the secretory pathway, there is evidence that β-secretase cleaves first, leading to the secretion of s-APPβ (sβ) and the retention of a 11 kDa membrane-bound carboxy terminal fragment (CTF). The latter is believed to give rise to Aβ peptides following cleavage by γ-secretase. The amount of the longer isoform, Aß42, is selectively increased in patients carrying certain mutations in the region of a particular gene coding in a particular protein (presenilin), and these mutations have been correlated with early-onset familial AD. Therefore, Aß42 is believed by many researchers to be the main culprit of the pathogenesis of AD.

It has now become clear that the γ-secretase activity cannot be ascribed to a single protein, but is in fact associated with an assembly of different proteins.

The gamma (γ)-secretase activity resides within a multiprotein complex containing at least four components: the presenilin (PS) heterodimer, nicastrin, aph-1 and pen-2. The PS heterodimer consists of the amino- and carboxyterminal PS fragments generated by endoproteolysis of the precursor protein. The two aspartates of the catalytic site are at the interface of this heterodimer. It has recently been suggested that nicastrin serves as a gamma-secretase-substrate receptor. The functions of the other members of gamma-secretase are unknown, but they are all required for activity (Steiner, 2004. Curr. Alzheimer Research 1(3): 175-181).

Thus, although the molecular mechanism of the second cleavage-step has remained elusive until now, the γ-secretase-complex has become one of the prime targets in the search for compounds for the treatment of AD.

Various strategies have been proposed for targeting γ-secretase in AD, ranging from targeting the catalytic site directly, developing substrate-specific inhibitors and modulators of γ-secretase activity (Marjaux et al., 2004. Drug Discovery Today: Therapeutic Strategies, Volume 1, 1-6). Accordingly, a variety of compounds were described that have secretases as targets (Larner, 2004. Secretases as therapeutics targets in AD: patents 2000-2004. Expert Opin. Ther. Patents 14, 1403-1420).

Indeed, this finding was supported by biochemical studies in which an effect of certain Non-Steroidal Anti-Inflammatory Drugs (NSAIDs) on γ-secretase was shown (US 2002/0128319; Eriksen (2003) J. Clin. Invest. 112, 440). Potential limitations for the use of NSAIDs to prevent or treat AD are their inhibition activity of cyclooxygenase (COX) enzymes, which can lead to unwanted side effects, and their low CNS penetration (Peretto et al., 2005, J. Med. Chem. 48, 5705-5720). More recently the NSAID R-flurbiprofen, an enantiomer lacking Cox-inhibitory activity and related gastric toxicity, has failed in large phase III trial since the drug did not improve thinking ability or the ability of patients to carry out daily activities significantly more than those patients on placebo.

WO-2010/100606 discloses phenyl imidazoles and phenyl triazoles for use as gamma-secretase modulators.

US20090062529 relates to polycyclic compounds effective as therapeutic or prophylactic agents for a disease caused by Aβ.

WO-2010/070008 is concerned with novel substituted bicyclic imidazole derivatives useful as γ-secretase modulators.

WO-2010/089292 is concerned with novel substituted bicyclic heterocyclic compounds useful as γ-secretase modulators.

WO-2011/006903 is concerned with novel substituted triazole and imidazole derivatives useful as γ-secretase modulators.

WO-2012/131539 relates to novel bicyclic pyridinones useful as brain-penetrable γ-secretase modulators.

There is a strong need for novel compounds which modulate γ-secretase activity thereby opening new avenues for the treatment of AD. It is an object of the present invention to overcome or ameliorate at least one of the disadvantages of the prior art, or to provide a useful alternative. The compounds of the present invention or part of the compounds of the present invention may have improved metabolic stability properties, improved central brain availability, improved solubilities, or reduced CYP inhibition compared with the compounds disclosed in the prior art. It is accordingly an object of the present invention to provide such novel compounds.

SUMMARY OF THE INVENTION

It has been found that the compounds of the present invention are useful as γ-secretase modulators. The compounds according to the invention and the pharmaceutically acceptable compositions thereof, may be useful in the treatment or prevention of AD.

The present invention concerns novel compounds of Formula (I):

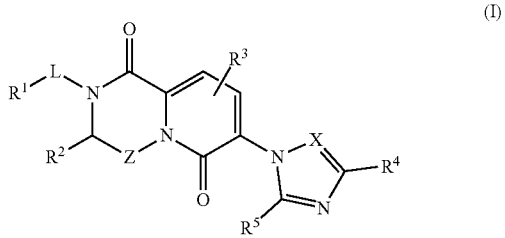

tautomers and stereoisomeric forms thereof, wherein
$R^1$ is $Ar^1$ or $Ar^2$;
$R^2$ is hydrogen, phenyl, cyclo$C_{3-7}$ alkyl, 3,4,5,6-tetrahydropyranyl, 3,4,5,6-tetrahydrothiopyranyl, piperidinyl, or $C_{1-4}$alkyl optionally substituted with one or more substituents each independently selected from the group consisting of halo, hydroxyl, $C_{1-4}$alkyloxy and $NR^7R^8$;
Z is methylene or 1,2-ethanediyl, wherein methylene or 1,2-ethanediyl is optionally substituted with one or two $C_{1-4}$alkyl substituents;
L is a covalent bond, 1,2-cyclopropanediyl, —C(=O)—$C_{1-6}$alkanediyl-,
  $C_{1-6}$alkanediyl optionally substituted with one or more substituents selected from the group consisting of 3,4,5,6-tetrahydropyranyl, phenyl and $C_{1-4}$alkyloxy-$C_{1-4}$alkyl, or
  $C_{1-6}$alkanediyl wherein two geminal hydrogen atoms are replaced by $C_{2-6}$alkanediyl;
$Ar^1$ is a ring system selected from the group consisting of imidazolyl, 1,2,4-triazolyl, 1,3,4-triazolyl, pyrrolyl, furanyl, isoxazolyl, isothiazolyl, thienyl, thiazolyl, pyrrolidinyl, piperidinyl, pyrazolyl, 4,5,6,7-tetrahydro-benzo[b]thienyl, 1,2-benzisoxazolyl, benzofuranyl, 2,3-dihydrobenzofuranyl, 1,3-dihydro-isobenzofuranyl, 5,6,7,8-tetrahydro-1,2,4-triazolo[4,3-a]pyridinyl, tetrahydropyrazolo[1,5-a]pyridinyl, 1,2,4-triazolo[4,3-a]pyridinyl, pyrazolo-[1,5-a]pyridinyl, 3,4-dihydro-1-benzopyranyl, 1,2-benzisothiazolyl, indazolyl, 1,2,3,4-tetrahydro-isoquinolinyl, 2,3-dihydro-benzo[b]thienyl, 1,3-dihydro-benzo[c]thienyl, 2-benzofuranyl, 3,4-dihydro-2-benzothiopyranyl, 3,4-dihydro-2-benzopyranyl and 1,2,3,4-tetrahydroquinolinyl;
  wherein said ring system is optionally substituted with one or more substituents each independently selected from the group consisting of halo, oxo, $Ar^3$, $R^0$, $C_{1-4}$alkyl optionally substituted with one or more substituents each independently selected from the group consisting of halo, $C_{1-4}$alkyloxy, and cyclo$C_{3-7}$alkyl, and $C_{1-4}$alkyloxy optionally substituted with one or more substituents each independently selected from the group consisting of halo and cyclo$C_{3-7}$alkyl;
$Ar^2$ is phenyl substituted with one substituent selected from the group consisting of $OR^9$ and 3-azabicyclo[3.1.0]hexanyl; and said phenyl is optionally substituted with one, two or three substituents each independently selected from the group consisting of halo, $C_{1-4}$alkyloxy optionally substituted with one or more halo substituents, and $C_{1-4}$alkyl optionally substituted with one or more halo substituents;
$Ar^3$ is phenyl optionally substituted with one or more substituents each independently selected from the group consisting of halo and $C_{1-4}$alkyl optionally substituted with one or more halo substituents;
$R^3$ is hydrogen, cyano, halo, $C_{1-4}$alkyloxy or $C_{1-4}$alkyl;
$R^4$ is hydrogen, halo or $C_{1-4}$alkyl;
$R^5$ is hydrogen or $C_{1-4}$alkyl;
X is $CR^6$ or N;
$R^6$ is hydrogen or $C_{1-4}$alkyl;
$R^7$ is hydrogen or $C_{1-4}$alkyl;
$R^8$ is hydrogen or $C_{1-4}$alkyl;
$R^9$ is hydrogen, cyclo$C_{3-7}$alkyl or phenyl;
$R^0$ is a ring system selected from the group consisting of piperidinyl, morpholinyl, cyclo$C_{3-7}$alkyl, pyrazolyl and pyrrolidinyl; wherein said ring system is optionally substituted with one or more substituents each independently selected from the group consisting of halo or $C_{1-4}$alkyl optionally substituted with one or more halo atoms;
and the pharmaceutically acceptable addition salts, and the solvates thereof.

The present invention also concerns methods for the preparation of compounds of the present invention and pharmaceutical compositions comprising them.

The compounds of the present invention were found to modulate the γ-secretase activity in vitro and in vivo, and therefore may be useful in the treatment or prevention of AD, traumatic brain injury (TBI), dementia pugilistica, mild cognitive impairment (MCI), senility, dementia, dementia with Lewy bodies, cerebral amyloid angiopathy, multi-infarct dementia, Down's syndrome, dementia associated with Parkinson's disease and dementia associated with beta-amyloid; preferably AD and other disorders with Beta-amyloid pathology (e.g. glaucoma).

In view of the aforementioned pharmacology of the compounds of Formula (I) and the pharmaceutically acceptable addition salts, and the solvates thereof, it follows that they may be suitable for use as a medicament.

More especially the compounds of Formula (I) and the pharmaceutically acceptable addition salts, and the solvates thereof, may be suitable in the treatment or prevention of AD, cerebral amyloid angiopathy, multi-infarct dementia, dementia pugilistica and Down syndrome.

The present invention also concerns the use of compounds according to the general Formula (I), and the pharmaceutically acceptable acid or base addition salts and the solvates thereof, for the manufacture of a medicament for the modulation of γ-secretase activity.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

DETAILED DESCRIPTION

When describing the compounds of the invention, the terms used are to be construed in accordance with the following definitions, unless a context dictates otherwise.

Whenever the term "substituted" is used in the present invention, it is meant, unless otherwise is indicated or is clear from the context, to indicate that one or more hydrogens, in particular from 1 to 3 hydrogens, preferably 1 or 2 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

The term "halo" as a group or part of a group is generic for fluoro, chloro, bromo, iodo unless otherwise is indicated or is clear from the context.

The term "$C_{1-4}$alkyl" as a group or part of a group refers to a hydrocarbyl radical of Formula $C_nH_{2n+1}$ wherein n is a number ranging from 1 to 4. $C_{1-4}$alkyl groups comprise from 1 to 4 carbon atoms, preferably from 1 to 3 carbon atoms, more preferably 1 to 2 carbon atoms. $C_{1-4}$alkyl groups may be linear or branched and may be substituted as indicated herein. When a subscript is used herein following a carbon atom, the subscript refers to the number of carbon atoms that the named group may contain. $C_{1-4}$alkyl includes all linear, or branched alkyl groups with between 1 and 4 carbon atoms, and thus includes such as for example methyl, ethyl, n-propyl, i-propyl, 2-methyl-ethyl, butyl and its isomers (e.g. n-butyl, isobutyl and tert-butyl), and the like.

The term "cyclo$C_{3-7}$alkyl" alone or in combination, refers to a cyclic saturated hydrocarbon radical having from 3 to 7 carbon atoms. Non-limiting examples of suitable cyclo$C_{3-7}$alkyl include cyclopropyl, cyclobutyl, cyclopentyl, cyclohexyl and cycloheptyl.

The term "$C_{1-4}$alkyloxy" as a group or part of a group refers to a radical having the Formula $OR^b$ wherein $R^b$ is $C_{1-4}$alkyl. Non-limiting examples of suitable $C_{1-4}$alkyloxy include methyloxy (also methoxy), ethyloxy (also ethoxy), propyloxy, isopropyloxy, butyloxy, isobutyloxy, sec-butyloxy and tert-butyloxy.

The term "$C_{1-6}$alkanediyl" as a group or part of a group defines bivalent straight or branched chained saturated hydrocarbon radicals having from 1 to 6 carbon atoms such as, for example, methylene or methanediyl, ethan-1,2-diyl, ethan-1,1-diyl or ethylidene, propan-1,3-diyl, propan-1,2-diyl, butan-1,4-diyl, pentan-1,5-diyl, pentan-1,1-diyl, hexan-1,6-diyl, 2-methylbutan-1,4-diyl, 3-methylpentan-1,5-diyl and the like.

The term "$C_{2-6}$alkanediyl" as a group or part of a group defines bivalent straight or branched chained saturated hydrocarbon radicals having from 2 to 6 carbon atoms such as, for example, ethan-1,2-diyl, ethan-1,1-diyl or ethylidene, propan-1,3-diyl, propan-1,2-diyl, butan-1,4-diyl, pentan-1,5-diyl, pentan-1,1-diyl, hexan-1,6-diyl, 2-methylbutan-1,4-diyl, 3-methylpentan-1,5-diyl and the like;

in particular "$C_{2-6}$alkanediyl" as a group or part of a group defines ethan-1,2-diyl.

Similarly, the term "$C_{1-2}$alkanediyl" as a group or part of a group defines bivalent straight or branched chained saturated hydrocarbon radicals having from 1 to 2 carbon atoms.

The term "oxo" means =O.

The term "3,4-dihydro-1-benzopyranyl" is equivalent to 3,4-dihydro-2H-1-benzopyranyl, "indazolyl" is equivalent to 1H-indazolyl, "3,4-dihydro-2-benzothiopyranyl" is equivalent to 3,4-dihydro-1H-2-benzothiopyranyl, "3,4-dihydro-2-benzopyranyl" is equivalent to 3,4-dihydro-1H-2-benzopyranyl, "3,4,5,6-tetrahydropyranyl" is equivalent to tetrahydro-2H-pyranyl, "3,4,5,6-tetrahydrothiopyranyl" is equivalent to tetrahydro-2H-thiopyranyl.

Whenever variable 'L' represents —C(=O)—$C_{1-6}$alkanediyl-, it is intended that the carbonyl group is attached to '$R^1$' and $C_{1-6}$alkanediyl is attached to the remainder of the molecule. This is illustrated by formula (I'):

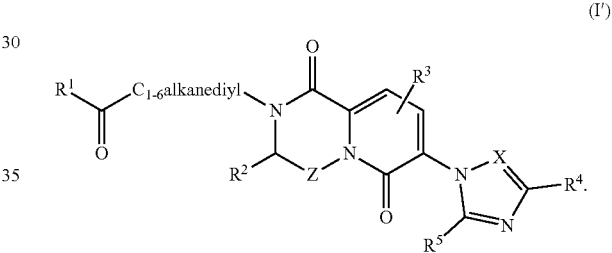

The chemical names of the compounds of the present invention were generated according to the nomenclature rules agreed upon by the Chemical Abstracts Service, using Advanced Chemical Development, Inc., nomenclature software (ACD/Labs Release 12.00 Product version 12.01; Build 33104, 27 May 2009). In case of tautomeric forms, the name of the depicted tautomeric form was generated. It should be clear that the other non-depicted tautomeric form is also included within the scope of the present invention.

Whenever one of the ring systems in the definition of $Ar^1$ or $R^0$ is substituted with one or more substituents, those substituents may replace any hydrogen atom bound to a carbon or nitrogen atom of the ring system.

The term "compounds of the invention" as used herein, is meant to include the compounds of Formula (I), and the salts and solvates thereof.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Hereinbefore and hereinafter, the term "compound of Formula (I)" is meant to include the stereoisomers thereof and the tautomeric forms thereof.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers.

Enantiomers are stereoisomers that are non-superimposable mirror images of each other. A 1:1 mixture of a pair of enantiomers is a racemate or racemic mixture.

Diastereomers (or diastereoisomers) are stereoisomers that are not enantiomers, i.e. they are not related as mirror images. If a compound contains a double bond, the substituents may be in the E or the Z configuration. Substituents on bivalent cyclic (partially) saturated radicals may have either the cis- or trans-configuration; for example if a compound contains a disubstituted cycloalkyl group, the substituents may be in the cis or trans configuration. Therefore, the invention includes enantiomers, diastereomers, racemates, E isomers, Z isomers, cis isomers, trans isomers and mixtures thereof, whenever chemically possible.

The meaning of all those terms, i.e. enantiomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of Formula (I) is for instance specified as (R), this means that the compound is substantially free of the (S) isomer; when a compound of Formula (I) is for instance specified as E, this means that the compound is substantially free of the Z isomer; when a compound of Formula (I) is for instance specified as cis, this means that the compound is substantially free of the trans isomer.

Some of the compounds according to Formula (I) may also exist in their tautomeric form. Such forms in so far as they may exist, although not explicitly indicated in the above Formula (I) are intended to be included within the scope of the present invention.

It follows that a single compound may exist in both stereoisomeric and tautomeric form.

For therapeutic use, salts of the compounds of Formula (I) and solvates thereof, are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove or hereinafter are meant to comprise the therapeutically active non-toxic acid and base addition salt forms which the compounds of Formula (I) and solvates thereof, are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I) and solvates thereof containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvate comprises the hydrates and solvent addition forms which the compounds of Formula (I) are able to form, as well as the pharmaceutically acceptable salts thereof. Examples of such forms are e.g. hydrates, alcoholates and the like.

The compounds of the invention as prepared in the processes described below may be synthesized in the form of mixtures of enantiomers, in particular racemic mixtures of enantiomers, that can be separated from one another following art-known resolution procedures. An manner of separating the enantiomeric forms of the compounds of Formula (I) and the pharmaceutically acceptable addition salts, and the solvates thereof, involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

In the framework of this application, an element, in particular when mentioned in relation to a compound according to Formula (I), comprises all isotopes and isotopic mixtures of this element, either naturally occurring or synthetically produced, either with natural abundance or in an isotopically enriched form. Radiolabelled compounds of Formula (I) may comprise a radioactive isotope selected from the group of $^3$H, $^{11}$C, $^{18}$F, $^{122}$I, $^{123}$I, $^{125}$I, $^{131}$I, $^{75}$Br, $^{76}$Br, $^{77}$Br and $^{82}$Br. Preferably, the radioactive isotope is selected from the group of $^3$H, $^{11}$C and $^{18}$F.

As used in the specification and the appended claims, the singular forms "a", "an," and "the" also include plural referents unless the context clearly dictates otherwise. For example, "a compound" means 1 compound or more than 1 compound.

In an embodiment, the present invention concerns novel compounds of Formula (I):

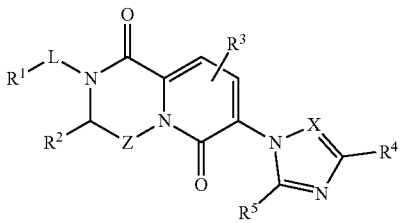

(I)

tautomers and stereoisomeric forms thereof, wherein
$R^1$ is $Ar^1$ or $Ar^2$;
$R^2$ is hydrogen, phenyl, cyclo$C_{3-7}$alkyl, 3,4,5,6-tetrahydropyranyl, 3,4,5,6-tetrahydrothiopyranyl, piperidinyl, or $C_{1-4}$alkyl optionally substituted with one or more substituents each independently selected from the group consisting of halo, hydroxyl, $C_{1-4}$alkyloxy and $NR^7R^8$;
Z is methylene or 1,2-ethanediyl, wherein methylene or 1,2-ethanediyl is optionally substituted with one or two $C_{1-4}$alkyl substituents;
L is a covalent bond, 1,2-cyclopropanediyl, —C(=O)—$C_{1-6}$alkanediyl-,
  $C_{1-6}$alkanediyl optionally substituted with one or more substituents selected from the group consisting of 3,4,5,6-tetrahydropyranyl, phenyl and $C_{1-4}$alkyloxy-$C_{1-4}$alkyl, or
  $C_{1-6}$alkanediyl wherein two geminal hydrogen atoms are replaced by $C_{2-6}$alkanediyl;
$Ar^1$ is a ring system selected from the group consisting of imidazolyl, 1,2,4-triazolyl, 1,3,4-triazolyl, pyrrolyl, furanyl, isoxazolyl, isothiazolyl, thienyl, thiazolyl, pyrrolidinyl, piperidinyl, pyrazolyl, 4,5,6,7-tetrahydro-benzo[b]thienyl, 1,2-benzisoxazolyl, benzofuranyl, 2,3-dihydrobenzofuranyl, 1,3-dihydro-isobenzofuranyl, 5,6,7,8-tetrahydro-1,2,4-triazolo[4,3-a]pyridinyl, 4,5,6,7-tetrahydro-pyrazolo[1,5-a]pyridinyl, 1,2,4-triazolo[4,3-a]pyridinyl, pyrazolo-[1,5-a]pyridinyl, 3,4-dihydro-1-benzopyranyl, 1,2-benzisothiazolyl, indazolyl, 1,2,3,4-tetrahydro-isoquinolinyl, 2,3-dihydro-benzo[b]thienyl, 1,3-dihydro-benzo[c]thienyl, 2-benzofuranyl, 3,4-dihydro-2-benzothiopyranyl, 3,4-dihydro-2-benzopyranyl and 1,2,3,4-tetrahydroquinolinyl;
  wherein said ring system is optionally substituted with one or more substituents each independently selected from the group consisting of halo, oxo, $Ar^3$, $R^0$, $C_{1-4}$alkyl optionally substituted with one or more substituents each independently selected from the group consisting of halo, $C_{1-4}$alkyloxy and cyclo$C_{3-7}$alkyl, and $C_{1-4}$alkyloxy optionally substituted with one or more substituents each independently selected from the group consisting of halo and cyclo$C_{3-7}$alkyl;
$Ar^2$ is phenyl substituted with one substituent selected from the group consisting of $OR^9$ and 3-azabicyclo[3.1.0]hexanyl; and said phenyl is optionally substituted with one, two or three substituents each independently selected from the group consisting of halo, $C_{1-4}$alkyloxy optionally substituted with one or more halo substituents, and $C_{1-4}$alkyl optionally substituted with one or more halo substituents;
$Ar^3$ is phenyl optionally substituted with one or more substituents each independently selected from the group consisting of halo and $C_{1-4}$alkyl optionally substituted with one or more halo substituents;
$R^3$ is hydrogen, cyano, halo, $C_{1-4}$alkyloxy or $C_{1-4}$alkyl;
$R^4$ is hydrogen, halo or $C_{1-4}$alkyl;
$R^5$ is hydrogen or $C_{1-4}$alkyl;
X is $CR^6$ or N;
$R^6$ is hydrogen or $C_{1-4}$alkyl;
$R^7$ is hydrogen or $C_{1-4}$alkyl;
$R^8$ is hydrogen or $C_{1-4}$alkyl;
$R^9$ is hydrogen, cyclo$C_{3-7}$alkyl or phenyl;
$R^0$ is a ring system selected from the group consisting of piperidinyl, morpholinyl, cyclo$C_{3-7}$alkyl, pyrazolyl and pyrrolidinyl; wherein said ring system is optionally substituted with one or more substituents each independently selected from the group consisting of halo or $C_{1-4}$alkyl optionally substituted with one or more halo atoms;
and the pharmaceutically acceptable addition salts, and the solvates thereof.

In an embodiment, the present invention concerns novel compounds of Formula (I), tautomers and stereoisomeric forms thereof, wherein:
$R^1$ is $Ar^1$;
$R^2$ is hydrogen, phenyl, cyclo$C_{3-7}$alkyl, 3,4,5,6-tetrahydropyranyl, 3,4,5,6-tetrahydrothiopyranyl, piperidinyl, or $C_{1-4}$alkyl optionally substituted with one or more substituents each independently selected from the group consisting of halo, hydroxyl, $C_{1-4}$alkyloxy and $NR^7R^8$;
Z is methylene or 1,2-ethanediyl, wherein methylene or 1,2-ethanediyl is optionally substituted with one or two $C_{1-4}$alkyl substituents;
L is a covalent bond, 1,2-cyclopropanediyl, —C(=O)—$C_{1-6}$alkanediyl-,
  $C_{1-6}$alkanediyl optionally substituted with one or more substituents selected from the group consisting of 3,4,5,6-tetrahydropyranyl, phenyl and $C_{1-4}$alkyloxy-$C_{1-4}$alkyl, or
  $C_{1-6}$alkanediyl wherein two geminal hydrogen atoms are replaced by $C_{2-6}$alkanediyl;
$Ar^1$ is a ring system selected from the group consisting of imidazolyl, 1,2,4-triazolyl, 1,3,4-triazolyl, pyrrolyl, furanyl, isoxazolyl, isothiazolyl, thienyl, thiazolyl, pyrrolidinyl, piperidinyl, pyrazolyl, 4,5,6,7-tetrahydro-benzo[b]thienyl, 1,2-benzisoxazolyl, benzofuranyl, 2,3-dihydrobenzofuranyl, 1,3-dihydro-isobenzofuranyl, 5,6,7,8-tetrahydro-1,2,4-triazolo[4,3-a]pyridinyl, 4,5,6,7-tetrahydro-pyrazolo[1,5-a]pyridinyl, 1,2,4-triazolo[4,3-a]pyridinyl, pyrazolo-[1,5-a]pyridinyl, 3,4-dihydro-1-benzopyranyl, 1,2-benzisothiazolyl, indazolyl, 1,2,3,4-tetrahydro-isoquinolinyl, 2,3-dihydro-benzo[b]thienyl, 1,3-dihydro-benzo[c]thienyl, 2-benzofuranyl, 3,4-dihydro-2-benzothiopyranyl, 3,4-dihydro-2-benzopyranyl and 1,2,3,4-tetrahydroquinolinyl;
  wherein said ring system is optionally substituted with one or more substituents each independently selected from the group consisting of halo, oxo, $Ar^3$, $R^0$, $C_{1-4}$alkyl optionally substituted with one or more substituents each independently selected from the group consisting of halo, $C_{1-4}$alkyloxy and cyclo$C_{3-7}$alkyl, and $C_{1-4}$alkyloxy optionally substituted with one or more substituents each independently selected from the group consisting of halo and cyclo$C_{3-7}$alkyl;
$Ar^3$ is phenyl optionally substituted with one or more substituents each independently selected from the group consisting of halo and $C_{1-4}$alkyl optionally substituted with one or more halo substituents;
$R^3$ is hydrogen, cyano, halo, $C_{1-4}$alkyloxy or $C_{1-4}$alkyl;
$R^4$ is hydrogen, halo or $C_{1-4}$alkyl;
$R^5$ is hydrogen or $C_{1-4}$alkyl;
X is $CR^6$ or N;
$R^6$ is hydrogen or $C_{1-4}$alkyl;
$R^7$ is hydrogen or $C_{1-4}$alkyl;

$R^8$ is hydrogen or $C_{1-4}$alkyl;

$R^0$ is a ring system selected from the group consisting of piperidinyl, morpholinyl, cyclo$C_{3-7}$alkyl, pyrazolyl and pyrrolidinyl; wherein said ring system is optionally substituted with one or more substituents each independently selected from the group consisting of halo or $C_{1-4}$alkyl optionally substituted with one or more halo atoms;

and the pharmaceutically acceptable addition salts, and the solvates thereof.

In an embodiment, the present invention concerns novel compounds of Formula (I), tautomers and stereoisomeric forms thereof, wherein:

$R^1$ is $Ar^2$;

$R^2$ is hydrogen, phenyl, cyclo$C_{3-7}$alkyl, 3,4,5,6-tetrahydropyranyl, 3,4,5,6-tetrahydrothiopyranyl, piperidinyl, or $C_{1-4}$alkyl optionally substituted with one or more substituents each independently selected from the group consisting of halo, hydroxyl, $C_{1-4}$alkyloxy and $NR^7R^8$;

Z is methylene or 1,2-ethanediyl, wherein methylene or 1,2-ethanediyl is optionally substituted with one or two $C_{1-4}$alkyl substituents;

L is a covalent bond, 1,2-cyclopropanediyl, —C(=O)—$C_{1-6}$alkanediyl-,
  $C_{1-6}$alkanediyl optionally substituted with one or more substituents selected from the group consisting of 3,4,5,6-tetrahydropyranyl, phenyl and $C_{1-4}$alkyloxy-$C_{1-4}$alkyl, or
  $C_{1-6}$alkanediyl wherein two geminal hydrogen atoms are replaced by $C_{2-6}$alkanediyl;

$Ar^2$ is phenyl substituted with one substituent selected from the group consisting of $OR^9$ and 3-azabicyclo[3.1.0]hexanyl; and said phenyl is optionally substituted with one, two or three substituents each independently selected from the group consisting of halo, $C_{1-4}$alkyloxy optionally substituted with one or more halo substituents, and $C_{1-4}$alkyl optionally substituted with one or more halo substituents;

$R^3$ is hydrogen, cyano, halo, $C_{1-4}$alkyloxy or $C_{1-4}$alkyl;

$R^4$ is hydrogen, halo or $C_{1-4}$alkyl;

$R^5$ is hydrogen or $C_{1-4}$alkyl;

X is $CR^6$ or N;

$R^6$ is hydrogen or $C_{1-4}$alkyl;

$R^7$ is hydrogen or $C_{1-4}$alkyl;

$R^8$ is hydrogen or $C_{1-4}$alkyl;

$R^9$ is hydrogen, cyclo$C_{3-7}$alkyl or phenyl;

and the pharmaceutically acceptable addition salts, and the solvates thereof.

In an embodiment, the present invention concerns novel compounds of Formula (I), tautomers and stereoisomeric forms thereof, wherein:

$R^1$ is $Ar^1$ or $Ar^2$;

$R^2$ is methyl;

Z is methylene or 1,2-ethanediyl, wherein methylene or 1,2-ethanediyl is optionally substituted with one or two $C_{1-4}$alkyl substituents;

L is a covalent bond, 1,2-cyclopropanediyl, —C(=O)—$C_{1-6}$alkanediyl-,
  $C_{1-6}$alkanediyl optionally substituted with one or more substituents selected from the group consisting of 3,4,5,6-tetrahydropyranyl, phenyl and $C_{1-4}$alkyloxy-$C_{1-4}$alkyl, or
  $C_{1-6}$alkanediyl wherein two geminal hydrogen atoms are replaced by $C_{2-6}$alkanediyl;

$Ar^1$ is a ring system selected from the group consisting of imidazolyl, 1,2,4-triazolyl, 1,3,4-triazolyl, pyrrolyl, furanyl, isoxazolyl, isothiazolyl, thienyl, thiazolyl, pyrrolidinyl, piperidinyl, pyrazolyl, 4,5,6,7-tetrahydro-benzo[b]thienyl, 1,2-benzisoxazolyl, benzofuranyl, 2,3-dihydrobenzofuranyl, 1,3-dihydro-isobenzofuranyl, 5,6,7,8-tetrahydro-1,2,4-triazolo[4,3-a]pyridinyl, 4,5,6,7-tetrahydro-pyrazolo[1,5-a]pyridinyl, 1,2,4-triazolo[4,3-a]pyridinyl, pyrazolo-[1,5-a]pyridinyl, 3,4-dihydro-1-benzopyranyl, 1,2-benzisothiazolyl, indazolyl, 1,2,3,4-tetrahydro-isoquinolinyl, 2,3-dihydro-benzo[b]thienyl, 1,3-dihydro-benzo[c]thienyl, 2-benzofuranyl, 3,4-dihydro-2-benzothiopyranyl, 3,4-dihydro-2-benzopyranyl and 1,2,3,4-tetrahydroquinolinyl;
  wherein said ring system is optionally substituted with one or more substituents each independently selected from the group consisting of halo, oxo, $Ar^3$, $R^0$, $C_{1-4}$alkyl optionally substituted with one or more substituents each independently selected from the group consisting of halo, $C_{1-4}$alkyloxy and cyclo$C_{3-7}$alkyl, and $C_{1-4}$alkyloxy optionally substituted with one or more substituents each independently selected from the group consisting of halo and cyclo$C_{3-7}$alkyl;

$Ar^2$ is phenyl substituted with one substituent selected from the group consisting of $OR^9$ and 3-azabicyclo[3.1.0]hexanyl; and said phenyl is optionally substituted with one, two or three substituents each independently selected from the group consisting of halo, $C_{1-4}$alkyloxy optionally substituted with one or more halo substituents, and $C_{1-4}$alkyl optionally substituted with one or more halo substituents;

$Ar^3$ is phenyl optionally substituted with one or more substituents each independently selected from the group consisting of halo and $C_{1-4}$alkyl optionally substituted with one or more halo substituents;

$R^3$ is hydrogen, cyano, halo, $C_{1-4}$alkyloxy or $C_{1-4}$alkyl;

$R^4$ is hydrogen, halo or $C_{1-4}$alkyl;

$R^5$ is hydrogen or $C_{1-4}$alkyl;

X is $CR^6$ or N;

$R^6$ is hydrogen or $C_{1-4}$alkyl;

$R^7$ is hydrogen or $C_{1-4}$alkyl;

$R^8$ is hydrogen or $C_{1-4}$alkyl;

$R^9$ is hydrogen, cyclo$C_{3-7}$alkyl or phenyl;

$R^0$ is a ring system selected from the group consisting of piperidinyl, morpholinyl, cyclo$C_{3-7}$alkyl, pyrazolyl and pyrrolidinyl; wherein said ring system is optionally substituted with one or more substituents each independently selected from the group consisting of halo or $C_{1-4}$alkyl optionally substituted with one or more halo atoms;

and the pharmaceutically acceptable addition salts, and the solvates thereof.

In an embodiment, the present invention concerns novel compounds of Formula (I), tautomers and stereoisomeric forms thereof, wherein:

$R^1$ is $Ar^1$ or $Ar^2$;

$R^2$ is hydrogen or $C_{1-4}$alkyl;

Z is methylene or 1,2-ethanediyl, wherein methylene or 1,2-ethanediyl is optionally substituted with one or two $C_{1-4}$alkyl substituents;

L is a covalent bond, 1,2-cyclopropanediyl, —C(=O)—$C_{1-6}$alkanediyl-, $C_{1-6}$alkanediyl or $C_{1-6}$alkanediyl wherein two geminal hydrogen atoms are replaced by $C_{2-6}$alkanediyl;

$Ar^1$ is a ring system selected from the group consisting of imidazolyl, 1,2,4-triazolyl, 1,3,4-triazolyl, pyrrolyl, furanyl, isoxazolyl, isothiazolyl, thienyl, thiazolyl, pyrrolidinyl, piperidinyl, pyrazolyl, 4,5,6,7-tetrahydro-benzo[b]thienyl, 1,2-benzisoxazolyl, benzofuranyl, 2,3-dihydrobenzofuranyl, 1,3-dihydro-isobenzofuranyl, 5,6,7,8-tetrahydro-1,2,4-triazolo[4,3-a]pyridinyl, 4,5,6,7-tetrahydro-pyrazolo[1,5-a]pyridinyl, 1,2,4-triazolo[4,3-a]

pyridinyl, pyrazolo-[1,5-a]pyridinyl, 3,4-dihydro-1-benzopyranyl, 1,2-benzisothiazolyl, indazolyl, 1,2,3,4-tetrahydro-isoquinolinyl, 2,3-dihydro-benzo[b]thienyl, 1,3-dihydro-benzo[c]thienyl, 2-benzofuranyl, 3,4-dihydro-2-benzothiopyranyl, 3,4-dihydro-2-benzopyranyl and 1,2,3,4-tetrahydroquinolinyl;
  wherein said ring system is optionally substituted with one or more substituents each independently selected from the group consisting of halo, oxo, $R^0$, $C_{1-4}$alkyl optionally substituted with one or more substituents each independently selected from the group consisting of halo, $C_{1-4}$alkyloxy and cyclo$C_{3-7}$alkyl, and $C_{1-4}$alkyloxy optionally substituted with one or more substituents each independently selected from the group consisting of halo and cyclo$C_{3-7}$alkyl;
$Ar^2$ is phenyl substituted with one substituent selected from the group consisting of $OR^9$ and 3-azabicyclo[3.1.0]hexanyl; and said phenyl is optionally substituted with one, two or three substituents each independently selected from the group consisting of halo, $C_{1-4}$alkyloxy optionally substituted with one or more halo substituents, and $C_{1-4}$alkyl optionally substituted with one or more halo substituents;
$R^3$ is hydrogen; $R^4$ is $C_{1-4}$alkyl; $R^5$ is hydrogen; X is $CR^6$; $R^6$ is hydrogen;
$R^9$ is hydrogen, cyclo$C_{3-7}$alkyl or phenyl;
$R^0$ is piperidinyl optionally substituted with one or more substituents each independently selected from the group consisting of halo or $C_{1-4}$alkyl optionally substituted with one or more halo atoms;
and the pharmaceutically acceptable addition salts, and the solvates thereof.

In an embodiment, the present invention concerns novel compounds of Formula (I), tautomers and stereoisomeric forms thereof, wherein:
$R^1$ is $Ar^1$ or $Ar^2$;
$R^2$ is methyl;
Z is methylene or 1,2-ethanediyl, wherein methylene or 1,2-ethanediyl is optionally substituted with one or two $C_{1-4}$alkyl substituents;
L is $C_{1-6}$alkanediyl;
$Ar^1$ is a ring system selected from the group consisting of imidazolyl, 1,2,4-triazolyl, 1,3,4-triazolyl, pyrrolyl, furanyl, isoxazolyl, isothiazolyl, thienyl, thiazolyl, pyrrolidinyl, piperidinyl, pyrazolyl, 4,5,6,7-tetrahydro-benzo[b]thienyl, 1,2-benzisoxazolyl, benzofuranyl, 2,3-dihydrobenzofuranyl, 1,3-dihydro-isobenzofuranyl, 5,6,7,8-tetrahydro-1,2,4-triazolo[4,3-a]pyridinyl, 4,5,6,7-tetrahydro-pyrazolo[1,5-a]pyridinyl, 1,2,4-triazolo[4,3-a]pyridinyl, pyrazolo-[1,5-a]pyridinyl, 3,4-dihydro-1-benzopyranyl, 1,2-benzisothiazolyl, indazolyl, 1,2,3,4-tetrahydro-isoquinolinyl, 2,3-dihydro-benzo[b]thienyl, 1,3-dihydro-benzo[c]thienyl, 2-benzofuranyl, 3,4-dihydro-2-benzothiopyranyl, 3,4-dihydro-2-benzopyranyl and 1,2,3,4-tetrahydroquinolinyl;
  wherein said ring system is optionally substituted with one or more substituents each independently selected from the group consisting of halo, oxo, $Ar^3$, $R^0$, $C_{1-4}$alkyl optionally substituted with one or more substituents each independently selected from the group consisting of halo, $C_{1-4}$alkyloxy and cyclo$C_{3-7}$alkyl, and $C_{1-4}$alkyloxy optionally substituted with one or more substituents each independently selected from the group consisting of halo and cyclo$C_{3-7}$alkyl;
$Ar^2$ is phenyl substituted with one substituent selected from the group consisting of $OR^9$ and 3-azabicyclo[3.1.0] hexanyl; and said phenyl is optionally substituted with one, two or three substituents each independently selected from the group consisting of halo, $C_{1-4}$alkyloxy optionally substituted with one or more halo substituents, and $C_{1-4}$alkyl optionally substituted with one or more halo substituents; Ara is phenyl optionally substituted with one or more substituents each independently selected from the group consisting of halo and $C_{1-4}$alkyl optionally substituted with one or more halo substituents;
$R^3$ is hydrogen, cyano, halo, $C_{1-4}$alkyloxy or $C_{1-4}$alkyl;
$R^4$ is hydrogen, halo or $C_{1-4}$alkyl;
$R^5$ is hydrogen or $C_{1-4}$alkyl;
X is $CR^6$ or N;
$R^6$ is hydrogen or $C_{1-4}$alkyl;
$R^7$ is hydrogen or $C_{1-4}$alkyl;
$R^8$ is hydrogen or $C_{1-4}$alkyl;
$R^9$ is hydrogen, cyclo$C_{3-7}$alkyl or phenyl;
$R^0$ is a ring system selected from the group consisting of piperidinyl, morpholinyl, cyclo$C_{3-7}$alkyl, pyrazolyl and pyrrolidinyl; wherein said ring system is optionally substituted with one or more substituents each independently selected from the group consisting of halo or $C_{1-4}$alkyl optionally substituted with one or more halo atoms;
and the pharmaceutically acceptable addition salts, and the solvates thereof.

In an embodiment, the present invention concerns novel compounds of Formula (I), tautomers and stereoisomeric forms thereof, wherein:
$R^1$ is $Ar^1$ or $Ar^2$;
$R^2$ is hydrogen or $C_{1-4}$alkyl;
Z is methylene;
L is a covalent bond, —C(=O)—$C_{1-6}$alkanediyl-, $C_{1-6}$alkanediyl, or $C_{1-6}$alkanediyl wherein two geminal hydrogen atoms are replaced by $C_{2-6}$alkanediyl;
$Ar^1$ is a ring system selected from the group consisting of thienyl, thiazolyl, pyrrolidinyl, piperidinyl, pyrazolyl, 4,5,6,7-tetrahydro-benzo[b]thienyl, 1,2-benzisoxazolyl, benzofuranyl, 2,3-dihydrobenzofuranyl, 1,3-dihydro-isobenzofuranyl, 5,6,7,8-tetrahydro-1,2,4-triazolo[4,3-a]pyridinyl, 4,5,6,7-tetrahydro-pyrazolo[1,5-a]pyridinyl, 1,2,4-triazolo[4,3-a]pyridinyl, pyrazolo[1,5-a]pyridinyl, 3,4-dihydro-1-benzopyranyl, 1,2-benzisothiazolyl, indazolyl, 1,2,3,4-tetrahydro-isoquinolinyl;
  wherein said ring system is optionally substituted with one or more substituents each independently selected from the group consisting of halo, $Ar^3$, oxo, $R^0$, $C_{1-4}$alkyl optionally substituted with one or more halo substituents, and $C_{1-4}$alkyloxy;
$Ar^2$ is phenyl substituted with one substituent selected from the group consisting of $OR^9$ and 3-azabicyclo[3.1.0]hexanyl; and said phenyl is optionally substituted with one, two or three substituents each independently selected from the group consisting of $C_{1-4}$alkyloxy optionally substituted with one or more halo substituents, and $C_{1-4}$alkyl optionally substituted with one or more halo substituents;
$Ar^3$ is phenyl optionally substituted with one or more $CF_3$ substituents;
$R^3$ is hydrogen;
$R^4$ is $C_{1-4}$alkyl;
$R^5$ is hydrogen;
X is $CR^6$;
$R^6$ is hydrogen;
$R^9$ is hydrogen, cyclo$C_{3-7}$alkyl or phenyl;
$R^0$ is a ring system selected from the group consisting of piperidinyl optionally substituted with one or more $C_{1-4}$alkyl groups optionally substituted with one or more halo atoms;

and the pharmaceutically acceptable addition salts, and the solvates thereof.

In an embodiment, the present invention concerns novel compounds of Formula (I), tautomers and stereoisomeric forms thereof, wherein:

$R^1$ is $Ar^1$ or $Ar^2$;
$R^2$ is hydrogen or methyl;
Z is methylene;
L is a covalent bond, —C(=O)—CH$_2$—, C$_{1-2}$alkanediyl, or C$_{1-2}$alkanediyl wherein two geminal hydrogen atoms are replaced by 1,2-ethanediyl;
$Ar^1$ is a ring system selected from the group consisting of imidazol-1-yl, 2-thienyl, 3-thienyl, 4-thiazolyl, 3-pyrrolidinyl, 1-piperidinyl, pyrazol-3-yl, pyrazol-5-yl, 4,5,6,7-tetrahydro-benzo[b]thien-3-yl, 4,5,6,7-tetrahydro-benzo[b]thien-2-yl, 1,2-benzisoxazol-3-yl, 2-benzofuranyl, 2,3-dihydro-3-benzofuranyl, 2,3-dihydro-7-benzofuranyl, 2,3-dihydro-2-benzofuranyl,1,3-dihydro-1-isobenzofuranyl, 5,6,7,8-tetrahydro-1,2,4-triazolo[4,3-a]pyridin-3-yl, 4,5,6,7-tetrahydro-pyrazolo[1,5-a]pyridin-3-yl, 1,2,4-triazolo[4,3-a]pyridin-3-yl, pyrazolo-3,4-dihydro-1-benzopyran-2-yl, 3,4-dihydro-1-benzopyran-6-yl, 1,2-benzisothiazol-3-yl, indazol-3-yl, 1,2,3,4-tetrahydro-2-isoquinolinyl; wherein said ring system is optionally substituted with 1, 2 or 3 substituents each independently selected from the group consisting of Br, Cl, $Ar^3$, oxo, $R^0$, isopropyloxy and C$_{1-4}$alkyl optionally substituted with 3 fluoro groups;
$Ar^2$ is phenyl substituted with one substituent selected from the group consisting of $OR^9$ and 3-azabicyclo[3.1.0]hexanyl; and said phenyl is optionally substituted with one substituent each independently selected from the group consisting of methyl, CF$_3$ and methoxy optionally substituted with 3 fluoro substituents;
$Ar^3$ is phenyl substituted with one CF$_3$ group;
$R^3$ is hydrogen;
$R^4$ is methyl;
$R^5$ is hydrogen;
X is CH;
$R^9$ is hydrogen, cyclopentyl, cyclopropyl or phenyl;
$R^0$ is a ring system selected from the group consisting of 1-piperidinyl substituted with one CF$_3$ group;
and the pharmaceutically acceptable addition salts, and the solvates thereof.

In an embodiment, the present invention concerns novel compounds of Formula (I) and the pharmaceutically acceptable addition salts, and the solvates thereof, or any subgroup thereof as mentioned in any of the other embodiments, wherein one or more of the following restrictions apply:
(a) $R^2$ is phenyl, cycloC$_{3-7}$alkyl, 3,4,5,6-tetrahydropyranyl, 3,4,5,6-tetrahydrothiopyranyl, piperidinyl, or C$_{1-4}$alkyl optionally substituted with one or more substituents each independently selected from the group consisting of hydroxyl, C$_{1-4}$alkyloxy and NR$^7$R$^8$;
(b) Z is methylene or 1,2-ethanediyl;
(c) L is C$_{1-6}$alkanediyl optionally substituted with one or more substituents selected from the group consisting of 3,4,5,6-tetrahydropyranyl, phenyl and C$_{1-4}$alkyloxy C$_{1-4}$alkyl;
(d) $R^3$ is hydrogen;
(e) $R^4$ is C$_{1-4}$alkyl;
(f) $R^5$ is hydrogen;
(g) X is CR$^6$;
(h) $R^6$ is hydrogen;
(i) $R^7$ is C$_{1-4}$alkyl;
(j) $R^8$ is C$_{1-4}$alkyl;
(k) $R^0$ is piperidinyl optionally substituted with one or more substituents each independently selected from the group consisting of halo or C$_{1-4}$alkyl optionally substituted with one or more halo atoms.

In an embodiment, the present invention relates to those compounds of formula (I) and the pharmaceutically acceptable addition salts, and the solvates thereof, or any subgroup thereof as mentioned in any of the other embodiments, wherein $R^1$ is $Ar^1$.

In an embodiment, the present invention relates to those compounds of formula (I) and the pharmaceutically acceptable addition salts, and the solvates thereof, or any subgroup thereof as mentioned in any of the other embodiments, wherein $R^1$ is Are.

In an embodiment, the present invention relates to those compounds of formula (I) and the pharmaceutically acceptable addition salts, and the solvates thereof, or any subgroup thereof as mentioned in any of the other embodiments, wherein $R^2$ is hydrogen, phenyl, cycloC$_{3-7}$ alkyl, 3,4,5,6-tetrahydropyranyl, 3,4,5,6-tetrahydrothiopyranyl, piperidinyl, or C$_{1-4}$alkyl optionally substituted with one or more substituents each independently selected from the group consisting of hydroxyl, C$_{1-4}$alkyloxy and NR$^7$R$^8$.

In an embodiment, the present invention relates to those compounds of formula (I) and the pharmaceutically acceptable addition salts, and the solvates thereof, or any subgroup thereof as mentioned in any of the other embodiments, wherein $R^2$ is hydrogen or C$_{1-4}$alkyl.

In an embodiment, the present invention relates to those compounds of formula (I) and the pharmaceutically acceptable addition salts, and the solvates thereof, or any subgroup thereof as mentioned in any of the other embodiments, wherein $R^2$ is hydrogen.

In an embodiment, the present invention relates to those compounds of formula (I) and the pharmaceutically acceptable addition salts, and the solvates thereof, or any subgroup thereof as mentioned in any of the other embodiments, wherein $R^2$ is C$_{1-4}$alkyl; in particular methyl.

In an embodiment, the present invention relates to those compounds of formula (I), or any subgroup thereof as mentioned in any of the other embodiments, wherein $R^2$ is hydrogen, phenyl, cycloC$_{3-7}$alkyl, or C$_{1-4}$alkyl optionally substituted with one or more substituents each independently selected from the group consisting of hydroxyl, C$_{1-4}$alkyloxy and NR$^7$R$^8$.

In an embodiment, the present invention relates to those compounds of formula (I) and the pharmaceutically acceptable addition salts, and the solvates thereof, or any subgroup thereof as mentioned in any of the other embodiments, wherein $R^2$ is phenyl, cycloC$_{3-7}$alkyl, 3,4,5,6-tetrahydropyranyl, 3,4,5,6-tetrahydrothiopyranyl, piperidinyl, or C$_{1-4}$alkyl optionally substituted with one or more substituents each independently selected from the group consisting of halo, hydroxyl, C$_{1-4}$alkyloxy and NR$^7$R$^8$.

In an embodiment, the present invention relates to those compounds of formula (I) and the pharmaceutically acceptable addition salts, and the solvates thereof, or any subgroup thereof as mentioned in any of the other embodiments, wherein $R^2$ is hydrogen or C$_{1-4}$alkyl optionally substituted with one or more substituents each independently selected from the group consisting of hydroxyl, C$_{1-4}$alkyloxy and NR$^7$R$^8$ methyl; in particular hydrogen or C$_{1-4}$alkyl; more in particular hydrogen or methyl; even more in particular methyl.

In an embodiment, the present invention relates to those compounds of formula (I) and the pharmaceutically acceptable addition salts, and the solvates thereof, or any subgroup thereof as mentioned in any of the other embodiments, wherein $R^2$ is $C_{1-4}$alkyl optionally substituted with one or more substituents each independently selected from the group consisting of halo, hydroxyl, $C_{1-4}$alkyloxy and $NR^7R^8$.

In an embodiment, the present invention relates to those compounds of formula (I) and the pharmaceutically acceptable addition salts, and the solvates thereof, or any subgroup thereof as mentioned in any of the other embodiments, wherein $R^2$ is phenyl, cyclo$C_{3-7}$alkyl, 3,4,5,6-tetrahydropyranyl, 3,4,5,6-tetrahydrothiopyranyl, piperidinyl, or $C_{1-4}$alkyl optionally substituted with one or more substituents each independently selected from the group consisting of halo, hydroxyl, $C_{1-4}$ alkyloxy and $NR^7R^8$.

In an embodiment, the present invention relates to those compounds of formula (I) and the pharmaceutically acceptable addition salts, and the solvates thereof, or any subgroup thereof as mentioned in any of the other embodiments, wherein $R^0$ is a ring system selected from the group consisting of piperidinyl, morpholinyl, cyclo$C_{3-7}$alkyl, pyrazolyl and pyrrolidinyl; wherein said ring system is optionally substituted with one or more $C_{1-4}$alkyl groups optionally substituted with one or more halo atoms.

In an embodiment, the present invention relates to those compounds of formula (I) and the pharmaceutically acceptable addition salts, and the solvates thereof, or any subgroup thereof as mentioned in any of the other embodiments, wherein $R^3$ is hydrogen or halo; in particular hydrogen.

In an embodiment, the present invention relates to those compounds of formula (I) and the pharmaceutically acceptable addition salts, and the solvates thereof, or any subgroup thereof as mentioned in any of the other embodiments, wherein $R^8$ is $C_{1-4}$alkyl.

In an embodiment, the present invention relates to those compounds of formula (I) and the pharmaceutically acceptable addition salts, and the solvates thereof, or any subgroup thereof as mentioned in any of the other embodiments, wherein Z is methylene or 1,2-ethanediyl, wherein methylene is optionally substituted with one or two $C_{1-4}$alkyl substituents.

In an embodiment, the present invention relates to those compounds of formula (I) and the pharmaceutically acceptable addition salts, and the solvates thereof, or any subgroup thereof as mentioned in any of the other embodiments, wherein L is $C_{1-6}$alkanediyl; in particular L is methylene, ethylidene or 1,2-ethanediyl; more in particular L is ethylidene.

In an embodiment, the present invention relates to those compounds of formula (I) and the pharmaceutically acceptable addition salts, and the solvates thereof, or any subgroup thereof as mentioned in any of the other embodiments, wherein L is methylene.

In an embodiment, the present invention relates to those compounds of formula (I) and the pharmaceutically acceptable addition salts, and the solvates thereof, or any subgroup thereof as mentioned in any of the other embodiments, wherein $R^2$ is methyl and L is ethylidene or methylene; in particular wherein $R^2$ is methyl and L is ethylidene.

In an embodiment, the present invention relates to those compounds of formula (I) and the pharmaceutically acceptable addition salts, and the solvates thereof, or any subgroup thereof as mentioned in any of the other embodiments, wherein $R^2$ is $C_{1-4}$alkyl and L is $C_{1-6}$alkanediyl.

In an embodiment, the present invention relates to those compounds of formula (I) and the pharmaceutically acceptable addition salts, and the solvates thereof, or any subgroup thereof as mentioned in any of the other embodiments, wherein $R^3$ is hydrogen; $R^4$ is methyl; $R^5$ is hydrogen; X is CH.

In an embodiment, the present invention relates to those compounds of formula (I) and the pharmaceutically acceptable addition salts, and the solvates thereof, or any subgroup thereof as mentioned in any of the other embodiments, wherein L is —C(=O)—$C_{1-6}$alkanediyl-, $C_{1-6}$alkanediyl optionally substituted with one or more substituents selected from the group consisting of 3,4,5,6-tetrahydropyranyl, phenyl and $C_{1-4}$alkyloxy$C_{1-4}$alkyl, or $C_{1-6}$alkanediyl wherein two geminal hydrogen atoms are replaced by $C_{2-6}$alkanediyl; in particular L is $C_{1-6}$alkanediyl optionally substituted with one or more substituents selected from the group consisting of 3,4,5,6-tetrahydropyranyl, phenyl and $C_{1-4}$alkyloxy$C_{1-4}$alkyl, or $C_{1-6}$alkanediyl wherein two geminal hydrogen atoms are replaced by $C_{2-6}$alkanediyl; more in particular L is $C_{1-6}$alkanediyl optionally substituted with one or more substituents selected from the group consisting of 3,4,5,6-tetrahydropyranyl, phenyl and $C_{1-4}$alkyloxy$C_{1-4}$alkyl.

An interesting group of compounds relates to those compounds wherein the position of $R^3$ is fixed as shown in (I-x)

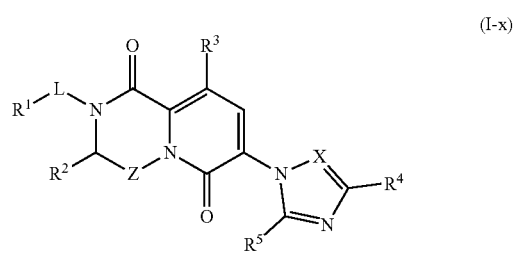

(I-x)

tautomers and stereoisomeric forms thereof,
wherein all the substituents have the same meaning as defined in any of the embodiments hereinbefore,
and the pharmaceutically acceptable addition salts and the solvates thereof.

An interesting group of compounds relates to those compounds of formula (I) and the pharmaceutically acceptable addition salts, and the solvates thereof, or any subgroups thereof, wherein the carbon atom substituted with $R^2$ has the R configuration.

In an embodiment, the present invention relates to those compounds of formula (I) and the pharmaceutically acceptable addition salts, and the solvates thereof, or any subgroup thereof as mentioned in any of the other embodiments, wherein $Ar^1$ is a ring system selected from the group consisting of imidazolyl, thienyl, thiazolyl, pyrrolidinyl, piperidinyl, pyrazolyl, 4,5,6,7-tetrahydro-benzo[b]thienyl, 1,2-benzisoxazolyl, benzofuranyl, 2,3-dihydrobenzofuranyl, 1,3-dihydro-isobenzofuranyl, 5,6,7,8-tetrahydro-1,2,4-triazolo[4,3-a]pyridinyl, 4,5,6,7-tetrahydro-pyrazolo-[1,5-a]pyridinyl, 1,2,4-triazolo[4,3-a]pyridinyl, pyrazolo[1,5-a]pyridinyl, 3,4-dihydro-1-benzopyranyl, 1,2-benzisothiazolyl, indazolyl, 1,2,3,4-tetrahydro-isoquinolinyl; it should be understood that any of these ring systems may be substituted as defined in any of the other embodiments.

In an embodiment, the present invention relates to those compounds of formula (I) and the pharmaceutically acceptable addition salts, and the solvates thereof, or any subgroup thereof as mentioned in any of the other embodiments, wherein $Ar^1$ is a ring system selected from the group consisting of imidazol-1-yl, 2-thienyl, 3-thienyl, 4-thiazolyl, 3-pyrrolidinyl, 1-piperidinyl, pyrazol-3-yl, pyrazol-5-yl, 4,5,6,7-tetrahydro-benzo[b]thien-3-yl, 4,5,6,7-tetrahydro-benzo[b]thien-2-yl, 1,2-benzisoxazol-3-yl, 2-benzofuranyl, 3-benzofuranyl, 2,3-dihydro-3-benzofuranyl, 2,3-dihydro-7-benzofuranyl, 2,3-dihydro-2-benzofuranyl, 1,3-dihydro-1-isobenzofuranyl, 5,6,7,8-tetrahydro-1,2,4-triazolo[4,3-a]pyridin-3-yl, 4,5,6,7-tetrahydro-pyrazolo[1,5-a]pyridin-3-yl, 1,2,4-triazolo[4,3-a]pyridin-3-yl, pyrazolo[1,5-a]pyridin-3-yl, 3,4-dihydro-1-benzopyran-2-yl, 3,4-dihydro-1-benzopyran-4-yl, 3,4-dihydro-1-benzopyran-6-yl, 1,2-benzisothiazol-3-yl, indazol-3-yl, 1,2,3,4-tetrahydro-2-isoquinolinyl;

it should be understood that any of these ring systems may be substituted as defined in any of the other embodiments.

In an embodiment, the present invention relates to those compounds of formula (I) and the pharmaceutically acceptable addition salts, and the solvates thereof, or any subgroup thereof as mentioned in any of the other embodiments, wherein $Ar^1$ is a ring system selected from the group consisting of imidazol-1-yl, 2-thienyl, 3-thienyl, 4-thiazolyl, 3-pyrrolidinyl, 1-piperidinyl, pyrazol-3-yl, pyrazol-5-yl, 4,5,6,7-tetrahydro-benzo[b]thien-3-yl, 4,5,6,7-tetrahydro-benzo[b]thien-2-yl, 1,2-benzisoxazol-3-yl, 2-benzofuranyl, 2,3-dihydro-3-benzofuranyl, 2,3-dihydro-7-benzofuranyl, 2,3-dihydro-2-benzofuranyl, 1,3-dihydro-1-isobenzofuranyl, 5,6,7,8-tetrahydro-1,2,4-triazolo-[4,3-a]pyridin-3-yl, 4,5,6,7-tetrahydro-pyrazolo[1,5-a]pyridin-3-yl, 1,2,4-triazolo-[4,3-a]pyridin-3-yl, pyrazolo[1,5-a]pyridin-3-yl, 3,4-dihydro-1-benzopyran-2-yl, dihydro-1-benzopyran-6-yl, 1,2-benzisothiazol-3-yl, indazol-3-yl, 1,2,3,4-tetrahydro-2-isoquinolinyl;

it should be understood that any of these ring systems may be substituted as defined in any of the other embodiments.

In an embodiment, the present invention relates to those compounds of formula (I) and the pharmaceutically acceptable addition salts, and the solvates thereof, or any subgroup thereof as mentioned in any of the other embodiments, wherein $Ar^1$ is a ring system selected from the group consisting of imidazolyl, thienyl, thiazolyl, pyrrolidinyl, piperidinyl, 4,5,6,7-tetrahydro-benzo[b]thienyl, benzofuranyl, 2,3-dihydrobenzofuranyl, 1,3-dihydro-isobenzofuranyl, 5,6,7,8-tetrahydro-1,2,4-triazolo[4,3-a]pyridinyl, 4,5,6,7-tetrahydro-pyrazolo[1,5-a]pyridinyl, 1,2,4-triazolo[4,3-a]pyridinyl, pyrazolo[1,5-a]pyridinyl, 3,4-dihydro-1-benzopyranyl, indazolyl, 1,2,3,4-tetrahydro-isoquinolinyl; it should be understood that any of these ring systems may be substituted as defined in any of the other embodiments.

In an embodiment, the present invention relates to those compounds of formula (I) and the pharmaceutically acceptable addition salts, and the solvates thereof, or any subgroup thereof as mentioned in any of the other embodiments, wherein $Ar^1$ is a ring system selected from the group consisting of imidazol-1-yl, 2-thienyl, 3-thienyl, 4-thiazolyl, 3-pyrrolidinyl, 1-piperidinyl, 4,5,6,7-tetrahydro-benzo[b]thien-3-yl, 4,5,6,7-tetrahydro-benzo[b]thien-2-yl, 2-benzofuranyl, 3-benzofuranyl, 2,3-dihydro-3-benzofuranyl, 2,3-dihydro-7-benzofuranyl, 2,3-dihydro-2-benzofuranyl, 1,3-dihydro-1-isobenzofuranyl, 5,6,7,8-tetrahydro-1,2,4-triazolo[4,3-a]pyridin-3-yl, 4,5,6,7-tetrahydro-pyrazolo[1,5-a]pyridin-3-yl, 1,2,4-triazolo[4,3-a]pyridin-3-yl, pyrazolo-[1,5-a]pyridin-3-yl, 3,4-dihydro-1-benzopyran-2-yl, 3,4-dihydro-1-benzopyran-4-yl, 3,4-dihydro-1-benzopyran-6-yl, indazol-3-yl, 1,2,3,4-tetrahydro-2-isoquinolinyl; it should be understood that any of these ring systems may be substituted as defined in any of the other embodiments.

In an embodiment, the present invention relates to those compounds of formula (I) and the pharmaceutically acceptable addition salts, and the solvates thereof, or any subgroup thereof as mentioned in any of the other embodiments, wherein $Ar^1$ is benzofuranyl, in particular 2-benzofuranyl and/or 3-benzofuranyl; it should be understood that the benzofuranyl ring system may be substituted as defined in any of the other embodiments.

In an embodiment, the present invention relates to those compounds of formula (I) and the pharmaceutically acceptable addition salts, and the solvates thereof, or any subgroup thereof as mentioned in any of the other embodiments, wherein one or more of the following heterocyclic groups in the $R^2$ definition are restricted: 3,4,5,6-tetrahydropyranyl is restricted to 3,4,5,6-tetrahydropyran-4-yl, 3,4,5,6-tetrahydrothiopyranyl is restricted to 3,4,5,6-tetrahydrothiopyran-4-yl, piperidinyl is restricted to 1-piperidinyl or 4-piperidinyl;

it should be understood that any of these heterocyclic groups may be substituted as defined in any of the other embodiments.

In an embodiment, the present invention relates to those compounds of formula (I) and the pharmaceutically acceptable addition salts, and the solvates thereof, or any subgroup thereof as mentioned in any of the other embodiments, wherein one or more of the following heterocyclic groups in the $R^0$ definition are restricted: piperidinyl is restricted to 1-piperidinyl, morpholinyl is restricted to 1-morpholinyl, pyrazolyl is restricted to 1-pyrazolyl, pyrrolidinyl is restricted to 1-pyrrolidinyl;

it should be understood that any of these heterocyclic groups may be substituted as defined in any of the other embodiments.

In an embodiment, the present invention relates to those compounds of formula (I) and the pharmaceutically acceptable addition salts, and the solvates thereof, or any subgroup thereof as mentioned in any of the other embodiments, wherein one or more of the heterocyclic groups in the $Ar^1$, $R^2$ and $R^0$ definitions are restricted as indicated in the embodiments hereabove.

In an embodiment, the present invention relates to compound of Formula (I), tautomers and stereoisomeric forms thereof, wherein:

$R^1$ is a ring system selected from the group consisting of imidazolyl, thienyl, piperidinyl, 4,5,6,7-tetrahydro-benzo[b]thienyl, benzofuranyl, 2,3-dihydrobenzofuranyl, 1,3-dihydro-isobenzofuranyl, 5,6,7,8-tetrahydro-1,2,4-triazolo[4,3-a]pyridinyl, 4,5,6,7-tetrahydro-pyrazolo[1,5-a]pyridinyl, 1,2,4-triazolo[4,3-a]pyridinyl, pyrazolo[1,5-a]pyridinyl, 3,4-dihydro-1-benzopyranyl, indazolyl;

wherein said ring system is optionally substituted with one, two or three substituents each independently selected from the group consisting of halo, $C_{1-4}$alkyl optionally substituted with one, two or three independently selected halo substituents, and $C_{1-4}$alkyloxy optionally substituted with one, two or three independently selected halo substituents; in particular, wherein said ring system is optionally substituted with one, two or three substituents each independently selected from the group consisting of F, Cl, Br, $CH_3$, $CF_3$, $CH_2CF_3$, $OCH(CH_3)_2$, and $OCF_3$;

$R^2$ is hydrogen or methyl; in particular methyl;

Z is methylene;

L is $C_{1-3}$alkanediyl, in particular methylene, ethylidene or 1,2-ethanediyl;

$R^3$ is hydrogen;

$R^4$ is methyl;

$R^5$ is hydrogen;

X is CH;
and the pharmaceutically acceptable addition salts, and the solvates thereof.

In an embodiment, the present invention relates to compound of Formula (I), tautomers and stereoisomeric forms thereof, wherein:
$R^1$ is a ring system selected from the group consisting of imidazol-1-yl, 2-thienyl, 3-thienyl, 1-piperidinyl, 4,5,6,7-tetrahydro-benzo[b]thien-3-yl, 4,5,6,7-tetrahydro-benzo[b]thien-2-yl, 2-benzofuranyl, 3-benzofuranyl, 2,3-dihydro-3-benzofuranyl, 2,3-dihydro-7-benzofuranyl, 2,3-dihydro-2-benzofuranyl, 1,3-dihydro-1-isobenzofuranyl, 5,6,7,8-tetrahydro-1,2,4-triazolo[4,3-a]pyridin-3-yl, 4,5,6,7-tetrahydro-pyrazolo-[1,5-a]pyridin-3-yl, pyrazolo[1,5-a]pyridin-3-yl, 3,4-dihydro-1-benzopyran-2-yl, 3,4-dihydro-1-benzopyran-4-yl, 3,4-dihydro-1-benzopyran-6-yl, indazol-3-yl;
wherein said ring system is optionally substituted with one, two or three substituents each independently selected from the group consisting of halo, $C_{1-4}$alkyl optionally substituted with one, two or three independently selected halo substituents, and $C_{1-4}$alkyloxy optionally substituted with one, two or three independently selected halo substituents; in particular, wherein said ring system is optionally substituted with one, two or three substituents each independently selected from the group consisting of F, Cl, Br, $CH_3$, $CF_3$, $CH_2CF_3$, $OCH(CH_3)_2$, and $OCF_3$;
$R^2$ is hydrogen or methyl; in particular methyl;
Z is methylene;
L is $C_{1-2}$alkanediyl, in particular methylene or ethylidene;
$R^3$ is hydrogen;
$R^4$ is methyl;
$R^5$ is hydrogen;
X is CH;
and the pharmaceutically acceptable addition salts, and the solvates thereof.

In an embodiment, the present invention relates to compound of Formula (I), tautomers and stereoisomeric forms thereof, wherein:
$R^1$ is 2-benzofuranyl or 3-benzofuranyl; substituted with one, two or three substituents each independently selected from the group consisting of halo, $C_{1-4}$alkyl optionally substituted with one, two or three independently selected halo substituents, and $C_{1-4}$alkyloxy optionally substituted with one, two or three independently selected halo substituents; in particular, said substituents are each independently selected from the group consisting of F, Cl, Br, $CH_3$, $CF_3$, $CH_2CF_3$, $OCH(CH_3)_2$, and $OCF_3$;
$R^2$ is hydrogen or methyl; in particular methyl;
Z is methylene;
L is $C_{1-2}$alkanediyl, in particular methylene or ethylidene;
$R^3$ is hydrogen;
$R^4$ is methyl;
$R^5$ is hydrogen;
X is CH;
and the pharmaceutically acceptable addition salts, and the solvates thereof.

In an embodiment, the present invention relates to compound of Formula (I), tautomers and stereoisomeric forms thereof, wherein:
$R^1$ is 2-benzofuranyl or 3-benzofuranyl, substituted with one or two substituents each independently selected from the group consisting of halo, and $C_{1-4}$alkyl substituted with one, two or three independently selected halo substituents; in particular, wherein said substituents are each independently selected from the group consisting of F, Cl, and $CF_3$;

$R^2$ is methyl; in particular, wherein the carbon atom substituted with $R^2$ has the R configuration;
Z is methylene;
L is methylene or ethylidene;
$R^3$ is hydrogen;
$R^4$ is methyl;
$R^5$ is hydrogen;
X is CH;
and the pharmaceutically acceptable addition salts, and the solvates thereof.

In an embodiment the compound of Formula (I) is selected from the group consisting of:
2-[[2,3-dihydro-4-(trifluoromethyl)-2-benzofuranyl]methyl]-3,4-dihydro-7-(4-methyl-1H-imidazol-1-yl)-2H-pyrido[1,2-a]pyrazine-1,6-dione (mixture of R and S),
(3R)-3,4-dihydro-3-methyl-7-(4-methyl-1H-imidazol-1-yl)-2-[(3-phenoxyphenyl)-methyl]-2H-pyrido[1,2-a]pyrazine-1,6-dione,
(3R)-2-[(5-bromo-2-benzofuranyl)methyl]-3,4-dihydro-3-methyl-7-(4-methyl-1H-imidazol-1-yl)-2H-pyrido[1,2-a]pyrazine-1,6-dione,
(3R)-2-[[3-(cyclopropyloxy)-5-(trifluoromethyl)phenyl]methyl]-3,4-dihydro-3-methyl-7-(4-methyl-1H-imidazol-1-yl)-2H-pyrido[1,2-a]pyrazine-1,6-dione,
(3R)-2-[[3-(cyclopentyloxy)-4-methoxyphenyl]methyl]-3,4-dihydro-3-methyl-7-(4-methyl-1H-imidazol-1-yl)-2H-pyrido[1,2-a]pyrazine-1,6-dione,
(3R)-2-[(2,3-dihydro-2,2-dimethyl-7-benzofuranyl)methyl]-3,4-dihydro-3-methyl-7-(4-methyl-1H-imidazol-1-yl)-2H-pyrido[1,2-a]pyrazine-1,6-dione,
(3R)-3,4-dihydro-3-methyl-7-(4-methyl-1H-imidazol-1-yl)-2-[[5-(2,2,2-trifluoroethyl)-3-thienyl]methyl]-2H-pyrido[1,2-a]pyrazine-1,6-dione,
(3R)-3,4-dihydro-3-methyl-7-(4-methyl-1H-imidazol-1-yl)-2-[[5-(trifluoromethyl)-3-thienyl]methyl]-2H-pyrido[1,2-a]pyrazine-1,6-dione,
(3R)-2-[(5-bromo-2,3-dihydro-7-benzofuranyl)methyl]-3,4-dihydro-3-methyl-7-(4-methyl-1H-imidazol-1-yl)-2H-pyrido[1,2-a]pyrazine-1,6-dione,
(3R)-2-[(4-bromo-2-thienyl)methyl]-3,4-dihydro-3-methyl-7-(4-methyl-1H-imidazol-1-yl)-2H-pyrido[1,2-a]pyrazine-1,6-dione,
(3R)-3,4-dihydro-3-methyl-7-(4-methyl-1H-imidazol-1-yl)-2-[2-[5-(2,2,2-trifluoroethyl)-3-thienyl]ethyl]-2H-pyrido[1,2-a]pyrazine-1,6-dione,
(3R)-2-[[2,3-dihydro-4-(1-methylethoxy)-7-benzofuranyl]methyl]-3,4-dihydro-3-methyl-7-(4-methyl-1H-imidazol-1-yl)-2H-pyrido[1,2-a]pyrazine-1,6-dione,
(3R)-2-[(3,4-dihydro-2,2-dimethyl-2H-1-benzopyran-6-yl)methyl]-3,4-dihydro-3-methyl-7-(4-methyl-1H-imidazol-1-yl)-2H-pyrido[1,2-a]pyrazine-1,6-dione,
(3R)-3,4-dihydro-3-methyl-7-(4-methyl-1H-imidazol-1-yl)-2-[[5-(trifluoromethyl)-2-benzofuranyl]methyl]-2H-pyrido[1,2-a]pyrazine-1,6-dione,
(3R)-2-[2-(3,4-dihydro-2(1H)-isoquinolinyl)-2-oxoethyl]-3,4-dihydro-3-methyl-7-(4-methyl-1H-imidazol-1-yl)-2H-pyrido[1,2-a]pyrazine-1,6-dione,
(3R)-2-[(5-bromo-1,2-benzisothiazol-3-yl)methyl]-3,4-dihydro-3-methyl-7-(4-methyl-1H-imidazol-1-yl)-2H-pyrido[1,2-a]pyrazine-1,6-dione,
(3R)-2-[(7-bromo-1,2-benzisothiazol-3-yl)methyl]-3,4-dihydro-3-methyl-7-(4-methyl-1H-imidazol-1-yl)-2H-pyrido[1,2-a]pyrazine-1,6-dione,
(3R)-2-[2-[3-(cyclopropyloxy)-5-(trifluoromethyl)phenyl]ethyl]-3,4-dihydro-3-methyl-7-(4-methyl-1H-imidazol-1-yl)-2H-pyrido[1,2-a]pyrazine-1,6-dione, (3R)-3,4-dihydro-3-methyl-7-(4-methyl-1H-imidazol-1-yl)-2-[[5-methyl-1-(2,2,2-trifluoroethyl)-1H-pyrazol-3-yl]methyl]-2H-pyrido[1,2-a]pyrazine-1,6-dione, (3R)-2-[(5-chloro-1-methyl-1H-indazol-3-yl)methyl]-3,4-dihydro-3-methyl-7-(4-methyl-1H-imidazol-1-yl)-2H-pyrido[1,2-a]pyrazine-1,6-dione, (3R)-2-(1,2-benzisothiazol-3-ylmethyl)-3,4-dihydro-3-methyl-7-(4-methyl-1H-imidazol-1-yl)-2H-pyrido[1,2-a]pyrazine-1,6-dione, (3R)-3,4-dihydro-3-methyl-2-[[3-(1-methylethyl)-1-(2,2,2-trifluoroethyl)-1H-pyrazol-5-yl]methyl]-7-(4-methyl-1H-imidazol-1-yl)-2H-pyrido[1,2-a]pyrazine-1,6-dione, (3R)-3,4-dihydro-3-methyl-2-[[5-(1-methylethyl)-1-(2,2,2-trifluoroethyl)-1H-pyrazol-3-yl]methyl]-7-(4-methyl-1H-imidazol-1-yl)-2H-pyrido[1,2-a]pyrazine-1,6-dione, (3R)-2-[[1-[3-(cyclopropyloxy)-5-(trifluoromethyl)phenyl]cyclopropyl]methyl]-3,4-dihydro-3-methyl-7-(4-methyl-1H-imidazol-1-yl)-2H-pyrido[1,2-a]pyrazine-1,6-dione, (3R)-3,4-dihydro-3-methyl-7-(4-methyl-1H-imidazol-1-yl)-2-[[5-(trifluoro-methyl)pyrazolo[1,5-a]pyridin-3-yl]methyl]-2H-pyrido[1,2-a]pyrazine-1,6-dione, (3R)-3,4-dihydro-3-methyl-7-(4-methyl-1H-imidazol-1-yl)-2-[[6-(trifluoromethyl)-1,2,4-triazolo[4,3-a]pyridin-3-yl]methyl]-2H-pyrido[1,2-a]pyrazine-1,6-dione, (3R)-2-[(5-chloro-1,2-benzisoxazol-3-yl)methyl]-3,4-dihydro-3-methyl-7-(4-methyl-1H-imidazol-1-yl)-2H-pyrido[1,2-a]pyrazine-1,6-dione, (3R)-2-[(6-Bromo-3,4-dihydro-2H-chromen-2-yl)methyl]-3-methyl-7-(4-methyl-1H-imidazol-1-yl)-3,4-dihydro-2H-pyrido[1,2-a]pyrazine-1,6-dione, (3R)-2-{[2-Chloro-5-(trifluoromethyl)-4,5,6,7-tetrahydro-1-benzothiophen-3-yl]methyl}-3-methyl-7-(4-methyl-1H-imidazol-1-yl)-3,4-dihydro-2H-pyrido[1,2-a]-pyrazine-1,6-dione, (3R)-2-[(5-Chloro-1-benzofuran-3-yl)methyl]-3-methyl-7-(4-methyl-1H-imidazol-1-yl)-3,4-dihydro-2H-pyrido[1,2-a]pyrazine-1,6-dione, (3R)-3-Methyl-7-(4-methyl-1H-imidazol-1-yl)-2-{[5-(trifluoromethyl)-1,2-benzisoxazol-3-yl]methyl}-3,4-dihydro-2H-pyrido[1,2-a]pyrazine-1,6-dione, (3R)-2-[(5-Chloro-6-fluoro-1-benzofuran-3-yl)methyl]-3-methyl-7-(4-methyl-1H-imidazol-1-yl)-3,4-dihydro-2H-pyrido[1,2-a]pyrazine-1,6-dione, (3R)-3-Methyl-7-(4-methyl-1H-imidazol-1-yl)-2-{[5-(trifluoromethyl)-1-benzofuran-3-yl]methyl}-3,4-dihydro-2H-pyrido[1,2-a]pyrazine-1,6-dione, (3R)-2-[(5,7-Dichloro-1-benzofuran-3-yl)methyl]-3-methyl-7-(4-methyl-1H-imidazol-1-yl)-3,4-dihydro-2H-pyrido[1,2-a]pyrazine-1,6-dione, 2-[(5-Chloro-3-methyl-2,3-dihydro-1-benzofuran-3-yl)methyl]-7-(4-methyl-1H-imidazol-1-yl)-3,4-dihydro-2H-pyrido[1,2-a]pyrazine-1,6-dione, (3R)-2-[(7-Bromo-1-benzofuran-3-yl)methyl]-3-methyl-7-(4-methyl-1H-imidazol-1-yl)-3,4-dihydro-2H-pyrido[1,2-a]pyrazine-1,6-dione, (3R)-3-Methyl-7-(4-methyl-1H-imidazol-1-yl)-2-{[5-(trifluoromethoxy)-1-benzofuran-3-yl]methyl}-3,4-dihydro-2H-pyrido[1,2-a]pyrazine-1,6-dione, 7-(4-Methyl-1H-imidazol-1-yl)-2-{[5-(trifluoromethoxy)-1-benzofuran-3-yl]methyl}-3,4-dihydro-2H-pyrido[1,2-a]pyrazine-1,6-dione, 7-(4-Methyl-1H-imidazol-1-yl)-2-{(1R or 1S)-1-[5-(trifluoromethoxy)-1-benzofuran-3-yl]ethyl}-3,4-dihydro-2H-pyrido[1,2-a]pyrazine-1,6-dione, 7-(4-Methyl-1H-imidazol-1-yl)-2-{(1S or 1R)-1-[5-(trifluoromethoxy)-1-benzofuran-3-yl]ethyl}-3,4-dihydro-2H-pyrido[1,2-a]pyrazine-1,6-dione, (3R)-2-{[5-Fluoro-6-(trifluoromethyl)-1-benzofuran-3-yl]methyl}-3-methyl-7-(4-methyl-1H-imidazol-1-yl)-3,4-dihydro-2H-pyrido[1,2-a]pyrazine-1,6-dione, (3R)-2-{[6-Fluoro-5-(trifluoromethyl)-1-benzofuran-3-yl]methyl}-3-methyl-7-(4-methyl-1H-imidazol-1-yl)-3,4-dihydro-2H-pyrido[1,2-a]pyrazine-1,6-dione, (3R)-3-Methyl-7-(4-methyl-1H-imidazol-1-yl)-2-{[6-(trifluoromethyl)-1-benzofuran-3-yl]methyl}-3,4-dihydro-2H-pyrido[1,2-a]pyrazine-1,6-dione, 2-[1-(5-Chloro-6-fluoro-1-benzofuran-3-yl)ethyl]-7-(4-methyl-1H-imidazol-1-yl)-3,4-dihydro-2H-pyrido[1,2-a]pyrazine-1,6-dione, (3R)-3-Methyl-7-(4-methyl-1H-imidazol-1-yl)-2-{[7-(trifluoromethyl)-1-benzofuran-3-yl]methyl}-3,4-dihydro-2H-pyrido[1,2-a]pyrazine-1,6-dione, 7-(4-Methyl-1H-imidazol-1-yl)-2-{[5-(trifluoromethyl)-1-benzofuran-3-yl]methyl}-3,4-dihydro-2H-pyrido[1,2-a]pyrazine-1,6-dione, 7-(4-Methyl-1H-imidazol-1-yl)-2-{(1R or 1S)-1-[6-(trifluoromethyl)-1-benzofuran-3-yl]ethyl}-3,4-dihydro-2H-pyrido[1,2-a]pyrazine-1,6-dione, 7-(4-Methyl-1H-imidazol-1-yl)-2-{(1S or 1R)-1-[6-(trifluoromethyl)-1-benzofuran-3-yl]ethyl}-3,4-dihydro-2H-pyrido[1,2-a]pyrazine-1,6-dione, 2-[(1S or 1R)-1-(5-Chloro-6-fluoro-1-benzofuran-3-yl)ethyl]-7-(4-methyl-1H-imidazol-1-yl)-3,4-dihydro-2H-pyrido[1,2-a]pyrazine-1,6-dione, 2-[(1R or 1S)-1-(5-Chloro-6-fluoro-1-benzofuran-3-yl)ethyl]-7-(4-methyl-1H-imidazol-1-yl)-3,4-dihydro-2H-pyrido[1,2-a]pyrazine-1,6-dione, (3R)-2-[(5-Chloro-6,7-difluoro-1-benzofuran-3-yl)methyl]-3-methyl-7-(4-methyl-1H-imidazol-1-yl)-3,4-dihydro-2H-pyrido[1,2-a]pyrazine-1,6-dione, (3R)-2-{[5-Chloro-7-(trifluoromethyl)-1-benzofuran-3-yl]methyl}-3-methyl-7-(4-methyl-1H-imidazol-1-yl)-3,4-dihydro-2H-pyrido[1,2-a]pyrazine-1,6-dione, 7-(4-Methyl-1H-imidazol-1-yl)-2-{(1R or 1S)-1-[5-(trifluoromethyl)-1-benzofuran-3-yl]ethyl}-3,4-dihydro-2H-pyrido[1,2-a]pyrazine-1,6-dione, 7-(4-Methyl-1H-imidazol-1-yl)-2-{(1S or 1R)-1-[5-(trifluoromethyl)-1-benzofuran-3-yl]ethyl}-3,4-dihydro-2H-pyrido[1,2-a]pyrazine-1,6-dione, (3R)-2-[(5-Chloro-7-fluoro-1-benzofuran-3-yl)methyl]-3-methyl-7-(4-methyl-1H-imidazol-1-yl)-3,4-dihydro-2H-pyrido[1,2-a]pyrazine-1,6-dione, 2-[(5-Chloro-7-fluoro-1-benzofuran-3-yl)methyl]-7-(4-methyl-1H-imidazol-1-yl)-3,4-dihydro-2H-pyrido[1,2-a]pyrazine-1,6-dione, (3R)-2-[(5,6-Dichloro-1-benzofuran-3-yl)methyl]-3-methyl-7-(4-methyl-1H-imidazol-1-yl)-3,4-dihydro-2H-pyrido[1,2-a]pyrazine-1,6-dione, 2-[(5,6-Dichloro-1-benzofuran-3-yl)methyl]-7-(4-methyl-1H-imidazol-1-yl)-3,4-dihydro-2H-pyrido[1,2-a]pyrazine-1,6-dione, tautomers and stereoisomeric forms thereof,
and the pharmaceutically acceptable addition salts, and the solvates thereof.

In an embodiment the compound of Formula (I) is selected from the group consisting of:

(3R)-2-{3-[(1R,5S)-3-Azabicyclo[3.1.0]hex-3-yl]-4-methylbenzyl}-3-methyl-7-(4-methyl-1H-imidazol-1-yl)-3,4-dihydro-2H-pyrido[1,2-a]pyrazine-1,6-dione, (3R)-3-Methyl-7-(4-methyl-1H-imidazol-1-yl)-2-{2-[3-(trifluoromethyl)piperidin-1-yl]ethyl}-3,4-dihydro-2H-pyrido[1,2-a]pyrazine-1,6-dione, (3R)-2-{(1S or 1R)-1-[3-Hydroxy-5-(trifluoromethyl)phenyl]ethyl}-3-methyl-7-(4-methyl-1H-imidazol-1-yl)-3,4-dihydro-2H-pyrido[1,2-a]pyrazine-1,6-dione, (3R)-2-{(1R or 1S)-1-[3-(Cyclopropyloxy)-5-(trifluoromethyl)phenyl]ethyl}-3-methyl-7-(4-methyl-1H-imidazol-1-yl)-3,4-dihydro-2H-pyrido[1,2-a]pyrazine-1,6-dione, (3R)-2-{(1S or 1R)-1-[3-(Cyclopropyloxy)-5-(trifluoromethyl)phenyl]ethyl}-3-methyl-7-(4-methyl-1H-imidazol-1-yl)-3,4-dihydro-2H-pyrido[1,2-a]pyrazine-1,6-dione, (3R)-2-{(1R or 1S)-1-[3-Hydroxy-4-(trifluoromethoxy)phenyl]ethyl}-3-methyl-7-(4-methyl-1H-imidazol-1-yl)-3,4-dihydro-2H-pyrido[1,2-a]pyrazine-1,6-dione, (3R)-2-{(1S or 1R)-1-[3-Hydroxy-4-(trifluoromethoxy)phenyl]ethyl}-3-methyl-7-(4-methyl-1H-imidazol-1-yl)-3,4-dihydro-2H-pyrido[1,2-a]pyrazine-1,6-dione, (3R)-3-Methyl-7-(4-methyl-1H-imidazol-1-yl)-2-({2-[3-(trifluoromethyl)piperidin-1-yl]-1,3-thiazol-4-yl}methyl)-3,4-dihydro-2H-pyrido[1,2-a]pyrazine-1,6-dione, (3R)-3-Methyl-7-(4-methyl-1H-imidazol-1-yl)-2-{(3R and 3S)-2-oxo-1-[3-(trifluoromethyl)phenyl]pyrrolidin-3-yl}-3,4-dihydro-2H-pyrido[1,2-a]pyrazine-1,6-dione (mixture of diastereomers), (3R)-3-Methyl-7-(4-methyl-1H-imidazol-1-yl)-2-{[(1R or 1S)-1-methyl-6-(trifluoromethyl)-1,3-dihydro-2-benzofuran-1-yl]methyl}-3,4-dihydro-2H-pyrido[1,2-a]pyrazine-1,6-dione, (3R)-3-Methyl-7-(4-methyl-1H-imidazol-1-yl)-2-{[(1S or 1R)-1-methyl-6-(trifluoromethyl)-1,3-dihydro-2-benzofuran-1-yl]methyl}-3,4-dihydro-2H-pyrido[1,2-a]pyrazine-1,6-dione, (3R)-2-[(6-Bromo-2-methyl-3,4-dihydro-2H-chromen-2-yl)methyl]-3-methyl-7-(4-methyl-1H-imidazol-1-yl)-3,4-dihydro-2H-pyrido[1,2-a]pyrazine-1,6-dione, (3R)-3-Methyl-7-(4-methyl-1H-imidazol-1-yl)-2-{[6-(trifluoromethyl)-4,5,6,7-tetrahydro-1-benzothiophen-3-yl]methyl}-3,4-dihydro-2H-pyrido[1,2-a]pyrazine-1,6-dione, (3R)-3-Methyl-7-(4-methyl-1H-imidazol-1-yl)-2-{[5-(trifluoromethyl)-4,5,6,7-tetrahydro-1-benzothiophen-2-yl]methyl}-3,4-dihydro-2H-pyrido[1,2-a]pyrazine-1,6-dione, (3R)-3-Methyl-7-(4-methyl-1H-imidazol-1-yl)-2-{[5-(trifluoromethyl)-4,5,6,7-tetrahydropyrazolo[1,5-a]pyridin-3-yl]methyl}-3,4-dihydro-2H-pyrido[1,2-a]pyrazine-1,6-dione, (3R)-3-Methyl-7-(4-methyl-1H-imidazol-1-yl)-2-{[(5R or 5S)-5-(trifluoromethyl)-4,5,6,7-tetrahydropyrazolo[1,5-a]pyridin-3-yl]methyl}-3,4-dihydro-2H-pyrido-[1,2-a]pyrazine-1,6-dione, (3R)-3-Methyl-7-(4-methyl-1H-imidazol-1-yl)-2-{[(5S or 5R)-5-(trifluoromethyl)-4,5,6,7-tetrahydropyrazolo[1,5-a]pyridin-3-yl]methyl}-3,4-dihydro-2H-pyrido-[1,2-a]pyrazine-1,6-dione, (3R)-3-Methyl-7-(4-methyl-1H-imidazol-1-yl)-2-{[6-(trifluoromethyl)-5,6,7,8-tetrahydro[1,2,4]triazolo[4,3-a]pyridin-3-yl]methyl}-3,4-dihydro-2H-pyrido-[1,2-a]pyrazine-1,6-dione, (3R)-3-Methyl-7-(4-methyl-1H-imidazol-1-yl)-2-{[(6R or 6S)-6-(trifluoromethyl)-5,6,7,8-tetrahydro[1,2,4]triazolo[4,3-a]pyridin-3-yl]methyl}-3,4-dihydro-2H-pyrido[1,2-a]pyrazine-1,6-dione, (3R)-3-Methyl-7-(4-methyl-1H-imidazol-1-yl)-2-{[(6S or 6R)-6-(trifluoromethyl)-5,6,7,8-tetrahydro[1,2,4]triazolo[4,3-a]pyridin-3-yl]methyl}-3,4-dihydro-2H-pyrido[1,2-a]pyrazine-1,6-dione, (3R)-2-[5,7-Bis(trifluoromethyl)-2,3-dihydro-1-benzofuran-3-yl]-3-methyl-7-(4-methyl-1H-imidazol-1-yl)-3,4-dihydro-2H-pyrido[1,2-a]pyrazine-1,6-dione, (3R)-3-Methyl-7-(4-methyl-1H-imidazol-1-yl)-2-{[(6R or 6S)-6-(trifluoromethyl)-4,5,6,7-tetrahydro-1-benzothiophen-3-yl]methyl}-3,4-dihydro-2H-pyrido[1,2-a]-pyrazine-1,6-dione, (3R)-3-Methyl-7-(4-methyl-1H-imidazol-1-yl)-2-{[(6S or 6R)-6-(trifluoromethyl)-4,5,6,7-tetrahydro-1-benzothiophen-3-yl]methyl}-3,4-dihydro-2H-pyrido[1,2-a]-pyrazine-1,6-dione, (3R)-3-Methyl-7-(4-methyl-1H-imidazol-1-yl)-2-{[5-(trifluoromethyl)-4,5,6,7-tetrahydro-1-benzothiophen-3-yl]methyl}-3,4-dihydro-2H-pyrido[1,2-a]pyrazine-1,6-dione, (3R)-3-Methyl-7-(4-methyl-1H-imidazol-1-yl)-2-{[(5R or 5S)-5-(trifluoromethyl)-4,5,6,7-tetrahydro-1-benzothiophen-3-yl]methyl}-3,4-dihydro-2H-pyrido[1,2-a]-pyrazine-1,6-dione, (3R)-3-Methyl-7-(4-methyl-1H-imidazol-1-yl)-2-{[(5S or 5R)-5-(trifluoromethyl)-4,5,6,7-tetrahydro-1-benzothiophen-3-yl]methyl}-3,4-dihydro-2H-pyrido[1,2-a]-pyrazine-1,6-dione, (3R)-3-Methyl-7-(4-methyl-1H-imidazol-1-yl)-2-{2-oxo-2-[3-(trifluoromethyl)-piperidin-1-yl]ethyl}-3,4-dihydro-2H-pyrido[1,2-a]pyrazine-1,6-dione, (3R)-3-Methyl-7-(4-methyl-1H-imidazol-1-yl)-2-{[(5R or 5S)-5-(trifluoromethyl)-4,5,6,7-tetrahydro-1-benzothiophen-2-yl]methyl}-3,4-dihydro-2H-pyrido[1,2-a]-pyrazine-1,6-dione, (3R)-3-Methyl-7-(4-methyl-1H-imidazol-1-yl)-2-{[(5S or 5R)-5-(trifluoromethyl)-4,5,6,7-tetrahydro-1-benzothiophen-2-yl]methyl}-3,4-dihydro-2H-pyrido[1,2-a]-pyrazine-1,6-dione, (3R)-2-[(6-Chloro-3,4-dihydro-2H-chromen-4-yl)methyl]-3-methyl-7-(4-methyl-1H-imidazol-1-yl)-3,4-dihydro-2H-pyrido[1,2-a]pyrazine-1,6-dione, (3R)-2-[(1R or 1S)-1-(5-Chloro-6-fluoro-1-benzofuran-3-yl)ethyl]-3-methyl-7-(4-methyl-1H-imidazol-1-yl)-3,4-dihydro-2H-pyrido[1,2-a]pyrazine-1,6-dione, (3R)-2-[(1S or 1R)-1-(5-Chloro-6-fluoro-1-benzofuran-3-yl)ethyl]-3-methyl-7-(4-methyl-1H-imidazol-1-yl)-3,4-dihydro-2H-pyrido[1,2-a]pyrazine-1,6-dione, (3R)-3-Methyl-7-(4-methyl-1H-imidazol-1-yl)-2-{(1R or 1S)-1-[5-(trifluoromethyl)-1-benzofuran-3-yl]ethyl}-3,4-dihydro-2H-pyrido[1,2-a]pyrazine-1,6-dione, (3R)-3-Methyl-7-(4-methyl-1H-imidazol-1-yl)-2-{(1S or 1R)-1-[5-(trifluoromethyl)-1-benzofuran-3-yl]ethyl}-3,4-dihydro-2H-pyrido[1,2-a]pyrazine-1,6-dione, (3R)-3-Methyl-7-(4-methyl-1H-imidazol-1-yl)-2-{(1R or 1S)-1-[5-(trifluoromethoxy)-1-benzofuran-3-yl]ethyl}-3,4-dihydro-2H-pyrido[1,2-a]pyrazine-1,6-dione, (3R)-3-Methyl-7-(4-methyl-1H-imidazol-1-yl)-2-{(1S or 1R)-1-[5-(trifluoromethoxy)-1-benzofuran-3-yl]ethyl}-3,4-dihydro-2H-pyrido[1,2-a]pyrazine-1,6-dione, (3R)-2-{(1R or 1S)-1-[5-Fluoro-6-(trifluoromethyl)-1-benzofuran-3-yl]ethyl}-3-methyl-7-(4-methyl-1H-imidazol-1-yl)-3,4-dihydro-2H-pyrido[1,2-a]pyrazine-1,6-dione, (3R)-2-{(1S or 1R)-1-[5-Fluoro-6-(trifluoromethyl)-1-benzofuran-3-yl]ethyl}-3-methyl-7-(4-methyl-1H-imidazol-1-yl)-3,4-dihydro-2H-pyrido[1,2-a]pyrazine-1,6-dione, (3R)-3-Methyl-7-(4-methyl-1H-imidazol-1-yl)-2-{(1S)-1-[6-(trifluoromethyl)-1-benzofuran-3-yl]ethyl}-3,4-dihydro-2H-pyrido[1,2-a]pyrazine-1,6-dione, (3R)-2-{(1R or 1S)-1-[6-Fluoro-5-(trifluoromethyl)-1-benzofuran-3-yl]ethyl}-3-methyl-7-(4-methyl-1H-imidazol-1-yl)-3,4-dihydro-2H-pyrido[1,2-a]pyrazine-1,6-dione, (3R)-2-{(1S or 1R)-1-[6-Fluoro-5-(trifluoromethyl)-1-benzofuran-3-yl]ethyl}-3-methyl-7-(4-methyl-1H-imidazol-1-yl)-3,4-dihydro-2H-pyrido[1,2-a]pyrazine-1,6-dione, (3R)-2-[(1R or 1S)-1-(5-Chloro-1-benzofuran-3-yl)ethyl]-3-methyl-7-(4-methyl-1H-imidazol-1-yl)-3,4-dihydro-2H-pyrido[1,2-a]pyrazine-1,6-dione, (3R)-2-[(1S or 1R)-1-(5-Chloro-1-benzofuran-3-yl)ethyl]-3-methyl-7-(4-methyl-1H-imidazol-1-yl)-3,4-dihydro-2H-pyrido[1,2-a]pyrazine-1,6-dione,
(3R)-2-[(1S or 1R)-1-(5-Chloro-7-fluoro-1-benzofuran-3-yl)ethyl]-3-methyl-7-(4-methyl-1H-imidazol-1-yl)-3,4-dihydro-2H-pyrido[1,2-a]pyrazine-1,6-dione,
(3R)-2-[(1R or 1S)-1-(5-Chloro-7-fluoro-1-benzofuran-3-yl)ethyl]-3-methyl-7-(4-methyl-1H-imidazol-1-yl)-3,4-dihydro-2H-pyrido[1,2-a]pyrazine-1,6-dione,
tautomers and stereoisomeric forms thereof,
and the pharmaceutically acceptable addition salts, and the solvates thereof.

In an embodiment the compound of Formula (I) is selected from the group consisting of:
2-[[3-(3-azabicyclo[3.1.0]hex-3-yl)-4-methylphenyl]methyl]-3,4-dihydro-3-methyl-7-(4-methyl-1H-imidazol-1-yl)-2H-pyrido[1,2-a]pyrazine-1,6-dione,
3,4-dihydro-3-methyl-7-(4-methyl-1H-imidazol-1-yl)-2-[2-[3-(trifluoromethyl)-1-piperidinyl]ethyl]-2H-pyrido[1,2-a]pyrazine-1,6-dione,
3,4-dihydro-2-[1-[3-hydroxy-5-(trifluoromethyl)phenyl]ethyl]-3-methyl-7-(4-methyl-1H-imidazol-1-yl)-2H-pyrido[1,2-a]pyrazine-1,6-dione,
2-[1-[3-(cyclopropyloxy)-5-(trifluoromethyl)phenyl]ethyl]-3,4-dihydro-3-methyl-7-(4-methyl-1H-imidazol-1-yl)-2H-pyrido[1,2-a]pyrazine-1,6-dione,
3,4-dihydro-2-[1-[3-hydroxy-4-(trifluoromethoxy)phenyl]ethyl]-3-methyl-7-(4-methyl-1H-imidazol-1-yl)-2H-pyrido[1,2-a]pyrazine-1,6-dione,
3,4-dihydro-3-methyl-7-(4-methyl-1H-imidazol-1-yl)-2-[[2-[3-(trifluoromethyl)-1-piperidinyl]-4-thiazolyl]methyl]-2H-pyrido[1,2-a]pyrazine-1,6-dione,
3,4-dihydro-3-methyl-7-(4-methyl-1H-imidazol-1-yl)-2-[2-oxo-1-[3-(trifluoro-methyl)phenyl]-3-pyrrolidinyl]-2H-pyrido[1,2-a]pyrazine-1,6-dione,
2-[[1,3-dihydro-1-methyl-6-(trifluoromethyl)-1-isobenzofuranyl]methyl]-3,4-dihydro-3-methyl-7-(4-methyl-1H-imidazol-1-yl)-2H-pyrido[1,2-a]pyrazine-1,6-dione,
2-[(6-bromo-3,4-dihydro-2-methyl-2H-1-benzopyran-2-yl)methyl]-3,4-dihydro-3-methyl-7-(4-methyl-1H-imidazol-1-yl)-2H-pyrido[1,2-a]pyrazine-1,6-dione,
3,4-dihydro-3-methyl-7-(4-methyl-1H-imidazol-1-yl)-2-[[4,5,6,7-tetrahydro-6-(trifluoromethyl)benzo[b]thien-3-yl]methyl]-2H-pyrido[1,2-a]pyrazine-1,6-dione,
3,4-dihydro-3-methyl-7-(4-methyl-1H-imidazol-1-yl)-2-[[4,5,6,7-tetrahydro-5-(trifluoromethyl)benzo[b]thien-2-yl]methyl]-2H-pyrido[1,2-a]pyrazine-1,6-dione,
3,4-dihydro-3-methyl-7-(4-methyl-1H-imidazol-1-yl)-2-[[4,5,6,7-tetrahydro-5-(trifluoromethyl)pyrazolo[1,5-a]pyridin-3-yl]methyl]-2H-pyrido[1,2-a]pyrazine-1,6-dione,
3,4-dihydro-3-methyl-7-(4-methyl-1H-imidazol-1-yl)-2-[[5,6,7,8-tetrahydro-6-(trifluoromethyl)-1,2,4-triazolo[4,3-a]pyridin-3-yl]methyl]-2H-pyrido[1,2-a]pyrazine-1,6-dione,
2-[2,3-dihydro-5,7-bis(trifluoromethyl)-3-benzofuranyl]-3,4-dihydro-3-methyl-7-(4-methyl-1H-imidazol-1-yl)-2H-pyrido[1,2-a]pyrazine-1,6-dione,
3,4-dihydro-3-methyl-7-(4-methyl-1H-imidazol-1-yl)-2-[[4,5,6,7-tetrahydro-5-(trifluoromethyl)benzo[b]thien-3-yl]methyl]-2H-pyrido[1,2-a]pyrazine-1,6-dione,
tautomers and stereoisomeric forms thereof,
and the pharmaceutically acceptable addition salts, and the solvates thereof.

All possible combinations of the above-indicated interesting embodiments are considered to be embraced within the scope of this invention.

Preparation of the Compounds

The present invention also encompasses processes for the preparation of compounds of Formula (I), intermediates and subgroups thereof. The person skilled in the art will notice that in the reactions described, it can be necessary to protect reactive functional groups, for example hydroxy, amino, or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1999.

Alternatively, in the presence of reactive functional groups, the person skilled in the art may consider tuning the general reaction conditions on the basis of standard chemistry knowledge, to avoid undesired side reactions.

When several methods are described to obtain the same structure, the choice of a method over another one may also minimize unwanted side reactions.

The compounds of Formula (I) and the subgroups thereof can be prepared by a succession of steps as described hereunder. They are generally prepared from starting materials which are either commercially available or prepared by standard means obvious to those skilled in the art. The compounds of the present invention can be also prepared using standard synthetic processes commonly used by those skilled in the art of organic chemistry.

The skilled person will realize that in some reactions microwave heating may be used instead of conventional heating to shorten the overall reaction time.

The general preparation of some typical examples is shown below. All the variables are defined as described in the scope of the invention unless otherwise mentioned or unless a context dictates otherwise. In the following examples, $R^{1a}$ is phenyl, p-methoxyphenyl, $Ar^1$ or $Ar^2$, unless otherwise mentioned or unless a context dictates otherwise.

Experimental Procedures—Scheme 1

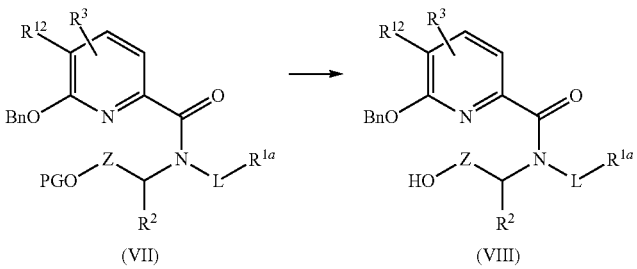

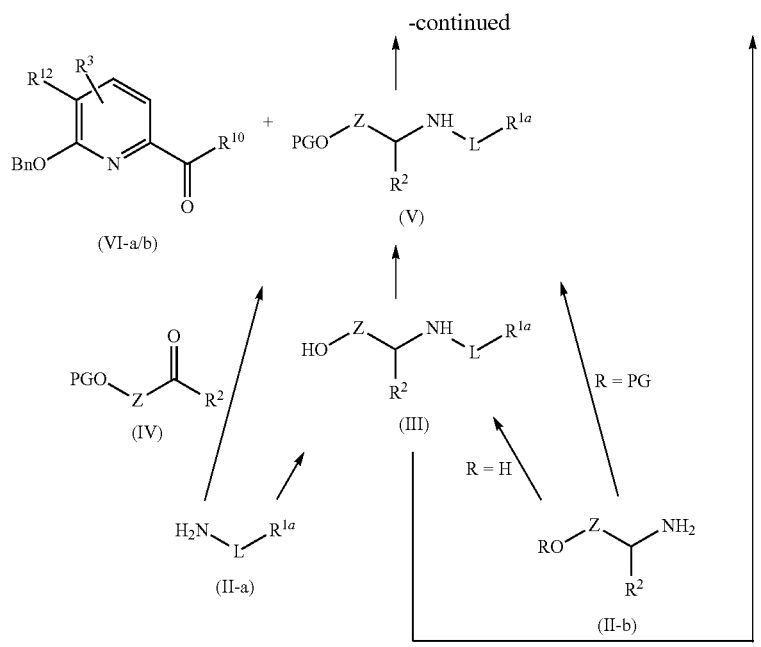

Experimental Procedure 1

An intermediate of formula (III), wherein all the variables are defined as described in the scope of the invention, can be prepared via nucleophilic substitution by an intermediate of formula (II-a) on an appropriate electrophile, such as for example an alkyl halide, such as for example an alkyl iodide, with methods known to the person skilled in the art, such as for example refluxing the mixture of nucleophile and electrophile in the presence or absence of solvent. Inert atmosphere may enhance the reaction outcome.

Alternatively, intermediate (III) can be obtained by reductive amination, starting from the appropriate aminoalcohol (II-b), in the presence of the desired carbonyl compound, such as for example a ketone or an aldehyde. The reaction can be typically performed in the presence of a suitable solvent, such as MeOH (methanol) and a reducing agent, such as $NaBH_4$ (sodium borohydride) or $NaCNBH_3$ (sodium cyanoborohydride). Pre-stirring of the mixture in the absence of the reducing agent under heating, and subsequent addition of the reducing agent at lower temperature, can enhance the reaction outcome.

Alternatively, intermediate (III) can be obtained by manipulation of any suitable precursor by methods known to the person skilled in the art, such as reduction of the corresponding α-aminoacid, for example by using borane-methyl sulphide in the presence of a suitable solvent, such as THF (tetrahydrofuran). Precooling of the reaction mixture, followed by heating after the addition of all the reagents, may enhance the reaction outcome.

Experimental Procedure 2

An intermediate of formula (V), wherein all the variables are defined as described in the scope of the invention, can be obtained via protection of the alcohol functionality of intermediate (III). The protection can be for example a silylation, that can be performed in the presence of a suitable solvent, such as DCM (dichloromethane), an additive, such as imidazole, and a silylating agent, such as TBSCl (tert-butyldimethylsilyl chloride) or TMSCl (trimethylsilyl chloride), following standard conditions known to the person skilled in the art.

Alternatively, intermediate (V) can be obtained by reductive amination of an appropriate amine (II-a) with a carbonyl intermediate such as (IV), where for example PG (the protecting group) can be tert-butyldimethylsilyl. Typical conditions involve stirring of the reagents in a suitable solvent, such as DCE (1,2-dichloroethane), in the presence of a reducing agent, such as $NaBH(OAc)_3$ (sodium triacetoxyborohydride). The person skilled in the art will notice that intermediate (V) can also be obtained via standard reductive amination conditions, starting from an intermediate of structure (II-b), where R is the desired protecting group (PG).

Experimental Procedure 3

An intermediate of formula (VII), wherein
PG is a protecting group;
and all the other variables are defined as described in the scope of the invention, can be obtained via acylation of intermediate (V) with an intermediate of structure (VI), where
$R^{12}$ is hydrogen or bromine;
$R^{10}$ is hydroxyl or chlorine.

Structure (VI) is hereby named (VI-a) when $R^{10}$ is hydroxyl, and (VI-b) when $R^{10}$ is a chlorine. Acylation using intermediate (VI-a) can be performed for example under classical peptide synthesis conditions. Typically, the reaction requests stirring of the starting materials (V) and (VI-a) in the presence of a base, such as DIPEA (diisopropylethyl amine) and a peptide coupling reagent, such as HBTU (O-benzotriazole-N,N,N',N'-tetramethyl-uronium-hexafluoro-phosphate), in a suitable solvent, such as DMF (N,N-dimethyl formamide).

Alternatively, acylation can be achieved by reacting intermediate (V) with an intermediate of formula (VI-b). The reaction can be performed for example by stirring the starting materials in the presence of a base, such as DIPEA, in a suitable solvent, such as DMF.

Experimental Procedure 4

An intermediate of formula (VIII), wherein R$^{12}$ is hydrogen or bromine; and all the other variables are defined as described in the scope of the invention, can be obtained by deprotection of intermediate (VII), by methods known to the person skilled in the art. In the case of a silyl protecting group, for example, one standard method would be treating intermediate (VII), dissolved in a suitable solvent, such as THF, with a fluoride source, such as TBAF (tetrabutylammonium fluoride).

Alternatively, an intermediate of formula (VIII) can be obtained by direct acylation of a suitable aminoalcohol of structure (III) with an acid of structure (VI-a). The reaction can be performed for example under peptide coupling conditions, in the presence of a base, such as DIPEA, and a peptide coupling reagent, such as HBTU, in a suitable solvent, such as DMF.

Experimental Procedures—Scheme 2

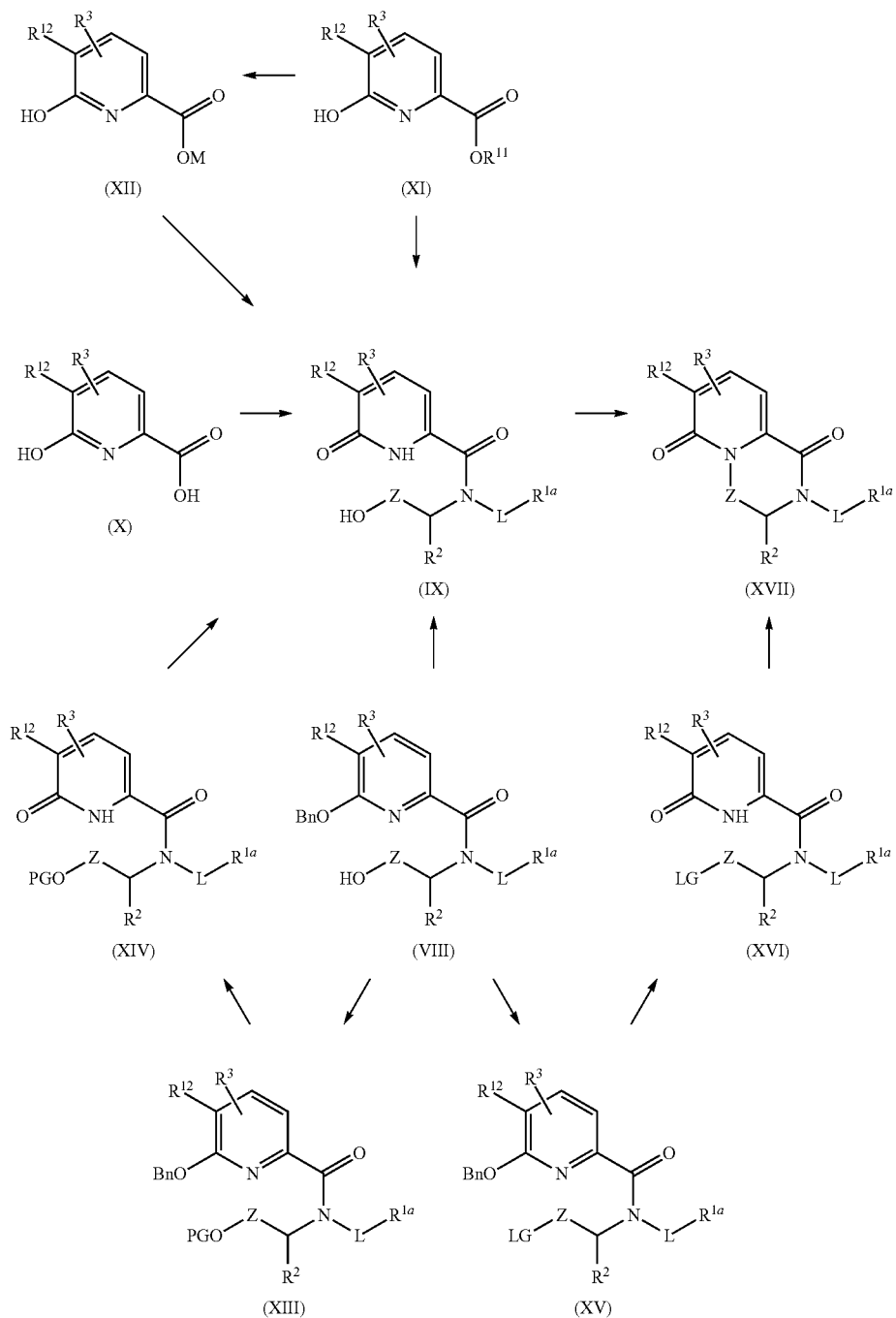

Experimental Procedure 5

An intermediate of formula (IX), wherein
$R^{12}$ is hydrogen or bromine;
and all the other variables are defined as described in the scope of the invention, can be obtained by debenzylation of intermediate (VIII), using standard methods known to the person skilled in the art. For example, the benzylation can be achieved by stirring a solution of intermediate (VIII) in a suitable solvent, such as MeOH or MeOH/THF, and in the presence of a hydrogenation catalyst, such as 10% Pd/C (palladium on carbon), under hydrogen atmosphere.

Alternatively, intermediate (IX) can be obtained by amide synthesis starting from a suitable ester, such as intermediate (XI), where $R^{11}$ is for example a methyl group. Typical conditions involve stirring a solution of the ester in a suitable solvent, such as MeOH, in the presence of a desired aminoalcohol of structure (III) under reflux. Alternatively, starting as well from intermediate (XI), intermediate (IX) can be obtained by using a 2-step method. First, ester (XI) can be saponified to give intermediate (XII), where M is a metal. The reaction can be performed for example by adding an hydroxide, such as LiOH (lithium hydroxide), to a solution of ester (XI) in a suitable polar solvent or in a mixture of miscible solvents of which one is highly polar, such as THF and water. Heating the reaction mixture can enhance the reaction outcome. In the second step, intermediate (XII) can be reacted with an aminoalcohol of structure (III), to afford intermediate (IX). Typically, peptide coupling conditions can be applied, such as stirring the starting material, dissolved in a suitable solvent, such as DMF, in the presence of a peptide coupling agent, such as HBTU. The skilled in the art will appreciate that when a base, such as DIPEA, is present in the mixture, the reaction affords directly the cyclised intermediate (XVII). Heating the reaction mixture can enhance the reaction outcome.

Alternatively, intermediate (IX) can be obtained starting from acid (X), using for example standard peptide coupling conditions, such as stirring intermediate (X) and the desired aminoalcohol (III), dissolved in a suitable solvent, such as DMF, in the presence of a peptide coupling reagent, such as HBTU.

Alternatively, intermediate (IX) can be obtained by using a 3-step synthesis starting from intermediate (VIII). First, the free alcohol functionality can be protected using standard protection methods, such as for example acylation to the ester. Typical conditions would be for example treating intermediate (VIII) with a suitable acylating agent, such as a combination of acetic anhydride and DMAP (dimethylaminopyridine), in the presence of a base, such as $Et_3N$ (triethylamine) in a suitable inert solvent, such as DCM. The so obtained intermediate (XIII) can subsequently undergo debenzylation using standard deprotection methods, such as stirring in a suitable solvent, such as MeOH, under hydrogen atmosphere in the presence of a hydrogenation catalyst, such as 10% Pd/C. Pyridone intermediate (XIV) can be finally converted into intermediate (IX) by using one of the available deprotection methods for the chosen protecting group. In the case of protection of the alcohol as an ester, saponification using a base, such as NaOH (sodium hydroxide) in a suitable solvent, such as MeOH, can afford the desired free alcohol (IX). The skilled in the art will recognize that this method is valuable when the alcohol functionality present in intermediate (VIII) could be liable under debenzylation conditions.

Experimental Procedure 6

An intermediate of formula (XVII), wherein
$R^{12}$ is hydrogen or bromine;
and all the other variables are defined as described in the scope of the invention, can be obtained via intramolecular cyclization, for example by applying Mitsunobu conditions to intermediate (IX). The reaction can be performed by treating a solution of intermediate (IX) in a suitable inert and dry solvent, such as THF, with an azadicarboxylate species, such as DIAD (diisopropyl azodicarboxylate), in the presence of a phosphine, such as triphenylphosphine, under inert atmosphere. Precooling of the solution may be used.

Alternatively, starting from intermediate (VIII) a 3-step method can be used. First, the free hydroxyl function in intermediate (VIII) can be converted into a suitable leaving group. For example, intermediate (XV-a), where LG=chlorine, can be obtained under mild conditions by dissolving intermediate (VIII) in a suitable solvent, such as DCM, and treating it with a chlorinating agent, such as thionyl chloride. Precooling of the solution before addition of the chlorinating agent can enhance the outcome of the reaction. Intermediate (XV) can then undergo debenzylation to give intermediate (XVI), using standard methods compatible with the presence of the leaving group. In the case of intermediate (XV-a), for example, debenzylation can be achieved by treating the intermediate, dissolved in a suitable and inert solvent, such as DCM, with a Lewis acid such as $BBr_3$ (boron tribromide). Precooling of the reaction mixture before addition of the Lewis acid can enhance the reaction outcome. Finally, intermediate (XVI) can be processed to intermediate (XVII) by using standard substitution conditions. For example, starting from intermediate (XVI-a), where LG=chlorine, the ring closure can be achieved by treating the substrate, dissolved in a suitable solvent, such as DMF, with a base, such as NaH (sodium hydride). Precooling of the reaction and a level of dilution high enough to avoid intermolecular reactions can enhance the reaction outcome.

Experimental Procedures—Scheme 3

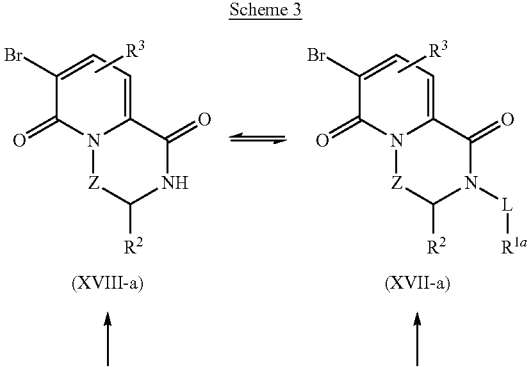

Scheme 3

(XVIII-a)     (XVII-a)

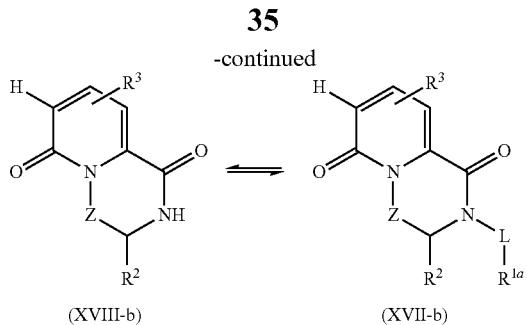

(XVIII-b)  (XVII-b)

Experimental Procedure 7

An intermediate of formula (XVIII-b), wherein all the variables are defined as described in the scope of the invention, can be obtained from an intermediate of structure (XVII-b), where all the variables are defined as mentioned hereabove, with the exception of the residual -L-$R^{1a}$, defined for structure (XVII-b) as any kind of protecting group suitable for an amidic nitrogen, such as, but not restricted to, a benzyl group (L=$CH_2$, $R^{1a}$=phenyl) or a PMB group (p-methoxybenzyl, L=$CH_2$, $R^{1a}$=p-methoxyphenyl).

Intermediate (XVII-b) can be converted into intermediate (XVIII-b) by means of deprotection methods known to the person skilled in the art. For example, when L=$CH_2$, $R^{1a}$=phenyl, deprotection can be achieved by treating intermediate (XVII-b), dissolved in a suitable solvent, such as dry toluene, with a strong acid, such as TfOH (trifluoromethansulfonic acid). Heating the reaction mixture under stirring can enhance the reaction outcome.

Experimental Procedure 8

An intermediate of formula (XVII-b), wherein all the variables are defined as described in the scope of the invention, can be obtained from intermediate (XVIII-b) by means of any manipulation known to the person skilled in the art for the functionalization of an amidic nitrogen. Two general examples are reported:

Example 1

When
$R^{1a}$ is attached to the remainder of the molecule on an aromatic carbon;
L is a covalent bond;
functionalization can be achieved for example by means of a copper catalyzed C—N coupling. Standard conditions, such as stirring a mixture of intermediate (XVIII-b), dissolved in a suitable solvent, such as DMF, in the presence of a base, such as $K_3PO_4$ (potassium phosphate), a ligand, such as N,N-dimethyl-1,2-cyclohexanediamine, an aryl halide and a copper catalyst, such as CuI, could be used. Degassing the reaction mixture with an inert gas, such as $N_2$ or argon, and heating the reaction mixture to high temperatures, such as reflux temperature, may enhance the reaction outcome.

Example 2

When
L is one of the variables described in the scope of the invention, with the exception of L being a covalent bond if $R^{1a}$ is attached to the remainder of the molecule on an aromatic carbon;
functionalization can be achieved for example by treating intermediate (XVIII-b), dissolved in a suitable and inert solvent, such as DMF, with a base, such as NaH, followed by addition of an electrophile. Precooling of the reaction mixture can enhance the reaction outcome.

Experimental Procedure 9

An intermediate of formula (XVIII-a), wherein all the variables are defined as described in the scope of the invention, can be obtained from an intermediate of structure (XVII-a), where all the variables are defined as mentioned hereabove, with the exception of
the residual -L-$R^{1a}$, defined for structure (XVII-a) as any kind of protecting group suitable for an amidic nitrogen, such as, but not restricted to, a benzyl group (L=$CH_2$, $R^{1a}$=phenyl) or a PMB group (p-methoxybenzyl, L=$CH_2$, $R^{1a}$=p-methoxyphenyl).

Intermediate (XVII-a) can be converted into intermediate (XVIII-a) by means of deprotection methods known to the person skilled in the art. For example, when L=$CH_2$, $R^{1a}$=phenyl, deprotection can be achieved by treating intermediate (XVII-a), dissolved in a suitable solvent, such as dry toluene, with a strong acid, such as TfOH. Heating the reaction mixture under stirring can enhance the reaction outcome.

Alternatively, an intermediate of formula (XVIII-a) can be obtained starting from an intermediate of formula (XVIII-b) by means of direct bromination. Different brominating agents can be used. For example, the reaction can be performed by dissolving intermediate (XVIII-b) in a mixture of solvents such as DCM/AcOH (acetic acid) and adding bromine to the mixture, or by adding NBS (N-bromosuccinimide) to a solution of intermediate (XVIII-b) in an appropriate solvent, such as acetonitrile. The reaction mixture may be stirred under heating and inert atmosphere.

Experimental Procedure 10

An intermediate of formula (XVII-a), wherein all the variables are defined as described in the scope of the invention, can be obtained from intermediate (XVIII-a) by means of any manipulation known to the person skilled in the art for the functionalization of an amidic nitrogen. One general example is reported:

Example 1

When
L is one of the variables described in the scope of the invention, with the exception of L being a covalent bond if $R^{1a}$ is attached to the remainder of the molecule on an aromatic carbon;
functionalization can be achieved for example by treating intermediate (XVIII-a), dissolved in a suitable and inert solvent, such as DMF, with a base, such as NaH, followed by an electrophile. Precooling of the reaction mixture can enhance the reaction outcome.

Alternatively, intermediate (XVII-a) can be obtained by direct bromination of intermediate (XVII-b), for example by adding bromine to a solution of intermediate (XVII-b), dissolved in a mixture of solvents such as DCM/AcOH.

Experimental Procedures—Scheme 4

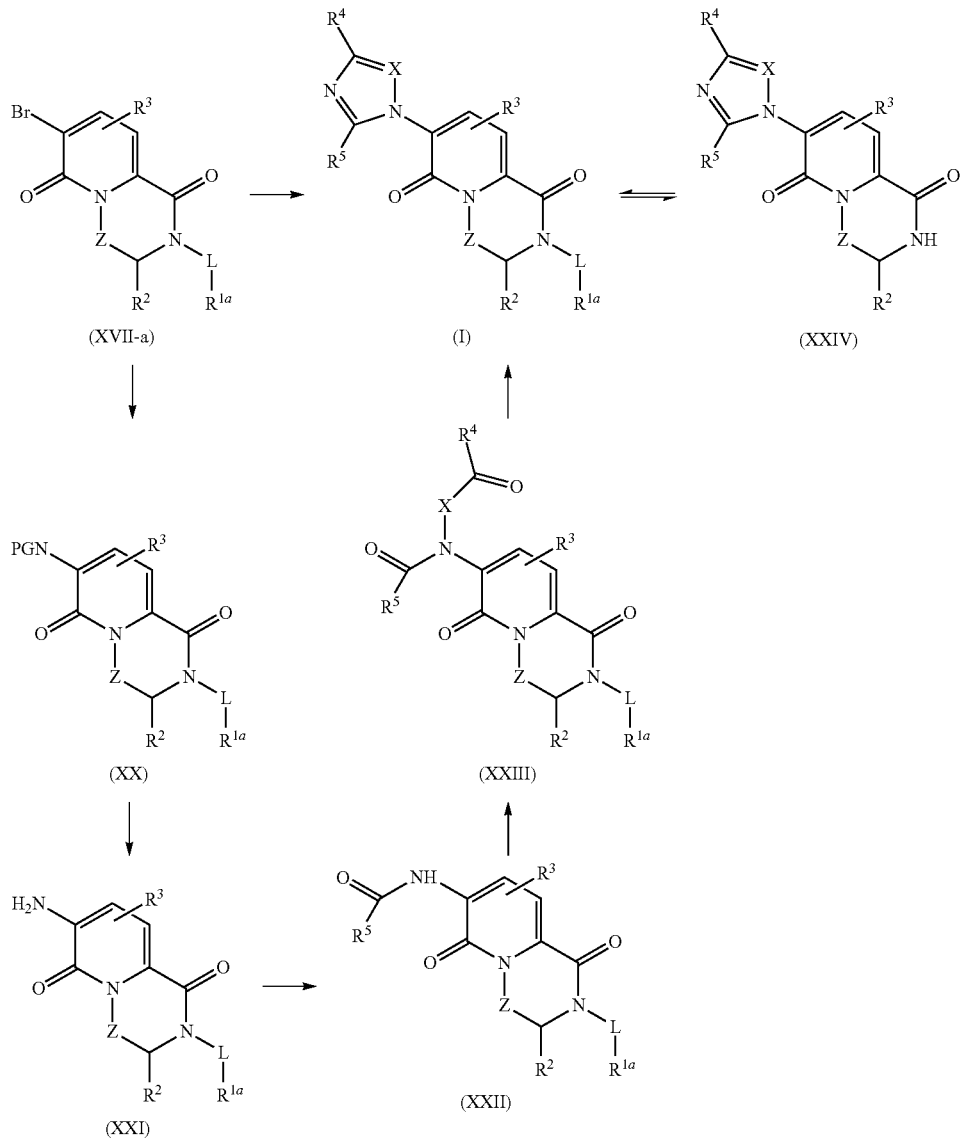

Scheme 4

Experimental Procedure 11

A compound of formula (I), wherein all the variables are defined as described in the scope of the invention, can be obtained for example by copper catalyzed C—N coupling. Standard conditions involve stirring of intermediate (XVII-a) in the presence of a copper catalyst, such as CuI, a base, such as $Cs_2CO_3$ (cesium carbonate), the coupling partner, such as for example 4-methylimidazole, and a ligand, such as N,N-dimethyl-1,2-cyclohexanediamine, in a suitable solvent, such as DMF. Degassing the reaction mixture with an inert gas, such as $N_2$ or argon, and heating the reaction mixture to high temperatures, such as reflux temperature, may enhance the reaction outcome.

Alternatively, a compound of formula (I), where $R^5$ is restricted to hydrogen, can be obtained by palladium catalyzed C—N coupling. Typically, an intermediate of formula (XVII-a) is stirred and heated in the presence of a base, such as $K_3PO_4$, a palladium source, such as $Pd_2(dba)_3$ (tris (dibenzylideneacetone)dipalladium(0)), a ligand, such as 2-di-tert-butylphosphino-3,4,5,6-tetramethyl-2',4',6'-triisopropyl-1,1'-biphenyl and the desired imidazole, in the presence of a solvent or a mixture of solvents, such as toluene/dioxane. Premixing of the catalyst and the ligand followed by heating before addition of the remaining reagents, degassing of the solution and heating can enhance the reaction outcome.

Alternatively, a compound of formula (I) can be obtained via a 5-step synthesis. In the first step, intermediate (XVII-a) can be converted into intermediate (XX), where PG is a mono or divalent nitrogen protecting group. For example, when PG=acetyl, the reaction can be performed using known amide coupling methodologies. For example, acetamide can be reacted with intermediate (XVII-a) in the presence of a base, such as $K_3PO_4$, a palladium source, such as $Pd_2(dba)_3$, a ligand, such as (9,9-dimethyl-9H-xanthene-4,5-diyl)bis[diphenylphosphine] (Xantphos), in a suitable solvent, such as dry THF. Degassing of the reaction mixture during the set-up with an inert gas, such as $N_2$ or argon, anhydrous conditions, and the use of high temperatures, such as reflux temperature, can enhance the reaction outcome. In the second step, intermediate (XX) can be converted into the free amine intermediate (XXI) by using any deprotection method tolerated by the other functionalities present in the molecule. For example, when PG in intermediate (XX)=acetyl, an acidic hydrolysis, using for example HCl (hydrochloric acid), in a suitable solvent, such as MeOH, can be used. In the third step, the amino group in intermediate (XXI) can be acylated to give intermediate (XXII). For example, if $R^5$ in compound (XVII) represents hydrogen, formylation of intermediate (XXI) can be obtained by adding to intermediate (XXI), dissolved in a suitable inert solvent, such as THF, a formylating agent, such as a mixture of acetic anhydride and formic acid. Stirring of the reaction under heating can enhance the reaction outcome. In the fourth step, intermediate (XXII) can be converted to the cyclization precursor (XXIII) with methodologies known to the person skilled in the art and depending on the desired functionalities X and $R^4$. For example, if in compound (XVII) X=CH and $R^4$=alkyl, the reaction can be performed by adding the desired α-haloketone, such as for example 1-bromo-2-butanone, to a mixture of intermediate (XXII), and a base, such as $K_2CO_3$, in a suitable solvent, such as DMF. If the halogen of the α-haloketone is different from iodine, the reaction can be improved by means of an in-situ Filkenstein reaction, performed by adding an iodine salt, such as KI, to the reaction mixture. Finally, intermediate (XXIII) can be converted into compound (I) by means of a classical imidazole synthesis. Diketo precursor (XXIII) can be cyclized into desired compound (I) in the presence of a nitrogen source, such as ammonium acetate, and an acid, such as AcOH. Heating the reaction to reflux temperature can enhance the reaction outcome.

Alternatively, when the residual -L-$R^{1a}$ in compound (I) corresponds to any kind of protecting group suitable for an amidic nitrogen, such as, but not restricted to, a benzyl group (L=$CH_2$, $R^{1a}$=phenyl) or a PMB group (p-methoxybenzyl, L=$CH_2$, $R^{1a}$=p-methoxyphenyl), the compound can be further converted via a two-step method to generate other structures that can be described as well with the general formula (I). In the first step, compound (I) can be converted into intermediate (XXIV) by means of deprotection methods known to the person skilled in the art. For example, when L=$CH_2$, $R^{1a}$=p-methoxyphenyl, deprotection can be achieved by treating compound (I), dissolved in a suitable solvent, such as dry toluene, with a strong acid, such as TfOH. Heating the reaction mixture under stirring can enhance the reaction outcome. In the second step, intermediate (XXIV) can be converted to a compound of general formula (I), by means of known N-functionalization methods.

For example, when
L is one of the variables described in the scope of the invention, with the exception of L being a covalent bond if $R^{1a}$ is attached to the remainder of the molecule on an aromatic carbon;
one possibility would be treating intermediate (XXIV), dissolved in a suitable and inert solvent, such as DMF, with a base, such as NaH, followed by an electrophile.

Precooling of the reaction mixture and anhydrous conditions can enhance the reaction outcome.

Alternatively, intermediate (XVII-a) wherein $R^3$ is restricted to halo (halo=Cl, Br, I), hereby called intermediate (XVII-b), may be obtained starting from intermediate (XVII-a) wherein $R^3$ is restricted to hydrogen, hereby called (XVII-a1), via a halogenation reaction. For example, if halo is Cl in intermediate (XVII-b), the reaction can be performed by treating intermediate (XVII-a1), dissolved in a suitable solvent, such as DMF, with a chlorine source, such as NCS (N-chlorosuccinimide).

Scheme 4a

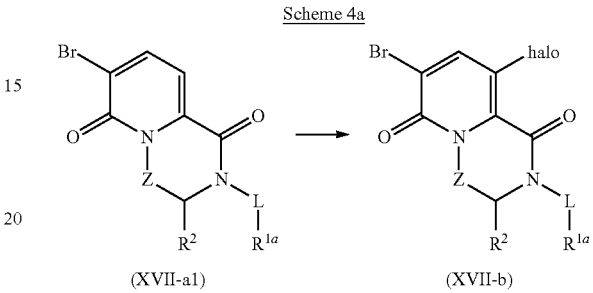

(XVII-a1)        (XVII-b)

Alternatively, a compound of formula (I) bearing an $R^{1a}$ group which can undergo further manipulation, could be converted into other compounds described as well with the general formula (I), by mean of one or several subsequent chemical transformations known to the person skilled in the art. For example, if $R^{1a}$ is an halogenated ring system, the corresponding dehalogenated compound can be obtained by stirring a solution of compound (I) in a suitable solvent, such as MeOH or MeOH/THF, and in the presence of a hydrogenation catalyst, such as 10% Pd/C (palladium on carbon), under hydrogen atmosphere. Heating the reaction mixture or a high pressure of hydrogen can enhance the reaction outcome.

Starting materials can be obtained commercially or can be prepared by those skilled in the art.

Where necessary or desired, any one or more of the following further steps in any order may be performed: Compounds of Formula (I) and any subgroup thereof may be converted into further compounds of Formula (I) and any subgroup thereof, using procedures known in the art.

It will be appreciated by those skilled in the art that in the processes described above the functional groups of intermediate compounds may need to be blocked by protecting groups. In case the functional groups of intermediate compounds were blocked by protecting groups, they can be deprotected after a reaction step.

In all these preparations, the reaction products may be isolated from the reaction medium and, if necessary, further purified according to methodologies generally known in the art such as, for example, extraction, crystallization, trituration and chromatography. In particular, stereoisomers can be isolated chromatographically using a chiral stationary phase such as, for example, Chiralpak® AD (amylose 3,5 dimethyl-phenyl carbamate) or Chiralpak® AS, both purchased from Daicel Chemical Industries, Ltd, in Japan, or by Supercritical Fluid Chromatography (SFC).

The chirally pure forms of the compounds of Formula (I) form a preferred group of compounds. It is therefore that the chirally pure forms of the intermediates and their salt forms are particularly useful in the preparation of chirally pure compounds of Formula (I). Also enantiomeric mixtures of the intermediates are useful in the preparation of compounds of Formula (I) with the corresponding configuration.

Pharmacology

It has been found that the compounds of the present invention modulate the γ-secretase activity. The compounds according to the invention and the pharmaceutically acceptable compositions thereof therefore may be useful in the treatment or prevention of AD, TBI, dementia pugilistica, MCI, senility, dementia, dementia with Lewy bodies, cerebral amyloid angiopathy, multi-infarct dementia, Down's syndrome, dementia associated with Parkinson's disease and dementia associated with beta-amyloid; preferably AD.

The compounds according to the present invention and the pharmaceutically acceptable compositions thereof may be useful in the treatment or prevention of a disease or condition selected from the group consisting of AD, TBI, dementia pugilistica, MCI, senility, dementia, dementia with Lewy bodies, cerebral amyloid angiopathy, multi-infarct dementia, Down's syndrome, dementia associated with Parkinson's disease and dementia associated with beta-amyloid.

A skilled person will be familiar with alternative nomenclatures, nosologies, and classification systems for the diseases or conditions referred to herein. For example, the fifth edition of the Diagnostic & Statistical Manual of Mental Disorders (DSM-5™) of the American Psychiatric Association utilizes terms such as neurocognitive disorders (NCDs) (both major and mild), in particular, neurocognitive disorders due to Alzheimer's disease, due to traumatic brain injury (TBI), due to Lewy body disease, due to Parkinson's disease or to vascular NCD (such as vascular NCD present with multiple infarctions). Such terms may be used as an alternative nomenclature for some of the diseases or conditions referred to herein by the skilled person.

As used herein, the term "modulation of γ-secretase activity" refers to an effect on the processing of APP by the γ-secretase-complex. Preferably it refers to an effect in which the overall rate of processing of APP remains essentially as without the application of said compounds, but in which the relative quantities of the processed products are changed, more preferably in such a way that the amount of the Aß42-peptide produced is reduced. For example a different Abeta species can be produced (e.g. Abeta-38 or other Abeta peptide species of shorter amino acid sequence instead of Abeta-42) or the relative quantities of the products are different (e.g. the ratio of Abeta-40 to Abeta-42 is changed, preferably increased).

It has been previously shown that the γ-secretase complex is also involved in the processing of the Notch-protein. Notch is a signaling protein which plays a crucial role in developmental processes (e.g. reviewed in Schweisguth F (2004) Curr. Biol. 14, R129). With respect to the use of γ-secretase modulators in therapy, it seems particularly advantageous not to interfere with the Notch-processing activity of the γ-secretase activity in order to avoid putative undesired side-effects. While γ-secretase inhibitors show side effects due to concomitant inhibition of Notch processing, γ-secretase modulators may have the advantage of selectively decreasing the production of highly aggregatable and neurotoxic forms of Aβ, i.e. Aβ42, without decreasing the production of smaller, less aggregatable forms of Aβ, i.e. Aβ38 and without concomitant inhibition of Notch processing. Thus, compounds are preferred which do not show an effect on the Notch-processing activity of the γ-secretase-complex.

As used herein, the term "treatment" is intended to refer to all processes, wherein there may be a slowing, interrupting, arresting, or stopping of the progression of a disease, or an alleviation of symptoms, but does not necessarily indicate a total elimination of all symptoms.

The term "subject" as used herein, refers to an animal, preferably a mammal, most preferably a human, who is or has been the object of treatment, observation or experiment.

The invention relates to compounds according to the general Formula (I), and the pharmaceutically acceptable acid or base addition salts and the solvates thereof, for use as a medicament.

The invention also relates to compounds according to the general Formula (I), and the pharmaceutically acceptable acid or base addition salts and the solvates thereof, for use in the modulation of γ-secretase activity.

The invention also relates to compounds according to the general Formula (I), and the pharmaceutically acceptable acid or base addition salts and the solvates thereof, for use in the treatment or prevention of diseases or conditions selected from the group consisting of AD, TBI, dementia pugilistica, MCI, senility, dementia, dementia with Lewy bodies, cerebral amyloid angiopathy, multi-infarct dementia, Down's syndrome, dementia associated with Parkinson's disease and dementia associated with beta-amyloid.

In an embodiment, said disease or condition is preferably AD.

The invention also relates to compounds according to the general Formula (I), and the pharmaceutically acceptable acid or base addition salts and the solvates thereof for use in the treatment or prevention of a disease or condition selected from neurocognitive disorder due to Alzheimer's disease, neurocognitive disorder due to traumatic brain injury, neurocognitive disorder due to Lewy body disease, neurocognitive disorder due to Parkinson's disease or vascular neurocognitive disorder.

The invention also relates to compounds according to the general Formula (I), and the pharmaceutically acceptable acid or base addition salts and the solvates thereof, for use in the treatment of said diseases.

The invention also relates to compounds according to the general Formula (I), and the pharmaceutically acceptable acid or base addition salts and the solvates thereof, for the treatment or prevention of said diseases.

The invention also relates to compounds according to the general formula (I), and the pharmaceutically acceptable acid or base addition salts and the solvates thereof, for the treatment or prevention, in particular treatment, of γ-secretase mediated diseases or conditions.

The invention also relates to the use of compounds according to the general Formula (I), and the pharmaceutically acceptable acid or base addition salts and the solvates thereof, for the manufacture of a medicament.

The invention also relates to the use of compounds according to the general Formula (I), and the pharmaceutically acceptable acid or base addition salts and the solvates thereof, for the manufacture of a medicament for the modulation of γ-secretase activity.

The invention also relates to the use of compounds according to the general Formula (I), and the pharmaceutically acceptable acid or base addition salts and the solvates thereof, for the manufacture of a medicament for the treatment or prevention of any one of the disease conditions mentioned hereinbefore.

The invention also relates to the use of compounds according to the general Formula (I), and the pharmaceutically acceptable acid or base addition salts and the solvates thereof, for the manufacture of a medicament for the treatment of any one of the disease conditions mentioned hereinbefore.

In the invention, particular preference is given to compounds of Formula (I), and the pharmaceutically acceptable acid or base addition salts and the solvates thereof, or any subgroup thereof with a $IC_{50}$ value for the inhibition of the production of Aß42-peptide of less than 1000 nM, preferably less than 100 nM, more preferably less than 50 nM, even more preferably less than 20 nM as determined by a suitable assay, such as the assay used in the Examples below.

The compounds of Formula (I), and the pharmaceutically acceptable acid or base addition salts and the solvates thereof, can be administered to mammals, preferably humans for the treatment or prevention of any one of the diseases mentioned hereinbefore.

In view of the utility of the compounds of Formula (I), and the pharmaceutically acceptable acid or base addition salts and the solvates thereof, there is provided a method of treating a subject, in particular warm-blooded animals, including humans, suffering from or a method of preventing a subject, in particular warm-blooded animals, including humans, to suffer from any one of the diseases mentioned hereinbefore.

Said methods comprise the administration, i.e. the systemic or topical administration, preferably oral administration, of a therapeutically effective amount of a compound of Formula (I), and the pharmaceutically acceptable acid or base addition salts and the solvates thereof, to a subject, in particular warm-blooded animals, including humans.

Therefore, the invention also relates to a method of treating or preventing a disease or condition selected from Alzheimer's disease, traumatic brain injury, mild cognitive impairment, senility, dementia, dementia with Lewy bodies, cerebral amyloid angiopathy, multi-infarct dementia, dementia pugilistica, Down's syndrome, dementia associated with Parkinson's disease and dementia associated with beta-amyloid, comprising administering to a subject in need thereof, a therapeutically effective amount of a compound or a pharmaceutical composition according to the invention.

The invention also relates to a method of treating or preventing a disease or condition selected from neurocognitive disorder due to Alzheimer's disease, neurocognitive disorder due to traumatic brain injury, neurocognitive disorder due to Lewy body disease, neurocognitive disorder due to Parkinson's disease or vascular neurocognitive disorder, comprising administering to a subject in need thereof, a therapeutically effective amount of a compound or a pharmaceutical composition according to the invention.

The present invention also concerns to the use of compounds of Formula (I), and the pharmaceutically acceptable acid or base addition salts and the solvates thereof, for the modulation of γ-secretase activity resulting in a decrease in the relative amount of Aß42-peptides produced.

An advantage of the compounds or a part of the compounds of the present invention may be their enhanced CNS-penetration.

Those of skill in the treatment of such diseases could determine the effective therapeutic daily amount from the test results presented hereinafter. An effective therapeutic daily amount would be from about 0.005 mg/kg to 50 mg/kg, in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, even more preferably from about 0.01 mg/kg to about 1 mg/kg, most preferably from about 0.05 mg/kg to about 1 mg/kg body weight. The amount of a compound according to the present invention, also referred to here as the active ingredient, which is required to achieve a therapeutically effect will of course, vary on case-by-case basis, for example with the particular compound, the route of administration, the age and condition of the recipient, and the particular disorder or disease being treated.

A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

The compounds of the present invention, that can be suitable to treat or prevent Alzheimer's disease or the symptoms thereof, may be administered alone or in combination with one or more additional therapeutic agents. Combination therapy includes administration of a single pharmaceutical dosage formulation which contains a compound of Formula (I), a pharmaceutically acceptable acid or base addition salt, or a solvate thereof, and one or more additional therapeutic agents, as well as administration of the compound of Formula (I), a pharmaceutically acceptable acid or base addition salt, or a solvate thereof, and each additional therapeutic agents in its own separate pharmaceutical dosage formulation. For example, a compound of Formula (I), a pharmaceutically acceptable acid or base addition salt, or a solvate thereof, and a therapeutic agent may be administered to the patient together in a single oral dosage composition such as a tablet or capsule, or each agent may be administered in separate oral dosage formulations.

While it is possible for the active ingredient to be administered alone, it is preferable to present it as a pharmaceutical composition.

Accordingly, the present invention further provides a pharmaceutical composition comprising a pharmaceutically acceptable carrier and, as active ingredient, a therapeutically effective amount of a compound according to Formula (I), a pharmaceutically acceptable acid or base addition salt, or a solvate thereof.

The carrier or diluent must be "acceptable" in the sense of being compatible with the other ingredients of the composition and not deleterious to the recipients thereof.

For ease of administration, the subject compounds may be formulated into various pharmaceutical forms for administration purposes. The compounds according to the invention, in particular the compounds according to Formula (I), and the pharmaceutically acceptable acid or base addition salts and the solvates thereof, or any subgroup or combination thereof may be formulated into various pharmaceutical forms for administration purposes. As appropriate compositions there may be cited all compositions usually employed for systemically administering drugs.

To prepare the pharmaceutical compositions of this invention, an effective amount of the particular compound as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions, for example, may be prepared in which the carrier comprises saline solution, glucose solution or a mixture of saline and glucose solution. Injectable solutions containing a compound of Formula (I), a pharmaceutically acceptable acid or base addition salt, or a solvate thereof, may be formulated in an oil for prolonged action. Appropriate oils for this purpose are, for example, peanut oil, sesame oil, cottonseed oil, corn oil, soybean oil, synthetic glycerol esters of long chain fatty acids and mixtures of these and other oils. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Acid or base addition salts of compounds of Formula (I) due to their increased water solubility over the corresponding base or acid form, are more suitable in the preparation of aqueous compositions.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Since the compounds according to the invention are potent orally administrable compounds, pharmaceutical compositions comprising said compounds for administration orally are especially advantageous.

In order to enhance the solubility and/or the stability of the compounds of Formula (I), pharmaceutically acceptable acid or base addition salts and the solvates thereof, in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the invention in pharmaceutical compositions.

Depending on the mode of administration, the pharmaceutical composition will preferably comprise from 0.05 to 99% by weight, more preferably from 0.1 to 70% by weight, even more preferably from 0.1 to 50% by weight of the compound of Formula (I), a pharmaceutically acceptable acid or base addition salt, or a solvate thereof, and from 1 to 99.95% by weight, more preferably from 30 to 99.9% by weight, even more preferably from 50 to 99.9% by weight of a pharmaceutically acceptable carrier, all percentages being based on the total weight of the composition.

The following examples illustrate the present invention. In case no specific stereochemistry is indicated for a stereocenter of a compound, this means that the compound was obtained as a mixture of the R and the S enantiomers.

EXAMPLES

Hereinafter, the term "NaH" means sodium hydride (60% in mineral oil); "DCM" means dichloromethane; "LiBr" means lithium bromide; "$POCl_3$" means phosphorus oxychloride; "MeOH" means methanol; "sat." means saturated; "LCMS" means Liquid Chromatography/Mass spectrometry; "HPLC" means high-performance liquid chromatography; "sol." means solution; "aq." means aqueous; "r.t." means room temperature; "tBu" means tert-butyl; "AcOH" means acetic acid; "TFA" means trifluoroacetic acid; "m.p." means melting point; "$N_2$" means nitrogen; "RP" means reversed phase; "min" means minute(s); "h" means hour(s); "$Na_2SO_3$" means sodium sulphite; "EtOAc" means ethyl acetate; "$Et_3N$" means triethylamine; "EtOH" means ethanol; "eq." means equivalent; "r.m." means reaction mixture(s); "DIPE" means diisopropyl ether; "THF" means tetrahydrofuran; "DMF" means N,N-dimethyl formamide; 'iPrOH" means 2-propanol; "LDA" means lithium diisopropylamide; "$NH_3$" means ammonia; "SFC" means Supercritical Fluid Chromatography; "TBAF" means tetrabutylammonium fluoride; "OR" means optical rotation; "DIPEA" means diisopropylethylamine; "$NH_4HCO_3$" means ammonium bicarbonate; "$NH_4OAc$" means ammonium acetate; "TfOH" means trifluoromethanesulfonic acid; "v/v" means volume/volume %; "w/v" means weight/volume; "$Cs_2CO_3$" means cesium carbonate; "DIAD" means diisopropyl azodicarboxylate; "DMAP" means 4-dimethylaminopyridine; "HBTU" means O-Benzotriazole-N,N,N',N'-tetramethyluronium-hexafluoro-phosphate; "$CO_2$" means carbon dioxide; "$iPrNH_2$" means isopropylamine; "$Na_2CO_3$" means sodium carbonate; "HCl" means hydrochloric acid; "$K_2CO_3$" means potassium carbonate; "$K_3PO_4$" means potassium phosphate; "$MgSO_4$" means magnesium sulphate; "$Na_2SO_4$" means sodium sulphate; "$NaBH_4$" means sodium borohydride; "$LiAlH_4$" means lithium aluminium hydride; "$Et_2O$" means diethyl ether; "$NaHCO_3$" means sodium hydrogencarbonate; "NaOH" means sodium hydroxide; "$NH_4Cl$" means ammonium chloride; "Pd/C" means palladium on carbon; "Et" means ethyl; "Me" means methyl; "$Pd_2(dba)_3$" means tris(dibenzylideneacetone)dipalladium(0); "Xantphos" means 4,5-Bis(diphenylphosphino)-9,9-dimethylxanthene; "$H_2$" means hydrogen; "TPP" means triphenylphospine; "X-Phos" means 2-dicyclohexylphosphino-2',4',6'-triisopropylbiphenyl; "MsCl" means methansulphonyl chloride; "TLC" means thin layer chromatography, "DDQ" means 2,3-dichloro-5,6-dicyano-1,4-benzoquinone and "DABCO" means 1,4-diazabicyclo[2.2.2]octane.

A. Preparation of the Intermediates

Example A1 a) Preparation of Intermediate 1

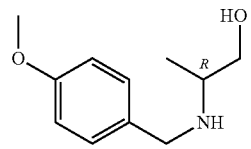

p-Anisaldehyde (7.4 mL, 61 mmol) was dissolved in MeOH (300 mL), then D-alaninol (5.0 g, 66 mmol) and NaHCO$_3$(10.2 g, 121 mmol) were added and the reaction stirred at 80° C. for 2 h. The r.m. was then cooled to 25° C. NaBH$_4$ (2.3 g, 61 mmol) was added portionwise while keeping the temperature below 25° C. The mixture was stirred at 25° C. for 1 additional h, then quenched with 2N HCl (pH=1) and NaHCO$_3$(pH=7-8). MeOH was evaporated in vacuo, then EtOAc was added. The organic layer was separated, dried over MgSO$_4$, filtered and the solvents evaporated in vacuo to yield intermediate 1 as a white solid (quantitative yield; R-enantiomer).

b) Preparation of Intermediate 2

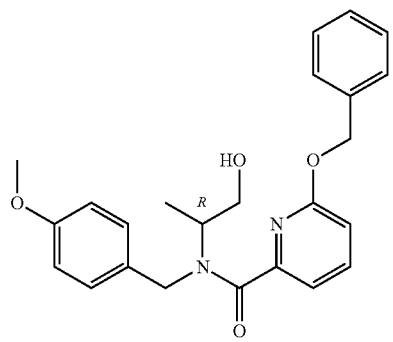

HBTU (2.15 g, 5.67 mmol) was added to a stirred solution of 6-(benzyloxy)pyridine-2-carboxylic acid (1 g, 4.36 mmol), DIPEA (1 mL, 5.68 mmol) and intermediate 1 (0.85 g, 4.36 mmol) in DMF (12 mL). The mixture was stirred at r.t. overnight. Sat. aq. NaHCO$_3$ sol. was added and the mixture was extracted with EtOAc. The combined extracts were dried over MgSO$_4$ and concentrated in vacuo. The crude product was purified by flash column chromatography (silica; hexanes/EtOAc 100/0 to 50/50). The desired fractions were collected and concentrated in vacuo to yield intermediate 2 as an oil (1.51 g, 85%; R-enantiomer).

c) Preparation of Intermediate 3

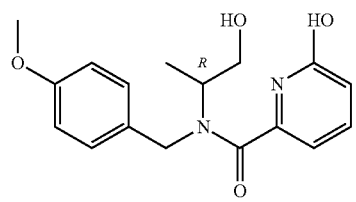

10% Pd/C (0.187 g) was added to a solution of intermediate 2 (1.87 g, 4.60 mmol) in MeOH (20 mL) at 0° C. The mixture was hydrogenated (atmospheric pressure) at r.t. for 6 h. The catalyst was filtered through diatomaceous earth and the solvent evaporated in vacuo to yield a colorless oil. The crude intermediate 3 was used as such in the next reaction step (quantitative yield; R-enantiomer).

d) Preparation of Intermediate 4

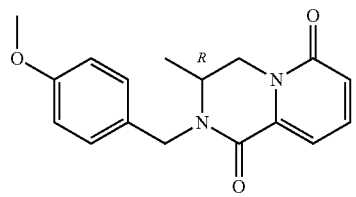

DIAD (1.36 mL, 6.90 mmol) was added to a stirred solution of intermediate 3 (crude material, 4.60 mmol) and TPP (1.8 g, 6.86 mmol) in dry THF (20 mL) under N$_2$. The mixture was stirred at r.t. overnight. The solvents were then evaporated in vacuo. The crude product was purified by flash column chromatography (silica; hexanes/EtOAc 100/0 to 0/100). The desired fractions were collected and concentrated in vacuo to afford intermediate 4 as a white solid (927 mg, 68% over two steps; R-enantiomer).

e) Preparation of Intermediate 5

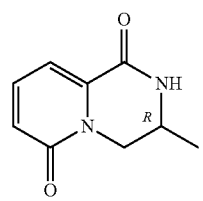

Trifluoromethanesulfonic acid (30 mL) was added dropwise to a warm (50° C.), stirred solution of intermediate 4 (10.5 g, 35 mmol) in TFA (175 mL) and anisole (4 g). After 2 h at this temperature the r.m. was cooled to r.t. and concentrated in vacuo. The dark purple residue was dissolved in acetonitrile (50 mL) and added dropwise to a cooled (−60° C.) sol. of 7 M NH$_3$ in MeOH (250 mL). The brownish suspension was filtered and silica was added to the filtrate. The mixture was concentrated in vacuo and the crude product was purified by column chromatography (silica, DCM/7 N NH$_3$ in MeOH 100/0 to 96/4), to give a brown solid, which was used without further purification in the subsequent reaction (4 g, R-enantiomer).

f) Preparation of Intermediate 6

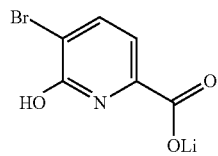

Lithium hydroxide monohydrate (0.766 g, 18.25 mmol) was added portionwise to a stirred solution of methyl 3-bromo-2-hydroxy-6-pyridinecarboxylate (3.85 g, 16.6 mmol) in a mixture of THF (66 mL) and water (17 mL). The mixture was stirred at 60° C. for 24 h and then the solvent was evaporated in vacuo. The crude intermediate 6 was dried in vacuo and used as such in the next reaction step (quantitative yield; R-enantiomer).

g) Preparation of Intermediate 7

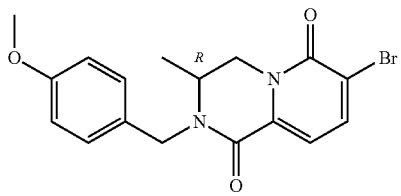

Bromine (0.17 mL, 3.32 mmol) was added dropwise slowly to a stirred solution of intermediate 11 (0.825 g, 2.76 mmol) in DCM/AcOH 4:1 (15 mL) under $N_2$. The mixture was stirred at r.t. overnight, then diluted with aq. sat. $NaHCO_3$ sol. and extracted with DCM. The organic layer was separated, dried over $MgSO_4$, filtered and the solvents evaporated in vacuo. The crude product was purified by flash column chromatography (silica; hexanes/EtOAc 100/0 to 50/50). The desired fractions were collected and concentrated in vacuo to yield intermediate 7 as an oil (530 mg, 51%; R-enantiomer).

g1) Alternative Preparation of Intermediate 7

HBTU (16.2 g, 42.66 mmol) was added portionwise to a stirred solution of intermediate 6 (crude material, 28.44 mmol), intermediate 1 (5.55 g, 28.44 mmol) and DIPEA (7.3 mL, 42 mmol) in DMF (24 mL). The mixture was stirred at r.t. for 14 h, then 0.5 additional eq. of HBTU and DIPEA were added. The mixture was stirred at r.t. for 4 h, then poured into aq. sat. $NaHCO_3$ sol. and extracted with EtOAc. The organic layer was separated, dried over $MgSO_4$, filtered and the solvents evaporated in vacuo. The crude product was purified by flash column chromatography (silica; EtOAc/ heptanes 0/100 to 50/50). The desired fractions were collected and concentrated in vacuo to yield intermediate 7 as an oil (7.03 g, 65% over two steps; R-enantiomer).

h) Preparation of Intermediate 8

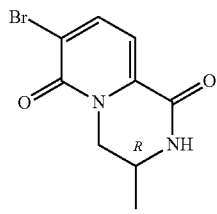

Trifluoromethanesulfonic acid (0.5 mL, 5.62 mmol) was added to a stirred solution of intermediate 7 (0.53 g, 1.4 mmol) in toluene (5 mL). The mixture was stirred at reflux for 2 h, then diluted with 1M NaOH to pH=8 and the solvents evaporated in vacuo. The crude product was purified by flash column chromatography (silica; DCM/EtOAc 100/0 to 0/100). The desired fractions were collected and concentrated in vacuo to yield intermediate 8 as a solid (0.297 g, quantitative yield, R-enantiomer).

h1) Alternative Preparation of Intermediate 8

To a stirred and ice-cooled mixture of intermediate 5 (4 g, 22.4 mmol) in DCM (50 mL) and AcOH (10 mL) was added dropwise bromine (1.6 mL, 31.4 mmol) in DCM (2.5 mL). After stirring for 4 h at r.t. the r.m. was diluted with DCM (200 mL) and successively treated with 20% $Na_2SO_3$ sol. until a colorless r.m. was obtained, and then with saturated aq. $NaHCO_3$ sol. until pH neutral. The layers were separated and the organic layer was dried over $MgSO_4$, filtered and concentrated in vacuo to afford an off white solid (4.5 g), which was used without further purification in the subsequent reaction.

Example A2 a) Preparation of Intermediate 9

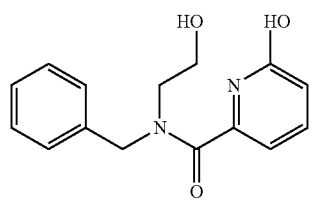 [SMILES: O=C(c1cccc(O)n1)N(CCO)Cc1ccccc1]

N-Benzylethanolamine (26.3 mL, 182.84 mmol) was added to a mixture of methyl 2-hydroxy-6-pyridinecarboxylate (14 g, 91.42 mmol) and MeOH (92 mL). The r.m. was stirred under reflux until completion of the reaction. Then the solvent was evaporated and the crude product purified by flash column chromatography (silica; DCM/MeOH 100/0 to 90/10). The desired fractions were collected and concentrated in vacuo to afford intermediate 9 (23.2 g, 93%).

b) Preparation of Intermediate 10

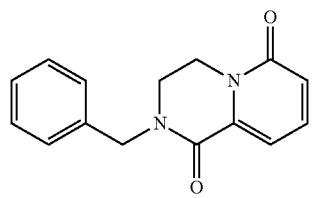 [SMILES: O=C1c2cccc(=O)n2CCN1Cc1ccccc1]

DIAD (19.0 mL, 96.12 mmol) was added to a stirred solution of intermediate 9 (17.45 g, 64.08 mmol) and TPP (25.21 g, 96.12 mmol) in dry THF (193 mL) under $N_2$. The mixture was stirred at r.t. for 2 h. The solvents evaporated in vacuo. The crude product was purified by flash column chromatography (silica; DCM/EtOAc 100/0 to 0/100). The desired fractions were collected and concentrated in vacuo to give intermediate 10 as a white solid (16.294 g, quantitative yield).

c) Preparation of Intermediate 11

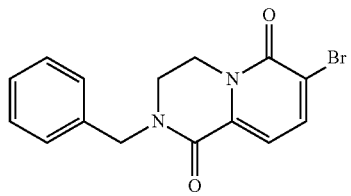 [SMILES: O=C1c2ccc(Br)c(=O)n2CCN1Cc1ccccc1]

Bromine (0.67 mL, 12.96 mmol) was added dropwise slowly to a stirred solution of intermediate 10 (2.75 g, 10.8 mmol) in DCM/AcOH 4:1 (50 mL) under $N_2$. The mixture was stirred at r.t. overnight, then diluted with aq. sat. $NaHCO_3$ sol. and extracted with DCM. The organic layer was separated, dried over $MgSO_4$, filtered and the solvents were evaporated in vacuo. The crude product was purified by flash column chromatography (silica; DCM/EtOAc 100/0 to 80/20). The desired fractions were collected and concentrated in vacuo to yield intermediate 11 as a yellow solid (quantitative yield).

d) Preparation of Intermediate 12

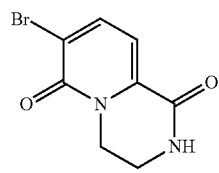

Trifluoromethanesulfonic acid (5.05 g, 15.15 mmol) was added to a stirred solution of intermediate 11 (5.4 mL, 60.6 mmol) in dry toluene (50 mL). The mixture was stirred at reflux for 24 h, then diluted with sat. $NH_3$ and the solvents were evaporated in vacuo.

The crude product was purified by flash column chromatography (silica; DCM/MeOH 100/0 to 94/6). The desired fractions were collected and concentrated in vacuo to yield intermediate 12 as a white solid (quantitative yield).

Example A3 a) Preparation of Intermediate 13

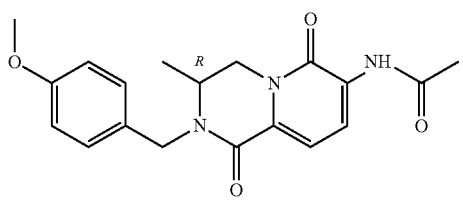

$K_3PO_4$ (0.731 g, 3.44 mmol), $Pd_2(dba)_3$ (63 mg, 0.06 mmol) and Xantphos (69 mg, 0.12 mmol) were added to a stirred solution of intermediate 7 (0.65 g, 1.72 mmol) in dry THF (5 mL) at r.t., while $N_2$ was bubbled through the mixture. After 10 min, acetamide (0.112 g, 1.89 mmol) was added and the mixture was stirred for another 10 min, then stirred for 3 h at 90° C. in a closed vessel. The reaction was then cooled to r.t. and sat. $NaHCO_3$ sol. and EtOAc were added. The phases were separated, the aqueous phase extracted once more with EtOAc, the combined organics were dried over $MgSO_4$, filtered and evaporated. The crude was purified by flash column chromatography (silica; hexanes/EtOAc 100/0 to 10/90). The desired fractions were collected and concentrated in vacuo to yield intermediate 13 as a pale yellow foam (0.335 g, 56%; R-enantiomer).

b) Preparation of Intermediate 14

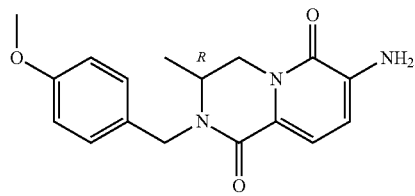

HCl (6N in 2-propanol, 0.5 mL, 2.82 mmol) was added to a solution of intermediate 13 (0.335 g, 0.94 mmol) in MeOH (5 mL) at r.t. and the mixture was stirred overnight. The solvent was then evaporated, sat. $NaHCO_3$ sol. and EtOAc were added, the phases were separated, the aqueous phase was extracted once more and the combined organics were dried over $MgSO_4$, filtered and evaporated. The crude intermediate 14 was used as such in the next reaction step, and the yield considered to be quantitative (R-enantiomer).

c) Preparation of Intermediate 15

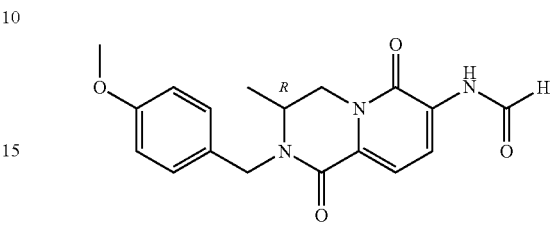

Acetic anhydride (0.34 mL, 3.58 mmol) was added dropwise to formic acid (0.5 mL, 14.13 mmol) at r.t. and stirred for 30 min at the same temperature. To this solution was added dropwise intermediate 14 (crude material, 0.94 mmol) in THF (6 mL). The r.m. was stirred 16 h at 60° C., then water and EtOAc were added. The phases were separated and the aqueous phase was extracted once more. The combined organics were dried over $MgSO_4$, filtered and evaporated. The crude intermediate 15 was used as such in the next reaction step, and the yield considered to be quantitative (R-enantiomer).

d) Preparation of Intermediate 16

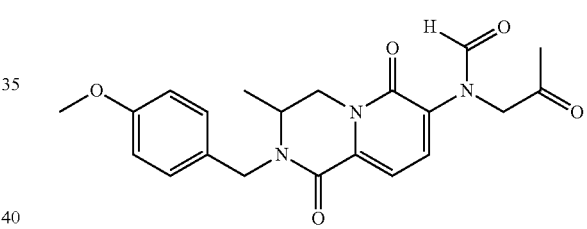

Chloroacetone (0.19 mL, 2.35 mmol) was added dropwise to a stirred suspension of intermediate 15 (crude material, 0.94 mmol), $K_2CO_3$ (0.456 g, 3.29 mmol) and potassium iodide (16 mg, 0.09 mmol) in DMF (3 mL) at r.t. The mixture was stirred for 16 h, then water and EtOAc were added. The phases were separated and the aq. phase was extracted once more. The combined organics were dried over $MgSO_4$, filtered and evaporated. The crude intermediate 16 was used as such to the next reaction step, and the yield considered to be quantitative (R-enantiomer).

e) Preparation of Intermediate 17

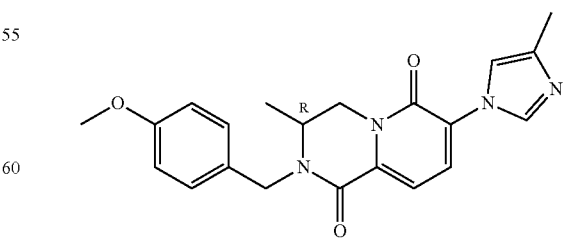

$NH_4OAc$ (0.362 g, 4.70 mmol) was added to a stirred solution of intermediate 16 (crude material, 0.94 mmol) in AcOH (2 mL) and the mixture was stirred for 1 h at reflux. The reaction was then cooled to r.t. and poured into water at 0° C. Aq. 50% NaOH sol. was added slowly until basic pH. The product was extracted with EtOAc (×2). The combined organics were dried over MgSO$_4$, filtered and evaporated. The crude was purified by flash column chromatography (silica; DCM/MeOH 100/0 to 90/10). The desired fractions were collected and concentrated in vacuo to yield intermediate 17 as a sticky brown oil (0.2 g, 57% over 4 steps; R-enantiomer).

f) Preparation of Intermediate 18

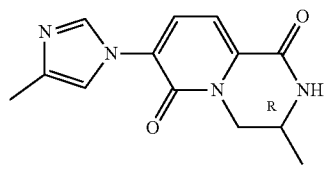

TfOH (0.2 mL, 2.11 mmol) was added to a stirred solution of intermediate 17 (0.2 g, 0.52 mmol) in dry toluene (2.5 mL) at r.t. and the mixture was stirred for 2 h at reflux. The solvent was then evaporated. Aq. 1N NaOH sol. was added until pH 8 and the solvents were evaporated. The crude was triturated with DCM-MeOH (9:1, v/v), dried over MgSO$_4$, filtered and evaporated. The crude intermediate 18 was used as such in the next reaction step, and the yield considered to be quantitative (R-enantiomer).

f1) Alternative Preparation of Intermediate 18

In a first vial equipped with a magnetic stir bar and a screw cap septum, a solution of Pd$_2$(dba)$_3$ (0.055 g, 0.06 mmol) and 2-di-tert-butylphosphino-3,4,5,6-tetramethyl-2',4',6'-triisopropyl-1,1'-biphenyl (0.06 g, 0.125 mmol) in dioxane (1.5 mL) and toluene (7 mL) was flushed with N$_2$ and then stirred at 120° C. for 3 min. A second vial, equipped with a magnetic stir bar and a screw cap septum, was charged with 4-methylimidazole (0.45 g, 5.5 mmol) and K$_3$PO$_4$ (2.12 g, 10 mmol), then with intermediate 8 (1.312 g, 5 mmol) and also flushed with N$_2$. The premixed catalyst solution was added by syringe to the second vial. The r.m. was heated at 120° C. for 5 h. The reaction was cooled to r.t, diluted with DCM, washed with brine and neutralized with NH$_4$Cl. The solvents were evaporated until dryness. The crude was purified by column chromatography (silica; DCM/MeOH 95/5 to 80/20). The fractions were collected to give intermediate 18 (1.33 g, 98%; R-enantiomer).

Example A4 a) Preparation of Intermediate 19

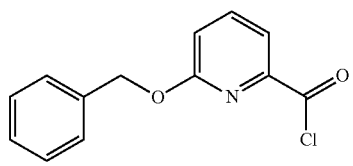 [SMILES: O=C(Cl)c1cccc(OCc2ccccc2)n1]

Thionyl chloride (0.4 mL, 4.86 mmol) was added to a solution of 6-(benzyloxy)-pyridine-2-carboxylic acid (0.724 g, 3.24 mmol) and a drop of DMF in DCM (15 mL). The mixture was stirred at r.t. for 2 h, then the solvent was removed under reduced pressure and the crude intermediate 19 used as such in the next reaction step, and the yield considered to be quantitative.

Example A5 a) Preparation of Intermediate 20

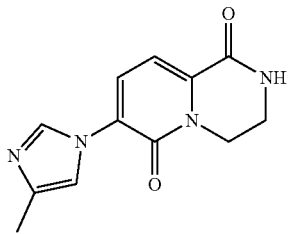 [SMILES: Cc1cn(-c2ccc3n(c2=O)CCNC3=O)cn1]

Intermediate 20 was obtained by following a synthetic procedure similar to the one reported for the synthesis of intermediate 18.

Example A6 a) Preparation of Intermediate 21

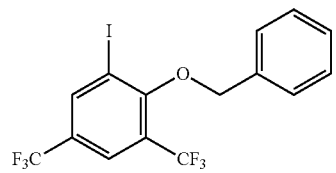 [SMILES: FC(F)(F)c1cc(I)c(OCc2ccccc2)c(C(F)(F)F)c1]

NaH (4.78 g, 119.61 mmol) was added to a stirred solution of benzyl alcohol (13.6 mL, 131.57 mmol) in dry THF (50 mL) at 0° C. After 30 min, this mixture was added to a stirred solution of 2-bromo-1-iodo-3,5-bis(trifluoromethyl)benzene (19.27 g, 23.92 mmol) in dry THF (80 mL). The mixture was stirred at r.t. overnight, then quenched with water and extracted with heptanes. The combined organics were dried over MgSO$_4$, filtered and concentrated in vacuo. The crude material was purified by flash column chromatography (silica; hexane). The desired fractions were collected and concentrated in vacuo to yield intermediate 21 (7.83 g, 73%).

b) Preparation of Intermediate 22

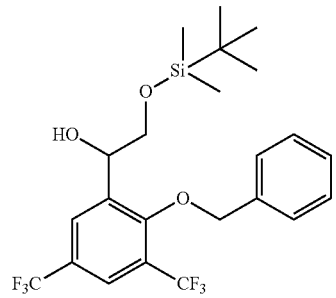 [SMILES: CC(C)(C)[Si](C)(C)OCC(O)c1cc(C(F)(F)F)cc(C(F)(F)F)c1OCc1ccccc1]

Buthyl lithium (2.5 M in hexane, 3.2 mL, 8.07 mmol) was added dropwise to a stirred solution of intermediate 21 (3 g, 6.72 mmol) in dry THF (20 mL) at −78° C. The mixture was stirred for 1 h at the same temperature, then t-butyldimethylsiloxyacetaldehyde (1.4 mL, 7.40 mmol) was added dropwise. The r.m. was stirred for 2 h, then quenched with sat. aq. NH₄Cl sol. and extracted with EtOAc. The combined organics were dried over MgSO₄, filtered and evaporated. The crude material was purified by flash column chromatography (silica; heptanes/DCM 0/100 to 50/50). The desired fractions were collected and concentrated in vacuo to yield intermediate 22 as a yellow oil (1.20 g, 36%, mixture of R and S enantiomers).

c) Preparation of Intermediate 23

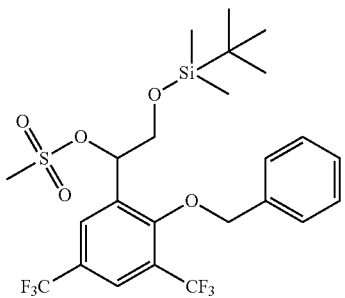 [SMILES: CC(C)(C)[Si](C)(C)OCC(OS(C)(=O)=O)c1cc(C(F)(F)F)cc(C(F)(F)F)c1OCc1ccccc1]

MsCl (0.23 mL, 2.91 mmol) was added dropwise to a stirred solution of intermediate 22 (1.2 g, 2.43 mmol) and DIPEA (0.7 mL, 4.12 mmol) in DCM (25 mL) at 0° C. The mixture was stirred overnight at r.t., then diluted with DCM and washed with sat. aq. NaHCO₃ sol. The organic phase was dried over MgSO₄, filtered and concentrated in vacuo. The crude material was used as such for the subsequent reaction step (1.389 g, quantitative yield; mixture of R and S enantiomers).

d) Preparation of Intermediate 24

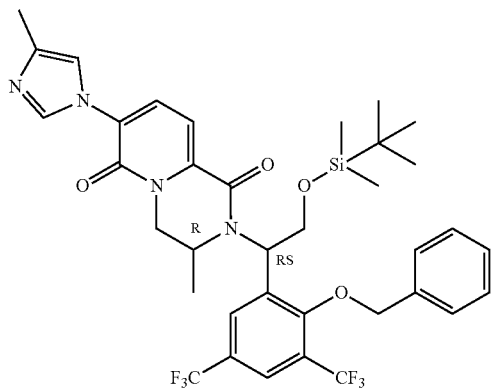

NaH (0.084 mg, 2.10 mmol) was added to a stirred solution of intermediate 18 (0.418 g, 1.62 mmol) and LiBr (0.168 mg, 1.94 mmol) in DMF (15 mL) at 0° C. under N₂ atmosphere. The mixture was stirred for 15 min and then intermediate 23 (1.389 g, crude material) was added dropwise. The r.m. was stirred overnight at r.t. and then 2 h at 50° C. The reaction was quenched with water and extracted with EtOAc. The organic phase was dried over MgSO₄, filtered and concentrated in vacuo. The crude was purified by flash column chromatography (silica; DCM/MeOH 100/0 to 90/10). The desired fractions were collected and concentrated in vacuo to afford intermediate 24 (96 mg, 8%; R, RS).

e) Preparation of Intermediate 25

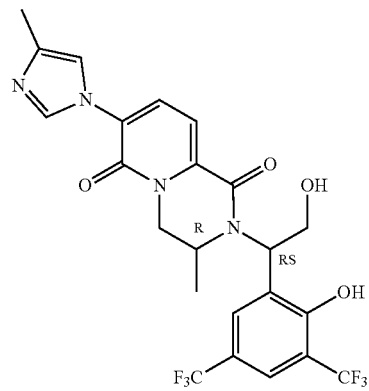

Boron tribromide (0.055 mL, 0.57 mmol) was added portionwise to a stirred solution of intermediate 24 (0.097 mg, 0.132 mmol) in DCM (10 mL) at 0° C. under N₂. The mixture was stirred at r.t. for 1 h, then diluted with aq. sat. NaHCO₃ and extracted with DCM. The organic layer was separated, dried over MgSO₄, filtered and the solvents evaporated in vacuo. The crude material was used as such for the subsequent reaction step (70 mg, quantitative yield; R, RS).

Example A7 a) Preparation of Intermediate 26

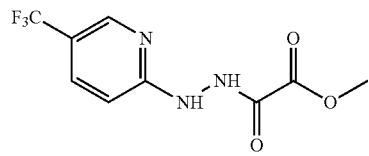 [SMILES: COC(=O)C(=O)NNc1ccc(C(F)(F)F)cn1]

2-Hydrazinyl-5-trifluoromethylpyridine (9.5 g, 53.63 mmol) was stirred in pyridine (261 mL) and DMF (261 mL). Methyl oxalyl chloride (7.885 g, 64.36 mmol) was added at 0° C. The r.m. was stirred for 1 h, then the solvents evaporated and the residue dissolved in DCM/water. The product precipitated and was filtered off and dried, to afford intermediate 26 (9.78 g, 69%).

b) Preparation of Intermediate 27

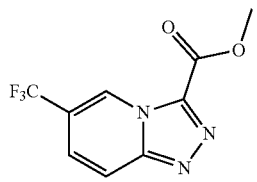

Intermediate 26 (9.78 g, 37.16 mmol) was stirred in POCl₃ (73 mL) and the r.m. was refluxed for 20 h, then allowed to cool down. Ice-water was added carefully at 0° C., then DCM was added until 2 layers were formed without any remaining solids. The mixture was basified with solid NaHCO₃. The organic layer was separated, dried over MgSO₄, filtered and the solvents evaporated in vacuo. The product was purified by flash column chromatography (silica; DCM/MeOH 100/0 to 99/1). The desired fractions were collected and concentrated in vacuo to afford intermediate 27 (2.03 g, 22%).

c) Preparation of Intermediate 28

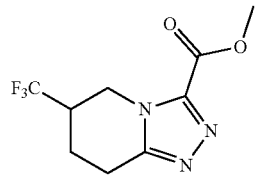 [SMILES: COC(=O)c1nnc2n1CC(C(F)(F)F)CC2]

10% Pd/C (0.43 g), was added to intermediate 27 (1 g, 4.08 mmol) and MeOH (50 mL). The mixture was hydrogenated (20 bar $H_2$) at 50° C. for 20 h. The catalyst was filtered off and the solvent evaporated in vacuo to yield intermediate 28 (1.05 g, used as such in the next step).

d) Preparation of Intermediate 29

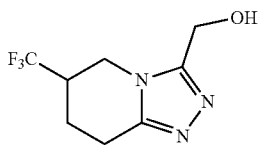 [SMILES: OCc1nnc2n1CC(C(F)(F)F)CC2]

Intermediate 28 (1.05 g, crude material) was stirred in THF (50 mL) and MeOH (50 mL) at r.t. under $N_2$. NaBH$_4$ (0.228 g, 6.02 mmol) was added and the mixture was stirred overnight at r.t., then sat. aq. NH$_4$Cl sol. was added and the solvent evaporated. DCM was added, the mixture dried over MgSO$_4$, filtered and the solvent evaporated in vacuo, to yield intermediate 29 (0.36 g).

e) Preparation of Intermediate 30

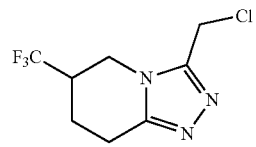 [SMILES: FC(F)(F)C1CCc2nnc(CCl)n2C1]

Intermediate 29 (0.36 g) was stirred in DCM (9 mL) at 0° C. under $N_2$ atmosphere. Thionyl chloride (0.387 g, 3.26 mmol) was added and the mixture was allowed to reach r.t. After TLC control, the mixture was evaporated and co-evaporated with toluene and used as such in the next step (0.39 g).

Example A8 a) Preparation of Intermediate 31

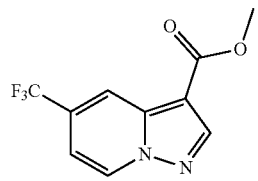 [SMILES: COC(=O)c1cnn2ccc(C(F)(F)F)cc12]

To 4-trifluoromethylpyridine (4.37 g, 29.73 mmol) in DCM (30 mL) at 0° C. was added o-mesitylenesulfonylhydroxylamine (6.40 g, 29.73 mmol) in small portions. The r.m. was stirred at 0° C. for 1 h, then at r.t. for 20 h. Heptane was then added. An oily solid was formed, which was filtered. After filtration, the collected white solid was dissolved in DMF (50 mL), then $K_2CO_3$ (6.16 g, 44.60 mmol) and methyl propiolate (2.50 g, 29.73 mmol) were added. The r.m. was stirred for 20 h at r.t., then filtered and the solvent evaporated in vacuo. The residue was treated with DCM/sat. aq. NaHCO$_3$ sol. The organic layer was separated, washed with 1N HCl sol., dried over MgSO$_4$, filtered and evaporated. The crude was purified by flash column chromatography (silica, heptanes/EtOAc 100/0 to 98/2) to afford intermediate 31 as a white solid (2 g, 28%).

b) Preparation of Intermediate 32

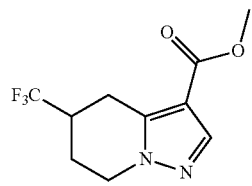 [SMILES: COC(=O)c1cnn2c1CC(C(F)(F)F)CC2]

By following a procedure similar to the one reported for the synthesis of intermediate 28, starting from intermediate 31 intermediate 32 was obtained and used as a crude for the subsequent synthetic step.

c) Preparation of Intermediate 33

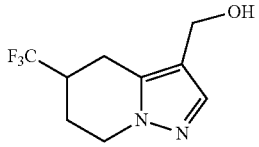 [SMILES: OCc1cnn2c1CC(C(F)(F)F)CC2]

Intermediate 32 (1.4 g, crude material) was dissolved in THF (0.5 mL) under $N_2$ atmosphere. LiAlH$_4$ (1 M in THF, 5.6 mL, 5.64 mmol) was added at r.t. and the r.m.

was stirred for 1 h. The r.m. was then cooled and water was carefully added (10 mL). The solvents were evaporated in vacuo and the residue treated with DCM. MeOH and water. The organic layer was separated, dried over MgSO$_4$, filtered and evaporated, to yield intermediate 33 (0.9 g).

d) Preparation of Intermediate 34

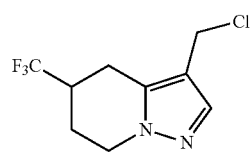 [SMILES: FC(F)(F)C1CCn2ncc(CCl)c2C1]

By following a procedure similar to the one reported for the synthesis of intermediate 30, starting from intermediate 33 intermediate 34 was obtained and used as a crude for the subsequent synthetic step.

Example A9 a) Preparation of Intermediate 35

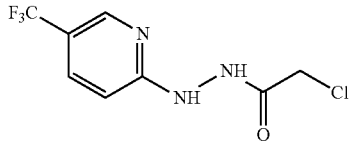 [SMILES: O=C(CCl)NNc1ccc(C(F)(F)F)cn1]

2-Hydrazinyl-5-trifluoromethylpyridine (5 g, 28.23 mmol) was stirred in dry THF (50 mL) and Et$_3$N (2.856 g, 28.23 mmol). Chloroacetyl chloride (3.188 g, 28.23 mmol) was added at 0° C. The r.m. was stirred at 0° C. for 3 h, then ice-water was added and the mixture extracted with DCM. The organic layer was washed with water, dried over MgSO$_4$, filtered and the solvent evaporated to afford intermediate 35 (6.16 g, 86%).

b) Preparation of Intermediate 36

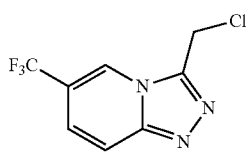 [SMILES: FC(F)(F)c1ccc2nnc(CCl)n2c1]

Intermediate 35 (3 g, 11.83 mmol) and POCl$_3$ (30 mL) were refluxed for 20 h, then the POCl$_3$ was evaporated and the residue was stirred in ice-water. The water layer was brought to pH=6 and the product was extracted with DCM. The organic layer was dried over MgSO$_4$, filtered and evaporated. The product was purified by flash column chromatography (silica; DCM/acetonitrile 98/2 to 90/10). The pure fractions were collected and the solvent was removed in vacuo at 35° C., yielding intermediate 36 (1 g, 36%).

Example A10

Following a procedure similar to the one described for the synthesis of intermediate 30, following intermediates were prepared starting from the commercially available or known corresponding alcohols:

| Structure | Intermediate number |
|---|---|
| 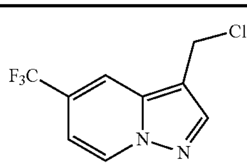 | 37 |
| 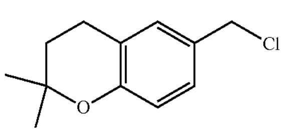 | 38 |

Example A11 a) Preparation of Intermediate 39

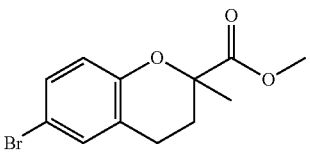 [SMILES: COC(=O)C1(C)CCc2cc(Br)ccc2O1]

6-Bromo-chroman-2-carboxylic acid methyl ester (3.5 g, 12.91 mmol) was dissolved in THF (88 mL) under N$_2$ atmosphere, then the solution was cooled to −72° C. LDA (2 M in THF, 8 mL, 16.14 mmol) was added dropwise, and the r.m. stirred at −70° C. for 1.5 h. Methyl iodide (8 mL, 129.1 mmol) in THF (5 mL) was then added dropwise, and the reaction mixture stirred for 20 h while reaching room temperature. After this time MeOH (10 mL) was added, followed by EtOAc and water. The organic layer was separated, filtered, dried over MgSO$_4$ and the solvent removed in vacuo. The crude was purified by flash column chromatography (silica; heptanes/EtOAc 100/0 to 98/2). The desired fractions were collected and the solvent evaporated to afford intermediate 39 (1.6 g, 43%).

b) Preparation of Intermediate 40

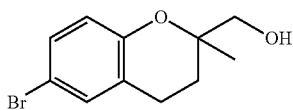

Intermediate 39 (1.6 g, 5.61 mmol) was dissolved in THF (0.5 mL) under N$_2$ atmosphere. Lithium borohydride (2 M in THF, 8.4 mL, 16 mmol) was added dropwise at r.t. and the r.m. stirred for 1 h. Extra lithium borohydride (4 mL) was added and the r.m. stirred for 1 h at r.t., then MeOH was added and the mixture allowed to stir for 5 min. After this time the volatiles were removed in vacuo and the residue was dissolved in DCM/water. The organic layer was separated, dried over MgSO$_4$, filtered and the solvent evaporated. Purification by flash column chromatography (silica; heptanes/EtOAc 100/0 to 98/2) afforded intermediate 40.

c) Preparation of Intermediate 41

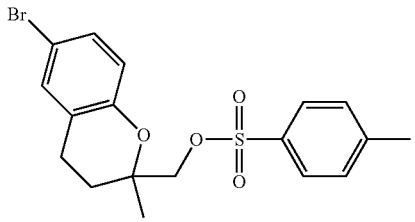 [SMILES: Cc1ccc(S(=O)(=O)OCC2(C)CCc3cc(Br)ccc3O2)cc1]

To a solution of intermediate 40 (0.7 g, 2.72 mmol) in pyridine (20 mL) at 0° C. was added p-toluenesulfonyl chloride (0.571 g, 3 mmol). The reaction mixture was stirred at r.t. overnight, then the solvent was removed in vacuo. Aq. NaHCO$_3$ sol. was added and the product was extracted with DIPE. The organic layer was dried on MgSO$_4$, filtered and evaporated. The product was purified by flash column chromatography (silica; DCM/MeOH from 100/0 to 99/1). The fractions containing the desired product were evaporated, to afford intermediate 41 (0.5 g, 45%).

Example A12 a) Preparation of Intermediates 42 and 43

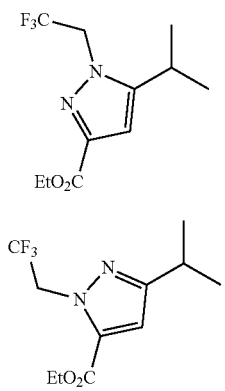

NaH (1.23 g, 31.15 mmol) was dissolved in DMF (200 mL) under N$_2$ atmosphere at 0° C. To this solution was added ethyl 5-isopropylpyrazole-3-carboxylate (5.16 g, 28.33 mmol) in DMF (50 mL) over 10 min at 0° C. After the addition, the r.m. was stirred for 10 min at 0° C. and then at r.t. for 40 min. 2,2,2-Trifluoroethyl trifluoromethanesulfonate (4.5 mL, 31.15 mmol) was subsequently added and the mixture was stirred at r.t. for 3 h. After this time the rm was quenched by addition of EtOH at 0° C. Water was added to the mixture and the water layer was extracted with EtOAc. The organic layer was then washed with brine, dried (MgSO$_4$), filtered and concentrated in vacuo. The resulting crude was purified by flash column chromatography (silica; heptanes/EtOAc 100/0 to 60/40) to afford intermediate 42 (4.05 g, 54%) and regioisomer intermediate 43 (1.52 g, 20%).

b) Preparation of Intermediate 44

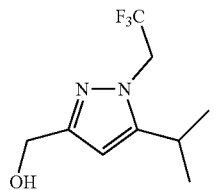

By following a procedure similar to the one reported for the synthesis of intermediate 33, starting from intermediate 42 intermediate 44 was obtained (68%).

c) Preparation of Intermediate 45

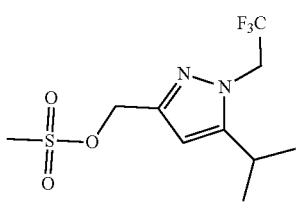 [SMILES: CC(C)c1cc(COS(C)(=O)=O)nn1CC(F)(F)F]

Intermediate 44 (0.86 mg, 3.87 mmol) was dissolved in DCM (25 mL). The solution was cooled down to 0° C. MsCl (0.33 mL, 4.26 mmol) and Et$_3$N (0.6 mL, 4.26 mmol) were added and the r.m. was stirred at r.t. until completion. Water was then added and the organic layer washed with aq. sat. Na$_2$CO$_3$ sol., dried over Na$_2$SO$_4$, filtered and concentrated in vacuo to give a crude, which was used in the subsequent step without further purification.

Example A13 a) Preparation of Intermediate 46

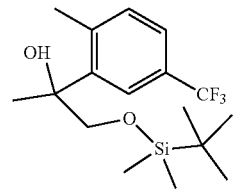 [SMILES: Cc1ccc(C(F)(F)F)cc1C(C)(O)CO[Si](C)(C)C(C)(C)C]

Butyl lithium (1.6 M in hexane, 2.6 mL, 4.18 mmol) was added dropwise to a solution of 2-methyl-5-(trifluoromethyl)bromobenzene (1 g, 4.18 mmol) in Et$_2$O (15 mL) at −78° C. The r.m. was stirred at −78° C. for 20 min and then 1-(tert-butyldimethylsilyloxy)-2-propanone (0.827 g, 4.39 mmol) in Et$_2$O (5 mL) was added and the r.m. was further stirred for 2 h at −78° C. The r.m. was then quenched with water and the product was extracted with EtOAc. The organic layer was dried over MgSO$_4$, filtered and the solvent was removed in vacuo. The crude product was purified by flash column chromatography (silica; heptanes/EtOAc 100/0 to 90/10). The fractions containing the product were collected and concentrated in vacuo to give intermediate 46 (1.036 g, 71%).

b) Preparation of Intermediate 47

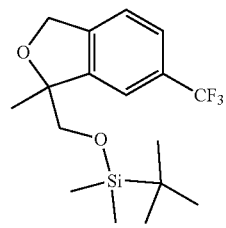 [SMILES: CC1(CO[Si](C)(C)C(C)(C)C)OCc2ccc(C(F)(F)F)cc21]

Intermediate 46 (4.84 g, 13.89 mmol) was stirred in carbon tetrachloride (194 mL). N-bromosuccinimide (2.719 g, 15.28 mmol) and 2,2'-azobis(2-methylpropionitrile) (0.228 g, 1.39 mmol) were added and the mixture was refluxed for 2 h. The reaction mixture was then washed with 1N NaOH sol., dried over MgSO$_4$, filtered and evaporated, yielding intermediate 47, which was used as such in the subsequent reaction step, and the yield considered to be quantitative (4.8 g).

c) Preparation of Intermediate 48

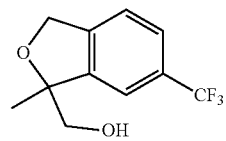

Intermediate 47 (4.8 g, crude material) and a solution of TBAF in THF (40 mL; 1 M) were stirred at r.t. for 2 h. Sat. NH$_4$Cl sol. was added and the product was extracted with EtOAc. The organic layer was washed with water (×2) and once with brine, dried over MgSO$_4$, filtered and evaporated, yielding intermediate 48. The crude material was used as such for the subsequent reaction step, and the yield considered to be quantitative (3.2 g).

d) Preparation of Intermediate 49

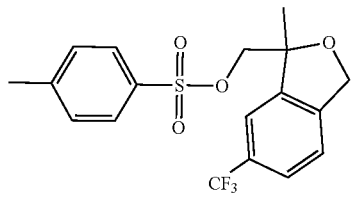 [SMILES: Cc1ccc(S(=O)(=O)OCC2(C)OCc3ccc(C(F)(F)F)cc32)cc1]

By following a procedure similar to the one reported for the synthesis of intermediate 41, starting from intermediate 48 intermediate 49 was obtained.

Example A14 a) Preparation of Intermediate 50

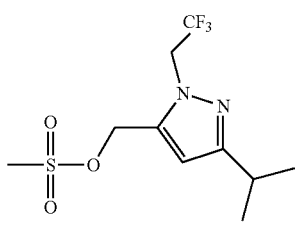 [SMILES: CC(C)c1cc(COS(C)(=O)=O)n(CC(F)(F)F)n1]

By following a procedure similar to the one reported for the synthesis of intermediate 45, starting from intermediate 43 intermediate 50 was obtained.

Example A15 a) Preparation of Intermediates 51 and 52

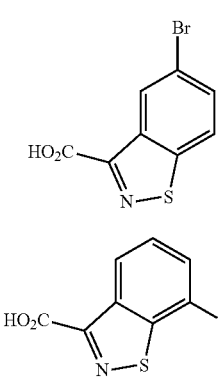

1,2-Benzisothiazole-3-carboxylic acid (4 g, 22.32 mmol) was dissolved in AcOH (64 mL). Nitric acid (19 mL) and sulfuric acid (3.8 mL) were added, followed by bromine (1.7 mL, 33.48 mmol). The reaction mixture was stirred overnight at 70° C., then allowed to reach r.t. The residue was poured into ice-water and the precipitate filtered off. The crude material was used as such for the subsequent step (7.5 g, mixture of intermediates 51 and 52 in a ratio of 17:7 by LC-MS).

b) Preparation of Intermediates 53 and 54

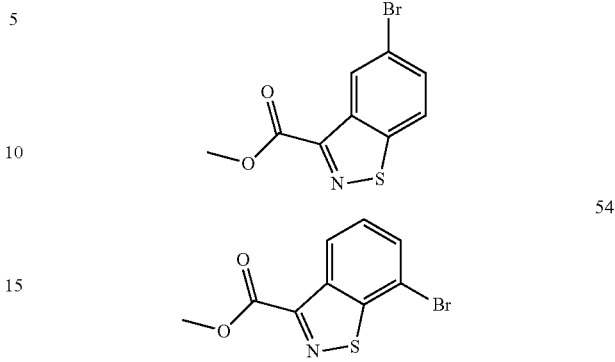

The crude mixture of intermediate 51 and intermediate 52 (5.7 g) was dissolved in MeOH (300 mL). Sulfuric acid (10 mL) was added and the r.m. stirred at 60° C. for 3 h. The solvent was evaporated in vacuo, DCM was added and the mixture cooled with an ice bath. NaHCO$_3$ sat. sol. was added carefully until pH ~8. The organic layer was separated, dried over MgSO$_4$, filtered and the solvent was evaporated in vacuo to afford a mixture of intermediates 53 and 54 in a ratio of 21:11 by LC-MS, which was used as such for the subsequent step (4.4 g).

c) Preparation of Intermediates 55 and 56

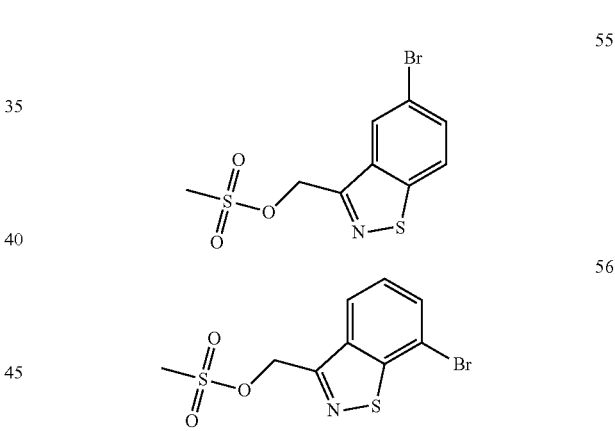

By following a synthetic procedure similar to the one reported for the synthesis of intermediate 40 and intermediate 45, starting from intermediates 53 and 54 intermediates 55 and 56 were obtained.

Example A16 a) Preparation of Intermediate 57

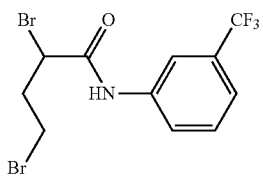 [SMILES: O=C(Nc1cccc(C(F)(F)F)c1)C(Br)CCBr]

Et$_3$N (1.2 mL, 8.87 mmol) and 3-aminobenzotrifluoride (1 mL, 8.07 mmol) in THF (10 mL) were added to 2,4- dibromobutyryl chloride (1.2 mL 9.41 mmol) in THF (10 mL) at 5° C. The r.m. was stirred at r.t. over the weekend, then sat. aq. NH₄Cl sol. was added and the r.m. extracted with EtOAc (×3). The combined organic layers were washed with water (×2) and brine, then dried over MgSO₄, filtered and evaporated to give the crude product as a brown solid, which was used without further purification in the subsequent step (2.92 g).

b) Preparation of Intermediate 58

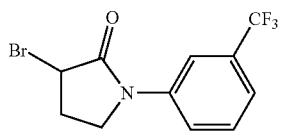 [SMILES: O=C1C(Br)CCN1c1cccc(C(F)(F)F)c1]

NaH (0.39 g, 9.75 mmol) was added portionwise to intermediate 57 (2.92 g, crude material) in THF (60 mL) at r.t. The r.m. was stirred at r.t. for 1 h, then additional NaH (0.075 g, 1.88 mmol) were added. The r.m. was stirred for 1 h, until completion. Water was carefully added, then the mixture extracted with EtOAc (×3). The combined organic layers were washed with brine, dried over MgSO₄ and the solvent was evaporated in vacuo to give an orange oily solid, which was purified by trituration in DIPE, to give intermediate 58 as a white solid (0.64 mg, 28%).

Example A17 a) Preparation of Intermediates 59 and 60

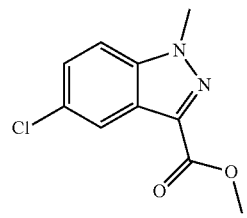

59

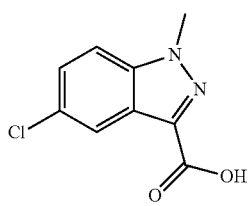

60

5-Chloro-3-indazolecarboxylic acid (1.34 g, 6.82 mmol) was dissolved in dry DMF (50 mL), then the r.m. was cooled to 0° C. under N₂ atmosphere. NaH (0.6 g, 15 mmol) was added in portions, and the r.m. stirred for 20 min at 0° C. Methyl iodide (0.9 mL, 15 mmol) was added dropwise, and the r.m. allowed to reach r.t. and stirred for 4 h. After this time the reaction was quenched with water, adjusted to pH=6 with 1N HCl sol. DCM was added and the organic layer was separated and dried over MgSO₄, filtered and the solvent was evaporated. The crude material showed to be a mixture of intermediate 59 and intermediate 60 (800 mg; LC-MS ratio ester/acid: 34/53), and was subsequently dissolved in MeOH (60 mL). Sulfuric acid (3 mL) was added, and the r.m. was heated at 60° C. for 4 h. The solvent was then evaporated. DCM was added and the reaction mixture was basified with sat.NaHCO₃ sol. The organic layer was separated and dried over MgSO₄, filtered and the solvent evaporated under reduced pressure, to afford intermediate 59 (0.4 g, 26% over two steps).

b) Preparation of Intermediate 61

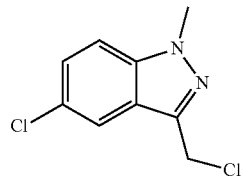

By following a synthetic procedure similar to the one reported for the synthesis of intermediate 34, intermediate 61 was obtained starting from intermediate 59.

Example A18 a) Preparation of Intermediates 62 and 63

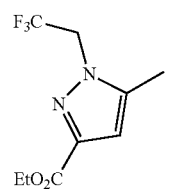

62

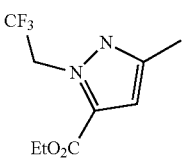

63

By following a synthetic procedure similar to the one reported for the synthesis of intermediates 42 and 43, intermediate 62 and intermediate 63 were obtained starting from ethyl 3-methylpyrazole-5-carboxylate. Intermediate 62 was obtained in 39% yield and intermediate 63 in 36% yield.

b) Preparation of Intermediate 64

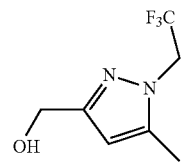

Diisobutylaluminum hydride (1.5 M in toluene, 68 mL, 102.12 mmol) was slowly added to intermediate 62 (8.04 g, 34.04 mmol) in DCM (161 mL) at −78° C. under N₂ atmosphere. After 2 h the reaction was quenched with MeOH and allowed to warm up to r.t., then it was diluted with DCM and treated with an aq. sol. of Rochelle's salt (10%), and the suspension left to stir vigorously for 20 min. The two layers were separated, and the organic layer dried over MgSO₄, filtered and evaporated, to give intermediate 64 (4.98 g, 73%).

c) Preparation of Intermediate 65

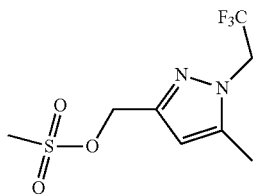 [SMILES: Cc1cc(COS(C)(=O)=O)nn1CC(F)(F)F]

By following a synthetic procedure similar to the one reported for the synthesis of intermediate 45, intermediate 65 was obtained starting from intermediate 64.

Example A19 a) Preparation of Intermediate 66

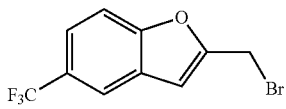

Phosphorus tribromide (0.12 mL, 1.22 mmol) was added to a stirred solution of 5-trifluoromethyl-2-benzofuran-methanol (0.24 g, 1.11 mmol) in DCM (5 mL) at 0° C. The mixture was stirred at 0° C. for 90 min, then it was neutralized with sat. aq. NaHCO$_3$ sol. and extracted with DCM. The organic layer was separated, washed with brine, dried over MgSO$_4$, filtered and the solvent evaporated in vacuo. The crude was purified by flash column chromatography (silica; heptane/EtOAc 100/0 to 75/25) to afford intermediate 66 (106 mg, 34%).

Example A20 a) Preparation of Intermediate 67

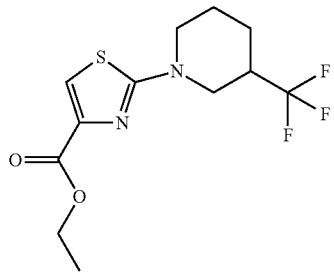 [SMILES: CCOC(=O)c1csc(N2CCCC(C(F)(F)F)C2)n1]

A solution of ethyl 2-bromothiazole-4-carboxylate (1 g, 4.24 mmol), 3-(trifluoro-methyl)piperidine (0.778 g, 5.08 mmol) and K$_2$CO$_3$ (1.463 g, 10.59 mmol) in dimethylacetamide (36 mL) was heated at 160° C. for 6 h, then the solvent was evaporated and the residue was dissolved in EtOAc and washed with water and brine. The organic layer was dried over MgSO$_4$, filtered and concentrated to give a crude product, which was purified by flash column chromatography (silica; heptane/EtOAc 100/0 to 50/50) to give intermediate 67 (0.622 g, 48%).

b) Preparation of Intermediate 68

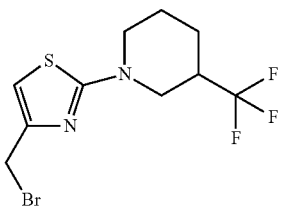 [SMILES: FC(F)(F)C1CCCN(c2nc(CBr)cs2)C1]

By following a synthetic sequence similar to the one reported for the synthesis of intermediate 33 and intermediate 66, intermediate 68 was obtained starting from intermediate 67.

Example A21 a) Preparation of Intermediate 69

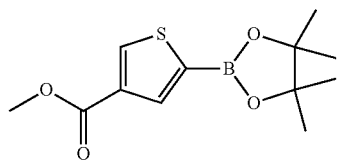

To a mixture of (1,5-cyclooctadiene)(methoxy)iridium(I) dimer (0.264 g, 0.40 mmol) and pinacolborane (4.8 mL, 32.82 mmol) was added 4,4'-di-tert-butyl-2,2'-dipyridyl (218 mg, 0.81 mmol) in hexane (10 mL). N$_2$ was bubbled through the solvent for 5 min, then a solution of methyl 3-thiophenecarboxylate (3.5 g, 24.62 mmol) in hexane (2 mL) was added. The resulting red solution was stirred for 6 h at 22° C. The solvent was then evaporated and the residue purified by flash column chromatography (silica, heptanes/EtOAc 100/0 to 98/2) to afford impure intermediate 69 (6.09 g), which was used without further purification for the subsequent reaction.

b) Preparation of Intermediate 70

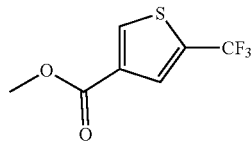

A flask was charged with 3 Å molecular sieves, cesium fluoride (2.606 g, 17.16 mmol), 1,10-phenanthroline (1.7 g, 9.44 mmol), and copper(II) acetate (1.575 g, 8.58 mmol) under N$_2$ and evacuated and backfilled with oxygen. Intermediate 69 (2.3 g) in isobutyronitrile (40 mL) and (trifluoromethyl)trimethylsilane (3.2 mL, 21.44 mmol) were added to the reaction mixture, then a balloon filled with oxygen was placed. After 90 min the mixture was dissolved in EtOAc and washed with water (×3). The organic layer was dried over MgSO$_4$, filtered and concentrated in vacuo to give a crude, which was purified by flash column chromatography (silica; heptane/EtOAc 100/0 to 70/30) to afford intermediate 70 (1 g, 55%).

c) Preparation of Intermediate 71

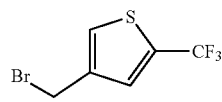

By following a synthetic sequence similar to the one reported for the synthesis of intermediate 68, intermediate 71 was obtained starting from intermediate 70.

Example A22 a) Preparation of Intermediate 72

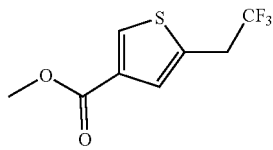

Pd$_2$(dba)$_3$ (0.116 g, 0.11 mmol), Xantphos (0.220 g, 0.38 mmol) and Cs$_2$CO$_3$ (7.29 g, 22.38 mmol) were added in a tube under N$_2$, then dioxane (12 mL) was added.

Intermediate 69 (1.5 g) and 2-iodo-1,1,1-trifluoroethane (1.1 mL, 1.19 mmol) were then dissolved in dioxane (24 mL) and added to the mixture. The r.m. was stirred for 1 min at r.t., then water (1.5 mL) was added and the mixture was stirred for 6 h at 80° C. The r.m. was poured into a EtOAc/water mixture and the two layers were separated. The aq. layer was extracted with EtOAc, then the organic layer was washed with brine, dried over MgSO$_4$, filtered and evaporated. Purification by flash column chromatography (silica; heptanes/EtOAc 100/0 to 98/2) afforded intermediate 72 (0.584 g, 47%).

b) Preparation of Intermediate 73

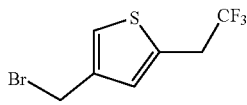 [SMILES: FC(F)(F)Cc1cc(CBr)cs1]

By following a synthetic sequence similar to the one reported for the synthesis of intermediate 68, intermediate 73 was obtained starting from intermediate 72.

Example A23 a) Preparation of Intermediate 74

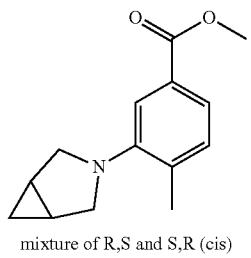 [SMILES: COC(=O)c1ccc(C)c(N2CC3CC3C2)c1]

mixture of R,S and S,R (cis)

3-Azabicyclo[3.1.0]hexane hydrochloride (0.246 g, 2.06 mmol) was added to a stirred solution of methyl 3-bromo-4-methylbenzoate (0.394 g, 1.72 mmol), X-Phos (0.072 g, 0.15 mmol), Pd$_2$(dba)$_3$ (0.064 g, 0.07 mmol) and Cs$_2$CO$_3$ (1.681 g, 5.16 mmol) in toluene (5 mL) while N$_2$ was bubbled through the r.m. The mixture was then stirred overnight at 100° C. in a sealed tube. Water and EtOAc were subsequently added. The aqueous phase was extracted once more with EtOAc and the combined organic layers were dried over MgSO$_4$, filtered and evaporated. The crude was purified by flash column chromatography (silica; heptanes/EtOAc 100/0 to 95/5). The desired fractions were collected and concentrated in vacuo to yield intermediate 74 as a sticky yellow oil (0.362 g, 93%).

b) Preparation of Intermediate 75

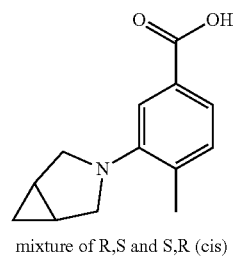 [SMILES: Cc1ccc(C(=O)O)cc1N1CC2CC2C1]

mixture of R,S and S,R (cis)

1N NaOH sol. (2.4 mL, 2.35 mmol) was added to a stirred solution of intermediate 74 (0.362 g, 1.56 mmol) in MeOH (5 mL) at r.t. The mixture was stirred overnight. After this time aq. 1N HCl sol. was added until pH=4. The solvents were evaporated in vacuo and the crude was used as such for the subsequent reaction step, and the yield considered to be quantitative (0.34 g).

c) Preparation of Intermediate 76

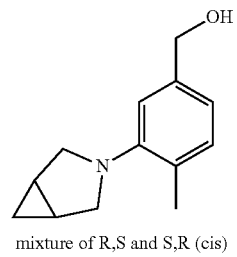

mixture of R,S and S,R (cis)

Borane dimethyl sulfide complex (2 M in THF, 1.9 mL, 3.91 mmol) was added dropwise to a stirred solution of intermediate 75 (0.34 g, crude material) in THF (5 mL) at 0° C. under N$_2$ atmosphere. The mixture was stirred overnight at 60° C., then the reaction was cooled to r.t. Na$_2$CO$_3$ was added portionwise at 0° C. The product was extracted with EtOAc (×2). The combined organic layers were dried over MgSO$_4$, filtered and evaporated. The crude was purified by flash column chromatography (silica; heptanes/EtOAc 100/0 to 80/20). The desired fractions were collected and concentrated in vacuo to yield intermediate 76 as a sticky pale brown oil (0.25 g, 83% over two steps).

d) Preparation of Intermediate 77

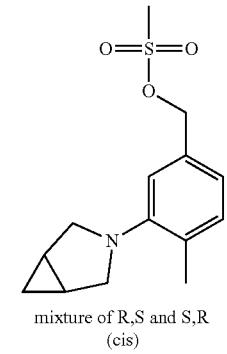 [SMILES: Cc1ccc(COS(C)(=O)=O)cc1N1CC2CC2C1]

mixture of R,S and S,R (cis)

By following a synthetic sequence similar to the one reported for the synthesis of intermediate 45, intermediate 77 was obtained starting from intermediate 76.

Example A24

Following a procedure similar to the one described for the synthesis of intermediate 45, following intermediate was prepared starting from the known corresponding alcohol.

| Structure | Intermediate number |
|---|---|
| 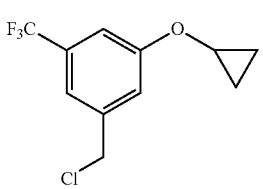 | 78 |

Example A25 a) Preparation of Intermediate 79

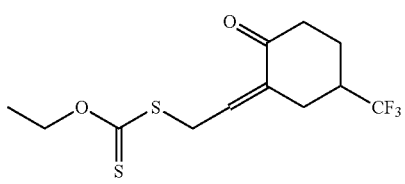

By following a synthetic sequence similar to the one reported for the synthesis of intermediate 76 and intermediate 30, intermediate 79 was obtained starting from commercially available 3-cyclopropoxy-5-(trifluoromethyl)benzoic acid.

Example A26 a) Preparation of Intermediate 80

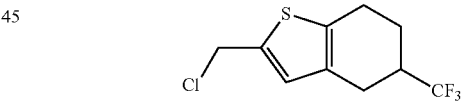

mixture of E and Z isomers

Butyl lithium (2.5 M in hexane, 2.7 mL, 6.62 mmol) was added dropwise at −78° C. to diisopropylamine (1.0 mL, 7.22 mmol) in THF (26 mL), over 20 min, and the resulting mixture was stirred for 1 h at this temperature. 4-(Trifluoromethyl)cyclohexanone (1 g, 6.02 mmol) in THF (5 mL) was added dropwise and the r.m. was stirred 1 h at this temperature. Carbonodithioic acid, O-ethyl S-(2-oxoethyl) ester (prepared as reported in Helv. Chim. Acta, 1992, 907; 0.989 g, 6.02 mmol) in THF (10 mL) was then added. The r.m. was stirred for 2 h. Subsequently, the mixture was quenched with sat. aq. NH$_4$Cl sol. and extracted with EtOAc. The organic layer was separated, dried (MgSO$_4$), filtered and the solvent was evaporated. The residue was purified by flash column chromatography (silica; heptane/EtOAc 100/0 to 75/25) gave intermediate 80 (0.88 g, 47%; mixture of E and Z isomers).

b) Preparation of Intermediate 81

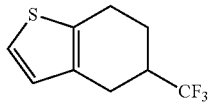

To N-methylpiperazine (25 mL, 225 mmol) at 0° C., intermediate 80 (5 g, 16 mmol) in DCM (8 mL) was added dropwise, under a N$_2$ flow. The r.m. was stirred at r.t. and the reaction as followed by TLC. When conversion to the free thiol was observed, the r.m. was cooled to 0° C. and HCl (37% in water, 35 mL, 419 mmol) was added cautiously dropwise. The r.m. was stirred 1 h at r.t., then diluted with water and extracted with DCM. The combined organic layers were dried, filtered and evaporated to give a crude, which was purified by flash column chromatography (silica; DCM/MeOH 100/0 to 95/5). The product fractions were collected and the solvent evaporated, to afford intermediate 81 (1.7 g, 51%).

c) Preparation of Intermediate 82

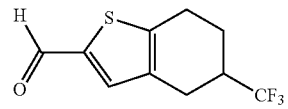 [SMILES: O=Cc1cc2c(s1)CCC(C(F)(F)F)C2]

To a solution of intermediate 81 (0.847 g, 4.11 mmol) in THF (23 mL) was added dropwise butyl lithium (2.5M in hexane, 2.1 mL, 5.34 mmol) at −30° C. under N$_2$ atmosphere. After 20 min of stirring at this temperature, DMF (2.5 mL) was added dropwise. The r.m. was then allowed to warm up to r.t. for 1 h, quenched with sat. NH$_4$Cl sol., then extracted with EtOAc. The organic layer was washed with brine, dried, filtered and concentrated in vacuo to give a crude, which was used without further purification in the subsequent step (0.815 g).

d) Preparation of Intermediate R$^3$

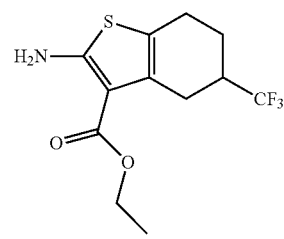 [SMILES: CCOC(=O)c1c(N)sc2c1CC(C(F)(F)F)CC2]

By following a synthetic sequence similar to the one reported for the synthesis of intermediate 30, intermediate 83 was obtained starting intermediate 82.

Example A27 a) Preparation of Intermediate 84

3-(Trifluoromethyl)cyclohexanone (0.79 g, 4.76 mmol) was dissolved in DMF (20 mL). Ethyl cyanoacetate (0.56 mL, 5.23 mmol) and sulfur (0.324 g, 9.51 mmol) were added, followed by L-proline (0.055 g, 0.48 mmol), and the r.m. stirred for 24 h at 60° C. After this time the mixture was cooled to r.t., diluted with EtOAc and washed with water and brine. The organic extracts were dried over MgSO$_4$, filtered and the solvent evaporated in vacuo to afford a crude, which was purified by flash column chromatography (silica; heptanes/EtOAc 100/0 to 75/25). The product fractions were collected and the solvent was evaporated to yield intermediate 84 (0.962 g, 69%).

b) Preparation of Intermediate 85

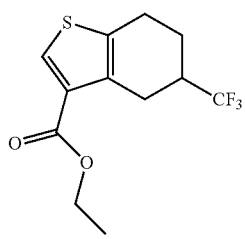 [SMILES: CCOC(=O)c1csc2c1CC(C(F)(F)F)CC2]

tert-Butyl nitrite (7.4 mL, 6.32 mmol) and copper (II) chloride (1.60 g, 11.88 mmol) were dissolved in MeOH (48 mL). To this mixture intermediate 84 (0.962 g, 3.28 mmol) was added in one portion and the reaction was stirred for 1 h, then quenched with sat. aq. NH$_4$Cl sol. and the solvent evaporated. The resulting slurry was partitioned between DCM and water. The organic sol. was separated and dried over MgSO$_4$, filtered and the solvent was evaporated in vacuo to give a crude, which was used without further purification for the subsequent reaction (0.9 g).

c) Preparation of Intermediate 86

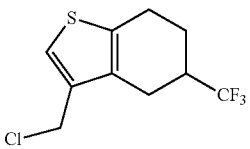 [SMILES: FC(F)(F)C1CCc2scc(CCl)c2C1]

By following a synthetic sequence similar to the one reported for the synthesis of intermediate 34, intermediate 86 was obtained starting intermediate 85.

Example A28 a) Preparation of Intermediate 87

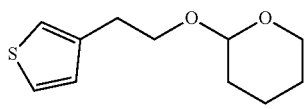 [SMILES: c1cc(CCOC2CCCCO2)cs1]

3,4-Dihydro-2H-pyran (1.7 mL, 19.02 mmol) in THF (10 mL) was added to a solution of 2-(3-thienyl)ethanol (2 mL, 18.11 mmol) in THF (10 mL). p-Toluenesulfonic acid (125 mg, 0.72 mmol) was then added and the mixture was stirred at r.t. overnight. Additional 3,4-dihydro-2H-pyran (0.2 eq) was added and the mixture was stirred for 1 h at r.t., then the solvent was removed in vacuo and the residue dissolved in EtOAc, washed with aq. K$_2$CO$_3$ sol. and water. The organic layers were combined, dried over MgSO$_4$ and the solvent evaporated to give a crude, which was purified by flash column chromatography (silica; DCM/EtOAc 100/0 to 75/25) to afford intermediate 87 (2.80 g, 73%).

b) Preparation of Intermediate 88

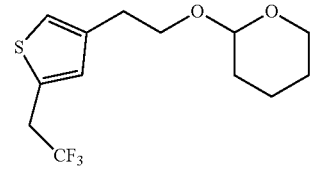 [SMILES: FC(F)(F)Cc1cc(CCOC2CCCCO2)cs1]

By following a synthetic sequence similar to the one reported for the synthesis of intermediate 69 and intermediate 72, intermediate 88 was obtained starting from intermediate 87.

c) Preparation of Intermediate 89

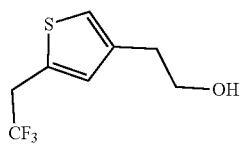 [SMILES: OCCc1csc(CC(F)(F)F)c1]

To a solution of intermediate 88 (0.64 g, 2.17 mmol) in MeOH (26 mL) was added p-toluensulfonic acid (0.187 g, 1.09 mmol). The r.m. was then stirred at r.t for 90 min.

After this time the mixture was concentrated in vacuo and the residue was dissolved in DCM. The solution was washed with aq. NaHCO$_3$ sol., dried over MgSO$_4$ and concentrated in vacuo to afford intermediate 89 (0.417 g, crude material).

d) Preparation of Intermediate 90

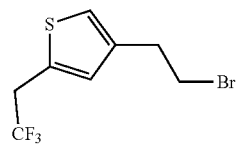

By following a synthetic procedure similar to the one reported for the synthesis of intermediate 66, intermediate 90 was obtained starting from intermediate 89.

Example A29 a) Preparation of Intermediate 91

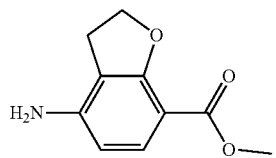

By following a synthetic procedure similar to the one reported for the synthesis of intermediate 28, in the presence of a thiophene solution in THF, intermediate 91 was obtained starting from methyl 4-amino-5-chloro-2,3-dihydrobenzofuran-7-carboxylate (described in ACS Symposium Series, 870 (Chemical Process Research), 125-139; 2004).

b) Preparation of Intermediate 92

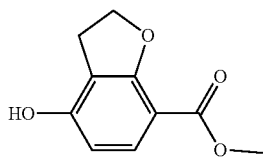

Water (60 mL) was stirred at 0° C. Sulfuric acid (30 mL, 55 mmol) was added dropwise at 0° C. Intermediate 91 (19.3 g, 100 mmol) was added. A solution of sodium nitrite (7.6 g, 110 mmol) in water (16 mL) was added dropwise at 0° C. The r.m. was stirred for 30 min at 0° C., then stirred for 1 h at 40° C. The precipitate obtained was filtered off, washed with water, and the residue was suspended in hot toluene. The suspension was cooled and the resulting precipitate was filtered off and dried to afford intermediate 92 (16.1 g), used as such in the subsequent reaction step.

c) Preparation of Intermediate 93

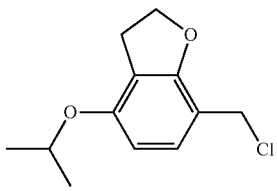

By following a synthetic sequence involving procedures similar to the ones used for the synthesis of (in the order) intermediate 24, intermediate 75, intermediate 53, intermediate 33 and intermediate 30, intermediate 93 was obtained starting from intermediate 92.

Example A30 a) Preparation of Intermediate 94

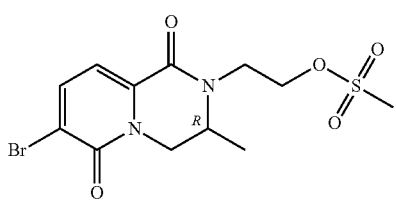

By following a synthetic sequence involving procedures similar to the ones used for the synthesis of (in the order) intermediate 24, intermediate 89 and intermediate 23, intermediate 94 was obtained starting from intermediate 8 and commercially available 2-(2-bromoethoxy)tetrahydro-2H-pyran.

b) Preparation of Intermediate 95

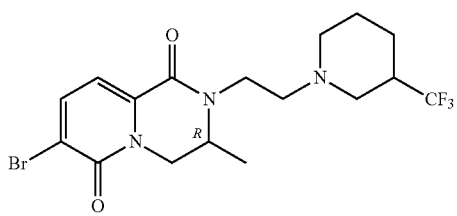

3-(Trifluoromethyl)piperidine (0.12 mL), 0.90 mmol), intermediate 94 (0.34 g, crude material) and DIPEA (0.23 mL, 1.35 mmol) in dimethylacetamide (5 mL) were stirred for 5 h at 80° C. Tetrabutylammonium iodide (0.066 g, 0.18 mmol) was then added and the r.m. heated overnight at 90° C. After this time the r.m. was allowed to cool down to r.t. and sat. NaHCO₃ sol. and EtOAc were added. The aqueous phase was extracted once more with EtOAc. The combined organic layers were dried over MgSO₄, filtered and the solvent evaporated. The crude was purified by flash column chromatography (silica; DCM/MeOH 100/0 to 93/7). The desired fractions were collected and concentrated in vacuo to yield intermediate 95 as a brown oil (0.392 g).

Example A31 a) Preparation of Intermediates 96 and 97

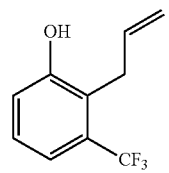

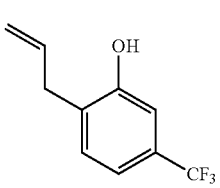

1-(Prop-2-en-1-yloxy)-3-(trifluoromethyl)benzene (3.9 g, 19.29 mmol) was heated at 240° C. for 1 h under microwave irradiation. The crude obtained was purified by flash column chromatography (silica; DCM/EtOAc 100/0 to 50/50). The desired fractions were collected and concentrated in vacuo to yield a mixture of intermediate 96 and 97, which was used without further purification in the subsequent reaction.

b) Preparation of Intermediates 98 and 99

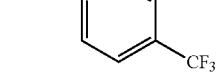

m-Chloroperbenzoic acid (1.585 g, 6.43 mmol) was added to a solution of intermediate 96 and intermediate 97 (1.3 g) in chloroform (15 mL). The reaction was stirred at reflux for 12 h, then it was diluted with sat. NaHCO₃ sol. and extracted with EtOAc. The organic layer was separated, dried over MgSO₄, filtered and the solvents evaporated in vacuo. The crude product was purified by flash column chromatography (silica; heptanes/EtOAc 100/0 to 90/10). The desired fractions were collected and concentrated in vacuo to yield intermediate 98 (0.267 g) and intermediate 99 (0.15 g) as colorless oils.

c) Preparation of Intermediate 100

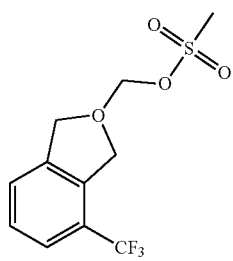

By following a synthetic procedure similar to the one reported for the synthesis of intermediate 23, intermediate 100 was obtained starting from intermediate 98.

d) Preparation of Intermediate 101

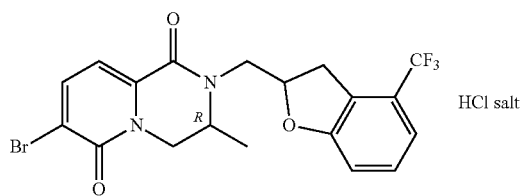

HCl salt

By following a synthetic procedure similar to the one reported for the synthesis of intermediate 59, intermediate 101 was obtained starting from intermediate 8 and intermediate 100.

Example A32 a) Preparation of Intermediates 102 and 103

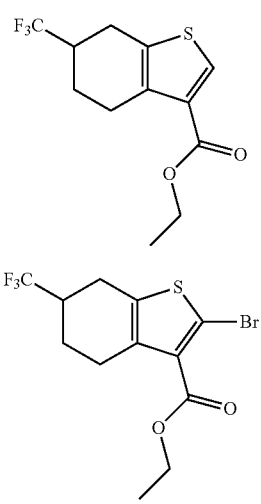

To a solution of benzo[b]thiophene-3-carboxylic acid, 2-amino-4,5,6,7-tetrahydro-6-(trifluoromethyl)-, ethyl ester (0.20 g, 0.68 mmol) in HBr (48% in water, 1.4 mL, 12.27 mmol) at 0° C. a solution of sodium nitrite (0.047 g, 0.68 mmol) in water (2 mL) was added dropwise over 45 min. The r.m. was warmed to r.t. and further stirred for 15 min, then cooled to 0° C. and copper (I) bromide (0.147 g, 1.02 mmol) was added portionwise. The mixture was stirred at 0° C. for 15 min, at r.t. for 15 min and at 140° C. for 40 min. The r.m. was then cooled to r.t. and neutralised with aq. sat. Na$_2$CO$_3$ sol. EtOAc was added and layers were separated. The organic phase was evaporated and the residue was purified by flash column chromatography (silica, heptanes/EtOAc 100/0 to 90/10). The product fractions were combined and evaporated in vacuo to give a mixture of intermediate 102 and intermediate 103, to which was added zinc (40 mg, 0.62 mmol). The mixture was heated at reflux in AcOH (4 mL) for 16 h. After cooling, the mixture was poured on onto ice and neutralized by cautious addition of aq. sat. NaHCO$_3$ sol. The resulting aqueous suspension was extracted with EtOAc (3×100 mL). The combined organic layers were washed with brine, dried over MgSO$_4$ and concentrated in vacuo to afford intermediate 102 (54 mg).

a1) Alternative Preparation of Intermediate 102 tert-Butyl nitrite (1.5 mL, 1.31 mmol) and copper (I) chloride (0.332 g, 2.47 mmol) were dissolved in MeOH (10 mL). Benzo[b]thiophene-3-carboxylic acid, 2-amino-4,5,6, 7-tetrahydro-6-(trifluoromethyl)-, ethyl ester (0.20 g, 0.68 mmol) was added in one portion and the reaction was stirred for 1 h, then it was quenched with sat. aq. NH$_4$Cl sol. and the solvent was evaporated. The resulting slurry was partitioned between DCM and water. The organic layer was separated and dried over MgSO$_4$, filtered and the solvent evaporated to give intermediate 102 (0.181 g, crude material).

b) Preparation of Intermediate 195

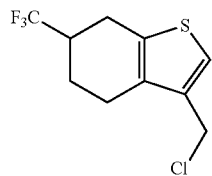

By following an analogous synthesis protocol as the one reported for the synthesis of intermediate 30, intermediate 104 was obtained starting from intermediate 102.

Example A33 a) Preparation of Intermediate 105

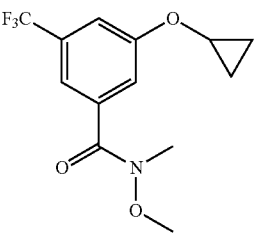 [SMILES: CON(C)C(=O)c1cc(OC2CC2)cc(C(F)(F)F)c1]

To a stirred solution of 3-cyclopropoxy-5-(trifluoromethyl)benzoic acid (1.21 g, crude) in DMF (25 mL) were added DIPEA (2.4 mL) and HBTU (2.24 g, 5.90 mmol) at 0° C. After 20 minutes, N,O-dimethylhydroxylamine hydrochloride (0.53 g, 5.41 mmol) was added and the solution was allowed to come to r.t. and stirred at the same temperature overnight. Sat. NaHCO₃ sol. was added and the solution was extracted with EtOAc. The organic layer was dried over MgSO₄, filtered and concentrated in vacuo. The crude product was purified by flash column chromatography (silica; heptanes/EtOAc 100/0 to 50/50) to yield intermediate 105 (1.28 g, 90%).

b) Preparation of Intermediate 106

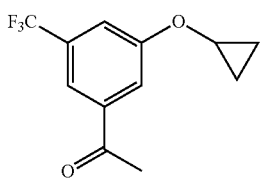 [SMILES: CC(=O)c1cc(OC2CC2)cc(C(F)(F)F)c1]

Methylmagnesium bromide (1.4 M in toluene/THF, 3.5 mL, 4.87 mmol) was added to a solution of intermediate 105 (1.28 g) in dry THF (25 mL) at 0° C. The r.m. was allowed to come to r.t. and stirred at the same temperature for 1 h. Additional methylmagnesium bromide (0.2 eq) was added. After reaction completion, aq. NH₄Cl sol. and EtOAc were added. The organic layer was separated, dried over MgSO₄, filtered and evaporated in vacuo. The crude product was purified by flash column chromatography (silica; heptanes/EtOAc 100/0 to 90/10) to afford intermediate 106 (0.93 g, 86%).

c) Preparation of Intermediate 107

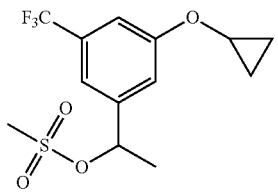 [SMILES: CC(OS(C)(=O)=O)c1cc(OC2CC2)cc(C(F)(F)F)c1]

By following a synthetic sequence involving procedures similar to the ones used for the synthesis of intermediate 29 and intermediate 23, intermediate 107 was obtained starting from intermediate 106.

d) Preparation of Intermediates 108 and 109

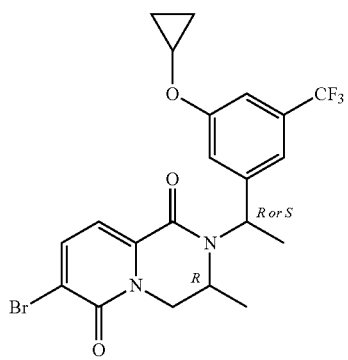

108

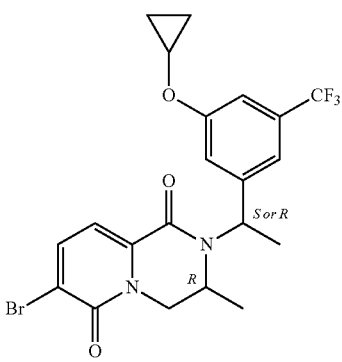

109

By following a synthetic procedure similar to the one reported for the synthesis of intermediate 59, a mixture of intermediate 108 and intermediate 109 was obtained starting from intermediate 8 and intermediate 107. The mixture was purified by flash column chromatography (silica; heptanes/EtOAc 100/0 to 80/20). The desired fractions were collected and concentrated in vacuo to yield intermediate 108 as a pale brown solid and intermediate 109 as a sticky brown solid.

Example A34 a) Preparation of Intermediate 110

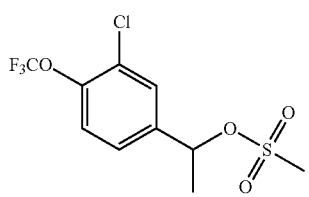 [SMILES: CC(OS(C)(=O)=O)c1ccc(OC(F)(F)F)c(Cl)c1]

By following a synthetic sequence involving procedures similar to the ones used for the synthesis of intermediate 107, intermediate 110 was obtained starting from commercially available 1-(3-chloro-4-(trifluoromethoxy)phenyl)ethanone.

b) Preparation of Intermediates 111 and 112.

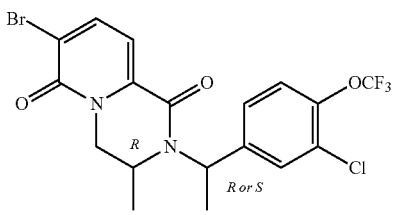

111

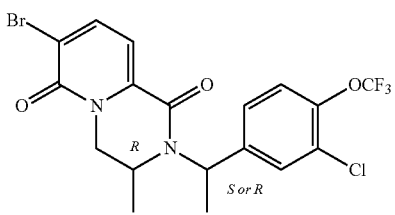

112

By following a synthetic procedure similar to the one reported for the synthesis of intermediate 59, a mixture of intermediate 111 and intermediate 112 was obtained starting from intermediate 8 and intermediate 110. The mixture was purified by flash column chromatography (silica; heptanes/EtOAc 100/0 to 75/25). The desired fractions were collected and concentrated in vacuo to yield intermediate 111 (0.322 g, 20%) and intermediate 112 (0.33 g, 21%) as pale yellow solids.

Example A35 a) Preparation of Intermediate 113

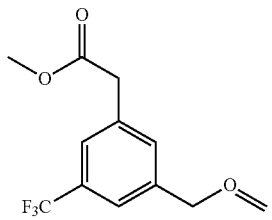

Methyl 3-hydroxy-5-(trifluoromethyl)phenylacetate (0.32 g, 1.36 mmol) and bis(1,5-cyclooctadiene)diiridium(I) dichloride (9 mg, 14 μmol) were added to a stirred solution of vinyl acetate (0.25 mL, 2.72 mmol) and $Na_2CO_3$ (86 mg, 0.82 mmol) in toluene (5 mL) while $N_2$ was bubbled through the r.m. The mixture was stirred for 3 h at 100° C. in a sealed tube, then water and EtOAc were added. The aqueous phase was extracted once more with EtOAc. The combined organics were dried over $MgSO_4$, filtered and evaporated. The crude was purified by flash column chromatography (silica; heptanes/EtOAc 100/0 to 90/10). The desired fractions were collected and concentrated in vacuo to yield intermediate 113 as a pale yellow oil (284 mg, 81%).

b) Preparation of Intermediate 114

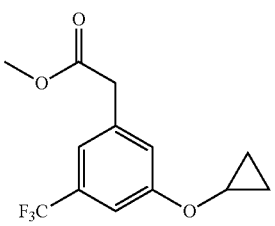 [SMILES: COC(=O)Cc1cc(OC2CC2)cc(C(F)(F)F)c1]

To a $N_2$ flushed round bottom flask, diethyl zinc (1M in heptanes, 8.3 mL, 8.3 mmol) was added to DCM (7 mL). The resulting solution was cooled with an ice bath. TFA (0.6 mL, 7.99 mmol) was added slowly by a syringe. The reaction mixture was then stirred at 0° C. for 10 min. Diiodomethane (0.7 mL, 8.61 mmol) was subsequently added by a syringe and the resulting r.m. was stirred at 0° C. for additional 10 min. Intermediate 113 (0.8 g, 3.07 mmol) in DCM (8 mL) was finally added. The reaction mixture was allowed to warm up to r.t. over 30 minutes, then quenched with water (15 mL) and 3 N HCl (15 mL). The layers were separated. The aqueous phase was extracted with EtOAc. The combined organics were dried over $MgSO_4$, filtered and concentrated. The crude was purified by flash column chromatography (silica; Heptane/EtOAc 100/0 to 90/10). The desired fractions were collected and concentrated in vacuo to yield intermediate 114 a pale yellow oil (0.73 g, 87%).

c) Preparation of Intermediate 115

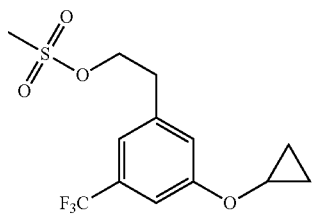 [SMILES: CS(=O)(=O)OCCc1cc(OC2CC2)cc(C(F)(F)F)c1]

By following a synthetic sequence similar to the one reported for the synthesis of intermediate 77, intermediate 115 was obtained starting from intermediate 114.

d) Preparation of Intermediate 116

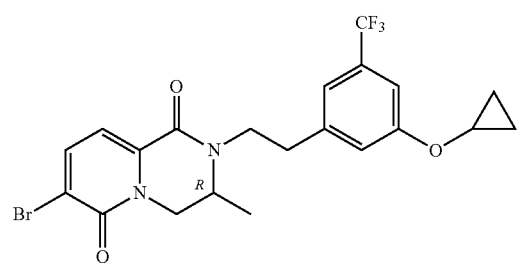

By following a synthetic sequence similar to the one reported for the synthesis of intermediate 24, intermediate 116 was obtained starting from intermediate 8 and intermediate 115.

Example A36 a) Preparation of Intermediate 117

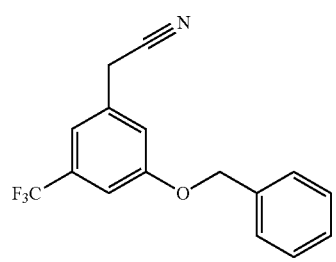 [SMILES: N#CCc1cc(OCc2ccccc2)cc(C(F)(F)F)c1]

Sodium cyanide (0.746 g, 15.23 mmol) was added dropwise to a stirred solution of 1-(benzyloxy)-3-(chloromethyl)-5-(trifluoromethyl)benzene (3.05 g, 10.15 mmol) in DMF (30 mL) at 0° C. under $N_2$ atmosphere. The mixture was stirred for 16 h at r.t. Then sat. $NaHCO_3$ sol. was added and the mixture extracted with EtOAc. The combined organics were dried over $MgSO_4$, filtered and concentrated in vacuo. The crude product was purified by flash column chromatography (silica; hexane/EtOAc 100/0 to 80/20). The desired fractions were collected and concentrated in vacuo to yield intermediate 117 as a colorless oil (2.11 g, 71%).

b) Preparation of Intermediate 118

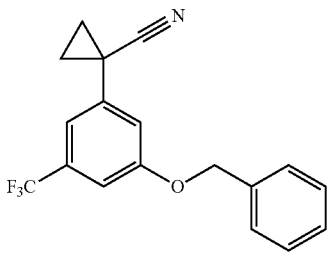 [SMILES: N#CC1(c2cc(OCc3ccccc3)cc(C(F)(F)F)c2)CC1]

NaOH (50% aq., 4.05 g, 50.64 mmol) was added dropwise to a mixture of intermediate 117 (2.12 g, 7.23 mmol), 1-bromo-2-chloroethane (2.1 mL, 25.32 mmol) and benzyltriethylammonium chloride (0.494 g, 2.17 mmol). The mixture was stirred at 50° C. for 15 h, then water was added and the organic layer was extracted with EtOAc. The organic phase was washed with 5% aq HCl sol., then dried over MgSO$_4$, filtered and the solvent was removed in vacuo. The crude product was purified by flash column chromatography (silica; hexane/EtOAc 100/0 to 90/10). The desired fractions were collected and concentrated in vacuo to yield intermediate 118 as a white solid (1.95 g, 85%).

c) Preparation of Intermediate 119

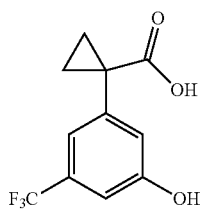

Intermediate 118 (1.95 g, 6.14 mmol) in AcOH (6 mL) and HCl (37% aq., 20 mL) was heated at 95° C. for 15 h in a sealed tube, then the mixture was diluted with water and extracted with EtOAc. The organic layer was washed with water, dried over MgSO$_4$, filtered and the solvents evaporated in vacuo. The crude material was used as such into the subsequent reaction step (1.51 g).

d) Preparation of Intermediate 120

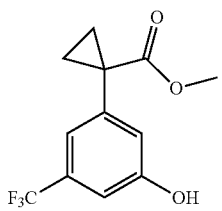

Thionyl chloride (1.3 mL, 18.41 mmol) was added to a stirred solution of intermediate 119 (1.51 g) in chloroform (20 mL) at 0° C., then DMF (48 µL) was added. The mixture was stirred overnight at r.t. The solvent was then evaporated and the residue was co-distilled with toluene several times. MeOH (20 mL) was added and the mixture was stirred overnight at r.t. The solvent was then evaporated. Sat. NaHCO$_3$ sol. and EtOAc were added and the phases separated. The aqueous phase was extracted once with EtOAc, then the combined organic layer was dried over MgSO$_4$, filtered and evaporated. The crude was purified by flash column chromatography (silica; heptanes/EtOAc 100/0 to 70/30). The desired fractions were collected and concentrated in vacuo to yield intermediate 120 as a white solid (1.44 g, 91%).

e) Preparation of Intermediate 121

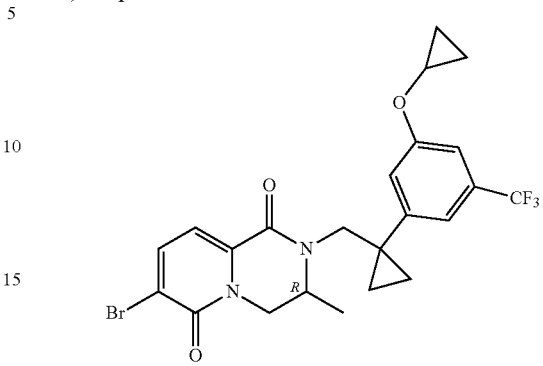

By following a synthetic sequence involving procedures similar to the ones used for the synthesis of (in the order) intermediate 113, intermediate 114, intermediate 75, intermediate 76, intermediate 23 and intermediate 24, intermediate 121 was obtained starting from intermediate 120 and intermediate 18.

Example A37 a) Preparation of Intermediate 122

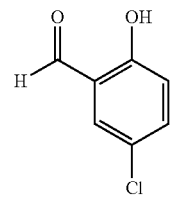

Hexamethylenetetramine (18.54 g, 132.24 mmol) was added to a mixture of 4-chloro-2-fluorophenol (8.5 g, 66.12 mmol) in methanesulfonic acid (50 mL, 771.02 mmol) at 0° C. The reaction mixture was then heated to 100° C. After completion of the reaction (1.5 h), the reaction mixture was allowed to cool to rt and was poured into ice water (50 mL). The precipitated yellow solid was collected by filtration and washed with water. This solid was dissolved in EtOAc, and then washed with water and brine. The organic phase was dried over MgSO$_4$, filtered and concentrated to yield intermediate 126 as a yellow oil (5.95 g, 28%), which solidified upon standing.

b) Preparation of Intermediate 123

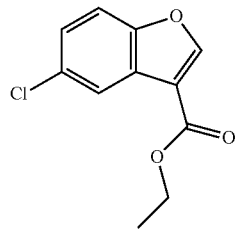

Intermediate 122 (3.17 g, 20.25 mmol) was stirred in DCM (7 mL). Then BF$_3$.OEt$_2$ (0.28 mL, 2.03 mmol) was added to the stirring solution. The reaction mixture was stirred during 10 min at rt. Ethyl diazoacetate (3.6 mL, 34.84 mmol) in DCM (21 mL) was added dropwise to the reaction mixture, resulting in steady evolution of nitrogen (total addition time 10 min) and an increase in temperature. Once gas evolution ceased, the solvents were evaporated in vacuo. With vigorous stirring, sulfuric acid (1.4 mL) was added dropwise to the oil. The addition is slightly exothermic. After 20 minutes of vigorously stirring, a solid precipitated. The acidic reaction mixture was then neutralized by slow addition of aq. sat. NaHCO$_3$ sol. The aqueous layer was extracted with EtOAc. The organic layer was then washed with brine, dried over MgSO$_4$, filtered and concentrated to afford an orange oil. This crude was purified by flash column chromatography (silica; heptanes/DCM 100/0 to 0/100). The desired fractions were collected and concentrated in vacuo to yield intermediate 123 (2.49 g, 55%).

c) Preparation of Intermediate 124

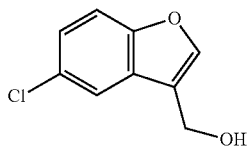 [SMILES: OCc1coc2ccc(Cl)cc12]

Diisobutylaluminum hydride (1 M in toluene, 22.4 mL, 33.25 mmol) was slowly added to intermediate 123 (2.49 g, 11.08 mmol) in DCM (37 mL) at −65° C. under N$_2$ atmosphere. After 20 min, the reaction was carefully quenched with aq. sat. Rochelle's salt sol. MeOH was added and the mixture was diluted with EtOAc and filtered through Celite. The volatiles were evaporated and the resulting crude was taken up in EtOAc. Water was added and the organic layer was separated. The organic layer was washed with water and brine, dried over MgSO$_4$, filtered and concentrated to give intermediate 124 (1.84 g, 91%).

d) Preparation of Intermediate 125

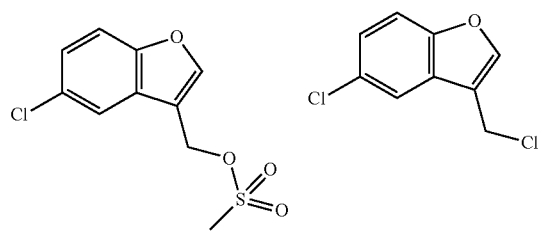 [SMILES: CS(=O)(=O)OCc1coc2ccc(Cl)cc12 ; ClCc1coc2ccc(Cl)cc12]

Intermediate 125 was prepared following a synthetic procedure similar to the one reported for the synthesis of intermediate 45. Starting from intermediate 124 (0.21 g, 1.15 mmol) intermediate 125 was obtained as a mixture of the mesylate and the chloro derivative (ratio 1:2 according to NMR), and the crude was used as such in the next step (0.31 g).

Example A38 a) Preparation of Intermediate 126

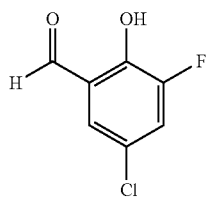

Hexamethylenetetramine (19.32 g, 136.47 mmol) was added to a mixture of 4-chloro-2-fluorophenol (10 g, 68.24 mmol) in methanesulfonic acid (51.6 mL, 796.05 mmol) at 0° C. The reaction mixture was then heated to 100° C. After completion of the reaction (1.5 h), the reaction mixture was allowed to cool to rt and was poured into ice water. The precipitated yellow solid was collected by filtration and washed with water. This solid was dissolved in DCM, dried over MgSO$_4$, filtered and concentrated to yield intermediate 126 as a yellow oil (7.554 g, 63% yield).

b) Preparation of Intermediate 127

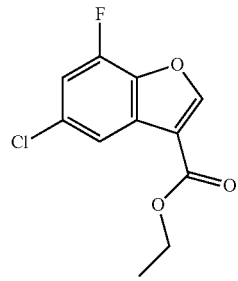 [SMILES: CCOC(=O)c1coc2c(F)cc(Cl)cc12]

Intermediate 127 was prepared following a synthetic procedure similar to the one reported for the synthesis of intermediate 123. Starting from intermediate 126 (7.554 g, 43.27 mmol) intermediate 127 was obtained as a pale yellow solid (4.904 g, 47%).

c) Preparation of Intermediate 128

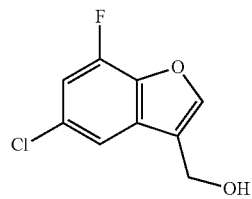 [SMILES: OCc1coc2c(F)cc(Cl)cc12]

Intermediate 128 was prepared following a synthetic procedure similar to the one reported for the synthesis of intermediate 124. Starting from intermediate 127 (4.904 g, 20.21 mmol) intermediate 128 was obtained as a white solid (4.095 g, quantitative yield).

d) Preparation of Intermediate 129

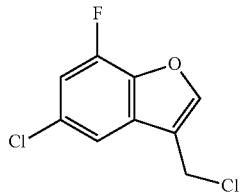 [SMILES: Fc1cc(Cl)cc2c(CCl)coc12]

Intermediate 129 was prepared following a synthetic procedure similar to the one reported for the synthesis of intermediate 45. Starting from intermediate 128 (1.368 g, 6.82 mmol) intermediate 129 was obtained and used as such in the next reaction step (2.648 g).

Example A39 a) Preparation of Intermediate 130

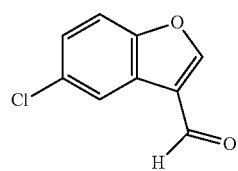 [SMILES: O=Cc1coc2ccc(Cl)cc12]

Intermediate 129 (1.83 g, 10.02 mmol) was dissolved in DCM (64 mL). Dess-Martin periodinane (6.40 g, 15.09 mmol) was added at 0° C. The reaction mixture was stirred at rt during 4 h. The reaction mixture was diluted with DCM and aq. Na$_2$S$_2$O$_3$ sol. (10%) and aq. sat. NaHCO$_3$ sol. were added. After 30 min stirring, the mixture was filtered through Celite and the layers were separated. The organic layer was washed respectively with aq. sat. NaHCO$_3$ sol., water and brine, dried over MgSO$_4$, filtered and concentrated in vacuo to afford intermediate 130 (1.55 g, 86%).

b) Preparation of Intermediate 131

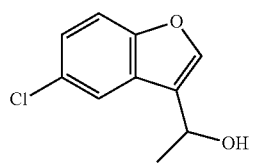

Methylmagnesium chloride (3 M in THF, 9.9 mL, 29.90 mmol) was added to a solution of intermediate 130 (1.35 g, 7.47 mmol) in dry THF (15 mL) at −78° C. The r.m. was stirred during 30 min and then warmed to rt. Aq. NH$_4$Cl sol. and EtOAc were added, The organic layer was separated, dried over MgSO$_4$, filtered and evaporated in vacuo to afford racemic intermediate 131 (1.2 g, 82%).

c) Preparation of Intermediate 132

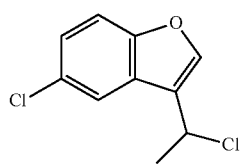

Intermediate 132 was prepared following a synthetic procedure similar to the one reported for the synthesis of intermediate 129. Starting from intermediate 131 (1.18 g, 6.00 mmol) intermediate 132 was obtained and used as such in the next reaction step (1.4 g).

Example A40 a) Preparation of Intermediate 133

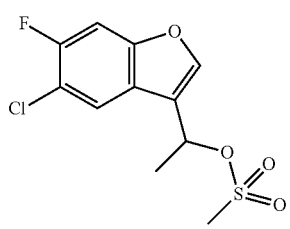 [SMILES: CC(OS(C)(=O)=O)c1coc2cc(F)c(Cl)cc12]

By following a synthetic sequence involving procedures similar to the ones used for the synthesis of (in the order) intermediate 122, intermediate 123, intermediate 124, intermediate 130, intermediate 131 and intermediate 132, intermediate 133 was obtained starting from commercially available 4-chloro-3-fluorophenol.

Example A41 a) Preparation of Intermediate 134

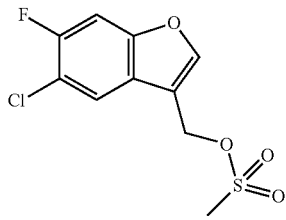 [SMILES: CS(=O)(=O)OCc1coc2cc(F)c(Cl)cc12]

By following a synthetic sequence involving procedures similar to the ones used for the synthesis of (in the order) intermediate 122, intermediate 123, intermediate 124, and intermediate 45, intermediate 134 was obtained starting from commercially available 4-chloro-3-fluorophenol.

Example A42 a) Preparation of Intermediate 135

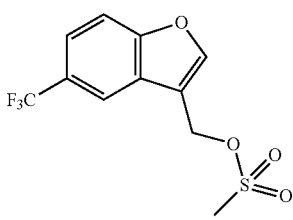 [SMILES: CS(=O)(=O)OCc1coc2ccc(C(F)(F)F)cc12]

By following a synthetic sequence involving procedures similar to the ones used for the synthesis of (in the order) intermediate 122, intermediate 123, intermediate 124, and intermediate 45, intermediate 135 was obtained starting from commercially available 4-trifluoromethylphenol.

Example A43 a) Preparation of Intermediate 136

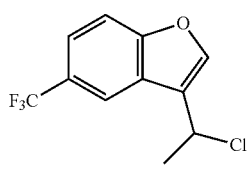 [SMILES: CC(Cl)c1coc2ccc(C(F)(F)F)cc12]

By following a synthetic sequence involving procedures similar to the ones used for the synthesis of (in the order) intermediate 122, intermediate 123, intermediate 124, intermediate 130, intermediate 131 and intermediate 132, intermediate 136 was obtained starting from commercially available 4-trifluoromethylphenol.

Example A44 a) Preparation of Intermediate 137

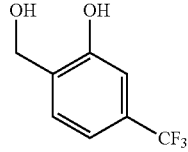 [SMILES: OCc1ccc(C(F)(F)F)cc1O]

Sodium borohydride (3.83 g, 101.31 mmol) and THF (97 mL) were mixed and added dropwise to dimethylsulfate (9.3 mL, 98.08 mmol) at 0° C. and stirred first for 1 h at this temperature and 4 h at rt until no gas generation was observed. A solution of 4-trifluoromethyl salicylic acid (10 g, 48.52 mmol) and trimethylborate (11.0 mL, 98.98 mmol) in THF (49 mL) was added dropwise to the rm at rt over 30 min. The mixture was stirred at the same temperature for 4.5 h. After the reaction was completed, $H_2O$ was added slowly at 0° C. and the resulting mixture was vigorously stirred for 30 min. Then THF was removed on a rotary evaporator. The residue was extracted with EtOAc (×3) and the combined organic layer was washed with sat. aq. $NaHCO_3$ sol. (×3) and brine (×3). The organic layer was then dried over $Na_2SO_4$, filtered, and concentrated in vacuo to give intermediate 137 as a crude, which was used as such in the next reaction (10.12 g, quantitative yield).

b) Preparation of Intermediate 138

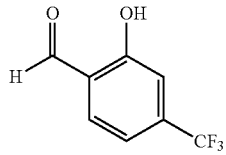

Intermediate 137 (9.55 g, 49.70 mmol) and DDQ (11.28 g, 49.70 mmol) were dissolved in DCM (76 mL) and THF (19 mL) at rt. After 4 h, the solvents were evaporated in vacuo and the black oily residue was adsorbed on silica gel and purified via filtration on a silica plug. The desired fractions were collected to afford intermediate 138 as a brown solid (8.17 g, 86%).

c) Preparation of Intermediate 139

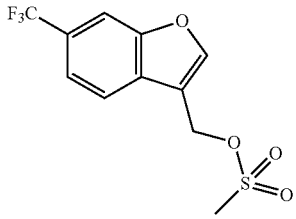 [SMILES: CS(=O)(=O)OCc1coc2cc(C(F)(F)F)ccc12]

By following a synthetic sequence involving procedures similar to the ones used for the synthesis of (in the order) intermediate 123, intermediate 124 and intermediate 45, intermediate 139 was obtained starting from intermediate 138.

Example A45 a) Preparation of Intermediate 140

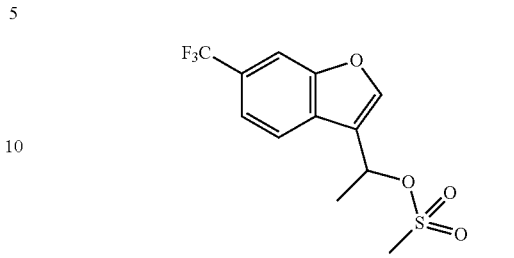

By following a synthetic sequence involving procedures similar to the ones used for the synthesis of (in the order) intermediate 123, intermediate 124, intermediate 130, intermediate 131 and intermediate 132, intermediate 140 was obtained starting from intermediate 138.

Example A46 a) Preparation of Intermediate 141

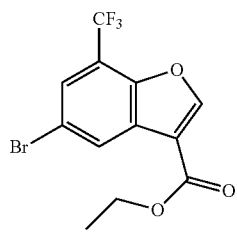 [SMILES: CCOC(=O)c1coc2c(C(F)(F)F)cc(Br)cc12]

By following a synthetic sequence involving procedures similar to the ones used for the synthesis of (in the order) intermediate 122 and intermediate 123, intermediate 141 was obtained starting from commercially available 4-bromo-2-(trifluoromethyl)phenol.

b) Preparation of Intermediate 142

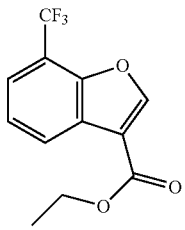 [SMILES: CCOC(=O)c1coc2c(C(F)(F)F)cccc12]

EtOH (400 mL) was added to Pd/C (10%, 1.578 g) under $N_2$ atm. Intermediate 141 (5 g, 14.83 mmol) was added and the resulting mixture was stirred at rt under $H_2$ atm (atmospheric pressure) for 2 h. The mixture was filtered through celite and the filtrate was evaporated in vacuo. Water was added and a solid precipitated. This solid was collected by filtration, washed with water and dried (vacuum oven) to afford intermediate 142 (3.56 g, 93%).

c) Preparation of Intermediate 143

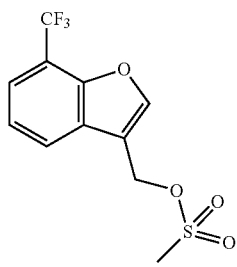

By following a synthetic sequence involving procedures similar to the ones used for the synthesis of (in the order) intermediate 124 and intermediate 45, intermediate 143 was obtained starting from intermediate 142.

Example A47 a) Preparation of Intermediate 144

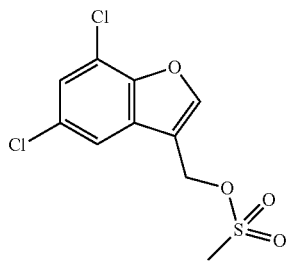 [SMILES: CS(=O)(=O)OCc1coc2c(Cl)cc(Cl)cc12]

By following a synthetic sequence involving procedures similar to the ones used for the synthesis of (in the order) intermediate 123, intermediate 124, and intermediate 45, intermediate 144 was obtained starting from commercially available 3,5-dichloro-2-hydroxybenzaldehyde.

Example A48 a) Preparation of Intermediate 145

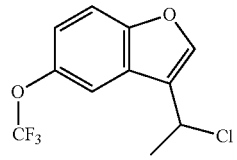 [SMILES: CC(Cl)c1coc2ccc(OC(F)(F)F)cc12]

By following a synthetic sequence involving procedures similar to the ones used for the synthesis of (in the order) intermediate 123, intermediate 124, intermediate 130, intermediate 131 and intermediate 132, intermediate 145 was obtained starting from commercially available 5-(trifluoromethoxy)salicylaldehyde.

Example A49 a) Preparation of Intermediate 146

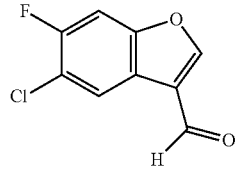 [SMILES: O=Cc1coc2cc(F)c(Cl)cc12]

By following a synthetic sequence involving procedures similar to the ones used for the synthesis of (in the order) intermediate 122, intermediate 123, intermediate 124 and intermediate 130, intermediate 146 was obtained starting from commercially available 4-chloro-3-fluorophenol.

b) Preparation of Intermediate 147

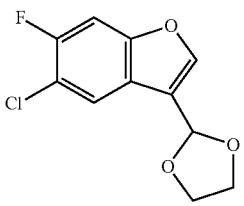 [SMILES: Fc1cc2occ(C3OCCO3)c2cc1Cl]

Intermediate 146 (2.2 g, 11.08 mmol), ethylene glycol (9.3 mL, 166.18 mmol), p-toluenesulfonic acid (0.09 g, 0.55 mmol) were refluxed in toluene (60 mL) overnight. The solvent was then evaporated and the residue was dissolved in EtOAc and washed with water. The organic layer was dried over MgSO$_4$, filtered and concentrated in vacuo to afford intermediate 147 (2.1 g, 55%), which was used as such in the next step.

c) Preparation of Intermediate 148

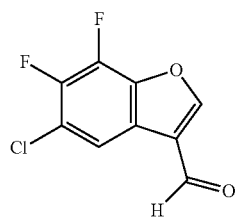 [SMILES: O=Cc1coc2c(F)c(F)c(Cl)cc12]

tert-Butyl lithium (1.7 M in pentane, 0.36 mL, 0.62 mmol) was added dropwise to a solution of intermediate 147 (0.1 g, 0.412 mmol) in THF (2 mL) at −78° C. The reaction mixture was stirred for 30 min at this temperature. N-Fluorobenzenesulfonimide (0.195 g, 0.62 mmol) in THF (10 mL) was added dropwise. The mixture was stirred at −78° C. during 4 h. The reaction was quenched with water and warmed to rt. The aqueous was extracted with EtOAc and the combined organic layers were dried over MgSO$_4$, filtered and concentrated in vacuo. The residue was dissolved in THF (2 mL) and treated with 1N HCl (2 mL). After 30 min deprotection was completed and the solvent was evaporated. The resulting residue was dissolved in EtOAc and washed with sat. NaHCO$_3$ sol., water and brine. The organic layer was separated, dried over MgSO$_4$, filtered and concentrated in vacuo to afford intermediate 148 (0.1 g), which was used as such in the next step.

d) Preparation of Intermediate 149

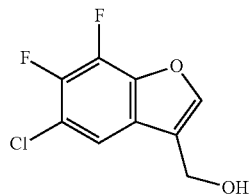 [SMILES: OCc1coc2c(F)c(F)c(Cl)cc12]

Sodium borohydride (0.035 g, 0.92 mmol) was added to a solution of intermediate 148 (0.1 g, 0.46 mmol) in MeOH (0.5 mL) at rt. The reaction mixture was stirred for 1 hour at this temperature. Aq. sat NaHCO₃ solution was added and the reaction was stirred during 30 min. EtOAc and water were added. The aqueous was extracted with EtOAc and the combined organic layers were washed with water and brine, then dried over MgSO₄, filtered and concentrated in vacuo. The crude product was purified by flash column chromatography to yield intermediate 149 (0.026 g).

e) Preparation of Intermediate 150

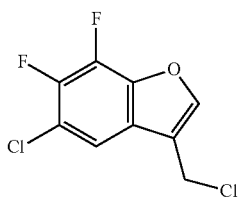 [SMILES: Fc1c(Cl)cc2c(CCl)coc2c1F]

Intermediate 150 was prepared following a synthetic procedure similar to the one reported for the synthesis of intermediate 45. Starting from intermediate 149 (0.026 g, 0.12 mmol) intermediate 150 was obtained and used as such in the next reaction step (0.045 g).

Example A50 a) Preparation of Intermediate 151

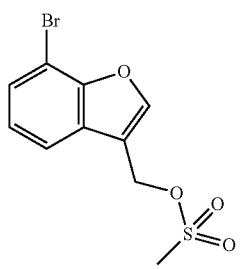 [SMILES: CS(=O)(=O)OCc1coc2c(Br)cccc12]

By following a synthetic sequence involving procedures similar to the ones used for the synthesis of (in the order) intermediate 123, intermediate 124 and intermediate 45, intermediate 151 was obtained starting from commercially available 3-bromo-2-hydroxybenzaldehyde.

Example A51 a) Preparation of Intermediate 152

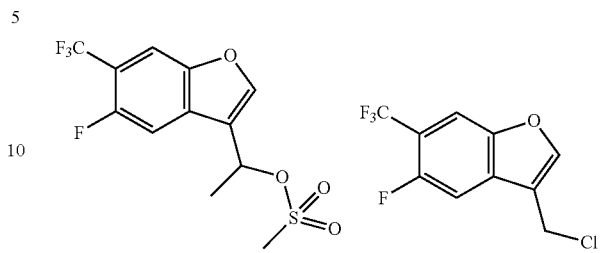

By following a synthetic sequence involving procedures similar to the ones used for the synthesis of (in the order) intermediate 122, intermediate 123, intermediate 124 and intermediate 45, intermediate 152 was obtained starting from commercially available 3-fluoro-4-(trifluoromethyl)phenol as a mixture of the mesylate and the chloro derivative.

Example A52 a) Preparation of Intermediate 153

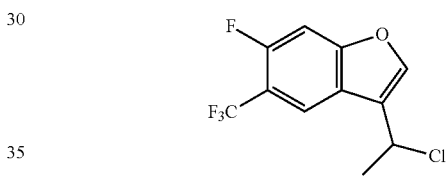

By following a synthetic sequence involving procedures similar to the ones used for the synthesis of (in the order) intermediate 122, intermediate 123, intermediate 124, intermediate 130, intermediate 131 and intermediate 132, intermediate 153 was obtained starting from commercially available 3-fluoro-4-(trifluoromethyl)phenol.

Example A53 a) Preparation of Intermediate 154

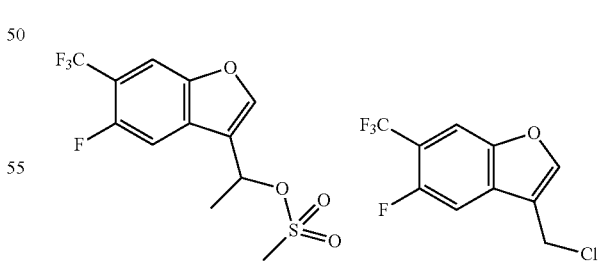

By following a synthetic sequence involving procedures similar to the ones used for the synthesis of (in the order) intermediate 122, intermediate 123, intermediate 124 and intermediate 45, intermediate 152 was obtained starting from commercially available 4-fluoro-3-(trifluoromethyl)phenol as a mixture of the mesylate and the chloro derivative.

Example A54 a) Preparation of Intermediate 155

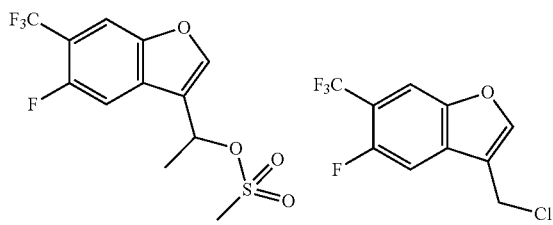

By following a synthetic sequence involving procedures similar to the ones used for the synthesis of (in the order) intermediate 122, intermediate 123, intermediate 124, intermediate 130, intermediate 131 and intermediate 132, intermediate 153 was obtained starting from commercially available 4-fluoro-3-(trifluoromethyl)phenol as a mixture of the mesylate and the chloro derivative (ratio 1:2 according to NMR).

Example A55 a) Preparation of Intermediate 156

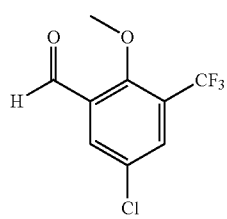

5-Chloro-2-fluorobenzotrifluoride (8.5 g, 42.81 mmol) in THF (57 mL) was treated with tetramethylethylenediamine (9.3 mL, 62.33 mmol) and cooled down to −78° C. n-Butyl lithium (1.6 M in hexane, 22.2 mL, 55.53 mmol) was added dropwise. After stirring at −78° C. for 90 min, the mixture was treated with DMF (4.4 mL) and stirred further 30 min. The reaction mixture was allowed to warn to rt and was quenched with aq. sat NH$_4$Cl solution and diluted with Et$_2$O. The organic layer was washed with brine, dried over MgSO$_4$, filtered and evaporated. The residue was then treated with sodium methoxide (30% in MeOH, 80 g, 1480.82 mmol). The reaction was stirred overnight at rt. Water was added and the aqueous phase was extracted with Et$_2$O. The combined organic layers were dried over MgSO$_4$, filtered and concentrated in vacuo to afford an oil. This crude was purified by flash column chromatography (silica; heptanes/DCM 100/0 to 50/50). The desired fractions were collected and concentrated in vacuo to yield intermediate 156 as a yellow oil (8.23 g, 85%).

b) Preparation of Intermediate 157

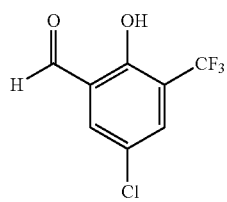

Boron tribromide (1 M in DCM, 19.3 mL, 16.33 mmol) was added dropwise to a solution of intermediate 156 (3.84 g, 16.11 mmol) in DCM (38 mL) at −78° C. The reaction was stirred at rt overnight. Water (20 mL) was added at −41° C. and the mixture was allowed to warm to rt. EtOAc was added and the organic phase was separated. The aqueous phase was extracted with EtOAc. The combined organic layers were dried over MgSO$_4$, filtered and concentrated in vacuo. This crude was purified by flash column chromatography (silica; heptanes/DCM 100/0 to 50/50). The desired fractions were collected and concentrated in vacuo to yield intermediate 157 as an orange oil (2.33 g, 64%), which solidifies upon standing.

c) Preparation of Intermediate 158

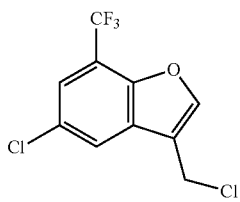 [SMILES: FC(F)(F)c1cc(Cl)cc2c(CCl)coc12]

By following a synthetic sequence involving procedures similar to the ones used for the synthesis of (in the order) intermediate 123, intermediate 124 and intermediate 45, intermediate 158 was obtained starting from intermediate 157.

Example A56 a) Preparation of Intermediate 159

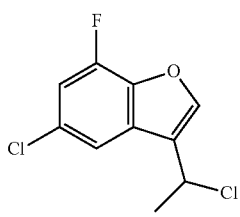

By following a synthetic sequence involving procedures similar to the ones used for the synthesis of (in the order) intermediate 122, intermediate 123, intermediate 124, intermediate 130, intermediate 131 and intermediate 132, intermediate 159 was obtained starting from commercially available 4-chloro-2-fluorophenol.

Example A57 a) Preparation of Intermediate 160

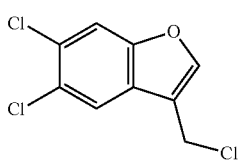 [SMILES: ClCc1coc2cc(Cl)c(Cl)cc12]

By following a synthetic sequence involving procedures similar to the ones used for the synthesis of (in the order) intermediate 122, intermediate 123, intermediate 124 and intermediate 45, intermediate 160 was obtained starting from commercially available 3,4-dichlorophenol.

Example A58 a) Preparation of Intermediate 161

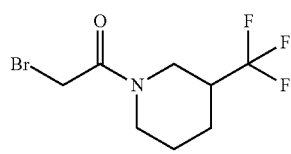 [SMILES: O=C(CBr)N1CCCC(C(F)(F)F)C1]

3-Trifluoromethylpiperidine (0.36 mL, 2.73 mmol) was added to a solution of bromoacetyl bromide (0.24 mL, 2.73 mmol) and potassium carbonate (0.47 g, 3.41 mmol) in THF (9 mL) at 0° C. The reaction mixture was then warmed up to rt and stirred 24 h. Water was added and the aqueous layer was extracted with EtOAc. The combined organic layers were washed with aq. sat. NaHCO$_3$ and brine, dried over MgSO$_4$, filtered and concentrated in vacuo. This crude was purified by flash column chromatography (silica; heptanes/DCM 100/0 to 60/40). The desired fractions were collected and concentrated in vacuo to yield intermediate 161 (0.29 g, 39%).

Example A59 a) Preparation of Intermediate 162

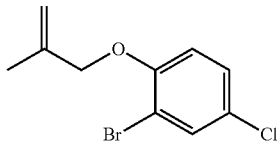

3-Chloro-2-methylpropene (2.35 g, 26 mmol) was added dropwise to a solution of 2-bromochlorophenol (4.15 g, 20 mmol) and K$_2$CO$_3$ (5.53 g, 39.99 mmol) in DMF (100 mL) at rt. The reaction mixture was stirred overnight at 70° C. After cooling down to rt, the reaction mixture was diluted with EtOAc and washed twice with water and once with brine. The organic layer was dried over MgSO$_4$, filtered and concentrated in vacuo to afford intermediate 162, which was used as such in the next reaction.

b) Preparation of Intermediate 163

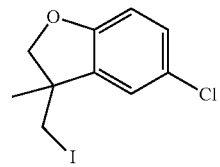

To a microwave vial equipped with a magnetic stir bar was added intermediate 162 (0.20 g, 0.76 mmol). The vial was purged with argon for 5 minutes, after which Pd(Q-Phos)2 (0.058 g, 0.038 mmol), potassium iodide (0.25 g, 1.53 mmol) and toluene (15 mL) were added. The vial was capped and added to an oil bath pre-heated to 100° C. After stirring for 6 hours, extra Pd(Q-Phos)2 (0.058 g, 0.038 mmol) (prepared as described in *Org. Lett.* 2010, 12, 3332) was added and the reaction mixture was stirred at 100° C. over the weekend. The vial was cooled and the contents filtered over a pad of silica gel, washing with ether. The crude material was loaded on to a silica gel column and purified by flash chromatography. This crude was purified by flash column chromatography (silica; heptanes/EtOAc 100/0 to 90/10). The desired fractions were collected and concentrated in vacuo to yield racemic intermediate 163 (0.11 g, 45%).

Example A60 a) Preparation of Intermediate 164

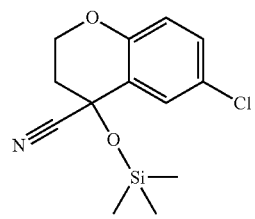 [SMILES: C[Si](C)(C)OC1(C#N)CCOc2ccc(Cl)cc21]

Zinc iodide (0.45 g, 1.42 mmol) was added to a solution of 6-chlorochroman-4-one (5 g, 27.38 mmol) in DCM (20 mL). Then trimethylsilyl cyanide (7.05 g, 71.1 mmol) was added dropwise and the reaction mixture was stirred at rt during 15 hours. The reaction mixture was washed three times with sat. aq. NaHCO$_3$ sol. The organic layer was dried over MgSO$_4$, filtered and concentrated in vacuo. The crude was purified by flash column chromatography (silica; heptanes/DCM 100/0 to 60/40). The desired fractions were collected and concentrated in vacuo to yield intermediate 164 (5.83 g, 76%).

b) Preparation of Intermediate 165

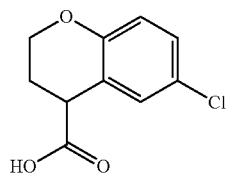 [SMILES: O=C(O)C1CCOc2ccc(Cl)cc21]

Intermediate 164 (3.8 g, 13.48 mmol) was stirred in acetic acid (15 mL) and HCl (15 mL) and then tin (II) chloride dihydrate (9.13 g, 40.45 mmol) was added. The reaction mixture was stirred at 125° C. during 24 hours. Water was added to the reaction mixture and the aqueous layer was then extracted with DCM (3×). The combined organic layers were dried over MgSO$_4$, filtered and concentrated in vacuo. The crude was purified by flash column chromatography (silica, DCM/MeOH 100/0 to 95/5). The desired fractions were collected and concentrated in vacuo to yield intermediate 165 (1.97 g, 69%).

c) Preparation of Intermediate 166

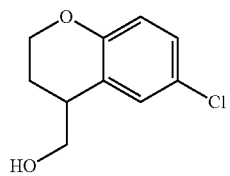 [SMILES: OCC1CCOc2ccc(Cl)cc21]

LiAlH$_4$ (1 M in THF, 26.5 mL, 26.52 mmol) was added to a solution of intermediate 165 (1.97 g, 8.84 mmol) in THF (45 mL) at −20° C. and then the reaction mixture was stirred at rt for 1 h. The r.m. was then cooled to −70° C. and water (4 mL) was carefully added dropwise followed by 1N NaOH (4 mL). THF (40 mL) was then added and the rm was stirred until it reached rt. The reaction mixture was filtered and the solid was washed with DCM. The filtrate was evaporated in vacuo to afford intermediate 166 (1.45 g, 83%).

d) Preparation of Intermediate 167

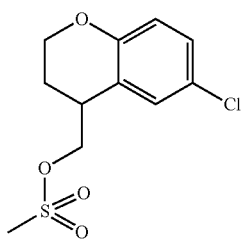 [SMILES: CS(=O)(=O)OCC1CCOc2ccc(Cl)cc21]

Intermediate 167 was prepared following a synthetic procedure similar to the one reported for the synthesis of intermediate 45. Starting from intermediate 166 (3.2 g, 16.11 mmol) racemic intermediate 167 was obtained and used as such in the next step.

Example A61 a) Preparation of Intermediate 168

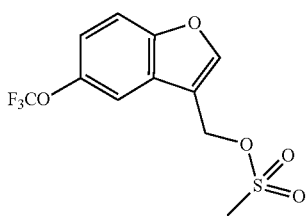 [SMILES: CS(=O)(=O)OCc1coc2ccc(OC(F)(F)F)cc12]

By following a synthetic sequence involving procedures similar to the ones used for the synthesis of (in the order) intermediate 123, intermediate 124 and intermediate 45, intermediate 168 was obtained starting from commercially available 5-(trifluoromethoxy)salicylaldehyde.

Example A62 a) Preparation of Intermediate 169

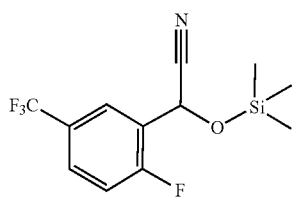 [SMILES: C[Si](C)(C)OC(C#N)c1cc(C(F)(F)F)ccc1F]

Trimethylsilyl cyanide (17.7 mL, 142 mmol) was added to a solution of 2-fluoro-5-(trifluoromethyl) benzaldehyde (25 g, 130 mmol) in DCM (100 mL) and DABCO (1 mL) at such rate that the mixture was maintained at a gentle reflux. After 1 h at rt, the reaction mixture was treated with water (3×50 mL) and brine (50 mL). The organic layer was dried over MgSO$_4$, filtered and concentrated in vacuo to yield intermediate 169 as an oil (34.7 g, 92%).

b) Preparation of Intermediate 170

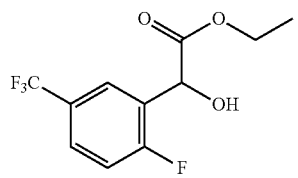 [SMILES: CCOC(=O)C(O)c1cc(C(F)(F)F)ccc1F]

A mixture of intermediate 169 (31.7 g, 109 mmol) in water (25 mL) was treated with HCl (37% in water, 75 mL, 989 mmol) and heated at reflux during 2 h. The r.m. was cooled down, diluted with ice water (300 mL), treated with NaOH (50% in water) until pH basic and washed with DCM (2×30 mL). The aqueous layer was acidified with conc HCl until pH=1 and extracted with DCM (3×250 mL). The combined organic layers were dried, filtered and evaporated to afford intermediate 170 as an oil (23.6 g, 91%), which solidifies upon standing.

c) Preparation of Intermediate 171

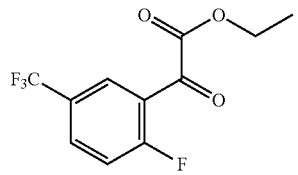 [SMILES: CCOC(=O)C(=O)c1cc(C(F)(F)F)ccc1F]

Intermediate 170 was dissolved in EtOH (500 mL). Sulfuric acid (10 mL) was added and the r.m. stirred overnight at reflux. The solvent was evaporated in vacuo, DCM was added and the mixture cooled with an ice bath. Aq. sat. NaHCO$_3$ sol. was added carefully until pH ~8. The organic layer was separated, dried over MgSO$_4$, filtered and concentrated in vacuo to afford intermediate 171 as an oil (23.8 g, 88%).

d) Preparation of Intermediate 172

A solution of intermediate 171 (23.8 g, 89.4 mmol) in 1,4-dioxane (250 mL) was treated with MnO$_2$ (60 g, 690 mmol) and stirred at reflux for 3 h and then at rt over the weekend. The reaction mixture was filtered over a small plug of Dicalite and concentrated in vacuo to afford intermediate 172 as an oil (18.5 g, 78%).

e) Preparation of Intermediate 173

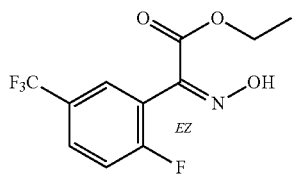

A stirred solution of intermediate 172 (18.5 g, 70 mmol) in EtOH (150 mL) was treated with hydroxylamine hydrochloride (5.84 g, 84 mmol) and sodium acetate (8.62 g, 105 mmol). The reaction mixture was heated at 50° C. for 5 h and then at rt for 16 h. The reaction mixture was filtered and concentrated in vacuo. The residue was treated with EtOAc (300 mL) and water (1 L) and the layers were separated. The aqueous layer was extracted with EtOAc. The combined organic layers were washed with brine, dried over MgSO$_4$, filtered and concentrated in vacuo. The residue was purified by flash column chromatography (silica; DCM/MeOH 100/0 to 95/5) to yield intermediate 173 as a white solid (17.6 g, 90%).

f) Preparation of Intermediate 174

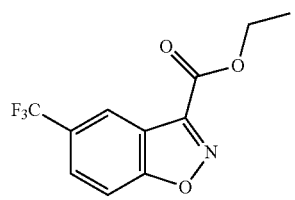 [SMILES: CCOC(=O)c1noc2ccc(C(F)(F)F)cc12]

K$_2$CO$_3$ (10 g, 72.4 mmol) was added to a solution of intermediate 173 (14 g, 50.1 mmol) in DMSO (50 mL) and the reaction mixture was stirred at rt for 16 h. The reaction mixture was diluted with EtOAc (300 mL) and water (100 mL) and the layers were separated. The aqueous layer was extracted with EtOAc (3×200 mL). The combined organic layers were washed with water (2×100 mL), brine (100 mL), dried over MgSO$_4$, filtered and concentrated in vacuo. The residue was purified by flash column chromatography (silica; DCM/MeOH 100/0 to 95/5) to yield intermediate 174 as a white solid (9.9 g, 76%).

g) Preparation of Intermediate 175

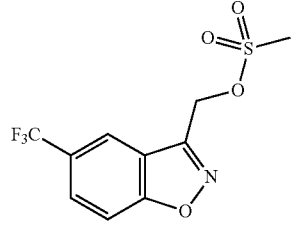 [SMILES: CS(=O)(=O)OCc1noc2ccc(C(F)(F)F)cc12]

By following a synthetic sequence involving procedures similar to the ones used for the synthesis of (in the order) intermediate 40 and intermediate 45, intermediate 175 was obtained starting from intermediate 174.

Example A66 a) Preparation of Intermediate 176

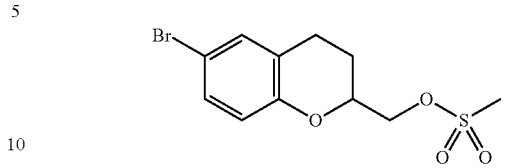

By following a synthetic sequence involving procedures similar to the ones used for the synthesis of (in the order) intermediate 40 and intermediate 45, intermediate 176 was obtained starting from 6-bromo-chroman-2-carboxylic acid methyl ester.

Example A67 a) Preparation of Intermediate 177

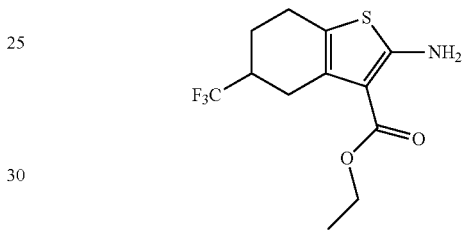

Ethyl cyanoacetate (0.6 mL, 5.23 mmol) and sulphur (0.32 g, 9.51 mmol) were added to 3-(trifluoromethyl) cyclohexanone (0.79 g, 4.76 mmol) in DMF (20 mL). Then L-proline (0.054 g, 0.47 mmol) was added and the reaction mixture was stirred at 60° C. for 24 h. After cooling to rt, the reaction mixture was diluted with EtOAc and washed with H$_2$O and brine. The organic layer was dried over MgSO$_4$, filtered and concentrated in vacuo. The residue was purified by flash column chromatography (silica; heptanes/EtOAc 100/0 to 75/25) to yield intermediate 177 (0.96 g, 69%).

b) Preparation of Intermediate 178

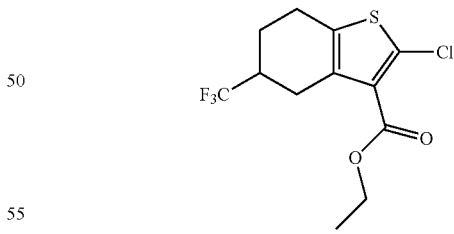

tert-Butyl nitrite (7.35 mL, 6.32 mmol) and copper (II) chloride (1.60 g, 11.88 mmol) were dissolved in MeOH (47 mL). To this mixture intermediate 177 (0.962 g, 3.28 mmol) was added in one portion and the reaction was stirred for 1 h, then quenched with sat. aq. NH$_4$Cl and the solvent evaporated. The resulting slurry was partitioned between DCM and water. The organic sol. was separated and dried over MgSO$_4$, filtered and the solvent was evaporated in vacuo to give a crude, which was used without further purification for the subsequent reaction (0.9 g).

c) Preparation of Intermediate 179

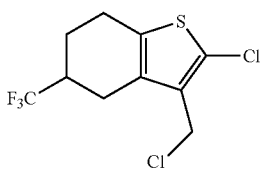 [SMILES: FC(F)(F)C1CCc2sc(Cl)c(CCl)c2C1]

By following a synthetic sequence involving procedures similar to the ones used for the synthesis of (in the order) intermediate 166 and intermediate 45, intermediate 179 was obtained starting from intermediate 178.

B. Preparation of the Final Compounds

Example B1 a) Preparation of Compound 1

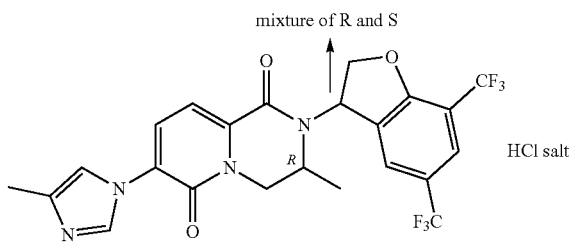

DIAD (0.039 mL, 0.20 mmol) was added to a stirred solution of intermediate 25 (70 mg, crude material) and TPP (52 mg, 0.20 mmol) in dry THF (20 mL) under $N_2$ at 0° C. The mixture was stirred at r.t. for 3 h, then the solvents were evaporated in vacuo. The product was purified by flash column chromatography (silica; DCM/MeOH 100/0 to 90/10). The desired fractions were collected and concentrated in vacuo. The compound was re-dissolved in DCM and 1.1 eq. of 4N HCl in dioxane was added. The solvent was evaporated and the solid triturated with DIPE to yield to give compound 1 as a beige solid (4 mg).

Example B2 a) Preparation of Compounds 2, 3 and 4

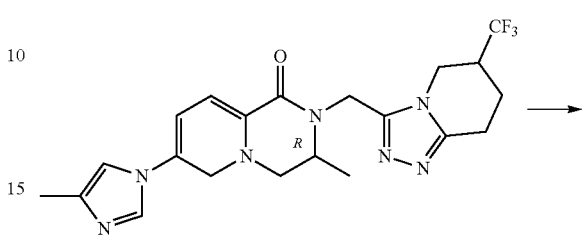

Compound 2: mixture of R and S
Compound 3: R or S
Compound 4: S or R

Intermediate 18 (429 mg, 1.661 mmol) was stirred in DMF (20 mL) under $N_2$ atmosphere. NaH (146 mg, 3.66 mmol) was added and the r.m. was stirred for 10 min. Intermediate 30 (390 mg, crude material) was added and the mixture was stirred at r.t. for 3 h. Ice was added and the solvents were evaporated. Water was added and the product was extracted with EtOAc. The organic layer was washed with brine, dried over $MgSO_4$, filtered and evaporated. The product was purified by flash column chromatography (silica; DCM/MeOH 97/3 to 90/10, then DCM/(7 N $NH_3$ in MeOH) 90/10). The pure fractions were collected and the solvent evaporated in vacuo, to give compound 2 (500 mg), which was separated into diastereoisomers by Prep HPLC (Stationary phase: RP SunFire Prep C18 OBD-10 μm, 30×150 mm; Mobile phase: 0.25% $NH_4HCO_3$ solution in water/MeOH), yielding compound 3 (114 mg) and compound 4 (69 mg).

Example B3 a) Preparation of Compounds 5, 6 and 7

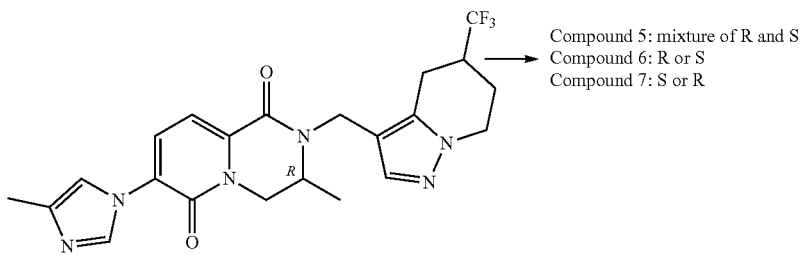

Compound 5: mixture of R and S
Compound 6: R or S
Compound 7: S or R

By following a procedure similar to the one reported for the synthesis of compound 2 (Example B2), starting from intermediate 18 and intermediate 34, compound 5 (240 mg) was obtained. Compound 5 was then separated into diastereoisomers by Prep SFC (Stationary phase: Chiralcel Diacel OD 20×250 mm; Mobile phase: $CO_2$, iPrOH with 0.2% $iPrNH_2$). The desired fractions were collected, the solvent evaporated in vacuo, the residue dissolved in MeOH and evaporated again. The two fractions were suspended in DIPE, filtered and dried in vacuo at 50° C., to afford compound 6 (57 mg) and compound 7 (49 mg).

Example B4 a) Preparation of Compound 14

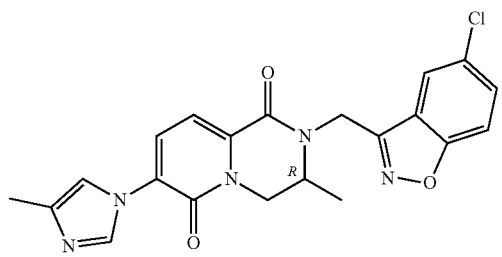

By following a procedure similar to the one reported for the synthesis of compound 2 (Example B2), starting from intermediate 18 and 3-(bromomethyl)-5-chloro-1,2-benzisoxazole compound 14 was obtained.

Example B5 a) Preparation of Compound 15

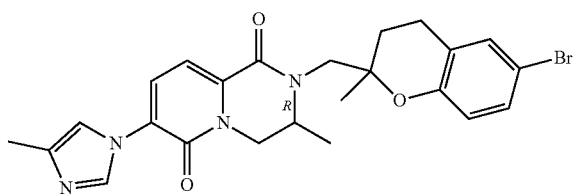

Intermediate 18 (287 mg, 1.11 mmol), NaH (89 mg, 2.23 mmol) and 18-crown-6 (197 mg, 0.75 mmol) were stirred in dry THF (5 mL) at 70° C. for 1 h under $N_2$ atmosphere. The r.m. was cooled to r.t. and then intermediate 41 (458 mg, 1.11 mmol) in DMF (3 mL) was added. The mixture was then heated to 90° C. and allowed to react at this temperature for 24 h. Water was then added and the product was extracted with EtOAc. The phases were separated, the organic layer was dried over $MgSO_4$, filtered and evaporated. The crude material was purified by Prep HPLC (Stationary phase: RP Vydac Denali C18-10 µm, 200 g, 5 cm; Mobile phase: 0.25% $NH_4HCO_3$ solution in water/acetonitrile). The desired fractions were collected, the solvent was evaporated, the residue dissolved in MeOH and the solvent evaporated again, yielding compound 15 (12 mg, 2%).

Example B6 a) Preparation of Compounds 17 and 18

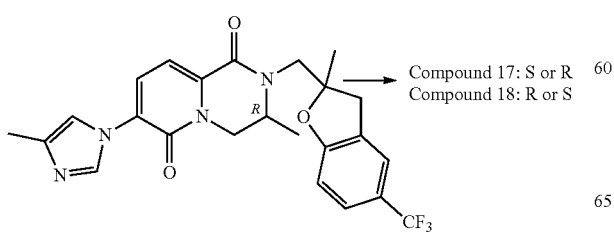

By following a procedure similar to the one reported for the synthesis of compound 15 (Example B5), starting from intermediate 18 and intermediate 49 a mixture of compound 17 and compound 18 was obtained. The mixture was separated into pure diastereoisomers by Prep HPLC (Stationary phase: RP SunFire Prep C18 OBD-10 µm, 30×150 mm; Mobile phase: 0.25% $NH_4HCO_3$ solution in water, MeOH), yielding compound 17 (6% yield) and compound 18 (5% yield) as foams.

Example B7 a) Preparation of Compounds 20 and 21

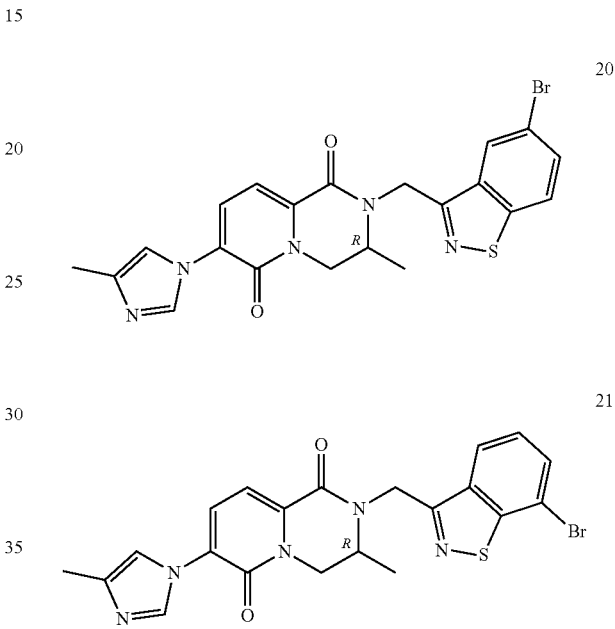

By following a procedure similar to the one reported for the synthesis of compound 2 (Example B2), starting from intermediate 18 and a mixture of intermediates 55 and 56, a mixture of compound 20 and compound 21 was obtained. The mixture was separated in the single regioisomers by Prep HPLC (Stationary phase: RP SunFire Prep C18 OBD-10 µm, 30×150 mm; Mobile phase: 0.25% $NH_4HCO_3$ solution in water/acetonitrile). The fractions containing the products were collected and the solvent evaporated in vacuo. The residue was suspended from DIPE, precipitated, filtered and dried in vacuo to afford compound 20 (48 mg, 10%) and compound 21 (20 mg, 4%).

Example B8 a) Preparation of Compound 22

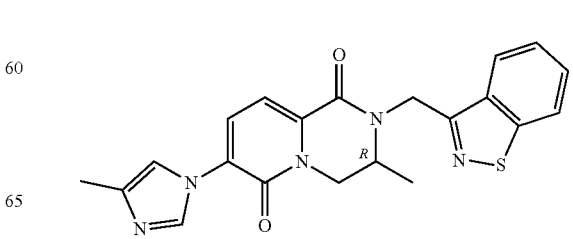

MeOH (40 mL) was added to 10% Pd/C (50 mg) under N₂ atmosphere. Thiophene solution (0.4% in MeOH) was added and the resulting mixture stirred under H₂ atmosphere for 30 min. Compound 20 (60 mg, 0.12 mmol) and potassium acetate (24 mg, 0.25 mmol) were added and the r.m. stirred at 25° C. under H₂ atmosphere until 1 eq. of H₂ was absorbed. The reaction mixture was then filtered over dicalite. The solvent was evaporated in vacuo and the residue purified by flash column chromatography (silica; DCM/MeOH 100/0 to 95/5). The product fractions were collected and the solvent was evaporated. The product was suspended in DIPE and dried in vacuo at 50° C., to afford compound 22 (24 mg, 48%).

Example B9 a) Preparation of Compound 23

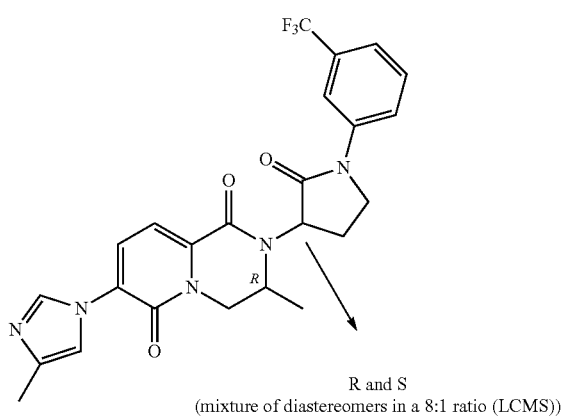

R and S
(mixture of diastereomers in a 8:1 ratio (LCMS))

Intermediate 18 (150 mg, 0.58 mmol), NaH (26 mg, 0.64 mmol) and 15-crown-5 (0.12 ml, 0.58 mmol) were stirred in dry DMF (7 mL) at r.t. for 1 h under N₂, then intermediate 58 (186 mg, 0.61 mmol) in DMF (2 ml) was added and the mixture stirred at r.t. After 90 min the reaction was quenched with water and extracted with EtOAc.

The combined organic layers were dried over MgSO₄, filtered and the solvent evaporated, to give a crude which was purified by flash column chromatography (silica; DCM/MeOH 100/0 to 95/5). The desired fractions were collected and the solvent was evaporated yielding compound 23 (28 mg, mixture of diastereomers in a 8:1 ratio (LCMS)).

Example B10 a) Preparation of Compound 32

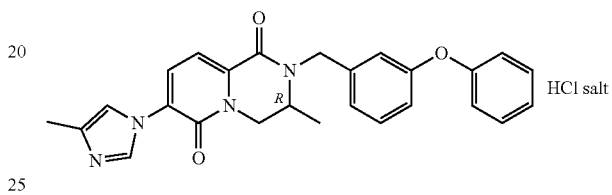

HCl salt

By following a procedure similar to the one reported for the synthesis of compound 2 (Example B2), starting from intermediate 18 and 3-phenoxybenzyl chloride compound 32 was obtained. After purification by flash column chromatography (silica; DCM/MeOH 99/1 to 95/5) the oil obtained after evaporation of the solvent was dissolved in MeOH. Subsequently, the compound was converted into the HCl salt. The salt obtained was recrystallized from Et₂O, to yield compound 32 (47%).

Example B11 a) Preparation of Compounds 35, 36 and 37

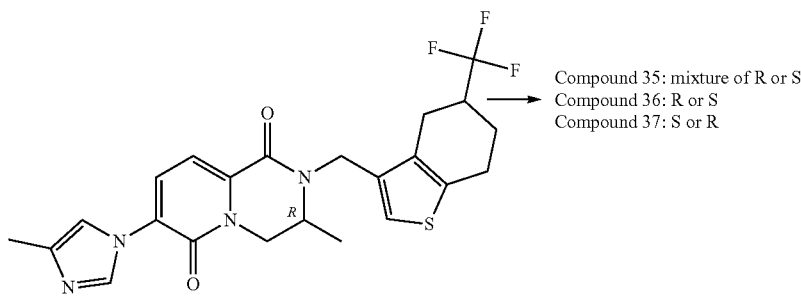

Compound 35: mixture of R or S
Compound 36: R or S
Compound 37: S or R

By following a procedure similar to the one reported for the synthesis of compound 2 (Example B2), starting from intermediate 18 and intermediate 86, compound 35 (626 mg, mixture of diastereoisomers) was obtained. The mixture was separated into the single diastereoisomers by Prep SFC (Stationary phase: Chiralpak Diacel AD 30×250 mm; Mobile phase: CO₂, EtOH with 0.4% iPrNH₂), yielding compound 36 (253 mg, 31%) and compound 37 (266 mg, 33%).

Example B12 a) Preparation of Compounds 45, 46 and 47

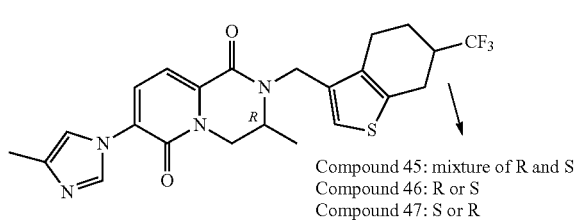

Compound 45: mixture of R and S
Compound 46: R or S
Compound 47: S or R

By following a procedure similar to the one reported for the synthesis of compound 2 (Example B2), starting from intermediate 18 and intermediate 104, 25 mg of compound 45 (mixture of diastereomers) was obtained. The mixture was separated into the single diastereoisomers by Prep SFC (Stationary phase: Chiralpak Diacel OJ 20×250 mm; Mobile phase: $CO_2$, MeOH with 0.4% iPrNH$_2$). The desired fractions were collected, evaporated, dissolved in MeOH and evaporated again, yielding compound 46 (5 mg, 7%) and compound 47 (6 mg, 8%).

Example B13 a) Preparation of Compound 51

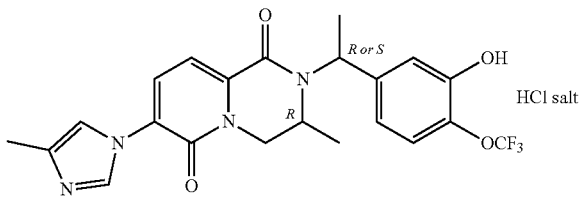

HCl salt

Pd$_2$(dba)$_3$ (25 mg, 0.027 mmol) and tetramethyl di-tBuX-Phos (23 mg, 0.047 mmol) were added to an oven-dried vial under N$_2$ atm and the vial was sealed. Dry toluene (10 mL) and dry dioxane (2 mL) were added and the resulting dark purple mixture was stirred at 120° C. for 3 min. 4-Methylimizazole (110 mg, 1.342 mmol) and K$_3$PO$_4$ (285 mg, 1.342 mmol) were added to a second oven-dried vial under N$_2$ atmosphere and the vial was sealed. Then, intermediate 111 (322 mg, 0.671 mmol) and the premixed catalyst solution were added to the second vial. The reaction mixture was stirred at 120° C. for 5 h, then it was cooled to room temperature, diluted with EtOAc, washed with brine, dried over MgSO$_4$, filtered and concentrated. The crude was purified by flash column chromatography (silica; DCM/MeOH 100/0 to 96/4). The desired fractions were collected and concentrated in vacuo. The product (92 mg) was dissolved in EtOAc (2 mL), then HCl (4 M in dioxane, 0.053 mL, 0.21 mmol) was added to obtain the hydrochloride. The solvent was evaporated and the product was triturated with Et$_2$O to yield 66 mg of compound 51 as a pale orange solid.

Example B14 a) Preparation of Compounds 57 and 58

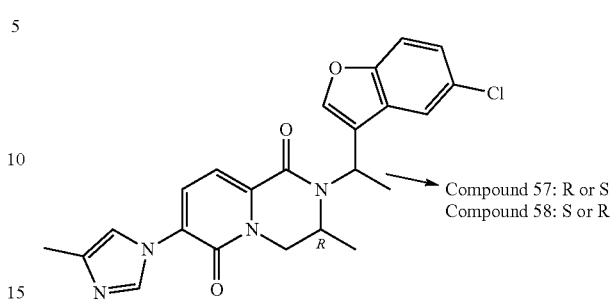

Compound 57: R or S
Compound 58: S or R

By following a procedure similar to the one reported for the synthesis of compound 2 (Example B2), starting from intermediate 18 and intermediate 132, 1.65 g of a mixture of diastereomers 57 and 57 was obtained. The mixture was separated into the single diastereoisomers by Prep HPLC (Stationary phase: XBridge C18 3.5 um, Mobile phase: 0.2% NH$_4$HCO$_3$ in water, MeOH). The desired fractions were collected, evaporated, dissolved in MeOH and evaporated again, yielding compound 57 (150 mg, 8%) and compound 58 (329 mg, 18%).

Example B15 a) Preparation of Compounds 65 and 66

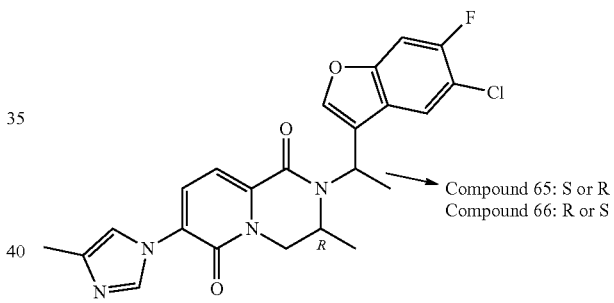

Compound 65: S or R
Compound 66: R or S

By following a procedure similar to the one reported for the synthesis of compound 2 (Example B2), starting from intermediate 18 and intermediate 133, 1 g of a mixture of diastereomers 65 and 66 was obtained. The crude was purified by flash column chromatography (silica; DCM/MeOH 100/0 to 95/5). The desired fractions were collected, evaporated, dissolved in MeOH and evaporated again, yielding compound 65 (0.45 g, 22%) and compound 66 (0.42 g, 20%).

Example B16 a) Preparation of Compounds 89 and 90ivelter 2326

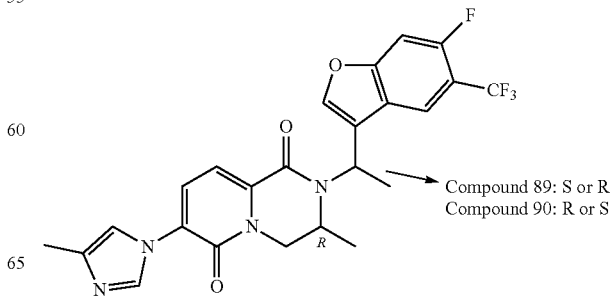

Compound 89: S or R
Compound 90: R or S

By following a procedure similar to the one reported for the synthesis of compound 2 (Example B2), starting from intermediate 18 and intermediate 153, a mixture of diastereomers 89 and 90 was obtained (429 mg). The mixture was separated into the single diastereoisomers by Prep SFC (Stationary phase: Chiralpak Diacel AD 30×250 mm; Mobile phase: $CO_2$, EtOH with 0.2% $iPrNH_2$). The desired fractions were collected, evaporated, dissolved in MeOH and and evaporated again, yielding compound 89 (25 mg, 4%) and compound 90 (54 mg, 8%).

Example B17 a) Preparation of Compound 100

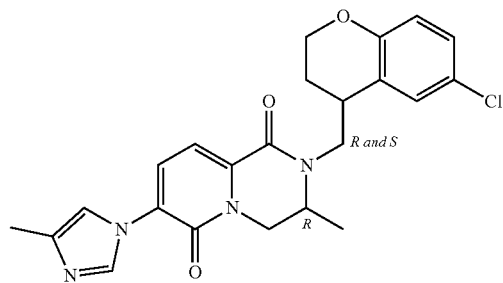

Intermediate 18 (1.48 g, 5.72 mmol) and lithium bromide (0.50 g, 5.72 mmol) were stirred in dry DMF (180 mL) at r.t. under $N_2$. NaH (1.37 g, 34.33 mmol) was added and the r.m. was stirred for 10 min. Intermediate 167 (1.9 g, 6.87 mmol) was added and the mixture was stirred at r.t. for 1 week. Two drops of water were added and the solvents were evaporated. Water was added and the aqueous layer was extracted with EtOAc. The combined organic layers were dried over $MgSO_4$, filtered and the solvent evaporated, to give a crude which was purified by flash column chromatography (silica; DCM/MeOH, 98/2 to 96/4). The desired fractions were collected and the solvent was evaporated yielding compound 100 (50 mg, 2%).

By using analogous reaction protocols as described in the foregoing examples, the compounds listed in the Tables below have been prepared.

'Co. No.' means compound number. 'cb' means covalent bond.

'Pr.' refers to the Example number in analogy to which protocol the compound was synthesized.

In case no specific stereochemistry is indicated for a stereocenter of a compound, this means that the compound was obtained as a mixture of the R and the S enantiomers. "HCl salt" means hydrochloric acid salt; the exact number of equivalents of HCl was not determined.

In case no salt form is indicated, the compound was obtained as a free base.

TABLE 1a

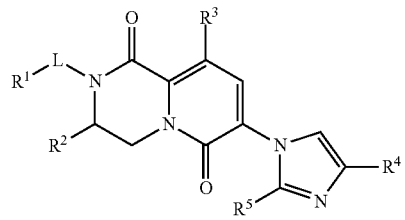

| Co. No. | Pr. | $R^1$ | L | $R^2$ | $R^3$ | $R^4$ | $R^5$ | Salt forms/ Stereo-chemistry/ Optical Rotation (OR) |
|---|---|---|---|---|---|---|---|---|
| 8 | B2 | ![structure] | $CH_2$ | $CH_3$ | H | $CH_3$ | H | R-enantiomer |
| 9 | B2 | ![structure] | $CH_2$ | $CH_3$ | H | $CH_3$ | H | R-enantiomer |
| 38 | B2 | ![structure] | ![structure] | $CH_3$ | H | $CH_3$ | H | R-enantiomer (OR: −42.91° (589 nm; 20° C.; 0.55 w/v %; DMF) |
| 39 | B2 | ![structure] | $CH_2$ | $CH_3$ | H | $CH_3$ | H | R-enantiomer |

TABLE 1a-continued

[Structure: core scaffold with R¹-L-N, R², R³, R⁴, R⁵ substituents on pyrido-pyrazine-dione with imidazole]

| Co. No. | Pr. | R¹ | L | R² | R³ | R⁴ | R⁵ | Salt forms/ Stereochemistry/ Optical Rotation (OR) |
|---|---|---|---|---|---|---|---|---|
| 10 | B2 | 4-bromothiophen-2-yl | CH₂ | CH₃ | H | CH₃ | H | R-enantiomer OR: +5.40° (589 nm; 20° C.; 0.5 w/v %; DMF) |
| 11 | B2 | 5-bromo-2,3-dihydrobenzofuran-7-yl | CH₂ | CH₃ | H | CH₃ | H | R-enantiomer |
| 12 | B2 | 2,2-dimethyl-2,3-dihydrobenzofuran-7-yl | CH₂ | CH₃ | H | CH₃ | H | R-enantiomer HCl salt |
| 13 | B2 | 5-bromobenzofuran-2-yl | CH₂ | CH₃ | H | CH₃ | H | R-enantiomer |
| 14 | B4 | 5-chlorobenzo[d]isoxazol-3-yl | CH₂ | CH₃ | H | CH₃ | H | R-enantiomer |
| 16 | B2 | 5-isopropyl-1-(2,2,2-trifluoroethyl)-1H-pyrazol-3-yl | CH₂ | CH₃ | H | CH₃ | H | R-enantiomer |
| 19 | B2 | 3-isopropyl-1-(2,2,2-trifluoroethyl)-1H-pyrazol-5-yl | CH₂ | CH₃ | H | CH₃ | H | R-enantiomer OR: +8.48° (589 nm; 20° C.; 0.495 w/v %; DMF) |
| 20 | B7 | 5-bromobenzo[d]isothiazol-3-yl | CH₂ | CH₃ | H | CH₃ | H | R-enantiomer OR: −85.14° (589 nm; 20° C.; 0.249 w/v %; DMF) |
| 21 | B7 | 7-bromobenzo[d]isothiazol-3-yl | CH₂ | CH₃ | H | CH₃ | H | R-enantiomer OR: −65.52° (589 nm; 20° C.; 0.174 w/v %; DMF) |

TABLE 1a-continued

| Co. No. | Pr. | R¹ | L | R² | R³ | R⁴ | R⁵ | Salt forms/ Stereochemistry/ Optical Rotation (OR) |
|---|---|---|---|---|---|---|---|---|
| 22 | B8 | benzisothiazol-3-yl | CH₂ | CH₃ | H | CH₃ | H | R-enantiomer OR: −78.37° (589 nm; 20° C.; 0.245 w/v %; DMF) |
| 24 | B2 | 5-chloro-1-methyl-1H-indazol-3-yl | CH₂ | CH₃ | H | CH₃ | H | R-enantiomer OR: −34.93° (589 nm; 20° C.; 0.375 w/v %; DMF) |
| 25 | B2 | 5-methyl-1-(2,2,2-trifluoroethyl)-1H-pyrazol-3-yl | CH₂ | CH₃ | H | CH₃ | H | R-enantiomer OR: +14.04° (589 nm; 20° C.; 0.4415 w/v %; DMF) |
| 26 | B2 | 5-(trifluoromethyl)benzofuran-2-yl | CH₂ | CH₃ | H | CH₃ | H | R-enantiomer OR: −37.29° (589 nm; 20° C.; 0.48 w/v %; DMF) |
| 28 | B2 | 5-(trifluoromethyl)thiophen-3-yl | CH₂ | CH₃ | H | CH₃ | H | R-enantiomer OR: −11.63° (589 nm; 20° C.; 0.49 w/v %; DMF) |
| 29 | B2 | 5-(2,2,2-trifluoroethyl)thiophen-3-yl | CH₂ | CH₃ | H | CH₃ | H | R-enantiomer OR: −7.45° (589 nm; 20° C.; 0.725 w/v %; DMF) |
| 31 | B2 | 3-(cyclopentyloxy)-4-methoxyphenyl | CH₂ | CH₃ | H | CH₃ | H | R-enantiomer |
| 32 | B10 | 3-phenoxyphenyl | CH₂ | CH₃ | H | CH₃ | H | R-enantiomer HCl salt |

TABLE 1a-continued
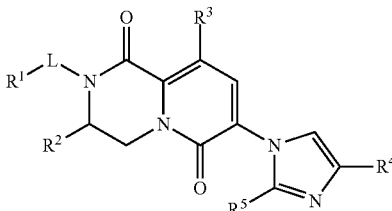
| Co. No. | Pr. | R¹ | L | R² | R³ | R⁴ | R⁵ | Salt forms/ Stereochemistry/ Optical Rotation (OR) |
|---|---|---|---|---|---|---|---|---|
| 33 | B2 | 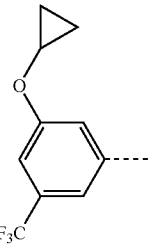 | CH₂ | CH₃ | H | CH₃ | H | R-enantiomer HCl salt |
| 41 | B2 | 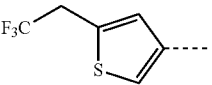 | 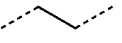 | CH₃ | H | CH₃ | H | R-enantiomer |
| 42 | B2 | 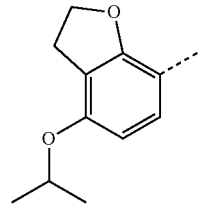 | CH₂ | CH₃ | H | CH₃ | H | R-enantiomer |
| 44 | B13 | 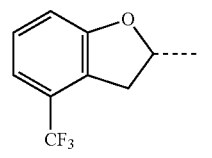 | CH₂ | H | H | CH₃ | H | Mixture of R and S |
| 40 | B13 | 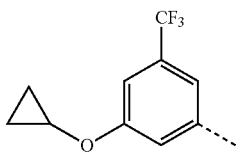 | 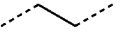 | CH₃ | H | CH₃ | H | R-enantiomer HCl salt |
| 53 | B13 | 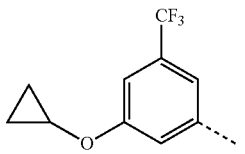 |  | CH₃ | H | CH₃ | H | R-enantiomer HCl salt |
| 54 | B2 | 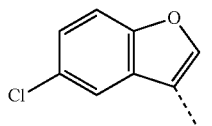 | CH₂ | H | H | CH₃ | H | |

TABLE 1a-continued
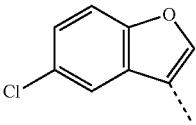
| Co. No. | Pr. | R¹ | L | R² | R³ | R⁴ | R⁵ | Salt forms/ Stereo- chemistry/ Optical Rotation (OR) |
|---|---|---|---|---|---|---|---|---|
| 55 | B2 | 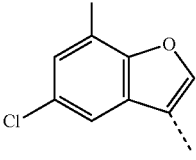 | CH₂ | CH₃ | H | CH₃ | H | R-enantiomer |
| 56 | B2 | 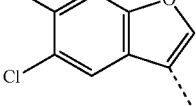 | CH₂ | H | H | CH₃ | H | |
| 59 | B2 |  | 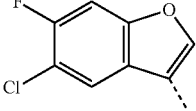 | H | H | CH₃ | H | Mixture of R and S |
| 60 | B2 |  | 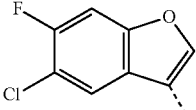 | H | H | CH₃ | H | R or S enantiomer |
| 61 | B2 |  | 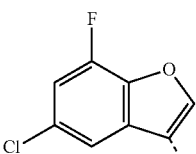 | H | H | CH₃ | H | S or R enantiomer |
| 62 | B2 | 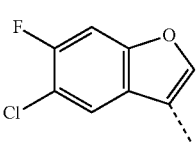 | CH₂ | CH₃ | H | CH₃ | H | R-enantiomer |
| 63 | B2 | 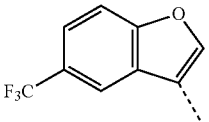 | CH₂ | CH₃ | H | CH₃ | H | R-enantiomer |
| 64 | B2 |  | CH₂ | H | H | CH₃ | H | |

TABLE 1a-continued
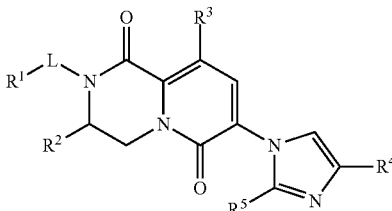
| Co. No. | Pr. | R¹ | L | R² | R³ | R⁴ | R⁵ | Salt forms/ Stereo- chemistry/ Optical Rotation (OR) |
|---|---|---|---|---|---|---|---|---|
| 67 | B5 | 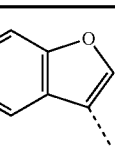 | CH₃ | H | H | CH₃ | H | S or R enantiomer |
| 68 | B5 | 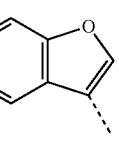 | CH₃ | H | H | CH₃ | H | R or S enantiomer |
| 69 | B2 | 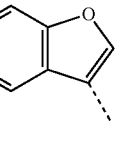 | CH₃ | H | H | CH₃ | H | S or R enantiomer |
| 70 | B2 | 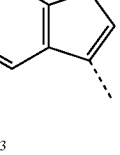 | CH₃ | H | H | CH₃ | H | R or S enantiomer |
| 71 | B2 | 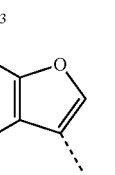 | CH₂ | CH₃ | H | CH₃ | H | R-enantiomer |
| 72 | B2 | 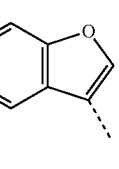 | CH₂ | CH₃ | H | CH₃ | H | R-enantiomer |
| 73 | B2 | 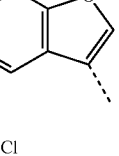 | CH₂ | CH₃ | H | CH₃ | H | R-enantiomer |
| 74 | B2 | 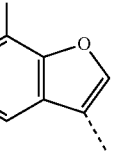 | CH₂ | CH₃ | H | CH₃ | H | R-enantiomer |

TABLE 1a-continued

| Co. No. | Pr. | R¹ | L | R² | R³ | R⁴ | R⁵ | Salt forms/ Stereochemistry/ Optical Rotation (OR) |
|---|---|---|---|---|---|---|---|---|
| 75 | B2 | 5-(OCF₃)-benzofuran-3-yl | CH₂ | H | H | CH₃ | H | |
| 76 | B2 | 5-Cl,6-F,7-F-benzofuran-3-yl | CH₂ | CH₃ | H | CH₃ | H | R-enantiomer |
| 77 | B2 | 7-Br-benzofuran-3-yl | CH₂ | CH₃ | H | CH₃ | H | R-enantiomer |
| 81 | B2 | 5-(OCF₃)-benzofuran-3-yl | CH(iPr) | H | H | CH₃ | H | S or R enantiomer |
| 82 | B2 | 5-(OCF₃)-benzofuran-3-yl | CH(iPr) | H | H | CH₃ | H | R or S enantiomer |
| 83 | B2 | 5-(OCF₃)-benzofuran-3-yl | CH₂ | CH₃ | H | CH₃ | H | R-enantiomer |
| 84 | B2 | 6-F,5-CF₃-benzofuran-3-yl | CH₂ | CH₃ | H | CH₃ | H | R-enantiomer |
| 85 | B2 | 6-CF₃,5-F-benzofuran-3-yl | CH₂ | CH₃ | H | CH₃ | H | R-enantiomer |

TABLE 1a-continued

| Co. No. | Pr. | R¹ | L | R² | R³ | R⁴ | R⁵ | Salt forms/ Stereo- chemistry/ Optical Rotation (OR) |
|---|---|---|---|---|---|---|---|---|
| 88 | B2 | 2-Cl-5-(trifluoromethyl)-4,5,6,7-tetrahydrobenzothiophen-3-yl | CH₂ | CH₃ | H | CH₃ | H | R-enantiomer |
| 93 | B2 | 5-chloro-7-(trifluoromethyl)benzofuran-3-yl | CH₂ | CH₃ | H | CH₃ | H | R-enantiomer |
| 94 | B2 | 5,6-dichlorobenzofuran-3-yl | CH₂ | H | H | CH₃ | H | |
| 97 | B2 | 6,7-dichlorobenzofuran-3-yl | CH₂ | CH₃ | H | CH₃ | H | R-enantiomer |
| 98 | B2 | 1-methyl-3-(trifluoromethyl)piperidin-3-yl | C(=O)CH₂ | CH₃ | H | CH₃ | H | R-enantiomer |
| 99 | B5 | 5-chloro-3-methylbenzofuran-3-yl | CH₂ | H | H | CH₃ | H | |
| 101 | B2 | 5-(trifluoromethyl)benzo[d]isoxazol-3-yl | CH₂ | CH₃ | H | CH₃ | H | R-enantiomer |
| 104 | B2 | 6-bromochroman-2-yl | CH₂ | CH₃ | H | CH₃ | H | R-enantiomer |

TABLE 1b
| Co. No. | Pr. | Structure | Salt forms |
|---|---|---|---|
| 1 | B1 | 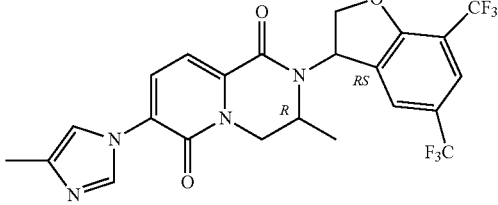 | HCl salt |
| 2 | B2 | 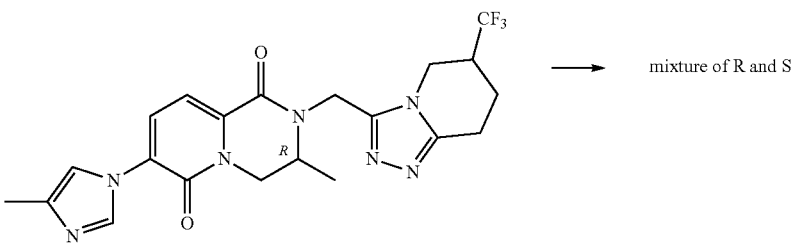 | → mixture of R and S |
| 3 | B2 | 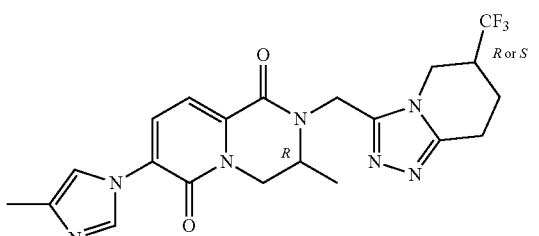 | |
| 4 | B2 | 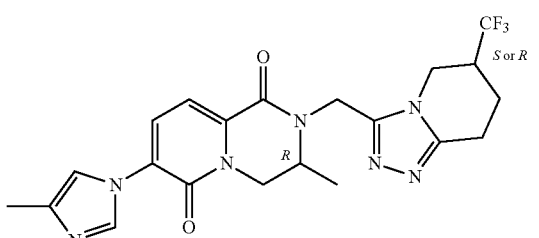 | |
| 5 | B3 | 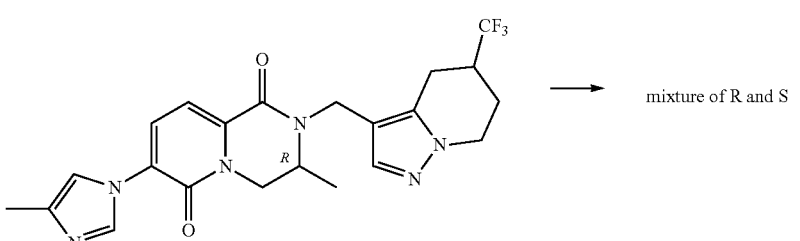 | → mixture of R and S |
| 6 | B3 | 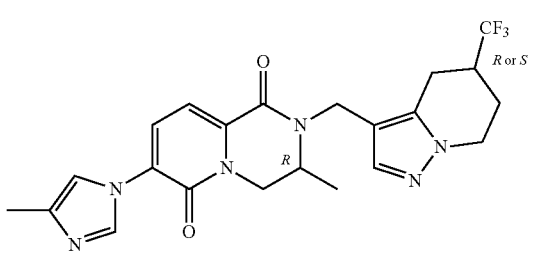 | |

TABLE 1b-continued

| Co. No. | Pr. | Structure | Salt forms |
|---|---|---|---|
| 7 | B3 | 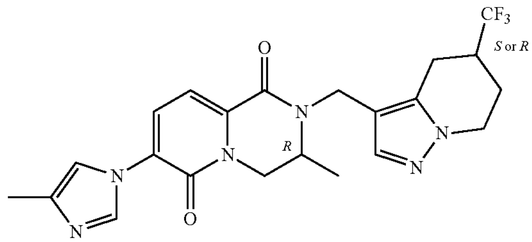 | |
| 15 | B5 | mixture of R and S (mixture of diastereoisomers 45/55 - NMR) | |
| 17 | B6 | 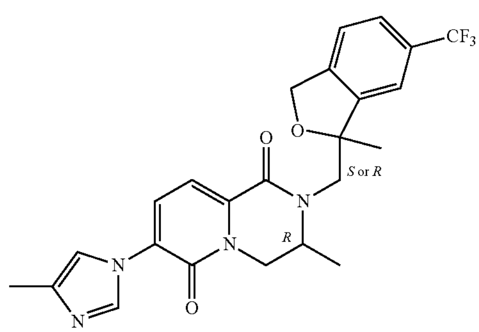 | |
| 18 | B6 | 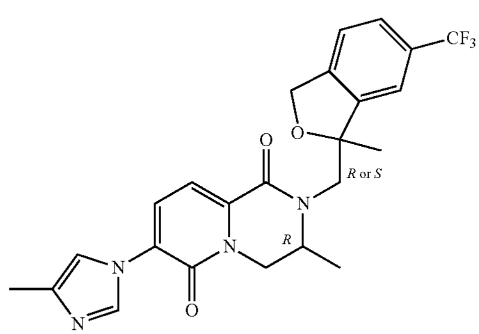 | |

TABLE 1b-continued

| Co. No. | Pr. | Structure | Salt forms |
|---|---|---|---|
| 34 | B2 | 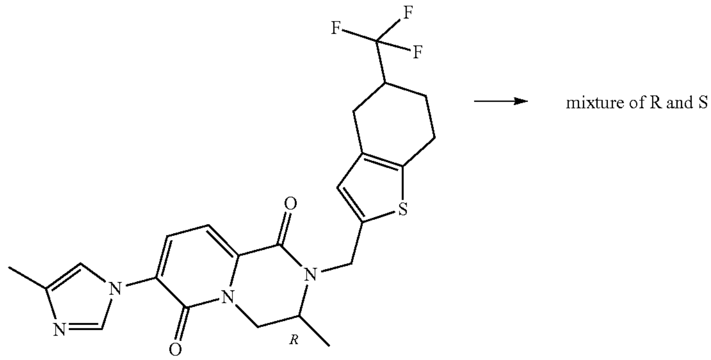 | mixture of R and S |
| 35 | B11 | 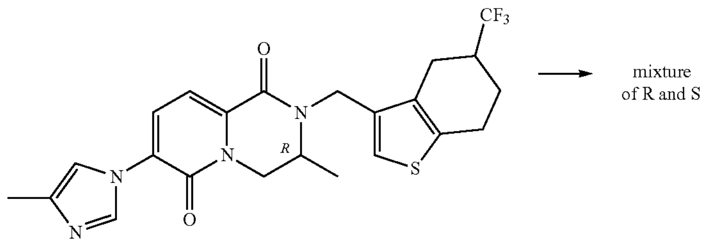 | mixture of R and S |
| 36 | B11 | 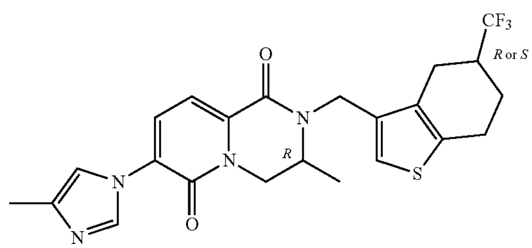 | R or S |
| 37 | B11 | 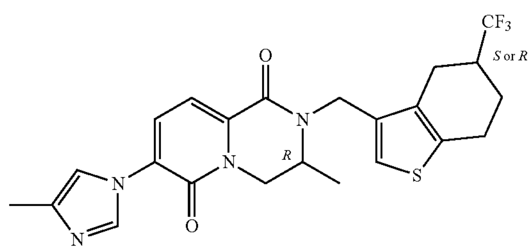 | S or R |
| 45 | B12 | 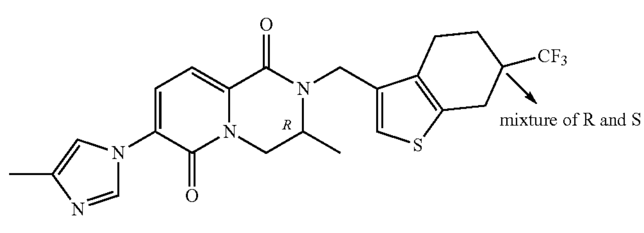 | mixture of R and S |
| 46 | B12 | 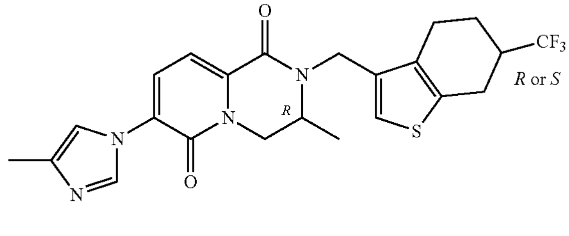 | R or S |

TABLE 1b-continued

| Co. No. | Pr. | Structure | Salt forms |
|---|---|---|---|
| 47 | B12 | 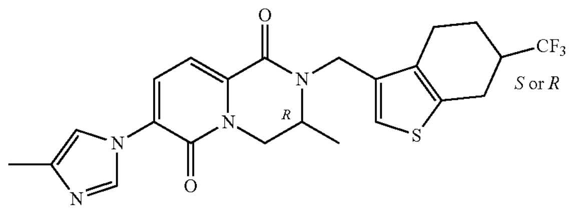 | |
| 48 | B13 | 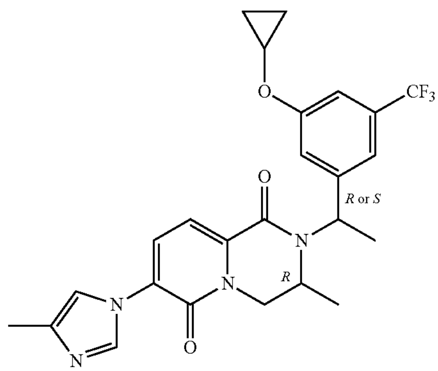 | HCl salt |
| 49 | B13 | 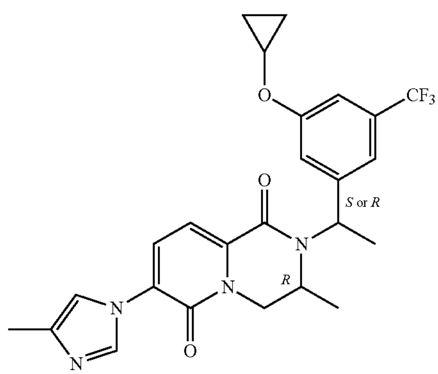 | HCl salt |
| 50* | B13 | 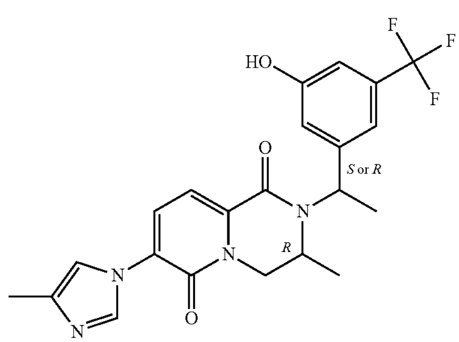 | HCl salt |
| 51 | B13 | 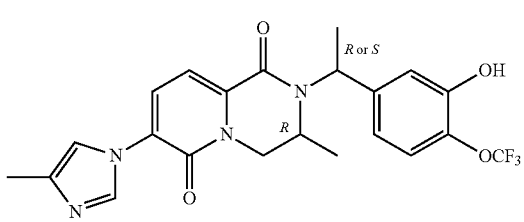 | HCl salt |

TABLE 1b-continued
| Co. No. | Pr. | Structure | Salt forms |
|---|---|---|---|
| 52 | B13 | 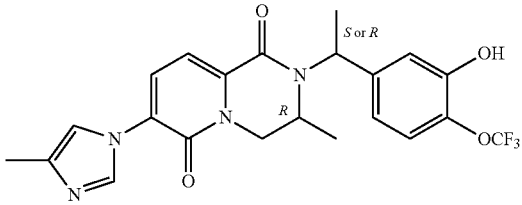 | HCl salt |
| 23 | B9 | 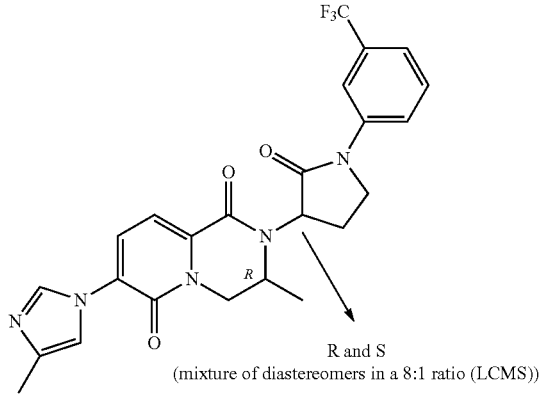 R and S (mixture of diastereomers in a 8:1 ratio (LCMS)) | |
| 27 | B2 | 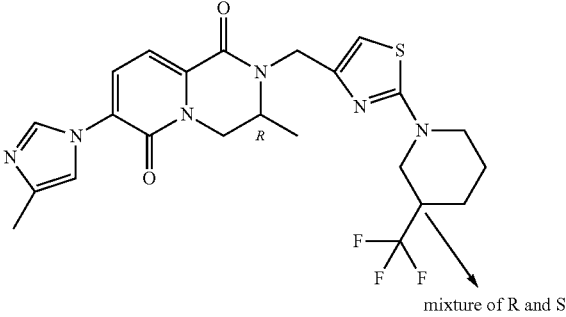 mixture of R and S | |
| 30 | B2 | 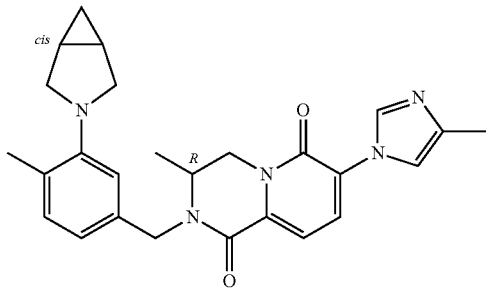 | HCl salt |
| 43 | B13 | 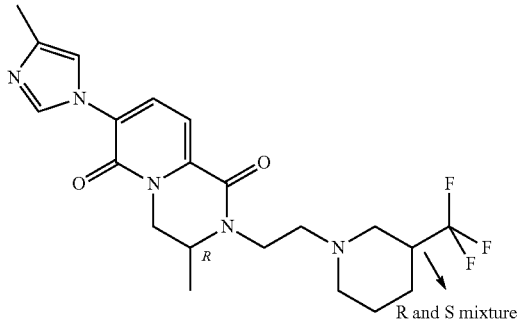 R and S mixture | HCl salt |

TABLE 1b-continued

| Co. No. | Pr. | Structure | Salt forms |
|---|---|---|---|
| 57 | B14 | 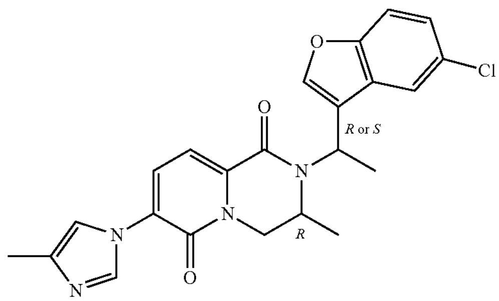 | |
| 58 | B14 | 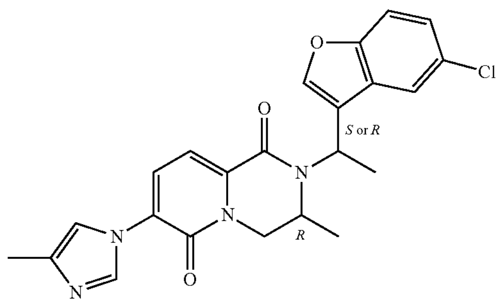 | |
| 65 | B15 | 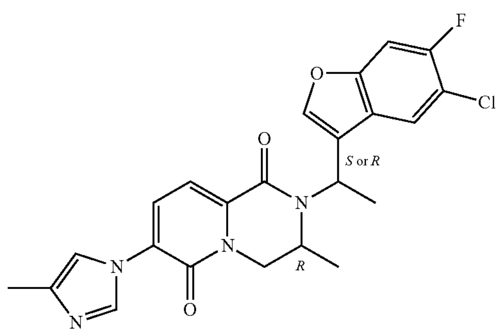 | |
| 66 | B15 | 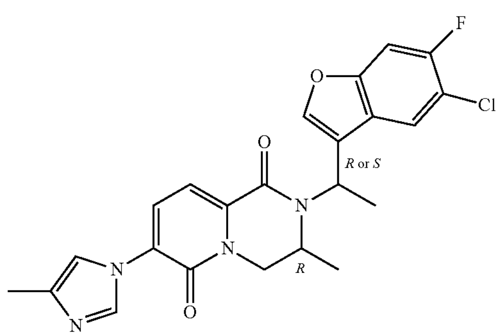 | |
| 78 | B2 | 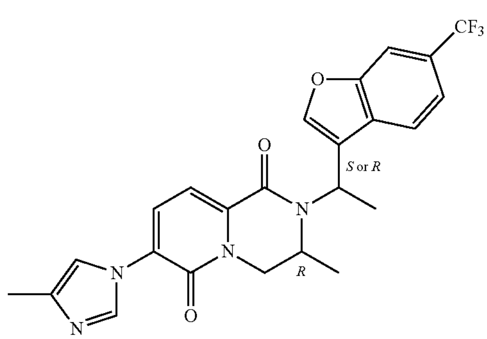 | |

TABLE 1b-continued

| Co. No. | Pr. | Structure | Salt forms |
|---|---|---|---|
| 79 | B2 | 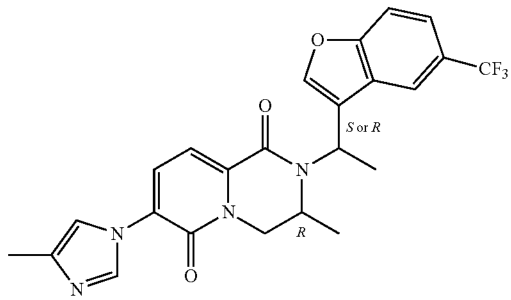 | |
| 80 | B2 | 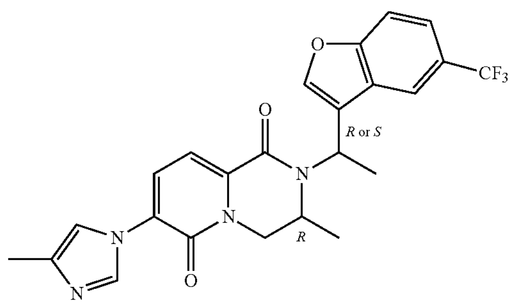 | |
| 86 | B2 | 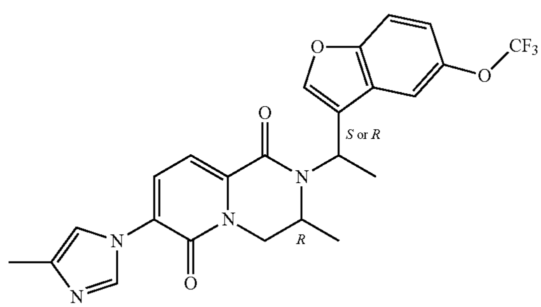 | |
| 87 | B2 | 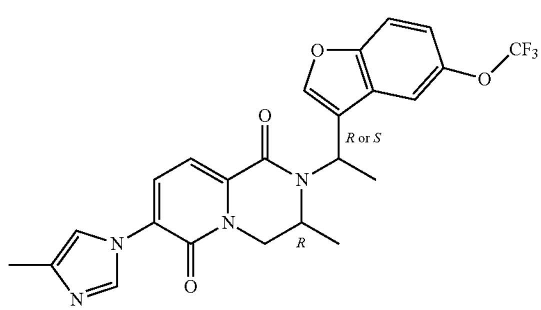 | |
| 88 | B2 | 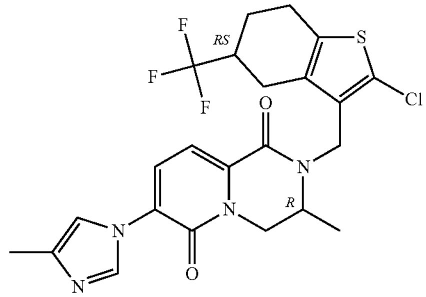 | |

TABLE 1b-continued

| Co. No. | Pr. | Structure | Salt forms |
|---|---|---|---|
| 89 | B16 | 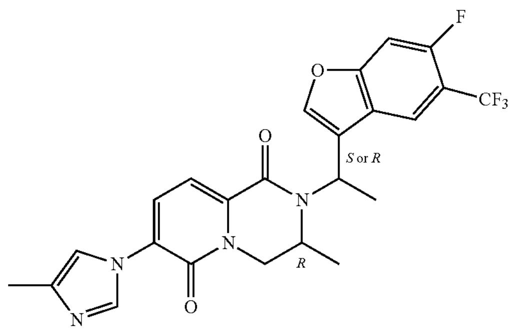 | |
| 90 | B16 | 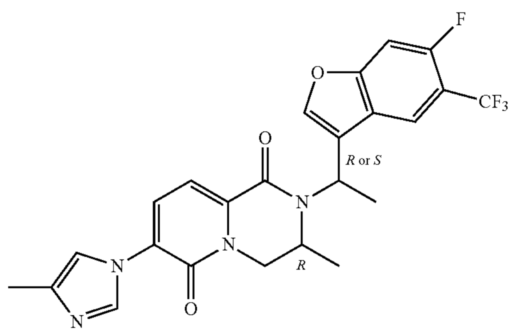 | |
| 91 | B2 | 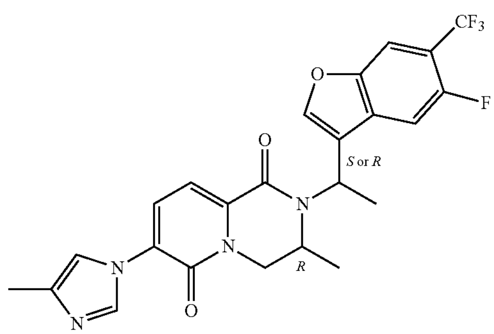 | |
| 92 | B2 | 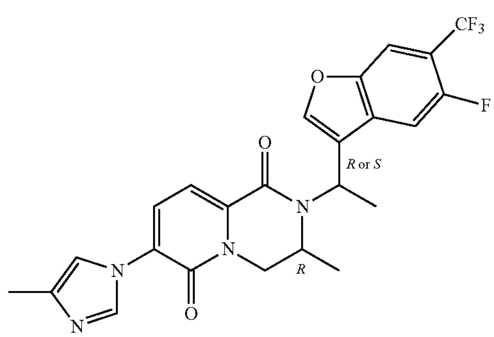 | |

TABLE 1b-continued

| Co. No. | Pr. | Structure | Salt forms |
|---|---|---|---|
| 95 | B2 | 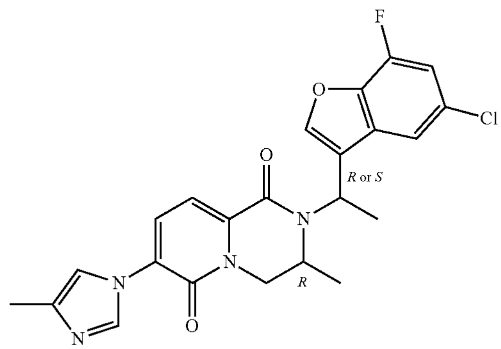 | |
| 96 | B2 | 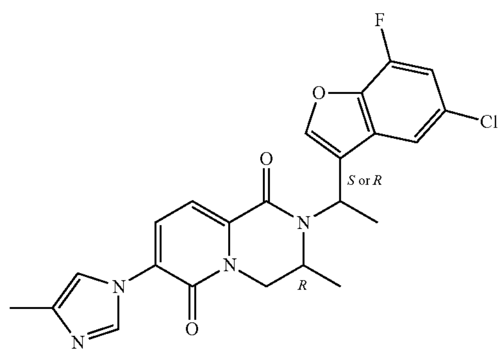 | |
| 100 | B17 | 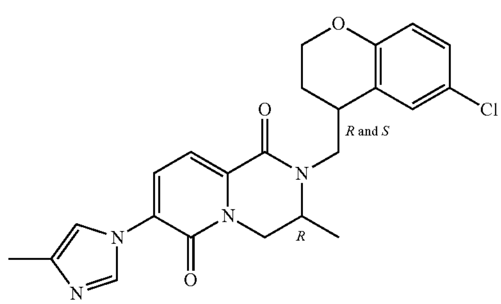 | |
| 102 | B2 | 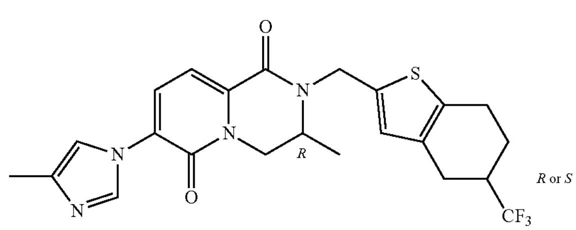 | |
| 103 | B2 | 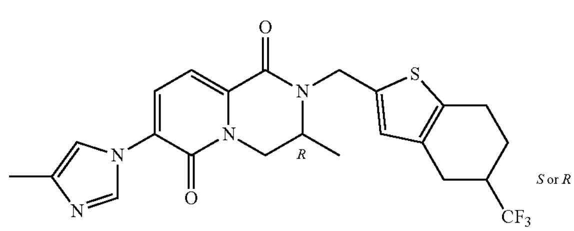 | |

*Compound 50 was obtained as a side-product during the reaction.

Analytical Part
LCMS (Liquid Chromatography/Mass Spectrometry)
LCMS General Procedure The High Performance Liquid Chromatography (HPLC) measurement was performed using a LC pump, a diode-array (DAD) or a UV detector and a column as specified in the respective methods. If necessary, additional detectors were included (see table of methods below).

Hereinafter, "SQD" means Single Quadrupole Detector, "MSD" Mass Selective Detector, "RT" room temperature, "BEH" bridged ethylsiloxane/silica hybrid, "DAD" Diode Array Detector, "HSS" High Strength silica., "Q-Tof" Quadrupole Time-of-flight mass spectrometers, "CLND", ChemiLuminescent Nitrogen Detector, "ELSD" Evaporative Light Scanning Detector.

TABLE 2

LCMS Method codes (Flow expressed in mL/min; column temperature (T) in ° C.; Run time in minutes)

| Method code | Instrument | Column | Mobile phase | Gradient | Flow Col T | Run time |
|---|---|---|---|---|---|---|
| 1 | Waters: Acquity® UPLC® - DAD and SQD | Waters: HSS T3 (1.8 μm, 2.1 * 100 mm) | A: 10 mM $CH_3COONH_4$ in 95% $H_2O$ + 5% $CH_3CN$ B: $CH_3CN$ | From 95% A to 0% A in 2.5 min, to 5% A in 0.5 min | 0.8 −55 | 3 |
| 2 | Waters: Acquity® UPLC® - DAD and SQD | Waters: HSS T3 (1.8 μm, 2.1 * 100 mm) | A: 10 mM $CH_3COONH_4$ in 95% $H_2O$ + 5% $CH_3CN$ B: $CH_3CN$ | From 100% A to 5% A in 2.10 min, to 0% A in 0.90 min, to 5% A in 0.5 min | 0.8 −55 | 3.5 |
| 3 | Waters: Alliance® - DAD - ZQ and ELSD 2000 Alltech | Waters: Xterra MS C18 (3.5 μm, 4.6 * 100 mm) | A: 25 mM $CH_3COONH_4$ in 95% $H_2O$ + 5% $CH_3CN$ B: $CH_3CN$ C: $CH_3OH$ D: (40% $CH_3CN$ and 40% $CH_3OH$ and 20% $H_2O$ with 0.25% $CH_3COOH$ | From 100% A to 1% A, 49% B and 50% C in 6.5 min, to 1% A and 99% B in 0.5 min, to 100% D in 1 min held for 1.0 min to 100% A in 0.5 min and held for 1.5 min. | 1.6 −40 | 11 |
| 4 | Waters: Acquity® UPLC® - DAD and SQD | Waters: BEH C18 (1.7 μm, 2.1 * 50 mm) | A: 10 mM $CH_3COONH_4$ in 95% $H_2O$ +5% $CH_3CN$ B: $CH_3CN$ | From 95% A to 5% A in 1.3 min, held for 0.7 min. | 0.8 −55 | 2 |
| 5 | Agilent 1100 - DAD-MSD G1956A | YMC-pack ODS-AQ C18 (50 x 4.6 mm, 3 μm) | A: 0.1% HCOOH in $H_2O$ B: $CH_3CN$ | From 95% A to 5% A in 4.8 min, held for 1.0 min, to 95% A in 0.2 min. | 2.6 −35 | 6.0 |
| 6 | Waters: Acquity® UPLC® - DAD and SQD | Waters: BEH C18 (1.7 μm, 2.1 * 50 mm) | A: 0.1% HCOOH + 5% $CH_3OH$ in $H_2O$ B: $CH_3CN$ | From 95% A to 0% A in 2.5 min, to 5% A in 0.5 min. | 0.8 −55 | 3 |
| 7 | Waters: Acquity® UPLC® - DAD and SQD | Waters: HSS T3 (1.8 μm, 2.1 * 100 mm) | A: 10 mM $CH_3COONH_4$ in 95% $H_2O$ + 5% $CH_3CN$ B: $CH_3CN$ | From 100% A to 5% A in 2.10 min, to 0% A in 0.90 min, to 5% A in 0.5 min | 0.7 −55 | 3.5 |

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software. Compounds are described by their experimental retention times ($R_t$) and ions. If not specified differently in the table of data, the reported molecular ion corresponds to the $[M+H]^+$ (protonated molecule) and/or $[M-H]^-$ (deprotonated molecule). For molecules with multiple isotopic patterns (e.g. Br, Cl), the reported value is the one obtained for the lowest isotope mass. All results were obtained with experimental uncertainties that are commonly associated with the method used.

Melting Points

For compounds 9, 13, 14, 19, 26, 28 and 29 melting points (m.p.) were determined with a DSC823e (Mettler-Toledo). The m.p. of compounds 13, 19, 26, 28 and 29 were measured with a temperature gradient of 10° C./min. The m.p. of compound 14 was measured with a temperature gradient of 30° C./min.

For compounds 30, 33, 40, 43, 44, 48, 51, 52 and 53 m.p. were determined in open capillary tubes on a Mettler FP62 apparatus. M.p. were measured with a temperature ranging from 50° C. to 300° C., using a gradient of 10° C./minute. The m.p. value was read from a digital display.

The results of the analytical measurements are shown in table 3.

TABLE 3

Retention time ($R_t$) in min., $[M + H]^+$ peak (protonated molecule), LCMS method and m.p. (melting point in °C.) (n.d. means not determined).

| Co. No. | $R_t$ | $[M + H]^+$ | LCMS Method | m.p. (°C.) |
|---|---|---|---|---|
| 1 | 2.79 | 513 | 5 | n.d. |
| 2 | 0.65 | 462 | 4 | n.d. |
| 3 | 0.64 | 462 | 4 | n.d. |
| 4 | 0.65 | 462 | 4 | n.d. |
| 5 | 0.77 | 461 | 4 | n.d. |
| 6 | 1.53 | 461 | 2 | n.d. |
| 7 | 1.53 | 461 | 2 | n.d. |
| 8 | 0.70 | 458 | 4 | n.d. |
| 9 | 1.62 | 457 | 2 | 170 |
| 38 | 0.80 | 432 | 4 | n.d. |
| 39 | 1.89 | 433 | 1 | n.d. |
| 10 | 0.87 | 433 | 4 | n.d. |
| 11 | 1.83 | 469 | 1 | n.d. |
| 12 | 0.96 | 418 | 4 | n.d. |
| 13 | 0.96 | 467 | 4 | 159 |
| 14 | 5.37 | 424 | 3 | 147 |
| 15 | 1.79 | 497 | 6 | n.d. |
| 16 | 0.87 | 463 | 4 | n.d. |
| 17 | 0.95 | 473 | 4 | n.d. |
| 18 | 0.96 | 473 | 4 | n.d. |
| 19 | 0.89 | 463 | 4 | 144 |
| 20 | 1.87 | 484 | 2 | n.d. |
| 21 | 1.85 | 484 | 2 | n.d. |
| 22 | 5.09 | 406 | 3 | n.d. |
| 23 | 1.61 | 486 | 2 | n.d. |
| 24 | 5.35 | 437 | 3 | n.d. |
| 25 | 0.76 | 435 | 4 | n.d. |
| 26 | 1.01 | 457 | 4 | 164 |
| 27 | 0.97 | 507 | 4 | n.d. |
| 28 | 0.91 | 423 | 4 | 162 |
| 29 | 0.89 | 437 | 4 | 110 |
| 30 | 2.36 | 444 | 5 | 122 |
| 31 | n.d. | n.d. | — | n.d. |
| 32 | 0.97 | 440 | 4 | n.d. |
| 33 | 2.52 | 473 | 5 | 149 |
| 34 | 1.90 | 477 | 2 | n.d. |
| 35 | 1.89 | 477 | 2 | n.d. |
| 36 | 1.89 | 477 | 2 | n.d. |
| 37 | 1.90 | 477 | 2 | n.d. |
| 41 | 0.92 | 451 | 4 | n.d. |
| 42 | 1.91 | 449 | 1 | n.d. |
| 43 | n.d. | n.d. | — | 138 |
| 44 | 2.21 | 445 | 5 | 128 |
| 45 | 1.04 | 477 | 4 | n.d. |
| 46 | 1.91 | 477 | 2 | n.d. |
| 47 | 1.90 | 477 | 2 | n.d. |
| 48 | 2.68 | 487 | 5 | 122 |
| 49 | 2.66 | 487 | 5 | n.d. |
| 50 | 2.09 | 447 | 5 | n.d. |
| 51 | n.d. | n.d. | — | 212 |
| 52 | n.d. | n.d. | — | 223 |
| 40 | 2.70 | 487 | 5 | 102 |
| 53 | 2.94 | 513 | 5 | 197 |
| 54 | 0.91 | 409 | 4 | n.d. |
| 55 | 0.94 | 423 | 4 | n.d. |
| 56 | 0.94 | 427 | 2 | 232 |
| 57 | 1.66 | 437 | 2 | n.d. |
| 58 | 1.64 | 437 | 2 | n.d. |
| 59 | 2.30 | 441 | 5 | n.d. |
| 60 | 1.63 | 441 | 2 | 234 |
| 61 | 1.63 | 441 | 2 | 231 |
| 62 | 1.67 | 441 | 2 | n.d. |
| 63 | 1.74 | 441 | 2 | n.d. |
| 64 | 1.60 | 443 | 2 | 211 |
| 65 | 2.43 | 455 | 5 | n.d. |
| 66 | 5.91 | 455 | 3 | n.d. |
| 67 | 1.68 | 457 | 2 | 200 |
| 68 | 1.68 | 457 | 2 | 204 |
| 69 | 1.74 | 457 | 2 | n.d. |
| 70 | 1.74 | 457 | 2 | n.d. |
| 71 | 1.72 | 457 | 2 | 225 |
| 72 | 1.72 | 457 | 2 | 215 |
| 73 | 1.75 | 457 | 2 | 187 |
| 74 | 1.87 | 457 | 2 | 202 |
| 75 | 1.73 | 459 | 2 | n.d. |
| 76 | 1.72 | 459 | 2 | n.d. |
| 77 | 1.68 | 467 | 2 | n.d. |
| 78 | 1.82 | 471 | 2 | n.d. |
| 79 | 1.79 | 471 | 2 | n.d. |
| 80 | 1.78 | 471 | 2 | n.d. |
| 81 | 1.68 | 473 | 2 | n.d. |
| 82 | 1.68 | 473 | 2 | n.d. |
| 83 | 1.79 | 473 | 2 | n.d. |
| 84 | 1.02 | 475 | 4 | 222 |
| 85 | 1.02 | 475 | 4 | 226 |
| 86 | 1.84 | 487 | 2 | n.d. |
| 87 | 1.82 | 487 | 2 | n.d. |
| 88 | 2.06 | 511 | 2 | n.d. |
| 89 | 1.73 | 489 | 2 | 230 |
| 90 | 1.71 | 489 | 2 | n.d. |
| 91 | 1.04 | 489 | 4 | n.d. |
| 92 | 1.03 | 489 | 4 | n.d. |
| 93 | 1.82 | 491 | 2 | n.d. |
| 94 | 1.88 | 443 | 7 | n.d. |
| 95 | 1.9 | 455 | 7 | n.d. |
| 96 | 1.92 | 455 | 7 | 201 |
| 97 | 1.05 | 457 | 4 | 227 |
| 98 | 0.8 | 452.8 | 4 | n.d. |
| 99 | 1.63 | 425 | 2 | n.d. |
| 100 | 1.72 | 439 | 2 | n.d. |
| 101 | 5.46 | 458 | 3 | 140 |
| 102 | 1.91 | 477 | 2 | n.d. |
| 103 | 1.91 | 477 | 2 | n.d. |
| 104 | 1.02 | 483 | 4 | n.d. |

NMR

For a number of compounds, $^1$H NMR spectra were recorded on a Bruker Avance III with a 300 MHz Ultrashield magnet, on a Bruker DPX-400 spectrometer operating at 400 MHz, on a Bruker DPX-360 operating at 360 MHz, or on a Bruker Avance 600 spectrometer operating at 600 MHz, using CHLOROFORM-d (deuterated chloroform, CDCl$_3$) or DMSO-d$_6$ (deuterated DMSO, dimethyl-d6 sulfoxide) as solvent. Chemical shifts (δ) are reported in parts per million (ppm) relative to tetramethylsilane (TMS), which was used as internal standard.

TABLE 4

$^1$H NMR results

| Co. No. | $^1$H NMR result |
|---|---|
| 3 | (360 MHz, DMSO-d$_6$) δ ppm 1.19 (d, J = 6.6 Hz, 3 H), 1.77-1.93 (m, 1 H), 2.15 (s, 4H), 2.87 (ddd, J = 17.2, 11.5, 6.0 Hz, 1 H), 2.96-3.24 (m, 2H), 3.84-4.04 (m, 3 H), 4.40 (dd, J = 12.3, 5.3 Hz, 1 H), 4.53 (d, J = 15.7 Hz, 1 H), 4.60 (dd, J = 13.9, 2.9 Hz, 1 H), 5.22 (d, J = 15.7 Hz, 1 H), 7.13 (d, J = 7.7 Hz, 1 H), 7.39-7.46 (m, 1 H), 7.81 (d, J = 7.7 Hz, 1 H), 8.28 (d, J = 1.5 Hz, 1 H) |

TABLE 4-continued

| | $^1$H NMR results |
|---|---|
| Co. No. | $^1$H NMR result |
| 4 | (360 MHz, DMSO-d$_6$) δ ppm 1.16 (d, J = 6.6 Hz, 3 H), 1.75-1.95 (m, 1 H), 2.10-2.26 (m, 4 H), 2.87 (ddd, J = 16.8, 11.0, 5.9 Hz, 1 H), 3.03 (dt, J = 16.6, 4.8 z, 1 H), 3.12-3.25 (m, 1 H), 3.89 (dd, J = 13.9, 4.0 Hz, 1 H), 3.93-4.13 (m, 2 H), 4.39 (dd, J = 12.4, 5.9 Hz, 1 H), 4.53-4.68 (m, 2 H), 5.15 (d, J = 15.7 Hz, 1 H), 7.03-7.24 (m, 1 H), 7.43 (s, 1 H), 7.81 (d, J = 8.1 Hz, 1H), 8.28 (d, J = 1.1 Hz, 1 H) |
| 6 | (360 MHz, CHLOROFORM-d) δ ppm 1.26 (d, J = 6.8 Hz, 3 H), 2.08 (qd, J = 12.4, 5.6 Hz, 1 H), 2.28 (s, 3 H), 2.38 (d, J = 13.9 Hz, 1 H), 2.55-2.67 (m, 1 H), 2.73 (dd, J = 16.1, 11.7 Hz, 1 H), 3.21 (dd, J = 16.1, 4.7 Hz, 1 H), 3.66 (dd, J = 14.1, 4.1 Hz, 1 H), 3.81-3.91 (m, 1 H), 4.01 (d, J = 15.0 Hz, 1 H), 4.11 (td, J = 12.5, 4.7 Hz, 1 H), 4.42 (dd, J = 13.4, 5.6 Hz, 1 H), 4.78 (d, J = 14.1 Hz, 1 H), 5.12 (d, J = 15.0 Hz, 1 H), 7.14 (s, 1 H), 7.21-7.31 (m, 1 H), 7.47 (d, J = 8.1 Hz, 1 H), 7.50 (s, 1 H), 8.23 (s, 1 H) |
| 7 | (360 MHz, CHLOROFORM-d) δ ppm 1.26 (d, J = 6.6 Hz, 3 H), 2.10 (dtd, J = 13.7, 11.7, 11.7, 5.6 Hz, 1 H), 2.29 (s, 3 H), 2.33-2.42 (m, 1 H), 2.56-2.69 (m, 1 H), 2.81 (dd, J = 16.5, 11.0 Hz, 1 H), 3.26 (ddd, J = 16.5, 5.3, 1.7 Hz, 1 H), 3.70 (dd, J = 14.2, 4.1 Hz, 1 H), 3.91 (qdd, J = 6.6, 6.6, 6.6, 4.2, 2.0 Hz, 1 H), 4.06 (d, J = 15.0 Hz, 1 H), 4.10 (td, J = 12.4, 4.8 Hz, 1 H), 4.42 (ddd, J = 13.1, 5.5, 2.7 Hz, 1 H), 4.80 (dd, J = 14.1, 2.3 Hz, 1 H), 5.04 (d, J = 15.1 Hz, 1 H), 7.14 (s, 1 H), 7.27 (d, J = 7.7 Hz, 1 H), 7.47 (d, J = 7.7 Hz, 1 H), 7.50 (s, 1 H), 8.24 (s, 1 H) |
| 8 | (400 MHz, DMSO-d$_6$) δ ppm 1.23 (d, J = 6.9 Hz, 3 H), 2.15 (s, 3 H), 3.81-3.98 (m, 1 H), 4.17 (br. s., 1 H), 4.59 (dd, J = 14.1, 2.8 Hz, 1 H), 5.08 (d, J = 15.7 Hz, 1 H), 5.59 (d, J = 15.7 Hz, 1 H), 7.13 (d, J = 8.1 Hz, 1 H), 7.42 (s, 1 H), 7.64 (d, J = 10.1 Hz, 1 H), 7.80 (d, J = 7.7 Hz, 1 H), 8.00 (d, J = 9.7 Hz, 1 H), 8.27 (s, 1 H), 9.19 (s, 1 H) |
| 9 | (360 MHz, DMSO-d$_6$) δ ppm 1.12 (d, J = 6.6 Hz, 3 H), 2.11-2.18 (m, 3 H), 3.76 (dd, J = 14.3, 4.0 Hz, 1 H), 4.07 (ddd, J = 6.5, 4.1, 2.2 Hz, 1 H), 4.59 (dd, J = 13.9, 2.2 Hz, 1 H), 4.67 (d, J = 15.0 Hz, 1 H), 5.17 (d, J = 15.0 Hz, 1 H), 7.11-7.18 (m, 2 H), 7.39-7.44 (m, 1 H), 7.81 (d, J = 7.7 Hz, 1 H), 8.26 (d, J = 1.5 Hz, 1 H), 8.31 (s, 1 H), 8.39-8.45 (m, 1 H), 8.90 (d, J = 7.3 Hz, 1 H) |
| 38 | (400 MHz, CHLOROFORM-d) δ ppm 1.28 (t, J = 6.3 Hz, 3 H), 2.29 (d, J = 1.2 Hz, 3 H), 2.90 (t, J = 5.9 Hz, 1 H), 2.99 (q, J = 6.1 Hz, 1 H), 3.67-3.78 (m, 1 H), 3.79-3.96 (m, 2 H), 3.98-4.14 (m, 1 H), 4.21 (dd, J = 14.1, 4.0 Hz, 1 H), 4.68 (m, J = 3.2 Hz, 1 H), 4.65-4.76 (m, 1 H), 5.10 (dd, J = 15.9, 10.3 Hz, 1 H), 7.08-7.25 (m, 6 H), 7.26 (s, 2 H), 7.44 (d, J = 7.7 Hz, 1 H), 8.24 (d, J = 1.2 Hz, 1 H) |
| 39 | (360 MHz, CHLOROFORM-d) δ ppm 1.22 (d, J = 6.6 Hz, 3 H), 1.33 (d, J = 6.6 Hz, 6 H), 1.76-1.85 (m, 2 H), 2.29 (s, 3 H), 2.76 (t, J = 6.8 Hz, 2 H), 3.62-3.70 (m, 1 H), 3.77-3.89 (m, 1 H), 3.98 (d, J = 14.6 Hz, 1 H), 4.76 (dd, J = 13.9, 2.2 Hz, 1 H), 5.31 (d, J = 14.6 Hz, 1 H), 6.76 (d, J = 9.1 Hz, 1 H), 6.99-7.06 (m, 2 H), 7.14 (s, 1 H), 7.31 (d, J = 7.7 Hz, 1 H), 7.47 (d, J = 7.7 Hz, 1 H), 8.23 (d, J = 1.5 Hz, 1 H) |
| 10 | (360 MHz, CHLOROFORM-d) δ ppm 1.27 (d, J = 6.6 Hz, 3 H), 2.29 (s, 3 H), 3.80 (dd, J = 14.1, 4.2 Hz, 1 H), 3.88-4.00 (m, 1 H), 4.37 (d, J = 15.4 Hz, 1 H), 4.77 (dd, J = 13.9, 2.6 Hz, 1 H), 5.34 (d, J = 15.4 Hz, 1 H), 7.01 (s, 1 H), 7.14 (s, 1 H), 7.20 (d, J = 1.5 Hz, 1 H), 7.31 (d, J = 7.7 Hz, 1 H), 7.47 (d, J = 7.7 Hz, 1 H), 8.25 (d, J = 1.1 Hz, 1 H) |
| 11 | (360 MHz, CHLOROFORM-d) δ ppm 1.25 (d, J = 6.6 Hz, 3 H), 2.24-2.33 (m, 3 H), 3.25 (t, J = 8.6 Hz, 2 H), 3.71-3.84 (m, 1 H), 3.95-4.06 (m, 1 H), 4.16 (d, J = 14.6 Hz, 1 H), 4.62 (td, J = 8.8, 2.9 Hz, 2 H), 4.78 (dd, J = 13.9, 2.2 Hz, 1 H), 5.11 (d, J = 15.0 Hz, 1 H), 7.14 (s, 1 H), 7.25-7.31 (m, 3 H), 7.46 (d, J = 7.7 Hz, 1 H), 8.23 (d, J = 1.1 Hz, 1 H) |
| 13 | (360 MHz, DMSO-d$_6$) δ ppm 1.12 (d, J = 6.6 Hz, 3 H), 2.15 (s, 3 H), 3.95 (dd, J = 14.1, 3.8 Hz, 1 H), 4.03-4.16 (m, 1 H), 4.63 (dd, J = 14.1, 2.4 Hz, 1 H), 4.75 (d, J = 16.1 Hz, 1 H), 5.07 (d, J = 16.1 Hz, 1 H), 6.96 (s, 1 H), 7.13 (d, J = 7.7 Hz, 1 H), 7.38-7.49 (m, 2 H), 7.56 (d, J = 8.4 Hz, 1 H), 7.77-7.90 (m, 2 H), 8.28 (d, J = 1.1 Hz, 1 H) |
| 14 | (360 MHz, CHLOROFORM-d) δ ppm 1.31 (d, J = 6.6 Hz, 3 H), 2.28 (s, 3 H), 3.69-3.81 (m, 1 H), 3.99-4.11 (m, 1 H), 4.62 (d, J = 15.0 Hz, 1 H), 4.75 (dd, J = 14.3, 2.9 Hz, 1 H), 5.57 (d, J = 15.4 Hz, 1 H), 7.14 (s, 1 H), 7.34 (d, J = 7.7 Hz, 1 H) 7.47 (d, J = 7.7 Hz, 1 H) 7.55 (s, 2 H) 7.87 (s, 1 H) 8.24 (s, 1 H) |
| 15 | (600 MHz, CHLOROFORM-d) δ ppm 1.19 (d, J = 6.7 Hz, 2 H), 1.28-1.34 (m, 6 H), 1.74-1.83 (m, 3 H), 1.84-1.95 (m, 4 H), 2.28 (d, J = 9.2 Hz, 4 H), 2.72 (dd, J = 5.7, 2.6 Hz, 1 H), 2.77-2.91 (m, 2 H), 3.16 (d, J = 14.2 Hz, 1 H), 3.24-3.32 (m, 1 H), 3.67 (dd, J = 14.2, 4.2 Hz, 1 H), 3.96 (dd, J = 14.1, 4.0 Hz, 1 H), 4.20-4.36 (m, 3 H), 4.25-4.29 (m, 1 H), 4.78 (dd, J = 14.2, 2.1 Hz, 1 H), 4.89 (dd, J = 14.1, 1.9 Hz, 1 H), 6.61-6.72 (m, 1 H), 7.11-7.29 (m, 7 H), 7.12-7.28 (m, 1 H), 7.12-7.19 (m, 1 H), 7.45 (dd, J = 17.2, 7.7 Hz, 1 H), 8.13-8.29 (m, 1 H)-mixture of diastereoisomers 45/55 |
| 17 | (360 MHz, CHLOROFORM-d) δ ppm 1.19 (d, J = 6.6 Hz, 3 H), 1.53 (s, 3 H), 2.25-2.32 (m, 3 H), 3.01 (d, J = 13.9 Hz, 1 H), 3.86 (dd, J = 14.3, 4.0 Hz, 1 H), 4.42 (dt, J = 4.4, 2.2 Hz, 1 H) 4.57 (d, J = 14.3 Hz, 1 H), 4.88 (dd, J = 14.3, 2.2 Hz, 1 H), 5.17 (d, J = 5.1 Hz, 2 H), 7.16 (t, J = 1.1 Hz, 1 H), 7.30 (d, J = 7.7 Hz, 1 H), 7.39 (d, J = 7.7 Hz, 1 H), 7.48 (d, J = 7.7 Hz, 1 H), 7.54 (s, 1 H), 7.62 (d, J = 8.1 Hz, 1 H), 8.26 (d, J = 1.5 Hz, 1 H) |

TABLE 4-continued

| Co. No. | ¹H NMR result |
|---|---|
| 18 | (360 MHz, CHLOROFORM-d) δ ppm 1.22 (d, J = 7.0 Hz, 3 H), 1.55 (s, 3 H), 2.27 (d, J = 1.1 Hz, 3 H), 3.28 (dd, J = 13.9, 4.0 Hz, 1 H), 3.35 (d, J = 14.6 Hz, 1 H), 4.29 (qdd, J = 6.7, 6.7, 6.7, 4.4, 2.2 Hz, 1 H), 4.63 (d, J = 14.3 Hz, 1 H), 4.68 (dd, J = 13.9, 2.2 Hz, 1 H), 5.15 (d, J = 3.3 Hz, 2 H), 7.08 (t, J = 1.1 Hz, 1 H), 7.14 (d, J = 7.7 Hz, 1 H), 7.29 (d, J = 8.1 Hz, 1 H), 7.37 (d, J = 7.7 Hz, 1 H), 7.53 (d, J = 7.0 Hz, 1 H), 7.60 (s, 1 H), 8.18 (d, J = 1.1 Hz, 1 H) |
| 19 | (360 MHz, CHLOROFORM-d) δ ppm 1.26 (d, J = 7.0 Hz, 9 H), 2.29 (s, 3 H), 2.97 (quin, J = 7.0 Hz, 1 H), 3.71 (dd, J = 14.3, 4.0 Hz, 1 H), 3.92-4.02 (m, 1 H), 4.30 (d, J = 15.7 Hz, 1 H), 4.77-4.86 (m, 2 H), 4.90-5.02 (m, 1 H), 5.20 (d, J = 15.7 Hz, 1 H), 6.18 (s, 1 H), 7.14 (s, 1 H), 7.29 (s, 1 H), 7.46 (d, J = 7.7 Hz, 1 H), 8.25 (d, J = 1.1 Hz, 1 H) |
| 20 | (400 MHz, DMSO-d₆) δ ppm 1.14 (d, J = 6.9 Hz, 3 H), 2.13-2.19 (m, 3 H), 3.93 (dd, J = 14.1, 4.0 Hz, 1 H), 4.09-4.17 (m, 1 H), 4.61 (dd, J = 14.1, 2.8 Hz, 1 H), 4.97 (d, J = 16.1 Hz, 1 H), 5.44 (d, J = 15.7 Hz, 1 H), 7.13 (d, J = 7.7 Hz, 1 H), 7.42 (s, 1 H), 7.77-7.83 (m, 2 H), 8.22 (d, J = 8.9 Hz, 1 H), 8.27 (d, J = 1.2 Hz, 1 H), 8.53 (d, J = 1.6 Hz, 1 H) |
| 21 | (400 MHz, DMSO-d₆) δ ppm 1.15 (d, J = 6.9 Hz, 3 H), 2.15 (d, J = 0.8 Hz, 3 H), 3.93 (dd, J = 14.1, 4.0 Hz, 1 H), 4.10-4.17 (m, 1 H), 4.61 (dd, J = 13.9, 3.0 Hz, 1 H), 4.99 (d, J = 16.1 Hz, 1 H), 5.47 (d, J = 16.1 Hz, 1 H), 7.13 (d, J = 7.7 Hz, 1 H), 7.42 (s, 1 H), 7.55 (dd, J = 8.1, 7.7 Hz, 1 H), 7.81 (d, J = 8.1 Hz, 1 H), 7.93 (dd, J = 7.3, 0.8 Hz, 1 H), 8.27 (d, J = 0.8 Hz, 1 H), 8.33 (dd, J = 8.1, 0.8 Hz, 1 H) |
| 22 | (360 MHz, DMSO-d₆) δ ppm 1.12 (d, J = 7.0 Hz, 3 H), 2.15 (s, 3 H), 3.92 (dd, J = 13.9, 4.0 Hz, 1 H), 4.07-4.18 (m, 1 H), 4.63 (dd, J = 13.9, 2.9 Hz, 1 H), 5.00 (d, J = 16.1 Hz, 1 H), 5.47 (d, J = 16.1 Hz, 1 H), 7.14 (d, J = 8.1 Hz, 1 H), 7.43 (s, 1 H), 7.56 (t, J = 7.5 Hz, 1 H), 7.62-7.69 (m, 1 H), 7.82 (d, J = 7.7 Hz, 1 H), 8.21-8.30 (m, 3 H) |
| 24 | (360 MHz, DMSO-d₆) δ ppm 1.09 (d, J = 7.0 Hz, 3 H), 2.15 (s, 3 H), 3.74 (dd, J = 14.1, 4.2 Hz, 1 H), 3.95-4.09 (m, 4 H), 4.57 (dd, J = 13.9, 2.6 Hz, 1 H), 4.74 (d, J = 15.0 Hz, 1 H), 5.25 (d, J = 15.0 Hz, 1 H), 7.17 (d, J = 7.7 Hz, 1 H), 7.38-7.46 (m, 2 H), 7.70 (d, J = 9.1 Hz, 1 H), 7.81 (d, J = 7.7 Hz, 1 H), 7.86-7.91 (m, 1 H), 8.26 (s, 1 H) |
| 25 | (360 MHz, CHLOROFORM-d) δ ppm 1.23 (d, J = 6.6 Hz, 3 H), 2.25-2.32 (m, 6 H), 3.76 (dd, J = 14.1, 4.2 Hz, 1 H), 3.97-4.05 (m, 1 H), 4.25 (d, J = 15.0 Hz, 1 H), 4.53-4.65 (m, 2 H), 4.74 (dd, J = 13.9, 2.6 Hz, 1 H), 5.13 (d, J = 14.6 Hz, 1 H), 6.11 (s, 1 H), 7.14 (s, 1 H), 7.29 (s, 1 H), 7.46 (d, J = 7.7 Hz, 1 H), 8.23 d, J = 1.5 Hz, 1 H) |
| 26 | (360 MHz, CHLOROFORM-d) δ ppm 1.31 (d, J = 6.6 Hz, 3 H), 2.29 (s, 3 H), 3.89 (dd, J = 14.1, 4.2 Hz, 1 H), 4.03-4.10 (m, 1 H), 4.52 (d, J = 15.7 Hz, 1 H), 4.78 (dd, J = 14.3, 2.9 Hz, 1 H), 5.27-5.35 (m, 1 H), 6.85 (s, 1 H), 7.14 (s, 1 H), 7.31 (d, J = 7.7 Hz, 1 H), 7.47 (d, J = 7.7 Hz, 1 H), 7.53-7.59 (m, 2 H), 7.86 (s, 1 H), 8.25 (d, J = 1.5 Hz, 1 H) |
| 28 | (360 MHz, CHLOROFORM-d) δ ppm 1.26 (d, J = 6.6 Hz, 3 H), 2.29 (d, J = 0.7 Hz, 3 H), 3.78 (dd, J = 14.1, 4.2 Hz, 1 H), 3.84-3.92 (m, 1 H), 4.27 (d, J = 15.4 Hz, 1 H), 4.78 (dd, J = 14.3, 2.6 Hz, 1 H), 5.17 (d, J = 15.0 Hz, 1 H), 7.14 (s, 1 H), 7.31 (d, J = 7.7 Hz, 1 H), 7.43 (s, 2 H), 7.48 (d, J = 7.7 Hz, 1 H), 8.25 (d, J = 1.5 Hz, 1 H) |
| 29 | (360 MHz, CHLOROFORM-d) δ ppm 1.22 (d, J = 7.0 Hz, 3 H), 2.29 (s, 3 H), 3.55 (q, J = 10.5 Hz, 2 H), 3.72 (dd, J = 14.1, 4.2 Hz, 1 H), 3.83-3.91 (m, 1 H), 4.23 (d, J = 15.0 Hz, 1 H), 4.78 (dd, J = 14.1, 2.4 Hz, 1 H), 5.16 (d, J = 15.0 Hz, 1 H), 6.99 (s, 1 H), 7.14 (s, 1 H), 7.18-7.21 (m, 1 H), 7.31 (d, J = 7.7 Hz, 1 H), 7.47 (d, J = 7.7 Hz, 1 H), 8.24 (d, J = 1.5 Hz, 1 H) |
| 30 | (300 MHz, DMSO-d₆) δ ppm 0.33 (td, J = 7.4, 4.3 Hz, 1 H), 0.52 (d, J = 3.3 Hz, 1 H), 0.92 (d, J = 6.5 Hz, 3 H), 1.39 (br. s., 2 H), 2.01 (s, 3 H), 2.18 (s, 3 H), 2.87 (br. s., 2 H), 3.18 (dd, J = 8.9, 4.2 Hz, 2 H), 3.69-3.79 (m, 2 H), 4.15 (d, J = 15.0 Hz, 1 H), 4.34-4.53 (m, 1 H), 4.83 (d, J = 14.8 Hz, 1 H), 6.58-6.83 (m, 2 H), 6.90 (d, J = 7.7 Hz, 1 H), 7.07 (d, J = 7.7 Hz, 1 H), 7.72 (t, J = 1.4 Hz, 1 H), 7.95 (d, J = 7.7 Hz, 1 H), 9.33-9.49 (m, 1 H) |
| 32 | (360 MHz, DMSO-d₆) δ ppm 1.11 (d, J = 6.6 Hz, 3 H), 2.33 (s, 3 H), 3.91 (dd, J = 14.1, 4.2 Hz, 1 H), 3.97 (d, J = 5.5 Hz, 1 H), 4.46 (d, J = 15.0 Hz, 1 H), 4.60 (dd, J = 13.7, 1.6 Hz, 1 H), 5.01 (d, J = 15.4 Hz, 1 H), 6.93 (dd, J = 8.2, 2.4 Hz, 1 H), 6.97-7.04 (m, 2 H), 7.06 (s, 1 H), 7.10-7.19 (m, 2 H), 7.21 (d, J = 7.7 Hz, 1 H), 7.34-7.44 (m, 3 H), 7.86 (s, 1 H), 8.09 (d, J = 7.7 Hz, 1 H), 9.50 (s, 1 H) |
| 33 | (300 MHz, DMSO-d₆) δ ppm 0.65-0.73 (m, 2 H), 0.78-0.88 (m, 2 H), 1.14 (d, J = 6.5 Hz, 3 H), 2.35 (s, 3 H), 3.91-4.09 (m, 3 H), 4.53 (d, J = 15.4 Hz, 1 H), 4.57-4.67 (m, 1 H), 5.08 (d, J = 15.3 Hz, 1 H), 7.25 (d, J = 7.7 Hz, 1 H), 7.28-7.39 (m, 3 H), 7.87 (s, 1 H), 8.11 (d, J = 7.7 Hz, 1 H), 9.51 (s, 1 H) |
| 34 | (600 MHz, CHLOROFORM-d) δ ppm 1.26 (d, J = 6.7 Hz, 3 H), 1.77 (qd, J = 12.5, 5.6 Hz, 1 H), 2.21-2.27 (m, 1 H), 2.29 (d, J = 1.1 Hz, 3 H), 2.42-2.51 (m, 1 H), 2.62 (dd, J = 14.7, 12.6 Hz, 1 H), 2.73-2.81 (m, 1 H), 2.87 (dd, J = 16.1, 5.3 Hz, 1 H), 2.88-2.93 (m, 1 H), 3.78 (dd, J = 14.1, 4.1 Hz, 1 H), 3.92-3.98 (m, 1 H), 4.26 (d, J = 15.3 Hz, 1 H), 4.76 (dt, J = 14.1, 2.3 Hz, 1 H), 5.34 (d, J = 15.3 Hz, 1 H), 6.74 (s, 1 H), 7.14 (s, 1 H), 7.30 (d, J = 8.4 Hz, 1 H), 7.46 (d, J = 7.6 Hz, 1 H), 8.24 (d, J = 1.4 Hz, 1 H) |

TABLE 4-continued

¹H NMR results

| Co. No. | ¹H NMR result |
|---|---|
| 36 | (360 MHz, CHLOROFORM-d) δ ppm 1.22 (d, J = 6.6 Hz, 3 H), 1.73-1.84 (m, 1 H), 2.22-2.31 (m, 4 H), 2.38-2.53 (m, 2 H), 2.78-2.91 (m, 2 H), 2.93-3.02 (m, 1 H) 3.70 (dd, J = 14.3, 4.0 Hz, 1 H), 3.78-3.86 (m, 1 H), 4.10 (d, J = 15.4 Hz, 1 H), 4.80 (dd, J = 14.3, 2.2 Hz, 1 H), 5.22 (d, J = 15.0 Hz, 1 H), 7.03 (s, 1 H), 7.15 (t, J = 1.1 Hz, 1 H), 7.32 (d, J = 7.7 Hz, 1 H), 7.48 (d, J = 7.7 Hz, 1 H), 8.24 (d, J = 1.5 Hz, 1 H) |
| 37 | (360 MHz, CHLOROFORM-d) δ ppm 1.20 (d, J = 7.0 Hz, 3 H), 1.72-1.85 (m, 1 H), 2.20-2.33 (m, 4 H), 2.39-2.60 (m, 2 H), 2.76-2.90 (m, 2 H), 2.90-3.02 (m, 1 H) 3.75 (dd, J = 14.1, 4.2 Hz, 1 H), 3.83-3.94 (m, 1 H), 4.21 (d, J = 15.4 Hz, 1 H), 4.77-4.87 (m, 1 H), 5.08 (d, J = 15.4 Hz, 1 H), 7.00 (s, 1 H), 7.14 (s, 1 H), 7.31 (d, J = 7.7 Hz, 1 H), 7.47 (d, J = 7.7 Hz, 1 H), 8.24 (d, J = 1.5 Hz, 1 H) |
| 41 | (360 MHz, CHLOROFORM-d) δ ppm 1.19 (d, J = 6.6 Hz, 3 H), 2.29 (s, 3 H), 2.91-3.10 (m, 2 H) 3.13-3.25 (m, 1 H) 3.50-3.62 (m, 4 H) 4.22-4.33 (m, 1 H), 4.64-4.71 (m, 1 H), 6.94 (s, 1 H), 7.00 (s, 1 H), 7.13 (s, 1 H), 7.24 (d, J = 7.7 Hz, 1 H), 7.45 (d, J = 7.7 Hz, 1 H), 8.23 (s, 1 H) |
| 42 | (360 MHz, DMSO-$d_6$) δ ppm 1.08 (d, J = 6.6 Hz, 3 H), 1.26 (d, J = 5.9 Hz, 6 H), 2.15 (s, 3 H), 3.06 (t, J = 8.8 Hz, 2 H), 3.74-3.85 (m, 1 H), 3.85-4.00 (m, 1 H) 4.24 (d, J = 14.6 Hz, 1 H), 4.48-4.70 (m, 4 H), 4.84 (d, J = 15.0 Hz, 1 H), 6.48 (d, J = 8.4 Hz, 1 H), 7.04 (d, J = 8.4 Hz, 1 H), 7.10 (d, J = 7.7 Hz, 1 H), 7.42 (s, 1 H), 7.81 (d, J = 8.1 Hz, 1 H), 8.23-8.33 (m, 1 H) |
| 44 | (300 MHz, DMSO-$d_6$) δ ppm 2.16 (s, 3 H), 3.17 (dd, J = 16.6, 6.7 Hz, 1 H), 3.51 (dd, J = 16.5, 9.2 Hz, 1 H), 3.71-3.93 (m, 4 H), 4.07 (ddd, J = 14.2, 7.7, 4.4 Hz, 1 H), 4.20-4.36 (m, 1 H), 5.13-5.28 (m, 1 H), 7.10 (d, J = 7.7 Hz, 2 H), 7.17 (d, J = 7.7 Hz, 1 H), 7.35 (t, J = 7.8 Hz, 1 H), 7.39-7.44 (m, 1 H), 7.79 (d, J = 7.8 Hz, 1 H), 8.26 (d, J = 1.0 Hz, 1 H) |
| 46 | (360 MHz, CHLOROFORM-d) δ ppm 1.21 (d, J = 6.6 Hz, 3 H), 1.70-1.79 (m, 1 H), 2.15-2.26 (m, 1 H), 2.29 (s, 3 H), 2.43 (d, J = 17.9 Hz, 2 H), 2.72-2.91 (m, 2 H), 3.07 (dd, J = 16.3, 5.3 Hz, 1 H), 3.64 (dd, J = 14.3, 4.4 Hz, 1 H), 3.82 (ddd, J = 6.9, 4.5, 2.2 Hz, 1 H), 4.06 (d, J = 15.0 Hz, 1 H), 4.76-4.86 (m, 1 H), 5.27 (d, J = 15.0 Hz, 1 H), 7.05 (s, 1 H), 7.15 (s, 1 H), 7.31 (d, J = 7.7 Hz, 1 H), 7.48 (d, J = 7.7 Hz, 1 H), 8.24 (s, 1 H) |
| 47 | (360 MHz, CHLOROFORM-d) δ ppm 1.17 (d, J = 7.0 Hz, 3 H), 1.72-1.81 (m, 1 H), 2.15-2.26 (m, 1 H), 2.29 (s, 3 H), 2.42-2.60 (m, 2 H), 2.69-2.91 (m, 2 H), 3.00-3.13 (m, 1 H), 3.68 (dd, J = 14.3, 4.4 Hz, 1 H), 3.79-3.92 (m, 1 H), 4.23 (d, J = 15.0 Hz, 1 H), 4.82 (dd, J = 14.3, 2.2 Hz, 1 H), 5.09 (d, J = 15.0 Hz, 1 H), 7.04 (s, 1 H), 7.14 (s, 1 H), 7.30 (d, J = 7.7 Hz, 1 H), 7.44-7.51 (m, 1 H), 8.24 (s, 1 H) |
| 48 | (300 MHz, DMSO-d6) δ ppm 0.64-0.72 (m, 2 H), 0.76-0.87 (m, 2 H), 1.18 (d, J = 6.6 Hz, 3 H), 1.66 (d, J = 7.1 Hz, 3 H), 2.31 (s, 3 H), 3.62 (dd, J = 13.9, 3.8 Hz, 1 H), 3.93-4.05 (m, 2 H), 4.60 (d, J = 14.0 Hz, 1 H), 5.69 (q, J = 7.1 Hz, 1 H), 7.19 (d, J = 7.7 Hz, 1 H), 7.29-7.36 (m, 3 H), 7.82 (s, 1 H), 8.07 (d, J = 7.8 Hz, 1 H), 9.41 (s, 1 H) |
| 49 | (300 MHz, DMSO-$d_6$) δ ppm 0.74 (d, J = 6.3 Hz, 5 H), 0.80-0.97 (m, 2 H), 1.76 (d, J = 7.1 Hz, 3 H), 2.38 (s, 3 H), 3.96 (dd, J = 14.0, 3.6 Hz, 1 H), 4.02-4.14 (m, 1 H), 4.25-4.43 (m, 1 H), 4.68 (d, J = 13.7 Hz, 1 H), 5.67-5.86 (m, 1 H), 7.29 (d, J = 7.7 Hz, 1 H), 7.35-7.49 (m, 3 H), 7.88 (s, 1 H), 8.13 (d, J = 7.7 Hz, 1 H), 9.45 (s, 1 H) |
| 51 | (300 MHz, DMSO-$d_6$) δ ppm 1.12 (br. s., 2 H), 1.20 (br. s., 2 H), 1.61 (br. s., 2 H), 2.35 (br. s., 2 H), 3.68 (d, J = 15.7 Hz, 2 H), 3.95 (br. s., 1 H), 4.64 (d, J = 15.3 Hz, 1 H), 5.67 (br. s., 1 H), 6.93 (br. s., 1 H), 7.10 (br. s., 1 H), 7.27 (br. s., 1 H), 7.88 (br. s., 1 H), 8.11 (br. s., 1 H), 9.52 (br. s., 1 H), 10.28 (br. s., 1 H) |
| 52 | (400 MHz, DMSO-d6) δ ppm 0.64 (d, J = 6.5 Hz, 3 H), 1.61 (d, J = 6.9 Hz, 3 H), 2.34 (s, 3 H), 3.89 (dd, J = 13.9, 3.8 Hz, 1 H), 4.10-4.22 (m, 1 H), 4.61 (d, J = 12.5 Hz, 1 H), 5.68 (q, J = 7.3 Hz, 1 H), 6.96 (dd, J = 8.5, 2.0 Hz, 1 H), 7.15 (d, J = 2.0 Hz, 1 H), 7.22 (d, J = 7.7 Hz, 1 H), 7.26 (dd, J = 8.3, 1.0 Hz, 1 H), 7.86 (s, 1 H), 8.11 (d, J = 7.7 Hz, 1 H), 9.52 (d, J = 1.6 Hz, 1 H), 10.32 (s, 1 H) |
| 56 | (360 MHz, DMSO-d6) δ ppm 2.15 (d, J = 1.1 Hz, 3 H), 3.69 (t, J = 5.9 Hz, 2 H) 4.21 (t, J = 5.5 Hz, 2 H), 4.81 (br. s, 2 H) 7.18 (d, J = 7.7 Hz, 1 H) 7.41 (t, J= 1.1 Hz, 1 H) 7.50 (dd, J = 10.7, 1.9 Hz, 1 H) 7.63 (d, J = 1.9 Hz, 1 H) 7.81 (d, J = 7.7 Hz, 1 H) 8.25 (d, J = 1.4 Hz, 1 H), 8.29 (s, 1 H) |
| 57 | (360 MHz, CHLOROFORM-d) δ ppm 0.62 (d, J = 6.6 Hz, 3 H) 1.72 (d, J = 6.9 Hz, 3 H) 2.29 (s, 3 H) 3.67 (dd, J = 14.1, 3.8 Hz, 1 H) 3.94-4.03 (m, 1 H) 4.87 (dd, J = 14.1, 1.7 Hz, 1 H) 6.22 (dd, J = 13.9, 6.6 Hz, 1 H) 7.13 (br. s, 1 H) 7.29 (dd, J = 8.8, 2.2 Hz, 1 H) 7.37-7.41 (m, 1 H) 7.42 (d, J = 8.8 Hz, 1 H) 7.50 (d, J = 7.7 Hz, 1 H) 7.58 (d, J = 2.2 Hz, 1 H) 7.71 (br. s, 1 H) 8.24 (d, J = 1.1 Hz, 1 H) |
| 61 | (360 MHz, CHLOROFORM-d) δ ppm 1.66 (d, J = 7.0 Hz, 3 H) 2.28 (s, 3 H) 3.26 (ddd, J = 13.4, 6.3, 4.0 Hz, 1 H) 3.47-3.60 (m, 1 H) 3.83-3.96 (m, 1 H) 4.41 (ddd, J = 14.3, 6.4, 3.8 Hz, 1 H) 6.23 (q, J = 6.9 Hz, 1 H) 7.13 (br. s, 1 H) 7.33 (d, J = 8.6 Hz, 1 H) 7.40 (d, J = 7.7 Hz, 1 H) 7.49 (d, J = 7.7 Hz, 1 H) 7.52 (d, J = 7.1 Hz, 1 H) 7.68 (d, J = 1.3 Hz, 1 H) 8.21 (br. s, 1 H) |
| 62 | (360 MHz, DMSO-d6) δ ppm 1.12 (d, J = 6.6 Hz, 3 H) 2.15 (d, J = 0.7 Hz, 3 H) 3.79 (dd, J = 14.1, 4.2 Hz, 1 H) 4.00-4.08 (m, 1 H) 4.53 (d, J = 15.4 Hz, 1 H) 4.60 (dd, J = 14.2, 2.2 Hz, 1 H) 5.09 (dd, J = 14.6, 0.73 Hz, 1 H) 7.18 (d, J = 7.7 Hz, 1 H) 7.43 (t, J = 1.1 Hz, 1 H) 7.50 (dd, J = 10.7, 1.9 Hz, 1 H) 7.67 (d, J = 1.8 Hz, 1 H) 7.83 (d, J = 7.7 Hz, 1 H) 8.27 (d, J = 1.4 Hz, 1 H) 8.31 (br. s, 1 H) |

TABLE 4-continued

¹H NMR results

| Co. No. | ¹H NMR result |
|---|---|
| 65 | (300 MHz, DMSO-d6) δ ppm 0.51 (d, J = 6.5 Hz, 3 H) 1.70 (d, J = 6.9 Hz, 3 H) 2.16 (s, 3 H) 3.84 (dd, J = 13.8, 3.37 Hz, 1 H) 4.19 (br. s., 1 H) 4.65 (d, J = 13.5 Hz, 1 H) 5.97 (q, J = 6.6 Hz, 1 H) 7.24 (d, J = 7.7 Hz, 1 H) 7.42 (s, 1 H) 7.68 (d, J = 7.4 Hz, 1 H) 7.83 (d, J = 7.8 Hz, 1 H) 7.88 (d, J = 9.4 Hz, 1 H) 8.27 (br. s., 1 H) 8.29 (s, 1 H) |
| 69 | (360 MHz, CHLOROFORM-d) δ ppm 1.71 (d, J = 7.0 Hz, 3 H) 2.28 (d, J = 0.9 Hz, 3 H) 3.24 (ddd, J = 13.4, 6.9, 3.9 Hz, 1 H) 3.55 (ddd, J = 13.2, 8.7, 3.9 Hz, 1 H) 3.96 (ddd, J = 14.3, 8.5, 3.9 Hz, 1 H) 4.35 (ddd, J = 10.7, 7.0, 3.5 Hz, 1 H) 6.31 (qd, J = 7.0, 1.2 Hz, 1 H) 7.12 (br. s, 1 H) 7.41 (d, J = 7.7 Hz, 1 H) 7.49 (d, J = 7.7 Hz, 1 H) 7.61 (d, J = 1.3 Hz, 2 H) 7.76 (d, J= 1.5 Hz, 1 H) 7.81 (s, 1 H) 8.21 (d, J = 1.2 Hz, 1 H) |
| 73 | (400 MHz, CHLOROFORM-d) δ ppm 1.25 (d, J = 6.7 Hz, 3 H) 2.28 (d, J = 0.9 Hz, 3 H) 3.65 (dd, J = 14.15, 4.15 Hz, 1 H) 3.84-3.95 (m, 1 H) 4.40 (d, J = 15.16 Hz, 1 H) 4.76 (dd, J = 14.15, 2.45 Hz, 1 H) 5.38 (dd, J = 15.16, 1.11 Hz, 1 H) 7.13 (t, J = 1.0 Hz, 1 H) 7.36 (d, J = 7.69 Hz, 1 H) 7.48 (d, J = 7.69 Hz, 1 H) 7.61 (d, J = 1.25 Hz, 2 H) 7.81 (s, 1 H) 7.97 (s, 1 H) 8.23 (d, J = 1.36 Hz, 1 H) |
| 78 | (360 MHz, CHLOROFORM-d) δ ppm 0.58 (d, J = 6.6 Hz, 3 H) 1.74 (d, J = 7.3 Hz, 3 H) 2.27 (s, 3 H) 3.68 (dd, J = 13.9, 3.3 Hz, 1 H) 3.95-4.03 (m, 1 H) 4.86 (dd, J = 13.9, 1.5 Hz, 1 H) 6.30 (dd, J = 13.5, 6.2 Hz, 1 H) 7.13 (s, 1 H) 7.37 (d, J = 7.7 Hz, 1 H) 7.48 (d, J = 7.7 Hz, 1 H) 7.52 (d, J = 8.8 Hz, 1 H) 7.73 (d, J = 8.4 Hz, 1 H) 7.78 (s, 1 H) 7.82 (s, 1 H) 8.23 (s, 1 H) |
| 89 | (360 MHz, CHLOROFORM-d) δ ppm 0.62 (d, J = 6.6 Hz, 3 H) 1.75 (d, J = 6.9 Hz, 3 H) 2.28 (s, 3 H) 3.69 (dd, J = 13.9, 3.7 Hz, 1 H) 3.94-4.07 (m, 1 H) 4.87 (dd, J = 13.9, 1.5 Hz, 1 H) 6.26 (dd, J = 13.5, 7.3 Hz, 1 H) 7.13 (br. s, 1 H) 7.35 (d, J = 9.9 Hz, 1 H) 7.39 (d, J = 7.7 Hz, 1 H) 7.50 (d, J = 7.7 Hz, 1 H) 7.77 (d, J = 1.1 Hz, 1 H) 7.91 (d, J = 6.6 Hz, 1 H) 8.20-8.28 (m, 1 H) |
| 94 | (360 MHz, CHLOROFORM-d) δ ppm 2.28 (br. s, 3 H) 3.61 (t, J = 5.8 Hz, 2 H) 4.29 (t, J = 5.5 Hz, 2 H) 4.84 (br. s, 2 H) 7.12 (s, 1 H) 7.38 (d, J = 7.7 Hz, 1 H) 7.47 (d, J = 7.7 Hz, 1 H) 7.65 (s, 1 H) 7.72 (s, 1 H) 7.75 (s, 1 H) 8.22 (s, 1 H) |
| 95 | (360 MHz, CHLOROFORM-d) δ ppm 1.30 (d, J = 6.7 Hz, 3 H) 1.74 (d, J = 7.1 Hz, 3 H) 2.30 (d, J = 0.7 Hz, 3 H) 3.18 (dd, J = 14.1, 3.8 Hz, 1 H) 3.63-3.89 (m, 1 H) 4.67 (dd, J = 14.0, 1.9 Hz, 1 H) 6.20 (qd, J = 6.8, 1.2 Hz, 1 H) 7.12 (dd, J = 10.1, 1.9 Hz, 1 H) 7.15 (s, 1 H) 7.21 (d, J = 1.9 Hz, 1 H) 7.36 (d, 7.7 Hz, 1 H) 7.51 (d, J = 7.7 Hz, 1 H) 7.76 (d, J = 1.3 Hz, 1 H) 8.28 (s, 1 H) |
| 96 | (360 MHz, CHLOROFORM-d) δ ppm 0.64 (d, J = 6.7 Hz, 3 H) 1.73 (d, J = 7.1 Hz, 3 H) 2.30 (d, J = 1.0 Hz, 3 H) 3.68 (dd, J = 14.0, 3.8 Hz, 1 H) 3.95-4.04 (m, 1 H) 4.87 (dd, J = 14.0, 1.9 Hz, 1 H) 6.21 (q, J = 6.8 Hz, 1 H) 7.11 (dd, J = 10.1, 1.9 Hz, 1 H) 7.14 (s, 1 H) 7.39 (d, J = 7.7 Hz, 1 H) 7.39 (d, J = 1.8 Hz, 1 H) 7.51 (d, J = 7.7 Hz, 1 H) 7.75 (d, J = 1.2 Hz, 1 H) 8.30 (s, 1 H) |
| 97 | (360 MHz, CHLOROFORM-d) δ ppm 1.12 (d, J = 6.6 Hz, 3 H) 2.15 (s, 3 H) 3.80 (dd, J = 14.1, 4.2 Hz, 1 H) 3.93-4.08 (m, 1 H) 4.51 (d, J = 15.3 Hz, 1 H) 4.60 (dd, J = 14.1, 2.2 Hz, 1 H) 5.08 (d, J = 15.3 Hz, 1 H) 7.18 (d, J = 7.7 Hz, 1 H) 7.43 (br. s, 1 H) 7.83 (d, J = 7.7 Hz, 1 H) 7.99 (s, 1 H) 8.06 (s, 1 H) 8.25 (s, 1 H) 8.27 (d, J = 1.1 Hz, 1 H) |

SFC-MS

For SFC-MS, an analytical SFC system from Berger Instruments (Newark, Del., USA) was used comprising a dual pump control module (FCM-1200) for delivery of $CO_2$ and modifier, a thermal control module for column heating (TCM2100) with temperature control in the range 1-150° C. and column selection valves (Valco, VICI, Houston, Tex., USA) for 6 different columns. The photodiode array detector (Agilent 1100, Waldbronn, Germany) is equipped with a high-pressure flow cell (up to 400 bar) and configured with a CTC LC Mini PAL auto sampler (Leap Technologies, Carrboro, N.C., USA). A ZQ mass spectrometer (Waters, Milford, Mass., USA) with an orthogonal Z-electrospray interface is coupled with the SFC-system. Instrument control, data collection and processing were performed with an integrated platform consisting of the SFC ProNTo software and Masslynx software.

Co. No. 6-7: SFC-MS was carried out on a OD-H column (250×4.6 mm) (Daicel Chemical Industries Ltd) with a flow rate of 3 ml/min. Two mobile phases (mobile phase A: $CO_2$; mobile phase B: 2-propanol containing 0.2% 2-propylamine) were employed. 45 B was hold for 15 min. Column temperature was set at 30° C. Under these conditions, Co. No. 6 had a shorter retention time ($R_t$) on the column than Co. No. 7. The measurement was compared against the mixture of compounds 6 and 7.

Co. No. 36-37: SFC-MS was carried out on a AD-H column (250×4.6 mm) (Daicel Chemical Industries Ltd) with a flow rate of 3 ml/min. Two mobile phases (mobile phase A: $CO_2$; mobile phase B: ethanol containing 0.2% 2-propylamine) were employed. 35% B was hold for 15 min. Column temperature was set at 30° C. Under these conditions, Co. No. 36 had a shorter retention time ($R_t$) on the column than Co. No. 37. The measurement was compared against the mixture of compounds 36 and 37.

Co. No. 46-47: SFC-MS was carried out on a OJ-H column (250×4.6 mm) (Daicel Chemical Industries Ltd) with a flow rate of 3 ml/min. Two mobile phases (mobile phase A: $CO_2$; mobile phase B: methanol containing 0.2% 2-propylamine) were employed. 10% B was hold for 15 min. Column temperature was set at 30° C. Under these conditions, Co. No. 46 had a shorter retention time ($R_t$) on the column than Co. No. 47. The measurement was compared against the mixture of compounds 46 and 47.

Pharmacology

A) Screening of the Compounds of the Invention for γ-Secretase-Modulating Activity Screening was carried out using SKNBE2 human neuroblastoma cells carrying the hAPP 695—wild type, grown in Dulbecco's Modified Eagle's Medium/Nutrient mixture F-12 (DMEM/NUT-mix F-12) (HAM) provided by Invitrogen (cat no. 10371-029) containing 5% Serum/Fe supplemented with 1% non-essential amino acids, 1-glutamine 2 mM, Hepes 15 mM, penicillin 50 U/ml (units/ml) and streptomycin 50 µg/ml. Cells were grown to near confluency.

The screening was performed using a modification of the assay as described in Citron et al (1997) Nature Medicine 3: 67. Briefly, cells were plated in a 384-well plate at $10^4$ cells/well in Ultraculture (Lonza, BE12-725F) supplemented with 1% glutamine (Invitrogen, 25030-024), 1% non-essential amino acid (NEAA), penicillin 50 U/ml en streptomycin 50 µg/ml in the presence of test compound at different test concentrations. The cell/compound mixture was incubated overnight at 37° C., 5% $CO_2$. The next day the media were assayed by two sandwich immuno-assays, for Aβ42 and Aβtotal.

Aβtotal and Aβ42 concentrations were quantified in the cell supernatant using the Aphalisa technology (Perkin Elmer). Alphalisa is a sandwich assay using biotinylated antibody attached to streptavidin coated donorbeads and antibody conjugated to acceptor beads. In the presence of antigen, the beads come into close proximity. The excitation of the donor beads provokes the release of singlet oxygen molecules that trigger a cascade of energy transfer in the acceptor beads, resulting in light emission. To quantify the amount of Aβ42 in the cell supernatant, monoclonal antibody specific to the C-terminus of Aβ42 (JRF/cAβ42/26) was coupled to the receptor beads and biotinylated antibody specific to the N-terminus of Aβ (JRF/AβN/25) was used to react with the donor beads. To quantify the amount of Aβtotal in the cell supernatant, monoclonal antibody specific to the N-terminus of Aβ (JRF/AβN/25) was coupled to the receptor beads and biotinylated antibody specific to the mid region of Aβ (biotinylated 4G8) was used to react with the donor beads.

To obtain the values reported in Table 3, the data are calculated as percentage of the maximum amount of amyloid Beta 42 measured in the absence of the test compound. The sigmoidal dose response curves were analyzed using non-linear regression analysis with percentage of the control plotted against the log concentration of the compound. A 4-parameter equation was used to determine the $IC_{50}$.

TABLE 3

("n.d." means not determined)

| Co. No. | IC50 Aβ42 (µM) | IC50 Aβtotal (µM) |
|---|---|---|
| 1 | 0.06 | >10 |
| 3 | >10 | >10 |
| 4 | >10 | >10 |
| 5 | 0.60 | >15 |
| 6 | 3.31 | >10 |
| 7 | 1.66 | >10 |
| 8 | 5.50 | >10 |
| 9 | 0.23 | >15 |
| 38 | 2.46 | >10 |
| 39 | 0.63 | >10 |
| 10 | 0.53 | >10 |
| 11 | 0.53 | >10 |
| 12 | 0.59 | >10 |
| 13 | 0.14 | >10 |
| 14 | 0.17 | >10 |
| 15 | 0.43 | >10 |
| 16 | 1.55 | >10 |
| 17 | 0.31 | >10 |
| 18 | 1.12 | >10 |
| 19 | 1.41 | >10 |
| 20 | 0.10 | >10 |
| 21 | n.d. | n.d. |
| 22 | 0.76 | >10 |
| 23 | 0.36 | >10 |
| 24 | 0.13 | >10 |
| 25 | 7.24 | >10 |
| 26 | 0.12 | >10 |
| 27 | 0.22 | >10 |
| 28 | 0.33 | >10 |
| 29 | 0.69 | >10 |
| 30 | 0.07 | >10 |
| 31 | 0.34 | >10 |
| 32 | 0.35 | >10 |
| 33 | 0.06 | >10 |
| 34 | 0.14 | >15 |
| 35 | 0.03 | >10 |
| 36 | 0.06 | >10 |
| 37 | 0.03 | >10 |
| 41 | 0.38 | >10 |
| 42 | 0.65 | >10 |
| 43 | 2.14 | >10 |
| 44 | 0.68 | >10 |
| 45 | n.d. | n.d. |
| 46 | 0.16 | >10 |
| 47 | 0.10 | >10 |
| 48 | 0.08 | >10 |
| 49 | 0.07 | >10 |
| 50 | 0.22 | >10 |
| 51 | 6.02 | >10 |
| 52 | 0.21 | >10 |
| 40 | 0.03 | >10 |
| 53 | 0.02 | >10 |
| 54 | 0.09 | >10 |
| 55 | 0.03 | >10 |
| 56 | 0.06 | >10 |
| 57 | 0.01 | 5.01 |
| 58 | 0.42 | >10 |
| 59 | 0.10 | >10 |
| 60 | 1.32 | >10 |
| 61 | 0.05 | 10 |
| 62 | 0.02 | >10 |
| 63 | 0.02 | 6.46 |
| 64 | 0.04 | >10 |
| 65 | 0.02 | 3.47 |
| 66 | 0.37 | >10 |
| 67 | 3.02 | >10 |
| 68 | 0.1 | >10 |
| 69 | 0.03 | >10 |
| 70 | 0.93 | >10 |
| 71 | 0.25 | >10 |
| 72 | 0.05 | >10 |
| 73 | 0.01 | 6.31 |
| 74 | 0.03 | >10 |
| 75 | 0.03 | >10 |
| 76 | 0.01 | >10 |
| 77 | 0.18 | >10 |
| 78 | 0.03 | >10 |
| 79 | 0.009 | 1.95 |
| 80 | 0.27 | 8.13 |
| 81 | 0.5 | >10 |
| 82 | 0.02 | 7.76 |
| 83 | 0.01 | 4.37 |
| 84 | 0.01 | 3.89 |
| 85 | 0.01 | 7.24 |
| 86 | 0.007 | 2.19 |
| 87 | 0.25 | 8.91 |
| 88 | 0.04 | >10 |
| 89 | 0.006 | 2.09 |
| 90 | 0.12 | >10 |
| 91 | 0.02 | 4.68 |
| 92 | 0.22 | >10 |
| 93 | 0.04 | >10 |

TABLE 3-continued ("n.d." means not determined)

| Co. No. | IC50 Aβ42 (µM) | IC50 Aβtotal (µM) |
|---|---|---|
| 94 | n.d. | n.d. |
| 95 | 0.24 | >10 |
| 96 | 0.02 | >10 |
| 97 | 0.007 | 6.76 |
| 98 | >10 | >10 |
| 99 | 0.59 | >10 |
| 100 | 0.34 | >10 |
| 101 | 0.1 | >10 |
| 102 | 0.12 | >10 |
| 103 | 0.12 | >10 |
| 104 | 0.19 | >10 |

B) Demonstration of In Vivo Efficacy

B-1) Aβ42

Aβ42 lowering agents of the invention can be used to treat AD in mammals such as humans or alternatively demonstrating efficacy in animal models such as, but not limited to, the mouse, rat, or guinea pig. The mammal may not be diagnosed with AD, or may not have a genetic predisposition for AD, but may be transgenic such that it overproduces and eventually deposits Aβ in a manner similar to that seen in humans afflicted with AD.

Aβ42 lowering agents can be administered in any standard form using any standard method. For example, but not limited to, Aβ42 lowering agents can be in the form of liquid, tablets or capsules that are taken orally or by injection. Aβ42 lowering agents can be administered at any dose that is sufficient to significantly reduce levels of Aβ42 in the blood, blood plasma, serum, cerebrospinal fluid (CSF), or brain.

To determine whether acute administration of an Aβ42 lowering agent would reduce Aβ42 levels in vivo, non-transgenic rodents, e.g. mice or rats were used. Animals treated with the Aβ42 lowering agent were examined and compared to those untreated or treated with vehicle and brain levels of soluble Aβ42, Aβ40, Aβ38, and Aβ37 were quantitated by Meso Scale Discovery's (MSD) electro-chemiluminescence detection technology. Treatment periods varied from hours (h) to days and were adjusted based on the results of the Aβ42 lowering once a time course of onset of effect could be established.

A typical protocol for measuring Aβ42 lowering in vivo is shown but it is only one of many variations that could be used to optimize the levels of detectable Aβ. For example, Aβ42 lowering compounds were formulated in 20% of Captisol® (a sulfobutyl ether of β-cyclodextrin) in water or 20% hydroxypropyl β cyclodextrin. The Aβ42 lowering agents were administered as a single oral dose or by any acceptable route of administration to overnight fasted animals. After 4 h, the animals were sacrificed and Aβ42 levels were analysed.

Blood was collected by decapitation and exsanguinations in EDTA-treated collection tubes. Blood was centrifuged at 1900 g for 10 minutes (min) at 4° C. and the plasma recovered and flash frozen for later analysis. The brain was removed from the cranium and hindbrain. The cerebellum was removed and the left and right hemisphere were separated. The left hemisphere was stored at −18° C. for quantitative analysis of test compound levels. The right hemisphere was rinsed with phosphate-buffered saline (PBS) buffer and immediately frozen on dry ice and stored at −80° C. until homogenization for biochemical assays.

Mouse brains from non-transgenic animals were resuspended in 8 volumes of 0.4% DEA (diethylamine)/50 mM NaCl containing protease inhibitors (Roche-11873580001 or 04693159001) per gram of tissue, e.g. for 0.158 g brain, add 1.264 ml of 0.4% DEA. All samples were homogenized in the FastPrep-24 system (MP Biomedicals) using lysing matrix D (MPBio #6913-100) at 6 m/s for 20 seconds. Homogenates were centrifuged at 20800×g for 5 min and supernatants collected. Supernatants were centrifuged at 221.300×g for 50 min. The resulting high speed supernatants were then transferred to fresh eppendorf tubes. Nine parts of supernatant were neutralized with 1 part 0.5 M Tris-HCl pH 6.8 and used to quantify Aβ.

To quantify the amount of Aβ42, Aβ40, Aβ38, and Aβ37 in the soluble fraction of the brain homogenates, simultaneous specific detection of Aβ42, Aβ40, Aβ38, and Aβ37 was performed using MSD's electro-chemiluminescence multiplex detection technology. In this assay purified monoclonal antibodies specific for Abeta37 (JRD/Aβ37/3), Abeta38 (J&JPRD/Aβ38/5), Abeta40 (JRF/cAβ40/28), and Abeta42 (JRF/cAβ42/26) were coated on MSD 4-plex plates. Briefly, the standards (a dilution of synthetic Aβ42, Aβ40, Aβ38, and Aβ37) were prepared in 1.5 ml Eppendorf tube in Ultraculture, with final concentrations ranging from 10000 to 0.3 pg/m. The samples and standards were co-incubated with Sulfo-tag labelled JRF/rAß/2 antibody to the N-terminus of Aβ as detector antibody. 50 µl of conjugate/sample or conjugate/standards mixtures were then added to the antibody-coated plate. The plate was allowed to incubate overnight at 4° C. in order to allow formation of the antibody-amyloid complex. Following this incubation and subsequent wash steps the assay was finished by adding read buffer according to the manufacturer's instructions (Meso Scale Discovery, Gaitherburg, Md.).

The SULFO-TAG emits light upon electrochemical stimulation initiated at the electrode. MSD Sector instrument SI6000 was used for signal read-out.

In this model a Aß42 lowering compared to untreated animals would be advantageous, in particular a Aß42 lowering with at least 10%, more in particular a Aß42 lowering with at least 20%.

B-2) Aβ38

Aβ38 increasing agents of the invention can be used to treat AD in mammals such as humans or alternatively demonstrating efficacy in animal models such as, but not limited to, the mouse, rat, or guinea pig. The mammal may not be diagnosed with AD, or may not have a genetic predisposition for AD, but may be transgenic such that it overproduces and eventually deposits Aβ in a manner similar to that seen in humans afflicted with AD.

Aβ38 increasing agents can be administered in any standard form using any standard method. For example, but not limited to, Aβ38 increasing agents can be in the form of liquid, tablets or capsules that are taken orally or by injection. Aβ38 increasing agents can be administered at any dose that is sufficient to significantly increase levels of Aβ38 in the blood, plasma, serum, cerebrospinal fluid (CSF), or brain.

To determine whether acute administration of an Aβ38 increasing agents would increase Aβ38 levels in vivo, non-transgenic rodents, e.g. mice or rats were used. Animals treated with the Aβ38 increasing agents were examined and compared to those untreated or treated with vehicle and brain levels of soluble Aβ42, Aβ40, Aβ38, and Aβ37 were quantitated by MSD electrochemiluminescence detection technology.

Treatment periods varied from hours (h) to days and were adjusted based on the results of the Aβ38 increase once a time course of onset of effect could be established.

A typical protocol for measuring Aβ38 increase in vivo is shown but it is only one of many variations that could be used to optimize the levels of detectable Aβ. For example, Aβ38 increasing agents were formulated in 20% of Captisol® (a sulfobutyl ether of β-cyclodextrin) in water or 20% hydroxypropyl β cyclodextrin. The Aβ38 increasing agents were administered as a single oral dose or by any acceptable route of administration to overnight fasted animals. After 4 h, the animals were sacrificed and Aβ38 levels were analysed.

Blood was collected by decapitation and exsanguinations in EDTA-treated collection tubes. Blood was centrifuged at 1900 g for 10 minutes (min) at 4° C. and the plasma recovered and flash frozen for later analysis. The brain was removed from the cranium and hindbrain. The cerebellum was removed and the left and right hemisphere were separated. The left hemisphere was stored at −18° C. for quantitative analysis of test compound levels. The right hemisphere was rinsed with phosphate-buffered saline (PBS) buffer and immediately frozen on dry ice and stored at −80° C. until homogenization for biochemical assays.

Mouse brains from non-transgenic animals were resuspended in 8 volumes of 0.4% DEA (diethylamine)/50 mM NaCl containing protease inhibitors (Roche-11873580001 or 04693159001) per gram of tissue, e.g. for 0.158 g brain, add 1.264 ml of 0.4% DEA. All samples were homogenized in the FastPrep-24 system (MP Biomedicals) using lysing matrix D (MPBio #6913-100) at 6 m/s for 20 seconds. Homogenates were centrifuged at 20800×g for 5 min and supernatants collected. Supernatants were centrifuged at 221.300×g for 50 min. The resulting high speed supernatants were then transferred to fresh eppendorf tubes. Nine parts of supernatant were neutralized with 1 part 0.5 M Tris-HCl pH 6.8 and used to quantify Aβ.

To quantify the amount of Aβ42, Aβ40, Aβ38, and Aβ37 in the soluble fraction of the brain homogenates, simultaneous specific detection of Aβ42, Aβ40, Aβ38, and Aβ37 was performed using MSD's electro-chemiluminescence multiplex detection technology. In this assay purified monoclonal antibodies specific for Abeta37 (JRD/Aβ37/3), Abeta38 (J&JPRD/Aβ38/5), Abeta40 (JRF/cAβ40/28), and Abeta42 (JRF/cAβ42/26) were coated on MSD 4-plex plates. Briefly, the standards (a dilution of synthetic Aβ42, Aβ40, Aβ38, and Aβ37) were prepared in 1.5 ml Eppendorf tube in Ultraculture, with final concentrations ranging from 10000 to 0.3 μg/m. The samples and standards were co-incubated with Sulfo-tag labelled JRF/rAβ/2 antibody to the N-terminus of Aβ as detector antibody. 50 μl of conjugate/sample or conjugate/standards mixtures were then added to the antibody-coated plate. The plate was allowed to incubate overnight at 4° C. in order to allow formation of the antibody-amyloid complex. Following this incubation and subsequent wash steps the assay was finished by adding read buffer according to the manufacturer's instructions (Meso Scale Discovery, Gaitherburg, Md.).

The SULFO-TAG emits light upon electrochemical stimulation initiated at the electrode. MSD Sector instrument SI6000 was used for signal read-out.

In this model a Aβ38 increase compared to untreated animals would be advantageous, in particular a Aβ38 increase with at least 10%, more in particular a Aβ38 increase with at least 20%.

B-3) Results

The results are shown in Table 4 (dose 30 mg/kg oral dosing) (value for untreated animals as control (Ctrl) was set at 100):

| Co. No. | Aβ40 (% vs Ctrl) _Mean | Aβ42 (% vs Ctrl) _Mean | Aβ38 (% vs Ctrl) _Mean |
| --- | --- | --- | --- |
| 13 | 101 | 77 | 117 |
| 30 | 126 | 118 | 121 |
| 33 | 79 | 57 | 132 |
| 34 | 128 | 104 | 102 |
| 35 | 108 | 112 | 116 |
| 48 | 91 | 60 | 161 |
| 49 | 101 | 85 | 123 |
| 53 | 121 | 120 | 124 |
| 55 | 113 | 93 | 142 |
| 57 | 105* | 100 | 134 |
| 61 | 90 | 86 | 192 |
| 62 | 87 | 82 | 113 |
| 63 | 62* | 58 | 135 |
| 64 | 132* | 108 | 155 |
| 65 | 52 | 58 | 165 |
| 72 | 88 | 64 | 130 |
| 73 | 114* | 97 | 110 |
| 74 | 100# | 83 | 144 |
| 79 | 62* | 54 | 175 |
| 83 | 41* | 40 | 166 |
| 84 | 21* | 25 | 237 |
| 85 | 69* | 51 | 194 |
| 89 | 67# | 58 | 132 |

*30 mpk sc;
10 mpk po

COMPOSITION EXAMPLES

"Active ingredient" (a.i.) as used throughout these examples relates to a compound of Formula (I), including any tautomer or stereoisomeric form thereof, or a pharmaceutically acceptable addition salt or a solvate thereof; in particular to any one of the exemplified compounds.

Typical examples of recipes for the formulation of the invention are as follows:

1. Tablets

| Active ingredient | 5 to 50 mg |
| --- | --- |
| Di-calcium phosphate | 20 mg |
| Lactose | 30 mg |
| Talcum | 10 mg |
| Magnesium stearate | 5 mg |
| Potato starch | ad 200 mg |

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 ml.

3. Injectable

A parenteral composition is prepared by stirring 1.5% (weight/volume) of active ingredient in 0.9% NaCl solution or in 10% by volume propylene glycol in water.

4. Ointment

| Active ingredient | 5 to 1000 mg |
| --- | --- |
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

The invention claimed is:
1. A compound of Formula (I):

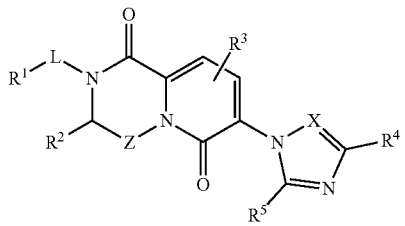

or a pharmaceutically acceptable addition salt, stereoisomer or tautomer thereof,
wherein:
X is $CR^6$ or N;
L is a covalent bond or $C_{1-6}$alkanediyl, wherein two geminal hydrogen atoms of the $C_{1-6}$alkanediyl may optionally be replaced by $C_{2-6}$alkanediyl;
$R^1$ is $Ar^1$ or $Ar^2$;
$R^2$ is hydrogen or $C_{1-4}$ alkyl;
$R^3$ is hydrogen;
$R^4$ is hydrogen, halo or $C_{1-4}$alkyl;
$R^5$ is hydrogen or $C_{1-4}$ alkyl;
$R^6$ is hydrogen or $C_{1-4}$ alkyl;
$R^9$ is hydrogen, $C_{3-7}$cycloalkyl or phenyl;
$Ar^1$ is benzofuranyl, optionally substituted with $C_{1-4}$alkyloxy, wherein the $C_{1-4}$alkyloxy is further optionally substituted with one or more halo substituents;
$Ar^2$ is phenyl, substituted with one substituent selected from the group consisting of $OR^9$ and 3-azabicyclo [3.1.0]hexanyl, and further optionally substituted with $C_{1-4}$alkyl, wherein the $C_{1-4}$alkyl is further optionally substituted with one or more halo substituents; and
Z is methylene.

2. The compound according to claim 1, or a pharmaceutically acceptable addition salt, stereoisomer or tautomer thereof, wherein $R^1$ is $Ar^2$.

3. The compound according to claim 1, or a pharmaceutically acceptable addition salt, stereoisomer or tautomer thereof, wherein the carbon atom substituted with $R^2$ has the (R)-configuration.

4. The compound according to claim 1, or a pharmaceutically acceptable addition salt, stereoisomer or tautomer thereof, wherein $R^2$ is $C_{1-4}$alkyl.

5. The compound according to claim 1, or a pharmaceutically acceptable addition salt, stereoisomer or tautomer thereof, wherein $R^2$ is $C_{1-4}$alkyl and L is $C_{1-6}$alkanediyl.

6. The compound according to claim 1, or a pharmaceutically acceptable addition salt, stereoisomer or tautomer thereof, wherein:
X is $CR^6$;
$R^4$ is $C_{1-4}$ alkyl;
$R^5$ is hydrogen; and
$R^6$ is hydrogen.

7. The compound according to claim 1, wherein the compound is selected from the group consisting of:
(3R)-2-[[3-(cyclopropyloxy)-5-(trifluoromethyl)phenyl]methyl]-3,4-dihydro-3-methyl-7-(4-methyl-1H-imidazol-1-yl)-2H-pyrido[1,2-a]pyrazine-1,6-dione;
(3R)-2-[2-[3-(cyclopropyloxy)-5-(trifluoromethyl)phenyl]ethyl]-3,4-dihydro-3-methyl-7-(4-methyl-1H-imidazol-1-yl)-2H-pyrido[1,2-a]pyrazine-1,6-dione;
(3R)-2-[[1-[3-(cyclopropyloxy)-5-(trifluoromethyl)phenyl]cyclopropyl]methyl]-3,4-dihydro-3-methyl-7-(4-methyl-1H-imidazol-1-yl)-2H-pyrido[1,2-a]pyrazine-1,6-dione;
7-(4-methyl-1H-imidazol-1-yl)-2-{[5-(trifluoromethoxy)-1-benzofuran-3-yl]methyl}-3,4-dihydro-2H-pyrido[1,2-a]pyrazine-1,6-dione;
(3R)-3-methyl-7-(4-methyl-1H-imidazol-1-yl)-2-{[5-(trifluoromethoxy)-1-benzofuran-3-yl]methyl}-3,4-dihydro-2H-pyrido[1,2-a]pyrazine-1,6-dione;
(3R)-2-{3-[(1R,5S)-3-azabicyclo[3.1.0]hex-3-yl]-4-methylbenzyl}-3-methyl-7-(4-methyl-1H-imidazol-1-yl)-3,4-dihydro-2H-pyrido[1,2-a]pyrazine-1,6-dione;
7-(4-methyl-1H-imidazol-1-yl)-2-{(1R)-1-[5-(trifluoromethoxy)-1-benzofuran-3-yl]ethyl}-3,4-dihydro-2H-pyrido[1,2-a]pyrazine-1,6-dione;
7-(4-methyl-1H-imidazol-1-yl)-2-{(1S)-1-[5-(trifluoromethoxy)-1-benzofuran-3-yl]ethyl}-3,4-dihydro-2H-pyrido[1,2-a]pyrazine-1,6-dione;
(3R)-2-{(1R)-1-[3-(cyclopropyloxy)-5-(trifluoromethyl)phenyl]ethyl}-3-methyl-7-(4-methyl-1H-imidazol-1-yl)-3,4-dihydro-2H-pyrido[1,2-a]pyrazine-1,6-dione;
(3R)-2-{(1S)-1-[3-(cyclopropyloxy)-5-(trifluoromethyl)phenyl]ethyl}-3-methyl-7-(4-methyl-1H-imidazol-1-yl)-3,4-dihydro-2H-pyrido[1,2-a]pyrazine-1,6-dione;
(3R)-2-{(1R)-1-[3-hydroxy-5-(trifluoromethyl)phenyl]ethyl}-3-methyl-7-(4-methyl-1H-imidazol-1-yl)-3,4-dihydro-2H-pyrido[1,2-a]pyrazine-1,6-dione;
(3R)-2-{(1S)-1-[3-hydroxy-5-(trifluoromethyl)phenyl]ethyl}-3-methyl-7-(4-methyl-1H-imidazol-1-yl)-3,4-dihydro-2H-pyrido[1,2-a]pyrazine-1,6-dione;
(3R)-3-methyl-7-(4-methyl-1H-imidazol-1-yl)-2-{(1R)-1-[5-(trifluoromethoxy)-1-benzofuran-3-yl]ethyl}-3,4-dihydro-2H-pyrido[1,2-a]pyrazine-1,6-dione;
(3R)-3-methyl-7-(4-methyl-1H-imidazol-1-yl)-2-{(1S)-1-[5-(trifluoromethoxy)-1-benzofuran-3-yl]ethyl}-3,4-dihydro-2H-pyrido[1,2-a]pyrazine-1,6-dione;
(3R)-3-methyl-7-(4-methyl-1H-imidazol-1-yl)-2-{(1R)-1-[5-(trifluoromethoxy)-1-benzofuran-3-yl]ethyl}-3,4-dihydro-2H-pyrido[1,2-a]pyrazine-1,6-dione; and
(3R)-3-methyl-7-(4-methyl-1H-imidazol-1-yl)-2-{(1S)-1-[5-(trifluoromethoxy)-1-benzofuran-3-yl]ethyl}-3,4-dihydro-2H-pyrido[1,2-a]pyrazine-1,6-dione,
or a pharmaceutically acceptable addition salt thereof.

8. A pharmaceutical composition comprising a pharmaceutically acceptable carrier and, as active ingredient, a therapeutically effective amount of a compound according to claim 1, or a pharmaceutically acceptable addition salt, stereoisomer or tautomer thereof.

9. A method for modulating γ-secretase activity in a subject having a disease or condition selected from the group consisting of Alzheimer's disease, traumatic brain injury, mild cognitive impairment, senility, dementia, dementia with Lewy bodies, cerebral amyloid angiopathy, multi-infarct dementia, dementia pugilistica, Down's syndrome, dementia associated with Parkinson's disease and dementia associated with beta-amyloid, comprising administering to the subject in need thereof a therapeutically effective amount of a compound according to claim 1, or a pharmaceutically acceptable addition salt, stereoisomer or tautomer thereof.

10. The method according to claim 9, wherein the subject has Alzheimer's disease.

11. A method for modulating γ-secretase activity in a subject suffering from a disease or condition selected from the group consisting of neurocognitive disorder due to Alzheimer's disease, neurocognitive disorder due to traumatic brain injury, neurocognitive disorder due to Lewy body disease, neurocognitive disorder due to Parkinson's disease and vascular neurocognitive disorder, comprising administering to the subject in need thereof a therapeutically effective amount of a compound according to claim 1, or a pharmaceutically acceptable addition salt, stereoisomer or tautomer thereof.

\* \* \* \* \*